(12) United States Patent
Montti et al.

(10) Patent No.: US 11,333,644 B2
(45) Date of Patent: May 17, 2022

(54) CHROMATOGRAPHY METHOD FOR QUANTIFYING A NONIONIC SURFACTANT IN A COMPOSITION COMPRISING THE NON-IONIC SURFACTANT AND A POLYPEPTIDE

(71) Applicant: Genentech, Inc., South San Francisco, CA (US)

(72) Inventors: Mary Montti, San Francisco, CA (US); Richard L. Beardsley, Pacifica, CA (US); Michael S. Chinn, Pleasanton, CA (US)

(73) Assignee: Genentech, Inc., South San Francisco, CA (US)

( * ) Notice: Subject to any disclaimer, the term of this patent is extended or adjusted under 35 U.S.C. 154(b) by 240 days.

(21) Appl. No.: 16/275,849

(22) Filed: Feb. 14, 2019

(65) Prior Publication Data
US 2019/0178859 A1 Jun. 13, 2019

Related U.S. Application Data

(63) Continuation of application No. PCT/US2017/046725, filed on Aug. 14, 2017.
(Continued)

(51) Int. Cl.
*A61K 47/10* (2017.01)
*A61K 47/26* (2006.01)
(Continued)

(52) U.S. Cl.
CPC ......... *G01N 30/96* (2013.01); *B01D 15/3847* (2013.01); *G01N 30/36* (2013.01); *A61K 47/10* (2013.01); *A61K 47/26* (2013.01)

(58) Field of Classification Search
CPC ........ G01N 30/96; G01N 30/36; A61K 47/10; A61K 47/26; B01D 15/3847
See application file for complete search history.

(56) References Cited

U.S. PATENT DOCUMENTS

| 4,676,980 A | 6/1987 | Segal et al. |
| 4,816,567 A | 3/1989 | Cabilly et al. |

(Continued)

FOREIGN PATENT DOCUMENTS

| EP | 0 404 097 A2 | 12/1990 |
| EP | 0 308 936 B1 | 7/1994 |

(Continued)

OTHER PUBLICATIONS

LCGC North America, "Understanding gradient HPLC", vol. 31, Issue 7. Jul. 1, 2013.*

(Continued)

*Primary Examiner* — Benjamin L Lebron
(74) *Attorney, Agent, or Firm* — Morrison & Foerster LLP

(57) ABSTRACT

The invention provides methods for quantifying a non-ionic surfactant in a composition comprising a polypeptide and the non-ionic surfactant, where the quantification exhibits reduced interference between the non-ionic surfactant and the polypeptide. Also provided are methods where the composition further includes N-acetyl tryptophan, and the quantification exhibits reduced interference between the non-ionic surfactant, the polypeptide, and N-acetyl tryptophan.

23 Claims, 33 Drawing Sheets

Related U.S. Application Data

(60) Provisional application No. 62/375,373, filed on Aug. 15, 2016.

(51) Int. Cl.
  *B01D 15/38* (2006.01)
  *G01N 30/36* (2006.01)
  *G01N 30/96* (2006.01)

(56) References Cited

U.S. PATENT DOCUMENTS

| | | | |
|---|---|---|---|
| 5,208,020 | A | 5/1993 | Chari et al. |
| 5,229,275 | A | 7/1993 | Goroff |
| 5,500,362 | A | 3/1996 | Robinson et al. |
| 5,534,615 | A | 7/1996 | Baker et al. |
| 5,545,807 | A | 8/1996 | Surani et al. |
| 5,565,332 | A | 10/1996 | Hoogenboom et al. |
| 5,567,610 | A | 10/1996 | Borrelbaeck et al. |
| 5,571,894 | A | 11/1996 | Wels et al. |
| 5,573,905 | A | 11/1996 | Lerner et al. |
| 5,587,458 | A | 12/1996 | King et al. |
| 5,589,369 | A | 12/1996 | Seidman et al. |
| 5,591,669 | A | 1/1997 | Krimpenfort et al. |
| 5,641,870 | A | 6/1997 | Rinderknecht et al. |
| 5,648,237 | A | 7/1997 | Carter |
| 5,693,780 | A | 12/1997 | Newman et al. |
| 5,712,374 | A | 1/1998 | Kuntsmann et al. |
| 5,731,168 | A | 3/1998 | Carter et al. |
| 5,789,199 | A | 8/1998 | Joly et al. |
| 5,821,337 | A | 10/1998 | Carter et al. |
| 5,840,523 | A | 11/1998 | Simmons et al. |
| 6,331,254 | B1 * | 12/2001 | White .............. G01N 30/90 210/198.3 |
| 7,776,360 | B2 * | 8/2010 | Kipp .............. C08L 71/02 424/489 |
| 2006/0067930 | A1 | 3/2006 | Adams et al. |
| 2008/0113443 | A1 | 5/2008 | Gulati et al. |
| 2013/0079272 | A1 | 3/2013 | Liu et al. |

FOREIGN PATENT DOCUMENTS

| | | |
|---|---|---|
| JP | H0943218 A | 2/1997 |
| JP | 2013530156 A | 7/2013 |
| WO | WO-1991/00360 A1 | 1/1991 |
| WO | WO-1992/20373 A1 | 11/1992 |
| WO | WO-1993/08829 A1 | 5/1993 |
| WO | WO-1993/11161 A1 | 6/1993 |
| WO | WO-1993/16185 A1 | 8/1993 |
| WO | WO-1994/04690 A1 | 3/1994 |
| WO | WO-1994/11026 A2 | 5/1994 |
| WO | WO-1994/11026 A3 | 5/1994 |
| WO | WO-2000/29004 A1 | 5/2000 |
| WO | WO-2002/051870 A2 | 7/2002 |
| WO | WO-2002/051870 A3 | 7/2002 |
| WO | WO-2003/035694 A2 | 5/2003 |
| WO | WO-2003/035694 A3 | 5/2003 |
| WO | WO-2005/035572 A2 | 4/2005 |
| WO | WO-2005/035572 A3 | 4/2005 |
| WO | 2011150110 A1 | 12/2011 |
| WO | 2012067090 A1 | 5/2012 |

OTHER PUBLICATIONS

Li, Y. et al. (Apr. 21, 2014). "Characterization and Stability Study of Polysorbate 20 in Therapeutic Monoclonal Antibody Formulation by Multidimensional Ultrahigh-Performance Liquid Chromatography—Charged Aerosol Detection-Mass Spectrometry," Anal. Chem. 86:5150-5157.
Adamo, M. et al. "A Simple Reversed Phase High-Performance Liquid Chromatography Method for Polysorbate 80 Quantitation in Monoclonal Antibody Drug Products," *J. of Chromatography B* 878(21):1865-1870, (Jul. 1, 2010, e-pub. May 4, 2010).

Anonymous "Ion Chromatography—Wikipedia," retrieved from <https://en.wikipedia.org/w/index.php?title=Ion_chromatogrpahy&oldid=734427855> last visited Oct. 13, 2017, 13 pages.
Brennan, M. et al. "Preparation of Bispecific Antibodies by Chemical Recombination of Monoclonal Immunoglobulin $G_1$ Fragments," *Science* 229:81-83, (Jul. 5, 1985).
Brodeur, B.R. et al."Mouse-Human Myeloma Partners for the Production of Heterohybridomas,"in *Monoclonal Antibody Production Techniques and Applications*, pp. 51-63 Marcel Dekker, Inc., New York, (1987).
Bruggermann, M. et al. "Designer Mice: The Production of Human Antibody Repertoires in Transgenic Animals," *Year in Immuno.* 7:33-40, (1993).
Capel, P.J.A. et al. "Heterogeneity of Human IgG Fc Receptors," *Immunomethods* 4:25-34, (1994).
Caron, P.C. et al. Engineered Humanized Dimerica Forms of IgG Are More Effective Antibodies, *J. Exp. Med.* 176:1191-1195 (Oct. 1, 1992).
Carter, P. et al. "High Level *Escherichia coli* Expression and Production of a Bivalent Humanized Antibody Fragment," *Biotech.* 10:163-167, (Feb. 1992).
Carter, P. et al. "Humanization of an Anti-p185$^{HER2}$ Antibody for Human Cancer Therapy," *Proc. Natl. Acad. Sci. USA* 89:4285-4289, (May 1992).
Charlton, K.A. "Expression and Isolation of Recombinant Antibody Fragments in *E. coli*," *Methods in Molecular Biology*, Humana Press 248:245-254, (2003).
Chothia, C. et al. "Canonical Structures for the Hypervariable Regions of Immunoglobulins," *J. Mol. Biol.* 196:901-917, (1987).
Clackson, T. et al. "Making Antibody Fragments Using Phage Display Libraries," *Nature* 352:624-628, (Aug. 15, 1991).
Clynes, R. et al. "Fc Receptors Are Required in Passive and Active Immunity to Melanoma," *Proc. Natl. Acad. Sci. USA* 95:652-656, (Jan. 1998).
Cunningham, B.C. et al. "High-Resolution Epitope Mapping of hGH-receptor Interactions by Alanine-Scanning Mutagenesis," *Science* 244:1081-1085, (Jun. 2, 1989).
Daeron, M. "Fc Receptor Biology," *Annu. Rev. Immunol.* 15:203-234, (1997).
Davies, J. et al. "'Camelising' Human Antibody Fragments: NMR Studies on VH Domains," *Febs Lett.* 339(3):285-290, (Feb. 1994).
De Haas, M. et al. "Fcγ Receptors of Phagocytes," *J. Lab. Clin. Med.* 126:330-341, (1995).
Dooley, H. et al. "Antibody Repertoire Development In Cartilaginous Fish," *Dev Comp Immunol* 30(1-2):43-56, (2006).
Edelhoch, H. "Spectroscopic Determination of Tryptophan and Tyrosine in Proteins," *Biochemistry* 6(7): 1948-1954, (Jul. 1967).
Gazzano-Santoro, H. et al. "A Non-Radioactive Complement-Dependent Cytotoxicity Assay for Anti-CD20 Monoclonal Antibody," *J. Immunol. Methods* 202:163-171, (1997).
Geng, X. et al. "Retention Model for Proteins in Reversed-Phase Liquid Chromatography," *Journal of Chromatography A*, 296:15-30, (Jul. 27, 1984).
Goding, J.W. *Monoclonal Antibodies: Principles and Practice* pp. 59-103, (1983).
Griffiths, A.D. et al. "Human Anti-Self Antibodies With High Specificity From Phage Display Libraries," *EMBO J.* 12(2)725-734, (1993).
Gruber, M. et al. "Efficient Tumor Cell Lysis Mediated by a Bispecific Single Chain Antibody Expressed in *Escherichia coli*," *J. Immunol.* 152:5368-5374, (1994).
Guyer, R.L. et al. "Immunoglobulin Binding by Mouse Intestinal Epithelial Cell Receptors," *J. Immunol.* 117(2):587-593, (Aug. 1976).
Hewitt, D. et al. "Quantitation of Polysorbate 20 in Protein Solutions Using Mixed-Mode Chromatography and Evaporative Light Scattering Detection," *Journal of Chromatography A*, 1215(1):156-160, (2008, e-pub. Nov. 14, 2008).
Hewitt, D. et al. "Mixed-Mode and reversed-Phase Liquid Chromatography-Tandem Mass Spectrometry Methodologies to Study Composition and Base Hydrolysis of Polysorbate 20 and 80," *J. Chromatography A*, 1218(15):2138-2145, (Apr. 15, 2011, e-pub. Sep. 29, 2010).

(56) References Cited

OTHER PUBLICATIONS

Holliger, P., et al. "Diabodies: Small Bivalent and Bispecific Antibody Fragments," *Proc. Natl. Acad. Sci. USA* 90:6444-6448, (Jul. 1993).

Holt, L.J. et al. "Domain Antibodies: Proteins for Therapy," *Trends Biotechnol.* 21 (11):484-490, (Nov. 2003).

Jakobovits, A. et al. "Germ-Line Transmission and Expression of a Human-Derived Yeast Artificial Chromosome," *Nature* 362:255-258, (Mar. 18, 1993).

Jakobovits, A. et al. "Analysis of Homozygous Mutant Chimeric Mice: Deletion of the Immunoglobulin Heavy-Chain Joining Region Blocks B-cell development and antibody production," *PNAS* 90:2551-2555, (Mar. 1993).

Johnson, K.S. et al. "Human Antibody Engineering," *Current Opinion in Structural Biology* 3:564-571, (1993).

Jones, P.T. et al. "Replacing the Complementarity—Determining Regions in a Human Antibody With Those From a Mouse," *Nature* 321:522-525, (May 29, 1986).

Kerwin, B.A. "Polysorbates 20 and 80 Used in the Formulation of Protein Biotherapeutics: Structure and Degradation Pathways," *J. Pharm. Sci.* 97(8): 2924-2935, (Aug. 2008).

Kim, J. et al. "Quantitation of Low Concentrations of Polysorbates in High Protein Concentration Formulations by Solid Phase Extraction and Cobalt-Thiocyanate Derivatization," *Analytica chimica acta* 806:144-151, (Jan. 2, 2014, e-pub. Nov. 15, 2013).

Kim, J.-K. et al. "Localization of the Site of the Murine IgG1 Molecule That is Involved in Binding to the Murine Intestinal Fc Receptor," *J. Immunol.* 24:2429-2434, (1994).

Kohler, G. et al. "Continuous Cultures of Fused Cells Secreting Antibody of Predefined Specificity," *Nature* 256:495-497, (Aug. 7, 1975).

Kostelny, S.A. et al. "Formation of a Bispecific Antibody by the Use of Leucine Zippers," *J. Immunol.* 148(5):1547-1553, (Mar. 1, 1992).

Kozbor, D. "A Human Hybrid Myeloma for Production of human Monoclonal Antibodies," *J. Immunol.* 133(6):3001-3005, (Dec. 1984).

Lehninger, A.L. *Biochemistry 2nd ed.*, pp. 73-75, Worth Publishers, New York, (1975).

Marks, J.D. et al. "By-passing immunization. Human Antibodies From V-Gene Libraries Displayed on Phage," *J. Mol. Biol.* 222:581-597, (1991).

Marks, J.D. et al. "By-Passing Immunization: Building High Affinity Human Antibodies by Chain Shuffling," *Bio/Technology* 10:779-783, (Jul. 19921992).

McCafferty, J. et al. "Phage Antibodies: Filamentous Phage Displaying Antibody Variable Domains," *Nature* 348:552-554, (Dec. 6, 1990).

Milstein, C. "Hybrid Hybridomas and Their Use in Immunohistochemistry," *Nature* 305:537-540, (Oct. 6, 1983).

Morimoto, K. et al. "Single-Step Purification Of F(ab')2 fragments of Mouse Monoclonal Antibodies (Immunoglobulins G1) by Hydrophobic Interaction High Performance Liquid Chromatography Using TSKgel Phenyl-5PW," *J. Biochem. and Biophysical Methods* 24:107-117, (1992).

Morrison, S.L. et al. "Chimeric Human Antibody Molecules: Mouse Antigen-Binding Domains With Human Constant Region Domains," *Proc. Natl. Acad. Sci. USA* 81:6851-6855, (Nov. 1984).

Munson, P.J. et al. "Ligand: A Versatile Computerized Approach for Characterization of Ligand-Binding Systems," *Anal. Biochem.* 107:220-239, (1980).

Muyldermans, S. et al. "Recognition of Antigens by Single-Domain Antibody Fragments: The Superfluous Luxury of Paired Domains," *Trend Biochem Sci* 26(4):230-235, (Apr. 2001).

Nair, L.M. et al. "Determination of Polysorbate 80 in Parenteral Formulations by High-Performance Liquid Chromatography and Evaporative Light Scattering Detection," *J. of Chromatograp.* 1012(1):81-86, (Sep. 12, 2003).

Pluckthun, A. "Antibodies from *Escherichia coli*," *The Pharmacology of Monoclonal Antibodies*, vol. 113 Rosenburg and Moore eds. Springer-Verlag, New York pp. 269-315, (1994).

Pluckthun, A. "Mono-and Bivalent Antibody Fragments Produced In *Escherichia coli*: Engineering, Folding and Antigen Binding," *Immunol. Revs.* 130:151-188 (1992).

Presta, L.G. "Antibody Engineering," *Curr. Op. Struct. Biol.* 2:593-596, (1992).

Presta, L.G. et al. "Humanization of an Antibody Directed Against IgE" *J. Immunol.* 151(5):2623-2632, (Sep. 1, 1993).

Ravetch, J.V. et al. "Fc Receptors," *Annu. Rev. Immunol.* 9:457-492, (1991).

*Remington's Pharmaceutical Sciences*, $16^{th}$ ed. Table of Contents (1980).

Riechmann et al. "Reshaping Human Antibodies for Therapy," *Nature* 332:323-329, (1988).

Shopes, B. "A Genetically Engineered Human IgG Mutant With Enhanced Cyolytic Activity," *Immunol.* 148(9):2918-2922, (May 1, 1992).

Sims, M.J. et al. "A Humanized CD18 Antibody Can Block Function Without Cell Destruction," *J. Immunol.* 151(4):2296-2308, (Aug. 15, 1993).

Skerra, A. "Bacterial Expression of Immunoglobulin Fragments," *Curr. Opinion in Immunol.* 5:256-262 (1993).

Stevenson, G.T. et al. "A Chimeric Antibody With Dual Fc Regions (bisFabFc) Prepared by Manipulations at the IgG Hinge," *Anti-Cancer Drug Design* 3:219-230, (1989).

Suresh, M.R. et al. "Bispecific Monoclonal Antibodies From Hybrid Hybridomas," *Meth. in Enzymology* 121:210-228, (1986).

Traunecker, A. et al. "Bispecific Single Chain Molecules (Janusins) Target Cytotoxic Lymphocytes on HIV Infected Cells," *EMBO J.* 10(12):3655-3659, (1991).

Tutt, A. et al. "Trispecific F(ab')3 Derivatives That Use Cooperative Signaling Via the TCR/CD3 Complex and CD2 to Activate and Redirect Resting Cytotoxic T Cells," *J. Immunol.* 147(1):60-69, (Jul. 1, 1991).

Verhoeyen, M. et al. "Reshaping Human Antibodies: Grafting an Antilysozyme Activity," *Science* 239:1534-1536, (Mar. 25, 1988).

Vitetta, E.S. et al., "Redesigning Nature's Poisons to Create Anti-Tumor Reagents," *Science* 238:1098-1104, (1987).

Ward, E.S. et al. "Binding Activities of a Repertoire of Single Immunoglobulin Variable Domains Secreted From *Escherichia coli*," *Nature* 341 (6242):544-546, (Oct. 12, 1989).

Waterhouse, P. et al. "Combinatorial Infection and in vivo Recombination: A Strategy for Making Large Phage Antibody Repertoires," *Nuc. Acids. Res.* 21(9):2265-2266, (1993).

Wolff, E.A. et al. "Monoclonal Antibody Homodimers: Enhanced Antitumor Activity In Nude Mice," *Cancer Research* 53:2560-2565, (Jun. 1, 1993).

Zapata, G. et al. "Engineering Linear $F(ab')_2$ Fragments for Efficient Production in *Escherichia coli* and Enhanced Antiproliferative Activity," *Protein Eng.* 8(10):1057-1062, (1995).

International Preliminary Report on Patentability, dated Feb. 19, 2019, for PCT Application No. PCT/US2017/046725, filed Aug. 14, 2017, 8 pages.

International Search Report for PCT Application No. PCT/US2017/046725, dated Oct. 24, 2017, filed Aug. 14, 2017, 5 pages.

Written Search Report for PCT Application No. PCT/US2017/046725, dated Oct. 24, 2017, filed Aug. 14, 2017, 9 pages.

Miyashita, M. et al. (2004). "Solid Phase Precipitation for Reversed Phase High Speed Chromatography of Iodinated Amino Acids," The Journal of the Japan Society for Analytical Chemistry 1167-1175. English Abstract.

Zhang et al. (Dec. 2000). "Common Eluting Agents for Reverse Phase Chromatography," in Handbook of Analytical Chemistry, vol. 6, Liquid Chromatography Analysis, pp. 20-21, with English Translation, 6 pages.

\* cited by examiner

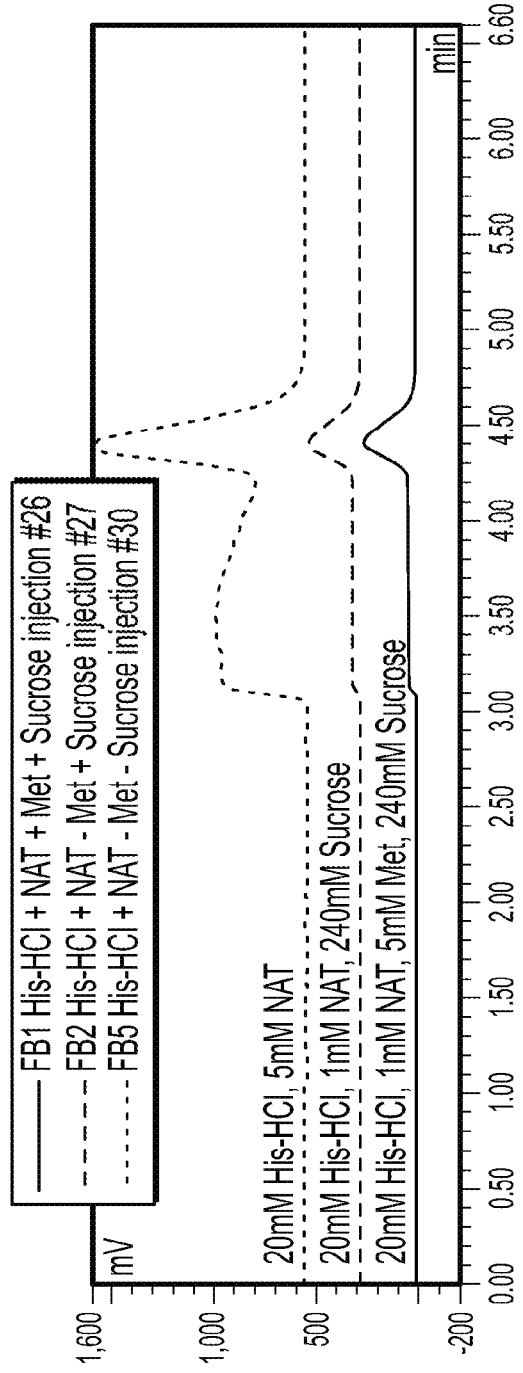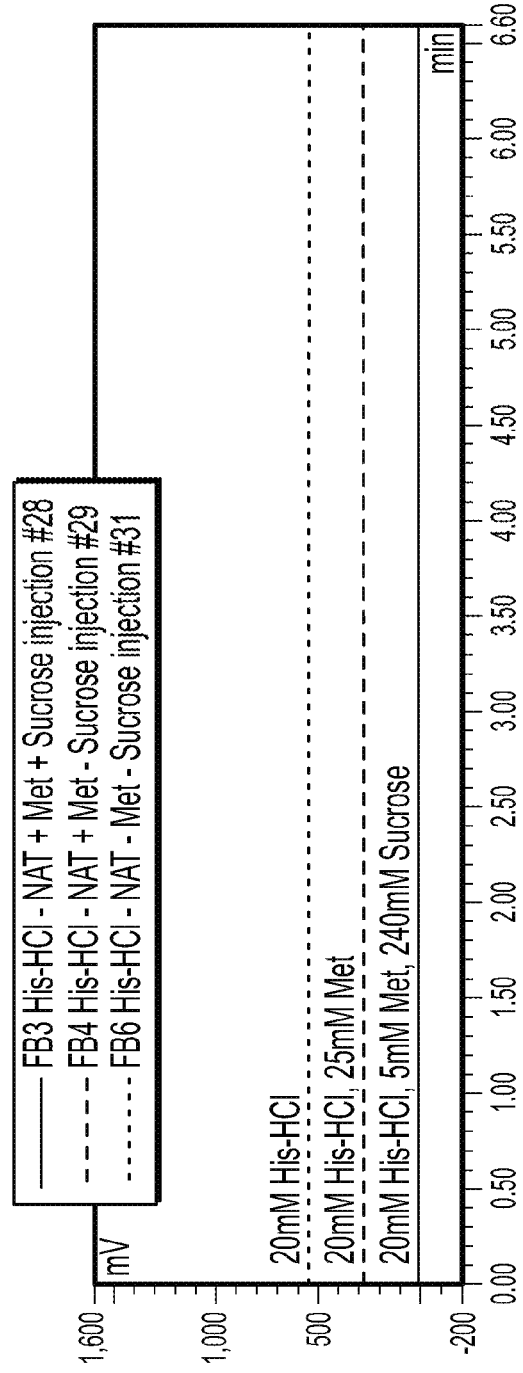
FIG. 12A
FIG. 12B

CHROMATOGRAPHY METHOD FOR QUANTIFYING A NONIONIC SURFACTANT IN A COMPOSITION COMPRISING THE NON-IONIC SURFACTANT AND A POLYPEPTIDE

CROSS-REFERENCE TO RELATED APPLICATIONS

This application is a continuation of International Application No. PCT/US2017/046725, filed on Aug. 14, 2017, which claims priority to U.S. Provisional Patent Application No. 62/375,373 filed Aug. 15, 2016, the disclosure of each of which is incorporated herein by reference in its entirety.

FIELD OF THE INVENTION

The present invention provides methods for analyzing formulations of polypeptides for the presence of polysorbates.

BACKGROUND OF THE INVENTION

Polysorbate 20 (PS20) is a surfactant commonly used in polypeptide formulations to protect product from physical damage during processing and storage (Kerwin, B., 2007, *J. Pharm. Sci.*, 97(8): 2924-2935). Due to its importance to product stability, PS20 must be accurately quantified in each product's control system. PS20 can be quantified by spectrophotometric assay, fluorescent micelle assay, or High Performance Liquid Chromatography-Evaporative Light Scattering Detector (HPLC-ELSD) assay (see for example Kim, J. and Qiu, J., *Analytica chimica acta* 806:144-151, 2014; Hewitt et al., *Journal of Chromatography A*, 1215(1): 156-160, 2008).

The evaporative light scattering detector (ELSD) assay is preferred as a control system assay because, relative to the fluorescent micelle assay, it does not require long conditioning times. The ELSD method may also obviate the requirement to use the same polysorbate lot for standard curve preparation as was used in production. Additionally, the fluorescent micelle assay is susceptible to non-specific protein interference, particularly for hydrophobic proteins and antibody drug conjugates (ADCs). The vcMMAE linker-drug of ADCs introduces additional hydrophobicity to the protein, which may lead to increased protein interference when quantifying PS20. In some cases, this non-specific protein interference can be mitigated by using the HPLC-ELSD assay.

Although the HPLC-ELSD assay may reduce the degree of protein interference, this interference is not completely eliminated. The protein interference issue becomes particularly problematic at low polysorbate concentrations and with more hydrophobic and/or concentrated proteins. Additionally, the effect of protein interference is highly dependent on the cartridge resin lot used. Strategies to mitigate these issues include a) spike addition of PS20 to dilute out protein interference without decreasing the PS20 response, and b) removal of protein from sample by protein precipitation.

The spike addition approach entails diluting a sample with a PS20 stock solution at the formulation target concentration. This sample preparation dilutes the protein concentration while maintaining an approximately unchanged PS20 concentration. The amount of PS20 spiked into the sample is then subtracted during data analysis. Because the relationship between ELSD response and the mass analyzed in the detector follows a power-law, spiking in PS20 disproportionally decreases the contribution of protein to the ELSD signal. The spike addition approach has been shown to improve the accuracy of PS20 quantitation in some cases, but in cases where this is not a viable solution, protein precipitation must be used. While it is effective in removing protein interference, the HPLC-ELSD precipitation method is not ideal due to overnight sample preparation time, large sample volumes, and sample preparation variability. By contrast, removal of protein uses the same HPLC-ELSD conditions, but without significant sample preparation procedures. What is needed is a more robust solution to eliminate protein interference and yield consistent PS20 quantitation across all chromatography conditions.

All references cited herein, including patent applications and publications, are incorporated by reference in their entirety.

BRIEF SUMMARY

In some aspects, the invention provides a method for quantifying a non-ionic surfactant in a composition comprising the non-ionic surfactant and a polypeptide, wherein interference between the non-ionic surfactant and the polypeptide during quantification is reduced, wherein the method comprises the steps of a) applying the composition to a mixed mode anion exchange chromatography material, wherein the composition is loaded onto the chromatography material in a solution comprising a mobile phase A and a mobile phase B, wherein mobile phase A comprises acid in water and mobile phase B comprises acid in methanol, wherein the polypeptide binds to the chromatography material specifically and non-specifically; b) eluting the specifically bound polypeptide from the mixed mode anion exchange chromatography material with a solution comprising mobile phase A and mobile phase B wherein the ratio of mobile phase B to mobile phase A is increased compared to step a); c) eluting the non-ionic surfactant and the non-specifically bound polypeptide from the chromatography material with a solution comprising mobile phase A and mobile phase B wherein the ratio of mobile phase B to mobile phase A is increased compared to step c); d) quantifying the non-ionic surfactant, wherein interference between the non-ionic surfactant and the polypeptide during quantitation is reduced. In some embodiments, the ratio of mobile phase B to mobile phase A in step a) is about 10:90. In some embodiments, the ratio of mobile phase B to mobile phase A is increased to about 40:60 in step b). In some embodiments, the ratio of mobile phase B to mobile phase A is increased to about 100:0 in step c). In some embodiments, mobile phase A comprises about 2% acid in water. In some embodiments, mobile phase B comprises about 2% acid in methanol. In some embodiments, the acid is formic acid. In some embodiments, the acid is acetic acid. In some embodiments, the flow rate of the chromatography is about 1.25 ml/minute. In some embodiments, step b) starts at about 1 min after the chromatography is initiated and ends at about 3.4 min after the chromatography is initiated. In some embodiments, step c) starts at about 3.5 min after the chromatography is initiated and ends at about 4.6 min after the chromatography is initiated. In some embodiments, the non-ionic surfactant is poloxamer (P188) or a polysorbate. In some embodiments, the polysorbate is polysorbate 20 or polysorbate 80. In some embodiments, the concentration of non-ionic surfactant in the composition is in the range of about 0.001% to 1.0% (w/v). In some embodiments, the protein concentration in the composition is about 1 mg/mL to about 250 mg/mL. In some embodiments, the formulation has a pH of about 4.5 to about 7.5. In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic polypeptide is a fusion protein, a polyclonal antibody, a monoclonal antibody, a humanized antibody, a human antibody, a chimeric antibody, a multispecific antibody, a glycoengineered antibody, an antibody fragment, an antibody drug conjugate, a THIOMAB™ or a THIOMAB™ drug conjugate. In some embodiments, the mixed mode anion exchange chromatography material comprises a reversed phase, strong anion exchange polymer. In some embodiments, the mixed mode anion exchange chromatography material comprises a quaternary amine moiety. In some embodiments, the mixed mode anion exchange chromatography material comprises a solid support. In some embodiments, the mixed mode anion exchange chromatography material is contained in a column. In some embodiments, the mixed mode anion exchange chromatography material is a high performance liquid chromatography (HPLC) material. In some embodiments, the mixed mode anion exchange chromatography material is an Oasis® MAX chromatography material. In some embodiments, the non-ionic detergent is quantified by Evaporative Light Scattering (ELSD) or by using a Charged Aerosol Detector (CAD).

In some aspects, the invention provides a method for quantifying a non-ionic surfactant in a composition comprising the non-ionic surfactant and a polypeptide, wherein the method comprises the steps of a) applying the composition to a mixed mode cation exchange chromatography material, wherein the composition is loaded onto the chromatography material in a solution comprising a mobile phase A and a mobile phase B, wherein mobile phase A comprises ammonium hydroxide in water and mobile phase B comprises ammonium hydroxide in an organic solvent; b) eluting the polypeptide from the mixed mode cation exchange chromatography material with a solution comprising mobile phase A and mobile phase B wherein the ratio of mobile phase B to mobile phase A is increased compared to step a); c) eluting the non-ionic surfactant from the chromatography material with a solution comprising mobile phase A and mobile phase B wherein the ratio of mobile phase B to mobile phase A is increased compared to step c); d) quantifying the non-ionic surfactant. In some embodiments, the organic solvent of mobile phase B is methanol. In some embodiments, the ratio of mobile phase B to mobile phase A in step a) is about 10:90. In some embodiments, the ratio of mobile phase B to mobile phase A is increased to about 45:55 in step b). In some embodiments, the ratio of mobile phase B to mobile phase A is increased to about 100:0 in step c). In some embodiments, mobile phase A comprises about 2% ammonium hydroxide in water. In some embodiments, mobile phase B comprises about 2% ammonium hydroxide in methanol. In some embodiments, the flow rate of the chromatography is about 1.4 mL/minute. In some embodiments, step b) starts at about 1 min after the chromatography is initiated and ends at about 4.4 min after the chromatography is initiated. In some embodiments, step c) starts at about 4.5 min after the chromatography is initiated and ends at about 7.6 min after the chromatography is initiated. In some embodiments, the non-ionic surfactant is a polysorbate. In some embodiments, the polysorbate is polysorbate 20 or polysorbate 80. In some embodiments, the concentration of polysorbate in the composition is in the range of about 0.001% to 1.0% (w/v). In some embodiments, the organic solvent of mobile phase B is acetonitrile. In some embodiments, the ratio of mobile phase B to mobile phase A in step a) is about 10:90. In some embodiments, the ratio of mobile phase B to mobile phase A is increased to about 40:60 is step b). In some embodiments, the ratio of mobile phase B to mobile phase A is increased to 100:0 is step c). In some embodiments, mobile phase A comprises about 2% ammonium hydroxide in water or in 43% methanol. In some embodiments, mobile phase B comprises about 2% ammonium hydroxide in acetonitrile. In some embodiments, the non-ionic surfactant is a poloxamer. In some embodiments, the poloxamer is poloxamer P188. In some embodiments, the concentration of poloxamer in the composition is in the range of about 0.001% to 1.0% (w/v). In some embodiments, the composition further comprises N-acetyl tryptophan and/or methionine. In some embodiments, the concentration of N-acetyl tryptophan in the composition ranges from about 0.1 mM to about 10 mM. In some embodiments, the concentration of methionine in the composition ranges from about 0.1 mM to about 100 mM. In some embodiments, the polypeptide concentration in the composition is about 1 mg/mL to about 250 mg/mL. In some embodiments, the formulation has a pH of about 4.5 to about 7.5. In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic polypeptide is a fusion protein, a polyclonal antibody, a monoclonal antibody, a humanized antibody, a human antibody, a chimeric antibody, a multispecific antibody, glycoengineered antibody, antibody fragment, an antibody drug conjugate, a THIOMAB™, a THIOMAB™ drug conjugate. In some embodiments, the mixed mode cation exchange chromatography material comprises a reversed phase, strong cation exchange polymer. In some embodiments, the mixed mode cation exchange chromatography material comprises a sulfonic acid moiety. In some embodiments, the mixed mode cation exchange chromatography material comprises a solid support. In some embodiments, the mixed mode cation exchange chromatography material is contained in a column. In some embodiments, the mixed mode cation exchange chromatography material is a high performance liquid chromatography (HPLC) material. In some embodiments, the mixed mode cation exchange chromatography material is an Oasis® MCX chromatography material. In some embodiments, the non-ionic detergent is quantified by Evaporative Light Scattering (ELSD) or by using a Charged Aerosol Detector (CAD).

BRIEF DESCRIPTION OF THE DRAWINGS

FIG. 1A shows ELSD and FIG. 1B shows UV (280 nm). Water (trace 1), PS20-free A16/A17 formulation buffer (trace 2) and PS20-free A16/A17 protein (trace 3) were assessed using Method 1 of Example 1.

FIGS. 12A and 12B show ELSD chromatograms of different A16/A17 buffer components using the method of Example 1. FIG. 12A shows buffers with NAT: 20 mM histidine-HCl, 1 mM NAT, 5 mM methionine, 240 mM sucrose (trace 1); 20 mM histidine-HCl, 1 mM NAT, 240 mM sucrose (trace 2); 20 mM histidine-HCl, 5 mM NAT (trace 3). FIG. 12B shows buffers without NAT: 20 mM histidine-HCl, 5 mM methionine, 240 mM sucrose (trace 1); 20 mM histidine-HCl, 25 mM methionine (trace 2); 20 mM histidine-HCl (trace 3). 50 µL buffer injections.

FIG. 13A shows buffers with NAT: 20 mM histidine-HCl, 1 mM NAT, 5 mM methionine, 240 mM sucrose (trace 1); 20 mM histidine-HCl, 1 mM NAT, 240 mM sucrose (trace 2); 20 mM histidine-HCl, 5 mM NAT (trace 3); and PS20-free protein with NAT (trace 4). FIG. 13B shows buffers without NAT: 20 mM histidine-HCl, 5 mM methionine, 240 mM sucrose (trace 1); 20 mM histidine-HCl, 25 mM methionine (trace 2); 20 mM histidine-HCl (trace 3), 50 µL injections.

FIG. 14A shows ELSD chromatograms.

FIG. 14B shows UV (280 nm) chromatograms. 50 µL injection of PS20-free A16/A17 protein with 0.15, 0.29, 0.73 and 1.5% ammonium hydroxide in the mobile phase (traces 1, 2, 3, and 4, respectively), and PS20-free A16/A17 formulation buffer with 1.5% ammonium hydroxide (trace 5).

FIG. 15A shows ELSD chromatograms. FIG. 15B shows UV (280 nm) chromatograms. 15 µL injection of PS20-free A16/A17 protein. 20, 30, 40, 50, and 60% mobile phase B (wash step), shown as traces 1, 2, 3, 4, and 5, respectively.

FIG. 17A shows ELSD chromatograms. FIG. 17B shows UV (280 nm) chromatograms. 25 µL injection of PS20-free A18/A19 (150 mg/mL) with different flow rates: 1.6, 1.4, 1.25, 1.0, and 0.8 mL/min, corresponding to traces 1, 2, 3, 4, and 5, respectively.

FIGS. 20A (A18/A19), 20C (A16/A17), and 20E (A14/A20) show ELSD chromatograms. FIGS. 20B (A18/A19), 20D (A16/A17), and 20F (A14/A20) show UV (280 nm) chromatograms. PS20-free formulation (trace 1). PS20-free protein (trace 2), and 0.1 mg/mL PS20 in water (trace 3).

using cartridge 4. FIG. 26A shows PS20 area vs injection number. FIG. 26B shows PS20 concentration vs injection number.

FIG. 27A shows PS20 area vs injection number. FIG. 27B shows PS20 concentration vs injection number.

FIG. 28A shows PS20 area vs injection number. FIG. 28B shows PS20 concentration vs injection number.

FIGS. 29A, 29C, and 29E show chromatograms for Method 1 with A21, A14/A15, and A14, respectively. FIGS. 29B, 29D, and 29F show chromatograms for Method 2 with A21, A14/A15, and A14, respectively.

DETAILED DESCRIPTION OF THE INVENTION

Figure 1:
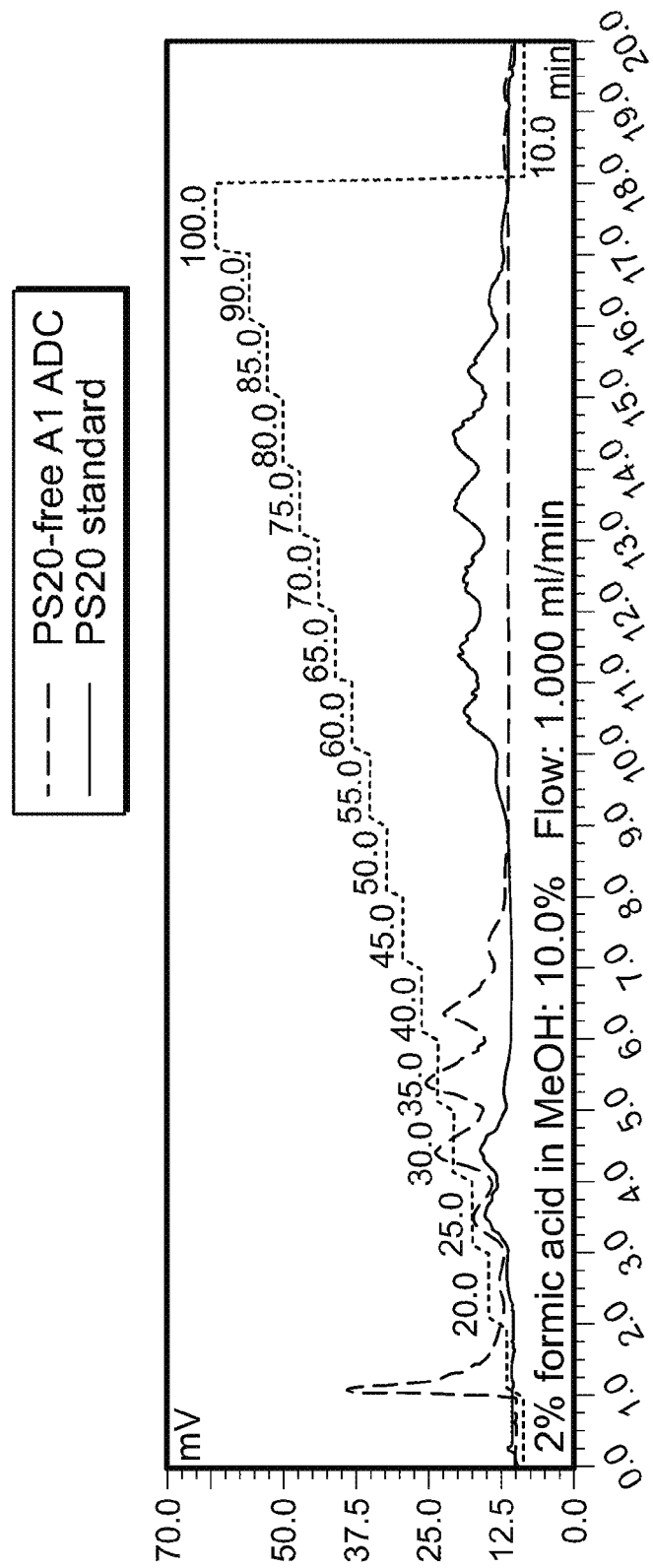
FIG. 1 is an overlay of PS20-free A1 ADC and a 0.6 mg/ml PS20 standard using the multi-step gradient of increasing 5% methanol. Elution solvent contains 2% formic acid.

The invention provides methods for quantifying a non-ionic surfactant in a composition comprising a polypeptide and the non-ionic surfactant, where the quantification exhibits reduced interference between the non-ionic surfactant and the polypeptide. Also provided are methods where the composition further includes N-acetyl tryptophan, and the quantification exhibits reduced interference between the non-ionic surfactant, the polypeptide, and N-acetyl tryptophan.

I. Definitions

The term "polypeptide" or "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component or toxin. Also included within the definition are, for example, polypeptides containing one or more analogs of an amino acid (including, for example, unnatural amino acids, etc.), as well as other modifications known in the art. The terms "polypeptide" and "protein" as used herein specifically encompass antibodies.

"Purified" polypeptide (e.g., antibody or immunoadhesin) means that the polypeptide has been increased in purity, such that it exists in a form that is more pure than it exists in its natural environment and/or when initially synthesized and/or amplified under laboratory conditions. Purity is a relative term and does not necessarily mean absolute purity.

The term "antagonist" is used in the broadest sense, and includes any molecule that partially or fully blocks, inhibits, or neutralizes a biological activity of a native polypeptide. In a similar manner, the term "agonist" is used in the broadest sense and includes any molecule that mimics a biological activity of a native polypeptide. Suitable agonist or antagonist molecules specifically include agonist or antagonist antibodies or antibody fragments, fragments or amino acid sequence variants of native polypeptides, etc. Methods for identifying agonists or antagonists of a polypeptide may comprise contacting a polypeptide with a candidate agonist or antagonist molecule and measuring a detectable change in one or more biological activities normally associated with the polypeptide.

A polypeptide "which binds" an antigen of interest, e.g. a tumor-associated polypeptide antigen target, is one that binds the antigen with sufficient affinity such that the polypeptide is useful as a diagnostic and/or therapeutic agent in targeting a cell or tissue expressing the antigen, and does not significantly cross-react with other polypeptides. In such embodiments, the extent of binding of the polypeptide to a "non-target" polypeptide will be less than about 10% of the binding of the polypeptide to its particular target polypeptide as determined by fluorescence activated cell sorting (FACS) analysis or radioimmunoprecipitation (RIA).

With regard to the binding of a polypeptide to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity. The term "immunoglobulin" (Ig) is used interchangeable with antibody herein.

Antibodies are naturally occurring immunoglobulin molecules which have varying structures, all based upon the immunoglobulin fold. For example, IgG antibodies have two "heavy" chains and two "light" chains that are disulphide-bonded to form a functional antibody. Each heavy and light chain itself comprises a "constant" (C) and a "variable" (V) region. The V regions determine the antigen binding specificity of the antibody, whilst the C regions provide structural support and function in non-antigen-specific interactions with immune effectors. The antigen binding specificity of an antibody or antigen-binding fragment of an antibody is the ability of an antibody to specifically bind to a particular antigen.

The antigen binding specificity of an antibody is determined by the structural characteristics of the V region. The variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" (HVRs) that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

Each V region typically comprises three HVRs, e.g. complementarity determining regions ("CDRs", each of which contains a "hypervariable loop"), and four framework regions. An antibody binding site, the minimal structural unit required to bind with substantial affinity to a particular desired antigen, will therefore typically include the three CDRs, and at least three, preferably four, framework regions interspersed there between to hold and present the CDRs in the appropriate conformation. Classical four chain antibodies have antigen binding sites which are defined by $V_H$ and $V_L$ domains in cooperation. Certain antibodies, such as camel and shark antibodies, lack light chains and rely on binding sites formed by heavy chains only. Single domain engineered immunoglobulins can be prepared in which the binding sites are formed by heavy chains or light chains alone, in absence of cooperation between $V_H$ and $V_L$.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health. Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" (HVR) when used herein refers to the amino acid residues of an antibody that are responsible for antigen binding. The hypervariable region may comprise amino acid residues from a "complementarity determining region" or "CDR" (e.g., around about residues 24-34 (L1), 50-56 (L2) and 89-97 (L3) in the $V_L$, and around about 31-35B (H1), 50-65 (H2) and 95-102 (H3) in the $V_H$ (Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 52A-55 (H2) and 96-101 (H3) in the $V_H$ (Chothia and Lesk *J. Mol. Biol.* 196:901-917 (1987)).

"Framework" or "FR" residues are those variable domain residues other than the hypervariable region residues as herein defined.

"Antibody fragments" comprise a portion of an intact antibody, preferably comprising the antigen binding region thereof. Examples of antibody fragments include Fab, Fab', F(ab')$_2$, and Fv fragments; diabodies; tandem diabodies (taDb), linear antibodies (e.g., U.S. Pat. No. 5,641,870, Example 2; Zapata et al., *Protein Eng.* 8(10):1057-1062 (1995)); one-armed antibodies, single variable domain antibodies, minibodies, single-chain antibody molecules; multispecific antibodies formed from antibody fragments (e.g., including but not limited to, Db-Fc, taDb-Fc, taDb-CH3, (scFV)4-Fc, di-scFv, bi-scFv, or tandem (di,tri)-scFv); and Bi-specific T-cell engagers (BiTEs).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called α, δ, ε, γ, and μ, respectively. The subunit structures and three-dimensional configurations of different classes of immunoglobulins are well known.

"Single-chain Fv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains that enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA,* 90:6444-6448 (1993).

The term "multispecific antibody" is used in the broadest sense and specifically covers an antibody that has polyepitopic specificity. Such multispecific antibodies include, but are not limited to, an antibody comprising a heavy chain variable domain ($V_H$) and a light chain variable domain ($V_L$), where the $V_H V_L$ unit has polyepitopic specificity, antibodies having two or more $V_L$ and $V_H$ domains with each $V_H V_L$ unit binding to a different epitope, antibodies having two or more single variable domains with each single variable domain binding to a different epitope, full length antibodies, antibody fragments such as Fab, Fv, dsFv, scFv, diabodies, bispecific diabodies, triabodies, tri-functional antibodies, antibody fragments that have been linked covalently or non-covalently. "Polyepitopic specificity" refers to the ability to specifically bind to two or more different epitopes on the same or different target(s). "Monospecific" refers to the ability to bind only one epitope. According to one embodiment the multispecific antibody is an IgG antibody that binds to each epitope with an affinity of 5 µM to 0.001 pM, 3 µM to 0.001 pM, 1 µM to 0.001 pM, 0.5 µM to 0.001 pM, or 0.001 µM to 0.001 µM.

The expression "single domain antibodies" (sdAbs) or "single variable domain (SVD) antibodies" generally refers to antibodies in which a single variable domain (VH or VL) can confer antigen binding. In other words, the single variable domain does not need to interact with another variable domain in order to recognize the target antigen. Examples of single domain antibodies include those derived from camelids (lamas and camels) and cartilaginous fish (e.g., nurse sharks) and those derived from recombinant methods from humans and mouse antibodies (*Nature* (1989) 341:544-546; *Dev Comp Immunol* (2006) 30:43-56; *Trend Biochem Sci* (2001) 26:230-235; *Trends Biotechnol* (2003): 21:484-490; WO 2005/035572; WO 03/035694; *Febs Lett* (1994) 339:285-290; WO00/29004; WO 02/051870).

The term "monoclonal antibody" as used herein refers to an antibody obtained from a population of substantially homogeneous antibodies. i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the methods provided herein may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA* 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992).

For the purposes herein, an "intact antibody" is one comprising heavy and light variable domains as well as an Fc region. The constant domains may be native sequence constant domains (e.g. human native sequence constant domains) or amino acid sequence variant thereof. Preferably, the intact antibody has one or more effector functions.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

A "naked antibody" is an antibody (as herein defined) that is not conjugated to a heterologous molecule, such as a cytotoxic moiety or radiolabel.

In some embodiments, antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet. *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., *Proc. Natl. Acad. Sci* (USA) 95:652-656 (1998).

"Human effector cells" are leukocytes that express one or more FcRs and perform effector functions. In some embodiments, the cells express at least FcγRIII and carry out ADCC effector function. Examples of human leukocytes that mediate ADCC include peripheral blood mononuclear cells (PBMC), natural killer (NK) cells, monocytes, cytotoxic T cells and neutrophils; with PBMCs and NK cells being preferred.

"Complement dependent cytotoxicity" or "CDC" refers to the ability of a molecule to lyse a target in the presence of complement. The complement activation pathway is initiated by the binding of the first component of the complement system (C1q) to a molecule (e.g. polypeptide (e.g., an antibody)) complexed with a cognate antigen. To assess complement activation, a CDC assay, e.g. as described in Gazzano-Santoro et al., *J. Immunol. Methods* 202:163 (1996) may be performed.

The terms "Fc receptor" or "FcR" are used to describe a receptor that binds to the Fc region of an antibody. In some embodiments, the FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor. FcRn, which is responsible for the transfer of maternal IgGs to the fetus (Guyer et al., *J. Immunol.* 117:587 (1976) and Kim et al., *J. Immunol.* 24:249 (1994)).

"Impurities" refer to materials that are different from the desired polypeptide product. In some embodiments of the invention, impurities include charge variants of the polypeptide. In some embodiments of the invention, impurities include charge variants of an antibody or antibody fragment. In other embodiments of the invention, the impurity includes, without limitation: host cell materials, such as CHOP; leached Protein A; nucleic acid; a variant, fragment, aggregate or derivative of the desired polypeptide; another polypeptide; endotoxin; viral contaminant; cell culture media component, etc.

As used herein, the term "immunoadhesin" designates antibody-like molecules which combine the binding specificity of a heterologous polypeptide with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes. IgA (including IgA-1 and IgA-2), IgE, IgD or IgM.

As used herein, a "surfactant" refers to a surface-active agent, preferably a nonionic surfactant. Examples of surfactants herein include polysorbate (for example, polysorbate 20 and, polysorbate 80); poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.); polyethyl glycol, polypropyl glycol, and copolymers of ethylene and propylene glycol (e.g. Pluronics, PF68 etc); etc. In one embodiment, the surfactant herein is polysorbate 20. In yet another embodiment, the surfactant herein is poloxamer 188.

The term "sequential" as used herein with regard to chromatography refers to having a first chromatography followed by a second chromatography. Additional steps may be included between the first chromatography and the second chromatography.

The term "continuous" as used herein with regard to chromatography refers to having a first chromatography material and a second chromatography material either directly connected or some other mechanism which allows for continuous flow between the two chromatography materials.

"Loading density" refers to the amount, e.g. grams, of composition put in contact with a volume of chromatography material, e.g. liters. In some examples, loading density is expressed in g/L.

The term "interference" as used herein with regard to quantification of a species (e.g., non-ionic surfactant) refers to contribution of some component other than the species (e.g., polypeptide) to the quantification. For example, an ELSD signal for a chromatographic fraction containing both polysorbate 20 and polypeptide will have contributions from both the polysorbate 20 and the polypeptide, and quantification of the polysorbate 20 in the fraction will have interference from the polypeptide.

As used herein "essentially the same" indicates that a value or parameter has not been altered by a significant effect. For example, an ionic strength of a chromatography mobile phase at column exit is essentially the same as the initial ionic strength of the mobile phase if the ionic strength has not changed significantly. For example, an ionic strength at column exit that is within 10%, 5% or 1% of the initial ionic strength is essentially the same as the initial ionic strength.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

II. Methods of Chromatography

In some aspects, the invention provides methods of analyzing compositions comprising a polypeptide and a non-ionic surfactant (e.g., polysorbate 20, or PS20), comprising binding the polypeptide and non-ionic surfactant to a mixed mode ion exchange chromatography material using a loading buffer, and eluting the polypeptide and non-ionic surfactant from the chromatography material using buffers such that the polypeptide and the non-ionic surfactant elute from the chromatography material in distinct fractions. In some embodiments, the chromatography methods are suitable for compositions comprising multiple polypeptides (e.g. polypeptide products), including polypeptides with varying pIs. For example, the methods can be used for analyzing compositions comprising a non-ionic surfactant and a number of different antibody products, such as antibody products with pIs ranging from 6.0 to 9.5. In other embodiments, the chromatography methods include use of optimal conditions (e.g., chromatography material buffers, gradients, step duration, flow rate, sample loading) identified by the methods described herein.

In some embodiments of any of the methods described herein, the chromatography material is a mixed mode material comprising functional groups capable of one of more of the following functionalities: anionic exchange, cation exchange, hydrogen bonding, and hydrophobic interactions. In some embodiments, the mixed mode material is a mixed mode anion exchange chromatography material. In some embodiments, the mixed mode anion exchange chromatography material comprises a reversed phase, strong anion exchange polymer. In some embodiments, the mixed mode anion exchange chromatography material comprises a quaternary amine moiety. In some embodiments, the mixed mode anion exchange chromatography material is an Oasis® MAX chromatography material. In some embodiments, the mixed mode material is a mixed mode cation exchange chromatography material. In some embodiments, the mixed mode cation exchange chromatography material comprises a reversed phase, strong cation exchange polymer. In some embodiments, the mixed mode cation exchange chromatography material comprises a sulfonic acid moiety. In some embodiments, the mixed mode cation exchange chromatography material is an Oasis® MCX chromatography material. In some embodiments, mixed mode material comprises a solid support. In some embodiments, the mixed mode material is contained in a column or cartridge. In some embodiments of the above, the mixed mode material is a mixed mode chromatography column or cartridge, such as a mixed mode anion exchange chromatography column or cartridge, or a mixed mode cation exchange chromatography column or cartridge. In some embodiments, the mixed mode material is a high performance liquid chromatography (HPLC) material.

In some embodiments of any of the methods described herein, the ion exchange material may utilize a conventional chromatography material or a convective chromatography material. The conventional chromatography materials include, for example, perfusive materials (e.g., poly(styrene-divinylbenzene) resin) and diffusive materials (e.g., cross-linked agarose resin). In some embodiments, the poly(styrene-divinylbenzene) resin can be Poros® resin. In some embodiments, the cross-linked agarose resin may be sulphopropyl-Sepharose® Fast Flow ("SPSFF") resin. The convective chromatography material may be a membrane (e.g., polyethersulfone) or monolith material (e.g. cross-linked polymer). The polyethersulfone membrane may be Mustang. The cross-linked polymer monolith material may be cross-linked poly(glycidyl methacrylate-co-ethylene dimethacrylate).

In some embodiments of any of the methods of the invention, the chromatography material is in a chromatography column or cartridge; for example a mixed mode cation exchange chromatography column or cartridge or a mixed mode anion exchange chromatography column or cartridge. In some embodiments, the chromatography column or cartridge is used for liquid chromatography. In some embodiments, the chromatography column or cartridge is used for high performance liquid chromatography (HPLC). In some embodiments, the chromatography column or cartridge is an HPLC chromatography column or cartridge; for example, a mixed mode cation exchange HPLC column or cartridge or a mixed mode anion exchange HPLC column or cartridge.

For example, in some embodiments, there is provided a method for quantifying a non-ionic surfactant in a composition comprising the non-ionic surfactant and a polypeptide, wherein the method comprises the steps of a) applying the composition to a mixed mode anion exchange chromatography material, wherein the composition is loaded onto the chromatography material in a solution comprising a first ratio of a mobile phase B to a mobile phase A, wherein mobile phase A comprises acid in water and mobile phase B comprises acid in methanol; b) eluting the polypeptide from the mixed mode anion exchange chromatography material with a solution comprising a second ratio of mobile phase B to mobile phase A, wherein the second ratio is greater than the first ratio; c) eluting the non-ionic surfactant from the chromatography material with a solution comprising a third ratio of mobile phase B to mobile phase A, wherein the third ratio is greater than the second ratio; and d) quantifying the non-ionic surfactant in the eluate of step c). In some embodiments, the polypeptide binds to the chromatography material specifically and non-specifically, and at least about 90% (such as at least about any of 91, 92, 93, 94, 95, 96, 97, 98, or 99%) of the polypeptide elutes in step b). In some embodiments, the eluate from step c) comprises non-specifically bound polypeptide. In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the first ratio of mobile phase B to mobile phase A is between about 0:100 and about 20:80 (such as about any of 2:98, 4:96, 6:94, 8:92, 10:90, 12:88, 14:86, 16:84, and 18:82, including any ranges between these ratios). In some embodiments, the second ratio is between about 30:70 and about 50:50 (such as about any of 32:68, 34:66, 36:64, 38:62, 40:60, 42:58, 44:56, 46:54, and 48:52, including any ranges between these ratios). In some embodiments, the third ratio is between about 80:20 and about 100:0 (such as about any of 82:18, 84:16, 86:14, 88:12, 90:10, 92:8, 94:6, 96:4, and 98:2, including any ranges between these values). In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) acid in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) acid in methanol. In some embodiments, the acid is formic acid. In some embodiments, the acid is acetic acid. In some embodiments, the flow rate of the chromatography is between about 0.5 and 2.5 (such as about any of 0.7, 0.9, 1.1, 1.2, 1.25, 1.3, 1.5, 1.7, 1.9, 2.1, and 2.3, including any ranges between these values) ml/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 1 (such as at least about any of 1.2, 1.4, 1.6, 1.8, 2, 2.2, 2.4, 2.6, 2.8, 3, 3.2, 3.4, 3.6, 3.8, 4 or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 0.5 (such as at least about any of 0.6, 0.7, 0.8, 0.9, 1, 1.1, 1.2, 1.3, 1.4, 1.5, 2, 3, or more) min. In some embodiments, the non-ionic surfactant is poloxamer (P188) or a polysorbate. In some embodiments, the polysorbate is polysorbate 20 or polysorbate 80. In some embodiments, the concentration of non-ionic surfactant in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the protein concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic polypeptide is a fusion protein, a polyclonal antibody, a monoclonal antibody, a humanized antibody, a human antibody, a chimeric antibody, a multispecific antibody, a glycoengineered antibody, an antibody fragment, an antibody drug conjugate, a THIOMAB™ or a THIOMAB™ drug conjugate. In some embodiments, the mixed mode anion exchange chromatography material comprises a reversed phase, strong anion exchange polymer. In some embodiments, the mixed mode anion exchange chromatography material comprises a quaternary amine moiety. In some embodiments, the mixed mode anion exchange chromatography material comprises a solid support. In some embodiments, the mixed mode anion exchange chromatography material is contained in a column or cartridge. In some embodiments, the mixed mode anion exchange chromatography material is a high performance liquid chromatography (HPLC) material. In some embodiments, the mixed mode anion exchange chromatography material is an Oasis® MAX chromatography material. In some embodiments, the non-ionic detergent is quantified by Evaporative Light Scattering (ELSD) or by using a Charged Aerosol Detector (CAD). In some embodiments, the quantification of the non-ionic surfactant comprises less than about 10% (such as less than about any of 9%, 8%, 7%, 6%, 5%, 4%, 3%, 2%, 1%, 0.5%, 0.1%, 0.05%, 0.01%, or less) interference from the polypeptide.

In some embodiments, there is provided a method for quantifying a non-ionic surfactant in a composition comprising the non-ionic surfactant and a polypeptide, wherein the method comprises the steps of a) applying the composition to a mixed mode anion exchange chromatography material wherein the composition is loaded onto the chromatography material in a solution comprising a first ratio of a mobile phase B to a mobile phase A, wherein mobile phase A comprises acid in water and mobile phase B comprises acid in methanol; b) eluting the polypeptide from the mixed mode anion exchange chromatography material with a solution comprising a second ratio of mobile phase B to mobile phase A, wherein the second ratio is greater than the first ratio; c) eluting the non-ionic surfactant from the chromatography material with a solution comprising a third ratio of mobile phase B to mobile phase A, wherein the third ratio is greater than the second ratio; and d) quantifying the non-ionic surfactant in the eluate of step c), wherein the quantification of the non-ionic surfactant comprises less than about 10% (such as less than about any of 9%, 8%, 7%, 6%, 5%, 4%, 3%, 2%, 1%, 0.5%, 0.1%, 0.05%, 0.01%, or less) interference from the polypeptide. In some embodiments, the polypeptide binds to the chromatography material specifically and non-specifically, and at least about 90% (such as at least about any of 91, 92, 93, 94, 95, 96, 97, 98, or 99%) of the polypeptide elutes in step b). In some embodiments, the eluate from step c) comprises non-specifically bound polypeptide. In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the first ratio of mobile phase B to mobile phase A is between about 0:100 and about 20:80 (such as about any of 2:98, 4:96, 6:94, 8:92, 10:90, 12:88, 14:86, 16:84, and 18:82, including any ranges between these ratios). In some embodiments, the second ratio is between about 30:70 and about 50:50 (such as about any of 32:68, 34:66, 36:64, 38:62, 40:60, 42:58, 44:56, 46:54, and 48:52, including any ranges between these ratios). In some embodiments, the third ratio is between about 80:20 and about 100:0 (such as about any of 82:18, 84:16, 86:14, 88:12, 90:10, 92:8, 94:6, 96:4, and 98:2, including any ranges between these values). In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) acid in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) acid in methanol. In some embodiments, the acid is formic acid. In some embodiments, the acid is acetic acid. In some embodiments, the flow rate of the chromatography is between about 0.5 and 2.5 (such as about any of 0.7, 0.9, 1.1, 1.2, 1.25, 1.3, 1.5, 1.7, 1.9, 2.1, and 2.3, including any ranges between these values) ml/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 1 (such as at least about any of 1.2, 1.4, 1.6, 1.8, 2, 2.2, 2.4, 2.6, 2.8, 3, 3.2, 3.4, 3.6, 3.8, 4 or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 0.5 (such as at least about any of 0.6, 0.7, 0.8, 0.9, 1, 1.1, 1.2, 1.3, 1.4, 1.5, 2, 3, or more) min. In some embodiments, the non-ionic surfactant is poloxamer (P188) or a polysorbate. In some embodiments, the polysorbate is polysorbate 20 or polysorbate 80. In some embodiments, the concentration of non-ionic surfactant in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the protein concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic polypeptide is a fusion protein, a polyclonal antibody, a monoclonal antibody, a humanized antibody, a human antibody, a chimeric antibody, a multispecific antibody, a glycoengineered antibody, an antibody fragment, an antibody drug conjugate, a THIOMAB™ or a THIOMAB™ drug conjugate. In some embodiments, the mixed mode anion exchange chromatography material comprises a reversed phase, strong anion exchange polymer. In some embodiments, the mixed mode anion exchange chromatography material comprises a quaternary amine moiety. In some embodiments, the mixed mode anion exchange chromatography material comprises a solid support. In some embodiments, the mixed mode anion exchange chromatography material is contained in a column or cartridge. In some embodiments, the mixed mode anion exchange chromatography material is a high performance liquid chromatography (HPLC) material. In some embodiments, the mixed mode anion exchange chromatography material is an Oasis® MAX chromatography material. In some embodiments, the non-ionic detergent is quantified by Evaporative Light Scattering (ELSD) or by using a Charged Aerosol Detector (CAD).

In some embodiments, there is provided a method for quantifying a non-ionic surfactant in a composition comprising the non-ionic surfactant and a polypeptide, wherein the method comprises the steps of a) applying the composition to a mixed mode anion exchange chromatography material, wherein the composition is loaded onto the chromatography material in a solution comprising a first ratio of a mobile phase B to a mobile phase A, wherein mobile phase A comprises acid in water and mobile phase B comprises acid in methanol; b) eluting the polypeptide from the mixed mode anion exchange chromatography material with a solution comprising a second ratio of mobile phase B to mobile phase A, wherein the second ratio is greater than the first ratio; c) eluting the non-ionic surfactant from the chromatography material with a solution comprising a third ratio of mobile phase B to mobile phase A, wherein the third ratio is greater than the second ratio; and d) quantifying the non-ionic surfactant in the eluate of step c), wherein the eluate comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the first ratio of mobile phase B to mobile phase A is between about 0:100 and about 20:80 (such as about any of 2:98, 4:96, 6:94, 8:92, 10:90, 12:88, 14:86, 16:84, and 18:82, including any ranges between these ratios). In some embodiments, the second ratio is between about 30:70 and about 50:50 (such as about any of 32:68, 34:66, 36:64, 38:62, 40:60, 42:58, 44:56, 46:54, and 48:52, including any ranges between these ratios). In some embodiments, the third ratio is between about 80:20 and about 100:0 (such as about any of 82:18, 84:16, 86:14, 88:12, 90:10, 92:8, 94:6, 96:4, and 98:2, including any ranges between these values). In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) acid in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) acid in methanol. In some embodiments, the acid is formic acid. In some embodiments, the acid is acetic acid. In some embodiments, the flow rate of the chromatography is between about 0.5 and 2.5 (such as about any of 0.7, 0.9, 1.1, 1.2, 1.25, 1.3, 1.5, 1.7, 1.9, 2.1, and 2.3, including any ranges between these values) mL/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 1 (such as at least about any of 1.2, 1.4, 1.6, 1.8, 2, 2.2, 2.4, 2.6, 2.8, 3, 3.2, 3.4, 3.6, 3.8, 4 or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 0.5 (such as at least about any of 0.6, 0.7, 0.8, 0.9, 1, 1.1, 1.2, 1.3, 1.4, 1.5, 2, 3, or more) min. In some embodiments, the non-ionic surfactant is poloxamer (P188) or a polysorbate. In some embodiments, the polysorbate is polysorbate 20 or polysorbate 80. In some embodiments, the concentration of non-ionic surfactant in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the protein concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic polypeptide is a fusion protein, a polyclonal antibody, a monoclonal antibody, a humanized antibody, a human antibody, a chimeric antibody, a multispecific antibody, a glycoengineered antibody, an antibody fragment, an antibody drug conjugate, a THIOMAB™ or a THIOMAB™ drug conjugate. In some embodiments, the mixed mode anion exchange chromatography material comprises a reversed phase, strong anion exchange polymer. In some embodiments, the mixed mode anion exchange chromatography material comprises a quaternary amine moiety. In some embodiments, the mixed mode anion exchange chromatography material comprises a solid support. In some embodiments, the mixed mode anion exchange chromatography material is contained in a column or cartridge. In some embodiments, the mixed mode anion exchange chromatography material is a high performance liquid chromatography (HPLC) material. In some embodiments, the mixed mode anion exchange chromatography material is an Oasis® MAX chromatography material. In some embodiments, the non-ionic detergent is quantified by Evaporative Light Scattering (ELSD) or by using a Charged Aerosol Detector (CAD). In some embodiments, the quantification of the non-ionic surfactant comprises less than about 10% (such as less than about any of 9%, 8%, 7%, 6%, 5%, 4%, 3%, 2%, 1%, 0.5%, 0.1%, 0.05%, 0.01%, or less) interference from the polypeptide.

In some embodiments, there is provided a method for quantifying a non-ionic surfactant in a composition comprising the non-ionic surfactant and a polypeptide, wherein the method comprises the steps of a) applying the composition to a mixed mode anion exchange chromatography material, wherein the composition is loaded onto the chromatography material in a solution comprising a first ratio of a mobile phase B to a mobile phase A, wherein mobile phase A comprises acetic acid in water and mobile phase B comprises acetic acid in methanol; b) eluting the polypeptide from the mixed mode anion exchange chromatography material with a solution comprising a second ratio of mobile phase B to mobile phase A, wherein the second ratio is greater than the first ratio; c) eluting the non-ionic surfactant from the chromatography material with a solution comprising a third ratio of mobile phase B to mobile phase A, wherein the third ratio is greater than the second ratio; and d) quantifying the non-ionic surfactant in the eluate of step c). In some embodiments, the polypeptide binds to the chromatography material specifically and non-specifically, and at least about 90% (such as at least about any of 91, 92, 93, 94, 95, 96, 97, 98, or 99%) of the polypeptide elutes in step b). In some embodiments, the eluate from step c) comprises non-specifically bound polypeptide. In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the first ratio of mobile phase B to mobile phase A is between about 0:100 and about 20:80 (such as about any of 2:98, 4:96, 6:94, 8:92, 10:90, 12:88, 14:86, 16:84, and 18:82, including any ranges between these ratios). In some embodiments, the second ratio is between about 30:70 and about 50:50 (such as about any of 32:68, 34:66, 36:64, 38:62, 40:60, 42:58, 44:56, 46:54, and 48:52, including any ranges between these ratios). In some embodiments, the third ratio is between about 80:20 and about 100:0 (such as about any of 82:18, 84:16, 86:14, 88:12, 90:10, 92:8, 94:6, 96:4, and 98:2, including any ranges between these values). In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) acetic acid in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) acetic acid in methanol. In some embodiments, the flow rate of the chromatography is between about 0.5 and 2.5 (such as about any of 0.7, 0.9, 1.1, 1.2, 1.25, 1.3, 1.5, 1.7, 1.9, 2.1, and 2.3, including any ranges between these values) ml/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 1 (such as at least about any of 1.2, 1.4, 1.6, 1.8, 2, 2.2, 2.4, 2.6, 2.8, 3, 3.2, 3.4, 3.6, 3.8, 4 or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 0.5 (such as at least about any of 0.6, 0.7, 0.8, 0.9, 1, 1.1, 1.2, 1.3, 1.4, 1.5, 2, 3, or more) min. In some embodiments, the non-ionic surfactant is poloxamer (P188) or a polysorbate. In some embodiments, the polysorbate is polysorbate 20 or polysorbate 80. In some embodiments, the concentration of non-ionic surfactant in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the protein concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic polypeptide is a fusion protein, a polyclonal antibody, a monoclonal antibody, a humanized antibody, a human antibody, a chimeric antibody, a multispecific antibody, a glycoengineered antibody, an antibody fragment, an antibody drug conjugate, a THIOMAB™ or a THIOMAB™ drug conjugate. In some embodiments, the mixed mode anion exchange chromatography material comprises a reversed phase, strong anion exchange polymer. In some embodiments, the mixed mode anion exchange chromatography material comprises a quaternary amine moiety. In some embodiments, the mixed mode anion exchange chromatography material comprises a solid support. In some embodiments, the mixed mode anion exchange chromatography material is contained in a column or cartridge. In some embodiments, the mixed mode anion exchange chromatography material is a high performance liquid chromatography (HPLC) material. In some embodiments, the mixed mode anion exchange chromatography material is an Oasis® MAX chromatography material. In some embodiments, the non-ionic detergent is quantified by Evaporative Light Scattering (ELSD) or by using a Charged Aerosol Detector (CAD). In some embodiments, the quantification of the non-ionic surfactant comprises less than about 10% (such as less than about any of 9%, 8%, 7%, 6%, 5%, 4%, 3%, 2%, 1%, 0.5%, 0.1%, 0.05%, 0.01%, or less) interference from the polypeptide.

In some embodiments, there is provided a method for quantifying a non-ionic surfactant in a composition comprising the non-ionic surfactant and a polypeptide, wherein the method comprises the steps of a) applying the composition to a mixed mode anion exchange chromatography material, wherein the composition is loaded onto the chromatography material in a solution comprising a first ratio of a mobile phase B to a mobile phase A between about 5:95 and about 15:85, wherein mobile phase A comprises acid in water and mobile phase B comprises acid in methanol; b) eluting the polypeptide from the mixed mode anion exchange chromatography material with a solution comprising a second ratio of mobile phase B to mobile phase A between about 35:65 and about 45:55; c) eluting the non-ionic surfactant from the chromatography material with a solution comprising a third ratio of mobile phase B to mobile phase A between about 90:10 and about 100:0; and d) quantifying the non-ionic surfactant in the eluate of step c). In some embodiments, the first ratio of mobile phase B to mobile phase A is about 10:90. In some embodiments, the second ratio is about 40:60. In some embodiments, the third ratio is about 100:0. In some embodiments, the polypeptide binds to the chromatography material specifically and non-specifically, and at least about 90% (such as at least about any of 91, 92, 93, 94, 95, 96, 97, 98, or 99%) of the polypeptide elutes in step b). In some embodiments, the eluate from step c) comprises non-specifically bound polypeptide. In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) acid in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) acid in methanol. In some embodiments, the acid is formic acid. In some embodiments, the acid is acetic acid. In some embodiments, the flow rate of the chromatography is between about 0.5 and 2.5 (such as about any of 0.7, 0.9, 1.1, 1.2, 1.25, 1.3, 1.5, 1.7, 1.9, 2.1, and 2.3, including any ranges between these values) mL/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 1 (such as at least about any of 1.2, 1.4, 1.6, 1.8, 2, 2.2, 2.4, 2.6, 2.8, 3, 3.2, 3.4, 3.6, 3.8, 4 or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 0.5 (such as at least about any of 0.6, 0.7, 0.8, 0.9, 1, 1.1, 1.2, 1.3, 1.4, 1.5, 2, 3, or more) min. In some embodiments, the non-ionic surfactant is poloxamer (P188) or a polysorbate. In some embodiments, the polysorbate is polysorbate 20 or polysorbate 80. In some embodiments, the concentration of non-ionic surfactant in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the protein concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic polypeptide is a fusion protein, a polyclonal antibody, a monoclonal antibody, a humanized antibody, a human antibody, a chimeric antibody, a multispecific antibody, a glycoengineered antibody, an antibody fragment, an antibody drug conjugate, a THIOMAB™ or a THIOMAB™ drug conjugate. In some embodiments, the mixed mode anion exchange chromatography material comprises a reversed phase, strong anion exchange polymer. In some embodiments, the mixed mode anion exchange chromatography material comprises a quaternary amine moiety. In some embodiments, the mixed mode anion exchange chromatography material comprises a solid support. In some embodiments, the mixed mode anion exchange chromatography material is contained in a column or cartridge. In some embodiments, the mixed mode anion exchange chromatography material is a high performance liquid chromatography (HPLC) material. In some embodiments, the mixed mode anion exchange chromatography material is an Oasis® MAX chromatography material. In some embodiments, the non-ionic detergent is quantified by Evaporative Light Scattering (ELSD) or by using a Charged Aerosol Detector (CAD). In some embodiments, the quantification of the non-ionic surfactant comprises less than about 10% (such as less than about any of 9%, 8%, 7%, 6%, 5%, 4%, 3%, 2%, 1%, 0.5%, 0.1%, 0.05%, 0.01%, or less) interference from the polypeptide.

In some embodiments, there is provided a method for quantifying a polysorbate in a composition comprising the polysorbate and a polypeptide, wherein the method comprises the steps of a) applying the composition to a mixed mode anion exchange chromatography material, wherein the composition is loaded onto the chromatography material in a solution comprising a first ratio of a mobile phase B to a mobile phase A, wherein mobile phase A comprises acid in water and mobile phase B comprises acid in methanol; b) eluting the polypeptide from the mixed mode anion exchange chromatography material with a solution comprising a second ratio of mobile phase B to mobile phase A, wherein the second ratio is greater than the first ratio; c) eluting the polysorbate from the chromatography material with a solution comprising a third ratio of mobile phase B to mobile phase A, wherein the third ratio is greater than the second ratio; and d) quantifying the polysorbate in the eluate of step c). In some embodiments, the polypeptide binds to the chromatography material specifically and non-specifically, and at least about 90% (such as at least about any of 91, 92, 93, 94, 95, 96, 97, 98, or 99%) of the polypeptide elutes in step b). In some embodiments, the eluate from step c) comprises non-specifically bound polypeptide. In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the first ratio of mobile phase B to mobile phase A is between about 0:100 and about 20:80 (such as about any of 2:98, 4:96, 6:94, 8:92, 10:90, 12:88, 14:86, 16:84, and 18:82, including any ranges between these ratios). In some embodiments, the second ratio is between about 30:70 and about 50:50 (such as about any of 32:68, 34:66, 36:64, 38:62, 40:60, 42:58, 44:56, 46:54, and 48:52, including any ranges between these ratios). In some embodiments, the third ratio is between about 80:20 and about 100:0 (such as about any of 82:18, 84:16, 86:14, 88:12, 90:10, 92:8, 94:6, 96:4, and 98:2, including any ranges between these values). In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) acid in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) acid in methanol. In some embodiments, the acid is formic acid. In some embodiments, the acid is acetic acid. In some embodiments, the flow rate of the chromatography is between about 0.5 and 2.5 (such as about any of 0.7, 0.9, 1.1, 1.2, 1.25, 1.3, 1.5, 1.7, 1.9, 2.1, and 2.3, including any ranges between these values) mL/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 1 (such as at least about any of 1.2, 1.4, 1.6, 1.8, 2, 2.2, 2.4, 2.6, 2.8, 3, 3.2, 3.4, 3.6, 3.8, 4 or more) min. In some embodiments, step c) starts at least about 0.05 (such as at least about any of 0.06, 0.07, 0.08. 0.09, 0.1, 0.2, 0.3, 0.4, 0.5, 1, 1.5, 2, or more) min after step b) ends and continues for at least about 0.5 (such as at least about any of 0.6, 0.7, 0.8, 0.9, 1, 1.1, 1.2, 1.3, 1.4, 1.5, 2, 3, or more) min. In some embodiments, the polysorbate is polysorbate 20 or polysorbate 80. In some embodiments, the concentration of polysorbate in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the protein concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic polypeptide is a fusion protein, a polyclonal antibody, a monoclonal antibody, a humanized antibody, a human antibody, a chimeric antibody, a multispecific antibody, a glycoengineered antibody, an antibody fragment, an antibody drug conjugate, a THIO-MAB™ or a THIOMAB™ drug conjugate. In some embodiments, the mixed mode anion exchange chromatography material comprises a reversed phase, strong anion exchange polymer. In some embodiments, the mixed mode anion exchange chromatography material comprises a quaternary amine moiety. In some embodiments, the mixed mode anion exchange chromatography material comprises a solid support. In some embodiments, the mixed mode anion exchange chromatography material is contained in a column or cartridge. In some embodiments, the mixed mode anion exchange chromatography material is a high performance liquid chromatography (HPLC) material. In some embodiments, the mixed mode anion exchange chromatography material is an Oasis® MAX chromatography material. In some embodiments, the non-ionic detergent is quantified by Evaporative Light Scattering (ELSD) or by using a Charged Aerosol Detector (CAD). In some embodiments, the quantification of the non-ionic surfactant comprises less than about 10% (such as less than about any of 9%, 8%, 7%, 6%, 5%, 4%, 3%, 2%, 1%, 0.5%, 0.1%, 0.05%, 0.01%, or less) interference from the polypeptide.

In some embodiments, there is provided a method for quantifying a polysorbate in a composition comprising the polysorbate and a polypeptide, wherein the method comprises the steps of a) applying the composition to a mixed mode anion exchange chromatography material, wherein the composition is loaded onto the chromatography material in a solution comprising a first ratio of a mobile phase B to a mobile phase A, wherein mobile phase A comprises acid in water and mobile phase B comprises acid in methanol; b) eluting the polypeptide from the mixed mode anion exchange chromatography material with a solution comprising a second ratio of mobile phase B to mobile phase A, wherein the second ratio is greater than the first ratio; c) eluting the polysorbate from the chromatography material with a solution comprising a third ratio of mobile phase B to mobile phase A, wherein the third ratio is greater than the second ratio; and d) quantifying the polysorbate in the eluate of step c), wherein the quantification of the non-ionic surfactant comprises less than about 10% (such as less than about any of 9%, 8%, 7%, 6%, 5%, 4%, 3%, 2%, 1%, 0.5%, 0.1%, 0.05%, 0.01%, or less) interference from the polypeptide. In some embodiments, the polypeptide binds to the chromatography material specifically and non-specifically, and at least about 90% (such as at least about any of 91, 92, 93, 94, 95, 96, 97, 98, or 99%) of the polypeptide elutes in step b). In some embodiments, the eluate from step c) comprises non-specifically bound polypeptide. In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the first ratio of mobile phase B to mobile phase A is between about 0:100 and about 20:80 (such as about any of 2:98, 4:96, 6:94, 8:92, 10:90, 12:88, 14:86, 16:84, and 18:82, including any ranges between these ratios). In some embodiments, the second ratio is between about 30:70 and about 50:50 (such as about any of 32:68, 34:66, 36:64, 38:62, 40:60, 42:58, 44:56, 46:54, and 48:52, including any ranges between these ratios). In some embodiments, the third ratio is between about 80:20 and about 100:0 (such as about any of 82:18, 84:16, 86:14, 88:12, 90:10, 92:8, 94:6, 96:4, and 98:2, including any ranges between these values). In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) acid in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) acid in methanol. In some embodiments, the acid is formic acid. In some embodiments, the acid is acetic acid. In some embodiments, the flow rate of the chromatography is between about 0.5 and 2.5 (such as about any of 0.7, 0.9, 1.1, 1.2, 1.25, 1.3, 1.5, 1.7, 1.9, 2.1, and 2.3, including any ranges between these values) mL/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 1 (such as at least about any of 1.2, 1.4, 1.6, 1.8, 2, 2.2, 2.4, 2.6, 2.8, 3, 3.2, 3.4, 3.6, 3.8, 4 or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 0.5 (such as at least about any of 0.6, 0.7, 0.8, 0.9, 1, 1.1, 1.2, 1.3, 1.4, 1.5, 2, 3, or more) min. In some embodiments, the polysorbate is polysorbate 20 or polysorbate 80. In some embodiments, the concentration of polysorbate in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the protein concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic polypeptide is a fusion protein, a polyclonal antibody, a monoclonal antibody, a humanized antibody, a human antibody, a chimeric antibody, a multispecific antibody, a glycoengineered antibody, an antibody fragment, an antibody drug conjugate, a THIO-MAB™ or a THIOMAB™ drug conjugate. In some embodiments, the mixed mode anion exchange chromatography material comprises a reversed phase, strong anion exchange polymer. In some embodiments, the mixed mode anion exchange chromatography material comprises a quaternary amine moiety. In some embodiments, the mixed mode anion exchange chromatography material comprises a solid support. In some embodiments, the mixed mode anion exchange chromatography material is contained in a column or cartridge. In some embodiments, the mixed mode anion exchange chromatography material is a high performance liquid chromatography (HPLC) material. In some embodiments, the mixed mode anion exchange chromatography material is an Oasis® MAX chromatography material. In some embodiments, the non-ionic detergent is quantified by Evaporative Light Scattering (ELSD) or by using a Charged Aerosol Detector (CAD).

In some embodiments, there is provided a method for quantifying a polysorbate in a composition comprising the polysorbate and a polypeptide, wherein the method comprises the steps of a) applying the composition to a mixed mode anion exchange chromatography material, wherein the composition is loaded onto the chromatography material in a solution comprising a first ratio of a mobile phase B to a mobile phase A, wherein mobile phase A comprises acid in water and mobile phase B comprises acid in methanol; b) eluting the polypeptide from the mixed mode anion exchange chromatography material with a solution comprising a second ratio of mobile phase B to mobile phase A, wherein the second ratio is greater than the first ratio; c) eluting the polysorbate from the chromatography material with a solution comprising a third ratio of mobile phase B to mobile phase A, wherein the third ratio is greater than the second ratio; and d) quantifying the polysorbate in the eluate of step c), wherein the eluate comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the first ratio of mobile phase B to mobile phase A is between about 0:100 and about 20:80 (such as about any of 2:98, 4:96, 6:94, 8:92, 10:90, 12:88, 14:86, 16:84, and 18:82, including any ranges between these ratios). In some embodiments, the second ratio is between about 30:70 and about 50:50 (such as about any of 32:68, 34:66, 36:64, 38:62, 40:60, 42:58, 44:56, 46:54, and 48:52, including any ranges between these ratios). In some embodiments, the third ratio is between about 80:20 and about 100:0 (such as about any of 82:18, 84:16, 86:14, 88:12, 90:10, 92:8, 94:6, 96:4, and 98:2, including any ranges between these values). In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) acid in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) acid in methanol. In some embodiments, the acid is formic acid. In some embodiments, the acid is acetic acid. In some embodiments, the flow rate of the chromatography is between about 0.5 and 2.5 (such as about any of 0.7, 0.9, 1.1, 1.2, 1.25, 1.3, 1.5, 1.7, 1.9, 2.1, and 2.3, including any ranges between these values) mL/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 1 (such as at least about any of 1.2, 1.4, 1.6, 1.8, 2, 2.2, 2.4, 2.6, 2.8, 3, 3.2, 3.4, 3.6, 3.8, 4 or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 0.5 (such as at least about any of 0.6, 0.7, 0.8, 0.9, 1, 1.1, 1.2, 1.3, 1.4, 1.5, 2, 3, or more) min. In some embodiments, the polysorbate is polysorbate 20 or polysorbate 80. In some embodiments, the concentration of polysorbate in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the protein concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic polypeptide is a fusion protein, a polyclonal antibody, a monoclonal antibody, a humanized antibody, a human antibody, a chimeric antibody, a multispecific antibody, a glycoengineered antibody, an antibody fragment, an antibody drug conjugate, a THIOMAB™ or a THIOMAB™ drug conjugate. In some embodiments, the mixed mode anion exchange chromatography material comprises a reversed phase, strong anion exchange polymer. In some embodiments, the mixed mode anion exchange chromatography material comprises a quaternary amine moiety. In some embodiments, the mixed mode anion exchange chromatography material comprises a solid support. In some embodiments, the mixed mode anion exchange chromatography material is contained in a column or cartridge. In some embodiments, the mixed mode anion exchange chromatography material is a high performance liquid chromatography (HPLC) material. In some embodiments, the mixed mode anion exchange chromatography material is an Oasis® MAX chromatography material. In some embodiments, the non-ionic detergent is quantified by Evaporative Light Scattering (ELSD) or by using a Charged Aerosol Detector (CAD). In some embodiments, the quantification of the non-ionic surfactant comprises less than about 10% (such as less than about any of 9%, 8%, 7%, 6%, 5%, 4%, 3%, 2%, 1%, 0.5%, 0.1%, 0.05%, 0.01%, or less) interference from the polypeptide.

In some embodiments, there is provided a method for quantifying a polysorbate in a composition comprising the polysorbate and a polypeptide, wherein the method comprises the steps of a) applying the composition to a mixed mode anion exchange chromatography material, wherein the composition is loaded onto the chromatography material in a solution comprising a first ratio of a mobile phase B to a mobile phase A, wherein mobile phase A comprises acetic acid in water and mobile phase B comprises acetic acid in methanol; b) eluting the polypeptide from the mixed mode anion exchange chromatography material with a solution comprising a second ratio of mobile phase B to mobile phase A, wherein the second ratio is greater than the first ratio; c) eluting the polysorbate from the chromatography material with a solution comprising a third ratio of mobile phase B to mobile phase A, wherein the third ratio is greater than the second ratio; and d) quantifying the polysorbate in the eluate of step c). In some embodiments, the polypeptide binds to the chromatography material specifically and non-specifically, and at least about 90% (such as at least about any of 91, 92, 93, 94, 95, 96, 97, 98, or 99%) of the polypeptide elutes in step b). In some embodiments, the eluate from step c) comprises non-specifically bound polypeptide. In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the first ratio of mobile phase B to mobile phase A is between about 0:100 and about 20:80 (such as about any of 2:98, 4:96, 6:94, 8:92, 10:90, 12:88, 14:86, 16:84, and 18:82, including any ranges between these ratios). In some embodiments, the second ratio is between about 30:70 and about 50:50 (such as about any of 32:68, 34:66, 36:64, 38:62, 40:60, 42:58, 44:56, 46:54, and 48:52, including any ranges between these ratios). In some embodiments, the third ratio is between about 80:20 and about 100:0 (such as about any of 82:18, 84:16, 86:14, 88:12, 90:10, 92:8, 94:6, 96:4, and 98:2, including any ranges between these values). In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) acetic acid in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) acetic acid in methanol. In some embodiments, the flow rate of the chromatography is between about 0.5 and 2.5 (such as about any of 0.7, 0.9, 1.1, 1.2, 1.25, 1.3, 1.5, 1.7, 1.9, 2.1, and 2.3, including any ranges between these values) mL/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) μL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 1 (such as at least about any of 1.2, 1.4, 1.6, 1.8, 2, 2.2, 2.4, 2.6, 2.8, 3, 3.2, 3.4, 3.6, 3.8, 4 or more) min. In some embodiments, step c) starts at least about 0.05 (such as at least about any of 0.06, 0.07, 0.08, 0.09, 0.1, 0.2, 0.3, 0.4, 0.5, 1, 1.5.2, or more) min after step b) ends and continues for at least about 0.5 (such as at least about any of 0.6, 0.7, 0.8, 0.9, 1, 1.1, 1.2, 1.3, 1.4, 1.5, 2, 3, or more) min. In some embodiments, the polysorbate is polysorbate 20 or polysorbate 80. In some embodiments, the concentration of polysorbate in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the protein concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic polypeptide is a fusion protein, a polyclonal antibody, a monoclonal antibody, a humanized antibody, a human antibody, a chimeric antibody, a multispecific antibody, a glycoengineered antibody, an antibody fragment, an antibody drug conjugate, a THIOMAB™ or a THIOMAB™ drug conjugate. In some embodiments, the mixed mode anion exchange chromatography material comprises a reversed phase, strong anion exchange polymer. In some embodiments, the mixed mode anion exchange chromatography material comprises a quaternary amine moiety. In some embodiments, the mixed mode anion exchange chromatography material comprises a solid support. In some embodiments, the mixed mode anion exchange chromatography material is contained in a column or cartridge. In some embodiments, the mixed mode anion exchange chromatography material is a high performance liquid chromatography (HPLC) material. In some embodiments, the mixed mode anion exchange chromatography material is an Oasis® MAX chromatography material. In some embodiments, the non-ionic detergent is quantified by Evaporative Light Scattering (ELSD) or by using a Charged Aerosol Detector (CAD). In some embodiments, the quantification of the non-ionic surfactant comprises less than about 10% (such as less than about any of 9%, 8%, 7%, 6%, 5%, 4%, 3%, 2%, 1%, 0.5%, 0.1%, 0.05%, 0.01%, or less) interference from the polypeptide.

In some embodiments, there is provided a method for quantifying a polysorbate in a composition comprising the polysorbate and a polypeptide, wherein the method comprises the steps of a) applying the composition to a mixed mode anion exchange chromatography material, wherein the composition is loaded onto the chromatography material in a solution comprising a first ratio of a mobile phase B to a mobile phase A between about 5:95 and about 15:85, wherein mobile phase A comprises acid in water and mobile phase B comprises acid in methanol; b) eluting the polypeptide from the mixed mode anion exchange chromatography material with a solution comprising a second ratio of mobile phase B to mobile phase A between about 35:65 and about 45:55; c) eluting the polysorbate from the chromatography material with a solution comprising a third ratio of mobile phase B to mobile phase A between about 90:10 and about 100:0; and d) quantifying the polysorbate in the eluate of step c). In some embodiments, the first ratio of mobile phase B to mobile phase A is about 10:90. In some embodiments, the second ratio is about 40.60. In some embodiments, the third ratio is about 100:0. In some embodiments, the polypeptide binds to the chromatography material specifically and non-specifically, and at least about 90% (such as at least about any of 91, 92, 93, 94, 95, 96, 97, 98, or 99%) of the polypeptide elutes in step b). In some embodiments, the eluate from step c) comprises non-specifically bound polypeptide. In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) acid in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) acid in methanol. In some embodiments, the acid is formic acid. In some embodiments, the acid is acetic acid. In some embodiments, the flow rate of the chromatography is between about 0.5 and 2.5 (such as about any of 0.7, 0.9, 1.1, 1.2, 1.25, 1.3, 1.5, 1.7, 1.9, 2.1, and 2.3, including any ranges between these values) mL/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) μL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 1 (such as at least about any of 1.2, 1.4, 1.6, 1.8, 2, 2.2, 2.4, 2.6, 2.8, 3, 3.2, 3.4, 3.6, 3.8, 4 or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 0.5 (such as at least about any of 0.6, 0.7, 0.8, 0.9, 1, 1.1, 1.2, 1.3, 1.4, 1.5, 2, 3, or more) min. In some embodiments, the polysorbate is polysorbate 20 or polysorbate 80. In some embodiments, the concentration of polysorbate in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the protein concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic polypeptide is a fusion protein, a polyclonal antibody, a monoclonal antibody, a humanized antibody, a human antibody, a chimeric antibody, a multispecific antibody, a glycoengineered antibody, an antibody fragment, an antibody drug conjugate, a THIOMAB™ or a THIOMAB™ drug conjugate. In some embodiments, the mixed mode anion exchange chromatography material comprises a reversed phase, strong anion exchange polymer. In some embodiments, the mixed mode anion exchange chromatography material comprises a quaternary amine moiety. In some embodiments, the mixed mode anion exchange chromatography material comprises a solid support. In some embodiments, the mixed mode anion exchange chromatography material is contained in a column or cartridge. In some embodiments, the mixed mode anion exchange chromatography material is a high performance liquid chromatography (HPLC) material. In some embodiments, the mixed mode anion exchange chromatography material is an Oasis® MAX chromatography material. In some embodiments, the non-ionic detergent is quantified by Evaporative Light Scattering (ELSD) or by using a Charged Aerosol Detector (CAD). In some embodiments, the quantification of the non-ionic surfactant comprises less than about 10% (such as less than about any of 9%, 8%, 7%, 6%, 5%, 4%, 3%, 2%, 1%, 0.5%, 0.1%, 0.05%, 0.01%, or less) interference from the polypeptide.

In some embodiments, there is provided a method for quantifying a polysorbate in a composition comprising the polysorbate and a polypeptide, wherein the method comprises the steps of a) applying the composition to a mixed mode anion exchange chromatography material, wherein the composition is loaded onto the chromatography material in a solution comprising a first ratio of a mobile phase B to a mobile phase A between about 5:95 and about 15:85, wherein mobile phase A comprises acetic acid in water and mobile phase B comprises acetic acid in methanol; b) eluting the polypeptide from the mixed mode anion exchange chromatography material with a solution comprising a second ratio of mobile phase B to mobile phase A between about 35:65 and about 45:55; c) eluting the polysorbate from the chromatography material with a solution comprising a third ratio of mobile phase B to mobile phase A between about 90:10 and about 100:0; and d) quantifying the polysorbate in the eluate of step c), wherein the quantification of the non-ionic surfactant comprises less than about 10% (such as less than about any of 9%, 8%, 7%, 6%, 5%, 4%, 3%, 2%, 1%, 0.5%, 0.1%, 0.05%, 0.01%, or less) interference from the polypeptide. In some embodiments, the first ratio of mobile phase B to mobile phase A is about 10:90. In some embodiments, the second ratio is about 40:60. In some embodiments, the third ratio is about 100:0. In some embodiments, the polypeptide binds to the chromatography material specifically and non-specifically, and at least about 90% (such as at least about any of 91, 92, 93, 94, 95, 96, 97, 98, or 99%) of the polypeptide elutes in step b). In some embodiments, the eluate from step c) comprises non-specifically bound polypeptide. In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) acetic acid in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) acetic acid in methanol. In some embodiments, the flow rate of the chromatography is between about 0.5 and 2.5 (such as about any of 0.7, 0.9, 1.1, 1.2, 1.25, 1.3, 1.5, 1.7, 1.9, 2.1, and 2.3, including any ranges between these values) ml/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 1 (such as at least about any of 1.2, 1.4, 1.6, 1.8, 2, 2.2, 2.4, 2.6, 2.8, 3, 3.2, 3.4, 3.6, 3.8, 4 or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 0.5 (such as at least about any of 0.6, 0.7, 0.8, 0.9, 1, 1.1, 1.2, 1.3, 1.4, 1.5, 2, 3, or more) min. In some embodiments, the polysorbate is polysorbate 20 or polysorbate 80. In some embodiments, the concentration of polysorbate in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the protein concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic polypeptide is a fusion protein, a polyclonal antibody, a monoclonal antibody, a humanized antibody, a human antibody, a chimeric antibody, a multispecific antibody, a glycoengineered antibody, an antibody fragment, an antibody drug conjugate, a THIOMAB™ or a THIOMAB™ drug conjugate. In some embodiments, the mixed mode anion exchange chromatography material comprises a reversed phase, strong anion exchange polymer. In some embodiments, the mixed mode anion exchange chromatography material comprises a quaternary amine moiety. In some embodiments, the mixed mode anion exchange chromatography material comprises a solid support. In some embodiments, the mixed mode anion exchange chromatography material is contained in a column or cartridge. In some embodiments, the mixed mode anion exchange chromatography material is a high performance liquid chromatography (HPLC) material. In some embodiments, the mixed mode anion exchange chromatography material is an Oasis® MAX chromatography material. In some embodiments, the non-ionic detergent is quantified by Evaporative Light Scattering (ELSD) or by using a Charged Aerosol Detector (CAD).

In some embodiments, there is provided a method for quantifying a polysorbate in a composition comprising the polysorbate and a polypeptide, wherein the method comprises the steps of a) applying the composition to a mixed mode anion exchange chromatography material, wherein the composition is loaded onto the chromatography material in a solution comprising a first ratio of a mobile phase B to a mobile phase A between about 5:95 and about 15:85, wherein mobile phase A comprises acetic acid in water and mobile phase B comprises acetic acid in methanol; b) eluting the polypeptide from the mixed mode anion exchange chromatography material with a solution comprising a second ratio of mobile phase B to mobile phase A between about 35:65 and about 45:55; c) eluting the polysorbate from the chromatography material with a solution comprising a third ratio of mobile phase B to mobile phase A between about 90:10 and about 100:0; and d) quantifying the polysorbate in the eluate of step c), wherein the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the first ratio of mobile phase B to mobile phase A is about 10:90. In some embodiments, the second ratio is about 40:60. In some embodiments, the third ratio is about 100:0. In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) acetic acid in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) acetic acid in methanol. In some embodiments, the flow rate of the chromatography is between about 0.5 and 2.5 (such as about any of 0.7, 0.9, 1.1, 1.2, 1.25, 1.3, 1.5, 1.7, 1.9, 2.1, and 2.3, including any ranges between these values) ml/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 1 (such as at least about any of 1.2, 1.4, 1.6, 1.8, 2, 2.2, 2.4, 2.6, 2.8, 3, 3.2, 3.4, 3.6, 3.8, 4 or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 0.5 (such as at least about any of 0.6, 0.7, 0.8, 0.9, 1, 1.1, 1.2, 1.3, 1.4, 1.5, 2, 3, or more) min. In some embodiments, the polysorbate is polysorbate 20 or polysorbate 80. In some embodiments, the concentration of polysorbate in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the protein concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic polypeptide is a fusion protein, a polyclonal antibody, a monoclonal antibody, a humanized antibody, a human antibody, a chimeric antibody, a multispecific antibody, a glycoengineered antibody, an antibody fragment, an antibody drug conjugate, a THIOMAB™ or a THIOMAB™ drug conjugate. In some embodiments, the mixed mode anion exchange chromatography material comprises a reversed phase, strong anion exchange polymer. In some embodiments, the mixed mode anion exchange chromatography material comprises a quaternary amine moiety. In some embodiments, the mixed mode anion exchange chromatography material comprises a solid support. In some embodiments, the mixed mode anion exchange chromatography material is contained in a column or cartridge. In some embodiments, the mixed mode anion exchange chromatography material is a high performance liquid chromatography (HPLC) material. In some embodiments, the mixed mode anion exchange chromatography material is an Oasis® MAX chromatography material. In some embodiments, the non-ionic detergent is quantified by Evaporative Light Scattering (ELSD) or by using a Charged Aerosol Detector (CAD). In some embodiments, the quantification of the non-ionic surfactant comprises less than about 10% (such as less than about any of 9%, 8%, 7%, 6%, 5%, 4%, 3%, 2%, 1%, 0.5%, 0.1%, 0.05%, 0.01%, or less) interference from the polypeptide.

In some embodiments, there is provided a method for quantifying polysorbate 20 in a composition comprising polysorbate 20 and a polypeptide, wherein the method comprises the steps of a) applying the composition to a mixed mode anion exchange chromatography material, wherein the composition is loaded onto the chromatography material in a solution comprising a ratio of about 10:90 of a mobile phase B to a mobile phase A, wherein mobile phase A comprises about 2% acetic acid in water and mobile phase B comprises about 2% acetic acid in methanol; b) eluting the polypeptide from the mixed mode anion exchange chromatography material with a solution comprising a ratio of about 40:60 of mobile phase B to mobile phase A; c) eluting the polysorbate 20 from the chromatography material with a solution comprising a ratio of about 100:0 of mobile phase B to mobile phase A; and d) quantifying the polysorbate in the eluate of step c). In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the flow rate of the chromatography is between about 0.5 and 2.5 (such as about any of 0.7, 0.9, 1.1, 1.2, 1.25, 1.3, 1.5, 1.7, 1.9, 2.1, and 2.3, including any ranges between these values) mL/minute. In some embodiments, the flow rate of the chromatography is about 1.25 mL/min. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, the volume of the composition applied to the chromatography material is about 20 µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 1 (such as at least about any of 1.2, 1.4, 1.6, 1.8, 2, 2.2, 2.4, 2.6, 2.8, 3, 3.2, 3.4, 3.6, 3.8, 4 or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 0.5 (such as at least about any of 0.6, 0.7, 0.8, 0.9, 1, 1.1, 1.2, 1.3, 1.4, 1.5, 2, 3, or more) min. In some embodiments, the concentration of polysorbate 20 in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the protein concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic polypeptide is a fusion protein, a polyclonal antibody, a monoclonal antibody, a humanized antibody, a human antibody, a chimeric antibody, a multispecific antibody, a glycoengineered antibody, an antibody fragment, an antibody drug conjugate, a THIOMAB™ or a THIOMAB™ drug conjugate. In some embodiments, the mixed mode anion exchange chromatography material comprises a reversed phase, strong anion exchange polymer. In some embodiments, the mixed mode anion exchange chromatography material comprises a quaternary amine moiety. In some embodiments, the mixed mode anion exchange chromatography material comprises a solid support. In some embodiments, the mixed mode anion exchange chromatography material is contained in a column or cartridge. In some embodiments, the mixed mode anion exchange chromatography material is a high performance liquid chromatography (HPLC) material. In some embodiments, the mixed mode anion exchange chromatography material is an Oasis® MAX chromatography material. In some embodiments, the non-ionic detergent is quantified by Evaporative Light Scattering (ELSD) or by using a Charged Aerosol Detector (CAD). In some embodiments, the quantification of the non-ionic surfactant comprises less than about 10% (such as less than about any of 9%, 8%, 7%, 6%, 5%, 4%, 3%, 2%, 1%, 0.5%, 0.1%, 0.05%, 0.01%, or less) interference from the polypeptide.

In some embodiments, there is provided a method for quantifying a non-ionic surfactant in a composition comprising the non-ionic surfactant and a polypeptide, wherein the method comprises the steps of a) applying the composition to a mixed mode cation exchange chromatography material, wherein the composition is loaded onto the chromatography material in a solution comprising a first ratio of a mobile phase B to a mobile phase A, wherein mobile phase A comprises ammonium hydroxide in water and mobile phase B comprises ammonium hydroxide in an organic solvent; b) eluting the polypeptide from the mixed mode cation exchange chromatography material with a solution comprising a second ratio of mobile phase B to mobile phase A, wherein the second ratio is greater than the first ratio; c) eluting the non-ionic surfactant from the chromatography material with a solution comprising a third ratio of mobile phase B to mobile phase A, wherein the third ratio is greater than the second ratio; and d) quantifying the non-ionic surfactant in the eluate of step c). In some embodiments, the polypeptide binds to the chromatography material specifically and non-specifically, and at least about 90% (such as at least about any of 91, 92, 93, 94, 95, 96, 97, 98, or 99%) of the polypeptide elutes in step b). In some embodiments, the eluate from step c) comprises non-specifically bound polypeptide. In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the organic solvent of mobile phase B is methanol. In some embodiments, the organic solvent of mobile phase B is acetonitrile. In some embodiments, the first ratio of mobile phase B to mobile phase A is between about 0:100 and about 20:80 (such as about any of 2:98, 4:96, 6:94, 8:92, 10:90, 12:88, 14:86, 16:84, and 18:82, including any ranges between these ratios). In some embodiments, the second ratio is between about 35:65 and about 55:45 (such as about any of 36:64, 38:62, 40:60, 42:58, 44:56, 46:54, 48:52, 50:50, 52:48, and 54:46, including any ranges between these ratios). In some embodiments, the third ratio is between about 80:20 and about 100:0 (such as about any of 82:18, 84:16, 86:14, 88:12, 90:10, 92:8, 94:6, 96:4, and 98:2, including any ranges between these values). In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in the organic solvent (e.g., methanol or acetonitrile). In some embodiments, the flow rate of the chromatography is between about 0.5 and 2.5 (such as about any of 0.7, 0.9, 1.1, 1.3, 1.4, 1.5, 1.7, 1.9, 2.1, and 2.3, including any ranges between these values) ml/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 2 (such as at least about any of 2.2, 2.4, 2.6, 2.8, 3, 3.2, 3.4, 3.6, 3.8, 4, 4.5, 5, or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 2 (such as at least about any of 2.2, 2.4, 2.6, 2.8, 3, 3.1, 3.2, 3.4, 3.6, 3.8, 4, 4.5, 5, or more) min. In some embodiments, the non-ionic surfactant is a polysorbate. In some embodiments, the polysorbate is polysorbate 20 or polysorbate 80. In some embodiments, the non-ionic surfactant is a poloxamer. In some embodiments, the poloxamer is poloxamer P188. In some embodiments, the concentration of the non-ionic surfactant (e.g., polysorbate or poloxamer) in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the composition further comprises N-acetyl tryptophan (also referred to as N-acetyl-DL-tryptophan) and/or methionine. In some embodiments, the concentration of N-acetyl tryptophan in the composition ranges from about 0.1 mM to about 10 mM (such as about any of 0.2, 0.5, 1, 2, 3, 4, 5, 6, 7, 8, or 9 mM, including any ranges between these values). In some embodiments, the concentration of methionine in the composition ranges from about 0.1 mM to about 100 mM (such as about any of 0.2, 0.5, 1, 2, 3, 4, 5, 6, 7, 8, 9, 10, 20, 30, 40, 50, 60, 70, 80, or 90 mM, including any ranges between these values). In some embodiments, the polypeptide concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic protein is a polyclonal antibody, a monoclonal antibody, a humanized antibody, a human antibody, a chimeric antibody, a multispecific antibody, glycoengineered antibody, antibody fragment, an antibody drug conjugate, a THIOMAB™, a THIOMAB™ drug conjugate. In some embodiments, the mixed mode cation exchange chromatography material comprises a reversed phase, strong cation exchange polymer. In some embodiments, the mixed mode cation exchange chromatography material comprises a sulfonic acid moiety. In some embodiments, the mixed mode cation exchange chromatography material comprises a solid support. In some embodiments, the mixed mode cation exchange chromatography material is contained in a column. In some embodiments, the mixed mode cation exchange chromatography material is a high performance liquid chromatography (HPLC) material. In some embodiments, the mixed mode cation exchange chromatography material is an Oasis® MCX chromatography material. In some embodiments, the non-ionic detergent is quantified by Evaporative Light Scattering (ELSD) or by using a Charged Aerosol Detector (CAD). In some embodiments, the quantification of the non-ionic surfactant comprises less than about 10% (such as less than about any of 9%, 8%, 7%, 6%, 5%, 4%, 3%, 2%, 1%, 0.5%, 0.1%, 0.05%, 0.01%, or less) interference from the polypeptide.

In some embodiments, there is provided a method for quantifying a non-ionic surfactant in a composition comprising the non-ionic surfactant and a polypeptide, wherein the method comprises the steps of a) applying the composition to a mixed mode cation exchange chromatography material, wherein the composition is loaded onto the chromatography material in a solution comprising a first ratio of a mobile phase B to a mobile phase A, wherein mobile phase A comprises ammonium hydroxide in water and mobile phase B comprises ammonium hydroxide in an organic solvent; b) eluting the polypeptide from the mixed mode cation exchange chromatography material with a solution comprising a second ratio of mobile phase B to mobile phase A, wherein the second ratio is greater than the first ratio; c) eluting the non-ionic surfactant from the chromatography material with a solution comprising a third ratio of mobile phase B to mobile phase A, wherein the third ratio is greater than the second ratio; and d) quantifying the non-ionic surfactant in the eluate of step c), wherein the quantification of the non-ionic surfactant comprises less than about 10% (such as less than about any of 9%, 8%, 7%, 6%, 5%, 4%, 3%, 2%, 1%, 0.5%, 0.1%, 0.05%, 0.01%, or less) interference from the polypeptide. In some embodiments, the polypeptide binds to the chromatography material specifically and non-specifically, and at least about 90% (such as at least about any of 91, 92, 93, 94, 95, 96, 97, 98, or 99%) of the polypeptide elutes in step b). In some embodiments, the eluate from step c) comprises non-specifically bound polypeptide. In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the organic solvent of mobile phase B is methanol. In some embodiments, the organic solvent of mobile phase B is acetonitrile. In some embodiments, the first ratio of mobile phase B to mobile phase A is between about 0:100 and about 20:80 (such as about any of 2:98, 4:96, 6:94, 8:92, 10:90, 12:88, 14:86, 16:84, and 18:82, including any ranges between these ratios). In some embodiments, the second ratio is between about 35:65 and about 55:45 (such as about any of 36:64, 38:62, 40:60, 42:58, 44:56, 46:54, 48:52, 50:50, 52:48, and 54:46, including any ranges between these ratios). In some embodiments, the third ratio is between about 80:20 and about 100:0 (such as about any of 82:18, 84:16, 86:14, 88:12, 90:10, 92:8, 94:6, 96:4, and 98:2, including any ranges between these values). In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in the organic solvent (e.g., methanol or acetonitrile). In some embodiments, the flow rate of the chromatography is between about 0.5 and 2.5 (such as about any of 0.7, 0.9, 1.1, 1.3, 1.4, 1.5, 1.7, 1.9, 2.1, and 2.3, including any ranges between these values) mL/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 2 (such as at least about any of 2.2, 2.4, 2.6, 2.8, 3, 3.2, 3.4, 3.6, 3.8, 4, 4.5, 5, or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 2 (such as at least about any of 2.2, 2.4, 2.6, 2.8, 3, 3.1, 3.2, 3.4, 3.6, 3.8, 4, 4.5, 5, or more) min. In some embodiments, the non-ionic surfactant is a polysorbate. In some embodiments, the polysorbate is polysorbate 20 or polysorbate 80. In some embodiments, the non-ionic surfactant is a poloxamer. In some embodiments, the poloxamer is poloxamer P188. In some embodiments, the concentration of the non-ionic surfactant (e.g., polysorbate or poloxamer) in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the composition further comprises N-acetyl tryptophan and/or methionine. In some embodiments, the concentration of N-acetyl tryptophan in the composition ranges from about 0.1 mM to about 10 mM (such as about any of 0.2, 0.5, 1, 2, 3, 4, 5, 6, 7, 8, or 9 mM, including any ranges between these values). In some embodiments, the concentration of methionine in the composition ranges from about 0.1 mM to about 100 mM (such as about any of 0.2, 0.5, 1, 2, 3, 4, 5, 6, 7, 8, 9, 10, 20, 30, 40, 50, 60, 70, 80, or 90 mM, including any ranges between these values). In some embodiments, the polypeptide concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic protein is a polyclonal antibody, a monoclonal antibody, a humanized antibody, a human antibody, a chimeric antibody, a multispecific antibody, glycoengineered antibody, antibody fragment, an antibody drug conjugate, a THIOMAB™, a THIOMAB™ drug conjugate. In some embodiments, the mixed mode cation exchange chromatography material comprises a reversed phase, strong cation exchange polymer. In some embodiments, the mixed mode cation exchange chromatography material comprises a sulfonic acid moiety. In some embodiments, the mixed mode cation exchange chromatography material comprises a solid support. In some embodiments, the mixed mode cation exchange chromatography material is contained in a column. In some embodiments, the mixed mode cation exchange chromatography material is a high performance liquid chromatography (HPLC) material. In some embodiments, the mixed mode cation exchange chromatography material is an Oasis® MCX chromatography material. In some embodiments, the non-ionic detergent is quantified by Evaporative Light Scattering (ELSD) or by using a Charged Aerosol Detector (CAD).

In some embodiments, there is provided a method for quantifying a non-ionic surfactant in a composition comprising the non-ionic surfactant and a polypeptide, wherein the method comprises the steps of a) applying the composition to a mixed mode cation exchange chromatography material, wherein the composition is loaded onto the chromatography material in a solution comprising a first ratio of a mobile phase B to a mobile phase A, wherein mobile phase A comprises ammonium hydroxide in water and mobile phase B comprises ammonium hydroxide in an organic solvent; b) eluting the polypeptide from the mixed mode cation exchange chromatography material with a solution comprising a second ratio of mobile phase B to mobile phase A, wherein the second ratio is greater than the first ratio; c) eluting the non-ionic surfactant from the chromatography material with a solution comprising a third ratio of mobile phase B to mobile phase A, wherein the third ratio is greater than the second ratio; and d) quantifying the non-ionic surfactant in the eluate of step c), wherein the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the organic solvent of mobile phase B is methanol. In some embodiments, the organic solvent of mobile phase B is acetonitrile. In some embodiments, the first ratio of mobile phase B to mobile phase A is between about 0:100 and about 20:80 (such as about any of 2:98, 4:96, 6:94, 8:92, 10:90, 12:88, 14:86, 16:84, and 18:82, including any ranges between these ratios). In some embodiments, the second ratio is between about 35:65 and about 55:45 (such as about any of 36:64, 38:62, 40:60, 42:58, 44:56, 46:54, 48:52, 50:50, 52:48, and 54:46, including any ranges between these ratios). In some embodiments, the third ratio is between about 80:20 and about 100:0 (such as about any of 82:18, 84:16, 86:14, 88:12, 90:10, 92:8, 94:6, 96:4, and 98:2, including any ranges between these values). In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in the organic solvent (e.g., methanol or acetonitrile). In some embodiments, the flow rate of the chromatography is between about 0.5 and 2.5 (such as about any of 0.7, 0.9, 1.1, 1.3, 1.4, 1.5, 1.7, 1.9, 2.1, and 2.3, including any ranges between these values) mL/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 2 (such as at least about any of 2.2, 2.4, 2.6, 2.8, 3, 3.2, 3.4, 3.6, 3.8, 4, 4.5, 5, or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 2 (such as at least about any of 2.2, 2.4, 2.6, 2.8, 3, 3.1, 3.2, 3.4, 3.6, 3.8, 4, 4.5, 5, or more) min. In some embodiments, the non-ionic surfactant is a polysorbate. In some embodiments, the polysorbate is polysorbate 20 or polysorbate 80. In some embodiments, the non-ionic surfactant is a poloxamer. In some embodiments, the poloxamer is poloxamer P188. In some embodiments, the concentration of the non-ionic surfactant (e.g., polysorbate or poloxamer) in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the composition further comprises N-acetyl tryptophan and/or methionine. In some embodiments, the concentration of N-acetyl tryptophan in the composition ranges from about 0.1 mM to about 10 mM (such as about any of 0.2, 0.5, 1, 2, 3, 4, 5, 6, 7, 8, or 9 mM, including any ranges between these values). In some embodiments, the concentration of methionine in the composition ranges from about 0.1 mM to about 100 mM (such as about any of 0.2, 0.5, 1, 2, 3, 4, 5, 6, 7, 8, 9, 10, 20, 30, 40, 50, 60, 70, 80, or 90 mM, including any ranges between these values). In some embodiments, the polypeptide concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic protein is a polyclonal antibody, a monoclonal antibody, a humanized antibody, a human antibody, a chimeric antibody, a multispecific antibody, glycoengineered antibody, antibody fragment, an antibody drug conjugate, a THIOMAB™, a THIOMAB™ drug conjugate. In some embodiments, the mixed mode cation exchange chromatography material comprises a reversed phase, strong cation exchange polymer. In some embodiments, the mixed mode cation exchange chromatography material comprises a sulfonic acid moiety. In some embodiments, the mixed mode cation exchange chromatography material comprises a solid support. In some embodiments, the mixed mode cation exchange chromatography material is contained in a column. In some embodiments, the mixed mode cation exchange chromatography material is a high performance liquid chromatography (HPLC) material. In some embodiments, the mixed mode cation exchange chromatography material is an Oasis® MCX chromatography material. In some embodiments, the non-ionic detergent is quantified by Evaporative Light Scattering (ELSD) or by using a Charged Aerosol Detector (CAD). In some embodiments, the quantification of the non-ionic surfactant comprises less than about 10% (such as less than about any of 9%, 8%, 7%, 6%, 5%, 4%, 3%, 2%, 1%, 0.5%, 0.1%, 0.05%, 0.01%, or less) interference from the polypeptide.

In some embodiments, there is provided a method for quantifying a non-ionic surfactant in a composition comprising the non-ionic surfactant and a polypeptide, wherein the method comprises the steps of a) applying the composition to a mixed mode cation exchange chromatography material, wherein the composition is loaded onto the chromatography material in a solution comprising a first ratio of a mobile phase B to a mobile phase A, wherein mobile phase A comprises ammonium hydroxide in water and mobile phase B comprises ammonium hydroxide in methanol; b) eluting the polypeptide from the mixed mode cation exchange chromatography material with a solution comprising a second ratio of mobile phase B to mobile phase A, wherein the second ratio is greater than the first ratio: c) eluting the non-ionic surfactant from the chromatography material with a solution comprising a third ratio of mobile phase B to mobile phase A, wherein the third ratio is greater than the second ratio; and d) quantifying the non-ionic surfactant in the eluate of step c). In some embodiments, the polypeptide binds to the chromatography material specifically and non-specifically, and at least about 90% (such as at least about any of 91, 92, 93, 94, 95, 96, 97, 98, or 99%) of the polypeptide elutes in step b). In some embodiments, the eluate from step c) comprises non-specifically bound polypeptide. In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the first ratio of mobile phase B to mobile phase A is between about 0:100 and about 20:80 (such as about any of 2:98, 4:96, 6:94, 8:92, 10:90, 12:88, 14:86, 16:84, and 18:82, including any ranges between these ratios). In some embodiments, the second ratio is between about 35:65 and about 55:45 (such as about any of 36:64, 38:62, 40:60, 42:58, 44:56, 46:54, 48:52, 50:50, 52:48, and 54:46, including any ranges between these ratios). In some embodiments, the third ratio is between about 80:20 and about 100:0 (such as about any of 82:18, 84:16, 86:14, 88:12, 90:10, 92:8, 94:6, 96:4, and 98:2, including any ranges between these values). In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in methanol. In some embodiments, the flow rate of the chromatography is between about 0.5 and 2.5 (such as about any of 0.7, 0.9, 1.1, 1.3, 1.4, 1.5, 1.7, 1.9, 2.1, and 2.3, including any ranges between these values) mL/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 2 (such as at least about any of 2.2, 2.4, 2.6, 2.8, 3, 3.2, 3.4, 3.6, 3.8, 4, 4.5, 5, or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 2 (such as at least about any of 2.2, 2.4, 2.6, 2.8, 3, 3.1, 3.2, 3.4, 3.6, 3.8, 4, 4.5, 5, or more) min. In some embodiments, the non-ionic surfactant is a polysorbate. In some embodiments, the polysorbate is polysorbate 20 or polysorbate 80. In some embodiments, the non-ionic surfactant is a poloxamer. In some embodiments, the poloxamer is poloxamer P188. In some embodiments, the concentration of the non-ionic surfactant (e.g., polysorbate or poloxamer) in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the composition further comprises N-acetyl tryptophan and/or methionine. In some embodiments, the concentration of N-acetyl tryptophan in the composition ranges from about 0.1 mM to about 10 mM (such as about any of 0.2, 0.5, 1, 2, 3, 4, 5, 6, 7, 8, or 9 mM, including any ranges between these values). In some embodiments, the concentration of methionine in the composition ranges from about 0.1 mM to about 100 mM (such as about any of 0.2, 0.5, 1, 2, 3, 4, 5, 6, 7, 8, 9, 10, 20, 30, 40, 50, 60, 70, 80, or 90 mM, including any ranges between these values). In some embodiments, the polypeptide concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic protein is a polyclonal antibody, a monoclonal antibody, a humanized antibody, a human antibody, a chimeric antibody, a multispecific antibody, glycoengineered antibody, antibody fragment, an antibody drug conjugate, a THIOMAB™, a THIOMAB™ drug conjugate. In some embodiments, the mixed mode cation exchange chromatography material comprises a reversed phase, strong cation exchange polymer. In some embodiments, the mixed mode cation exchange chromatography material comprises a sulfonic acid moiety. In some embodiments, the mixed mode cation exchange chromatography material comprises a solid support. In some embodiments, the mixed mode cation exchange chromatography material is contained in a column. In some embodiments, the mixed mode cation exchange chromatography material is a high performance liquid chromatography (HPLC) material. In some embodiments, the mixed mode cation exchange chromatography material is an Oasis® MCX chromatography material. In some embodiments, the non-ionic detergent is quantified by Evaporative Light Scattering (ELSD) or by using a Charged Aerosol Detector (CAD). In some embodiments, the quantification of the non-ionic surfactant comprises less than about 10% (such as less than about any of 9%, 8%, 7%, 6%, 5%, 4%, 3%, 2%, 1%, 0.5%, 0.1%, 0.05%, 0.01%, or less) interference from the polypeptide.

In some embodiments, there is provided a method for quantifying a non-ionic surfactant in a composition comprising the non-ionic surfactant and a polypeptide, wherein the method comprises the steps of a) applying the composition to a mixed mode cation exchange chromatography material wherein the composition is loaded onto the chromatography material in a solution comprising a first ratio of a mobile phase B to a mobile phase A, wherein mobile phase A comprises ammonium hydroxide in water and mobile phase B comprises ammonium hydroxide in acetonitrile; b) eluting the polypeptide from the mixed mode cation exchange chromatography material with a solution comprising a second ratio of mobile phase B to mobile phase A, wherein the second ratio is greater than the first ratio; c) eluting the non-ionic surfactant from the chromatography material with a solution comprising a third ratio of mobile phase B to mobile phase A, wherein the third ratio is greater than the second ratio; and d) quantifying the non-ionic surfactant in the eluate of step c). In some embodiments, the polypeptide binds to the chromatography material specifically and non-specifically, and at least about 90% (such as at least about any of 91, 92, 93, 94, 95, 96, 97, 98, or 99%) of the polypeptide elutes in step b). In some embodiments, the eluate from step c) comprises non-specifically bound polypeptide. In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the first ratio of mobile phase B to mobile phase A is between about 0:100 and about 20:80 (such as about any of 2:98, 4:96, 6:94, 8:92, 10:90, 12:88, 14:86, 16:84, and 18:82, including any ranges between these ratios). In some embodiments, the second ratio is between about 35:65 and about 55:45 (such as about any of 36:64, 38:62, 40:60, 42:58, 44:56, 46:54, 48:52, 50:50, 52:48, and 54:46, including any ranges between these ratios). In some embodiments, the third ratio is between about 80:20 and about 100:0 (such as about any of 82:18, 84:16, 86:14, 88:12, 90:10, 92:8, 94:6, 96:4, and 98:2, including any ranges between these values). In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in acetonitrile. In some embodiments, the flow rate of the chromatography is between about 0.5 and 2.5 (such as about any of 0.7, 0.9, 1.1, 1.3, 1.4, 1.5, 1.7, 1.9, 2.1, and 2.3, including any ranges between these values) ml/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) μL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 2 (such as at least about any of 2.2, 2.4, 2.6, 2.8, 3, 3.2, 3.4, 3.6, 3.8, 4, 4.5, 5, or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 2 (such as at least about any of 2.2, 2.4, 2.6, 2.8, 3, 3.1, 3.2, 3.4, 3.6, 3.8, 4, 4.5, 5, or more) min. In some embodiments, the non-ionic surfactant is a polysorbate. In some embodiments, the polysorbate is polysorbate 20 or polysorbate 80. In some embodiments, the non-ionic surfactant is a poloxamer. In some embodiments, the poloxamer is poloxamer P188. In some embodiments, the concentration of the non-ionic surfactant (e.g., polysorbate or poloxamer) in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the composition further comprises N-acetyl tryptophan and/or methionine. In some embodiments, the concentration of N-acetyl tryptophan in the composition ranges from about 0.1 mM to about 10 mM (such as about any of 0.2, 0.5, 1, 2, 3, 4, 5, 6, 7, 8, or 9 mM, including any ranges between these values). In some embodiments, the concentration of methionine in the composition ranges from about 0.1 mM to about 100 mM (such as about any of 0.2, 0.5, 1, 2, 3, 4, 5, 6, 7, 8, 9, 10, 20, 30, 40, 50, 60, 70, 80, or 90 mM, including any ranges between these values). In some embodiments, the polypeptide concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic protein is a polyclonal antibody, a monoclonal antibody, a humanized antibody, a human antibody, a chimeric antibody, a multispecific antibody, glycoengineered antibody, antibody fragment, an antibody drug conjugate, a THIOMAB™, a THIOMAB™ drug conjugate. In some embodiments, the mixed mode cation exchange chromatography material comprises a reversed phase, strong cation exchange polymer. In some embodiments, the mixed mode cation exchange chromatography material comprises a sulfonic acid moiety. In some embodiments, the mixed mode cation exchange chromatography material comprises a solid support. In some embodiments, the mixed mode cation exchange chromatography material is contained in a column. In some embodiments, the mixed mode cation exchange chromatography material is a high performance liquid chromatography (HPLC) material. In some embodiments, the mixed mode cation exchange chromatography material is an Oasis® MCX chromatography material. In some embodiments, the non-ionic detergent is quantified by Evaporative Light Scattering (ELSD) or by using a Charged Aerosol Detector (CAD). In some embodiments, the quantification of the non-ionic surfactant comprises less than about 10% (such as less than about any of 9%, 8%, 7%, 6%, 5%, 4%, 3%, 2%, 1%, 0.5%, 0.1%, 0.05%, 0.01%, or less) interference from the polypeptide.

In some embodiments, there is provided a method for quantifying a non-ionic surfactant in a composition comprising the non-ionic surfactant and a polypeptide, wherein the method comprises the steps of a) applying the composition to a mixed mode cation exchange chromatography material, wherein the composition is loaded onto the chromatography material in a solution comprising a first ratio of a mobile phase B to a mobile phase A between about 5:95 and about 15:85, wherein mobile phase A comprises ammonium hydroxide in water and mobile phase B comprises ammonium hydroxide in an organic solvent; b) eluting the polypeptide from the mixed mode cation exchange chromatography material with a solution comprising a second ratio of mobile phase B to mobile phase A between about 40:60 and about 50:50; c) eluting the non-ionic surfactant from the chromatography material with a solution comprising a third ratio of mobile phase B to mobile phase A between about 90:10 and about 100:0; and d) quantifying the non-ionic surfactant in the eluate of step c). In some embodiments, the polypeptide hinds to the chromatography material specifically and non-specifically, and at least about 90% (such as at least about any of 91, 92, 93, 94, 95, 96, 97, 98, or 99%) of the polypeptide elutes in step b). In some embodiments, the eluate from step c) comprises non-specifically bound polypeptide. In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the organic solvent of mobile phase B is methanol. In some embodiments, the organic solvent of mobile phase B is acetonitrile. In some embodiments, the first ratio of mobile phase B to mobile phase A is between about 0:100 and about 20:80 (such as about any of 2:98, 4:96, 6:94, 8:92, 10:90, 12:88, 14:86, 16:84, and 18:82, including any ranges between these ratios). In some embodiments, the second ratio is between about 35:65 and about 55:45 (such as about any of 36:64, 38:62, 40:60, 42:58, 44:56, 46:54, 48:52, 50:50, 52:48, and 54:46, including any ranges between these ratios). In some embodiments, the third ratio is between about 80:20 and about 100:0 (such as about any of 82:18, 84:16, 86:14, 88:12, 90:10, 92:8, 94:6, 96:4, and 98:2, including any ranges between these values). In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in the organic solvent (e.g., methanol or acetonitrile). In some embodiments, the flow rate of the chromatography is between about 0.5 and 2.5 (such as about any of 0.7, 0.9, 1.1, 1.3, 1.4, 1.5, 1.7, 1.9, 2.1, and 2.3, including any ranges between these values) ml/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 2 (such as at least about any of 2.2, 2.4, 2.6, 2.8, 3, 3.2, 3.4, 3.6, 3.8, 4, 4.5, 5, or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 2 (such as at least about any of 2.2, 2.4, 2.6, 2.8, 3, 3.1, 3.2, 3.4, 3.6, 3.8, 4, 4.5, 5, or more) min. In some embodiments, the non-ionic surfactant is a polysorbate. In some embodiments, the polysorbate is polysorbate 20 or polysorbate 80. In some embodiments, the non-ionic surfactant is a poloxamer. In some embodiments, the poloxamer is poloxamer P188. In some embodiments, the concentration of the non-ionic surfactant (e.g., polysorbate or poloxamer) in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the composition further comprises N-acetyl tryptophan and/or methionine. In some embodiments, the concentration of N-acetyl tryptophan in the composition ranges from about 0.1 mM to about 10 mM (such as about any of 0.2, 0.5, 1, 2, 3, 4, 5, 6, 7, 8, or 9 mM, including any ranges between these values). In some embodiments, the concentration of methionine in the composition ranges from about 0.1 mM to about 100 mM (such as about any of 0.2, 0.5, 1, 2, 3, 4, 5, 6, 7, 8, 9, 10, 20, 30, 40, 50, 60, 70, 80, or 90 mM, including any ranges between these values). In some embodiments, the polypeptide concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic protein is a polyclonal antibody, a monoclonal antibody, a humanized antibody, a human antibody, a chimeric antibody, a multispecific antibody, glycoengineered antibody, antibody fragment, an antibody drug conjugate, a THIOMAB™, a THIOMAB™ drug conjugate. In some embodiments, the mixed mode cation exchange chromatography material comprises a reversed phase, strong cation exchange polymer. In some embodiments, the mixed mode cation exchange chromatography material comprises a sulfonic acid moiety. In some embodiments, the mixed mode cation exchange chromatography material comprises a solid support. In some embodiments, the mixed mode cation exchange chromatography material is contained in a column. In some embodiments, the mixed mode cation exchange chromatography material is a high performance liquid chromatography (HPLC) material. In some embodiments, the mixed mode cation exchange chromatography material is an Oasis® MCX chromatography material. In some embodiments, the non-ionic detergent is quantified by Evaporative Light Scattering (ELSD) or by using a Charged Aerosol Detector (CAD). In some embodiments, the quantification of the non-ionic surfactant comprises less than about 10% (such as less than about any of 9%, 8%, 7%, 6%, 5%, 4%, 3%, 2%, 1%, 0.5%, 0.1%, 0.05%, 0.01%, or less) interference from the polypeptide.

When a product containing N-acetyl tryptophan (NAT) in the formulation is tested using HPLC-ELSD conditions there is significant interference observed in the PS20 region. Thus, in some circumstances, alternative conditions are needed to eliminate both NAT and protein related interference.

In some embodiments, there is provided a method for quantifying a non-ionic surfactant in a composition comprising the non-ionic surfactant, a polypeptide, and N-acetyl tryptophan, wherein the method comprises the steps of a) applying the composition to a mixed mode cation exchange chromatography material, wherein the composition is loaded onto the chromatography material in a solution comprising a first ratio of a mobile phase B to a mobile phase A, wherein mobile phase A comprises ammonium hydroxide in water and mobile phase B comprises ammonium hydroxide in an organic solvent; b) eluting the polypeptide from the mixed mode cation exchange chromatography material with a solution comprising a second ratio of mobile phase B to mobile phase A, wherein the second ratio is greater than the first ratio; c) eluting the non-ionic surfactant from the chromatography material with a solution comprising a third ratio of mobile phase B to mobile phase A, wherein the third ratio is greater than the second ratio; and d) quantifying the non-ionic surfactant in the eluate of step c). In some embodiments, the polypeptide binds to the chromatography material specifically and non-specifically, and at least about 90% (such as at least about any of 91, 92, 93, 94, 95, 96, 97, 98, or 99%) of the polypeptide elutes in step b). In some embodiments, the eluate from step c) comprises non-specifically bound polypeptide. In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the eluate from step c) comprises less than about 5% (such as less than about any of 4%, 3%, 2%, 1%, 0.5%, 0.1%, 0.05%, 0.01%, or less) of the total NAT in the composition. In some embodiments, the organic solvent of mobile phase B is methanol. In some embodiments, the organic solvent of mobile phase B is acetonitrile. In some embodiments, the first ratio of mobile phase B to mobile phase A is between about 0:100 and about 20:80 (such as about any of 2:98, 4:96, 6:94, 8:92, 10:90, 12:88, 14:86, 16:84, and 18:82, including any ranges between these ratios). In some embodiments, the second ratio is between about 35:65 and about 55:45 (such as about any of 36:64, 38:62, 40:60, 42:58, 44:56, 46:54, 48:52, 50:50, 52:48, and 54:46, including any ranges between these ratios). In some embodiments, the third ratio is between about 80:20 and about 100:0 (such as about any of 82:18, 84:16, 86:14, 88:12, 90:10, 92:8, 94:6, 96:4, and 98:2, including any ranges between these values). In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in the organic solvent (e.g., methanol or acetonitrile). In some embodiments, the flow rate of the chromatography is between about 0.5 and 2.5 (such as about any of 0.7, 0.9, 1.1, 1.3, 1.4, 1.5, 1.7, 1.9, 2.1, and 2.3, including any ranges between these values) mL/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 2 (such as at least about any of 2.2, 2.4, 2.6, 2.8, 3, 3.2, 3.4, 3.6, 3.8, 4, 4.5, 5, or more) min. In some embodiments, step c) starts at least about 0.05 (such as at least about any of 0.06, 0.07, 0.08, 0.09, 0.1, 0.2, 0.3.0.4, 0.5, 1, 1.5, 2, or more) min after step b) ends and continues for at least about 2 (such as at least about any of 2.2, 2.4, 2.6, 2.8, 3, 3.1, 3.2, 3.4, 3.6, 3.8, 4, 4.5, 5, or more) min. In some embodiments, the non-ionic surfactant is a polysorbate. In some embodiments, the polysorbate is polysorbate 20 or polysorbate 80. In some embodiments, the non-ionic surfactant is a poloxamer. In some embodiments, the poloxamer is poloxamer P188. In some embodiments, the concentration of the non-ionic surfactant (e.g., polysorbate or poloxamer) in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the concentration of N-acetyl tryptophan in the composition ranges from about 0.1 mM to about 10 mM (such as about any of 0.2, 0.5, 1, 2, 3, 4, 5, 6, 7, 8, or 9 mM, including any ranges between these values). In some embodiments, the composition further comprises methionine. In some embodiments, the concentration of methionine in the composition ranges from about 0.1 mM to about 100 mM (such as about any of 0.2, 0.5, 1, 2, 3, 4, 5, 6, 7, 8, 9, 10, 20, 30, 40, 50, 60, 70, 80, or 90 mM, including any ranges between these values). In some embodiments, the polypeptide concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic protein is a polyclonal antibody, a monoclonal antibody, a humanized antibody, a human antibody, a chimeric antibody, a multispecific antibody, glycoengineered antibody, antibody fragment, an antibody drug conjugate, a THIOMAB™, a THIOMAB™ drug conjugate. In some embodiments, the mixed mode cation exchange chromatography material comprises a reversed phase, strong cation exchange polymer. In some embodiments, the mixed mode cation exchange chromatography material comprises a sulfonic acid moiety. In some embodiments, the mixed mode cation exchange chromatography material comprises a solid support. In some embodiments, the mixed mode cation exchange chromatography material is contained in a column. In some embodiments, the mixed mode cation exchange chromatography material is a high performance liquid chromatography (HPLC) material. In some embodiments, the mixed mode cation exchange chromatography material is an Oasis® MCX chromatography material. In some embodiments, the non-ionic detergent is quantified by Evaporative Light Scattering (ELSD) or by using a Charged Aerosol Detector (CAD). In some embodiments, the quantification of the non-ionic detergent comprises less than about 10% (such as less than about any of 9%, 8%, 7%, 6%, 5%, 4%, 3%, 2%, 1%, 0.5%, 0.1%, 0.05%, 0.01%, or less) interference from the polypeptide.

In some embodiments, there is provided a method for quantifying a polysorbate in a composition comprising the polysorbate and a polypeptide, wherein the method comprises the steps of a) applying the composition to a mixed mode cation exchange chromatography material, wherein the composition is loaded onto the chromatography material in a solution comprising a first ratio of a mobile phase B to a mobile phase A, wherein mobile phase A comprises ammonium hydroxide in water and mobile phase B comprises ammonium hydroxide in an organic solvent; b) eluting the polypeptide from the mixed mode cation exchange chromatography material with a solution comprising a second ratio of mobile phase B to mobile phase A, wherein the second ratio is greater than the first ratio; c) eluting the polysorbate from the chromatography material with a solution comprising a third ratio of mobile phase B to mobile phase A, wherein the third ratio is greater than the second ratio; and d) quantifying the polysorbate in the eluate of step c). In some embodiments, the polypeptide binds to the chromatography material specifically and non-specifically, and at least about 90% (such as at least about any of 91, 92, 93, 94, 95, 96, 97, 98, or 99%) of the polypeptide elutes in step b). In some embodiments, the eluate from step c) comprises non-specifically bound polypeptide. In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the organic solvent of mobile phase B is methanol. In some embodiments, the organic solvent of mobile phase B is acetonitrile. In some embodiments, the first ratio of mobile phase B to mobile phase A is between about 0:100 and about 20:80 (such as about any of 2:98, 4:96, 6:94, 8:92, 10:90, 12:88, 14:86, 16:84, and 18:82, including any ranges between these ratios). In some embodiments, the second ratio is between about 35:65 and about 55:45 (such as about any of 36:64, 38:62, 40:60, 42:58, 44:56, 46:54, 48:52, 50:50, 52:48, and 54:46, including any ranges between these ratios). In some embodiments, the third ratio is between about 80:20 and about 100:0 (such as about any of 82:18, 84:16, 86:14, 88:12, 90:10, 92:8, 94:6, 96:4, and 98:2, including any ranges between these values). In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in the organic solvent (e.g., methanol or acetonitrile). In some embodiments, the flow rate of the chromatography is between about 0.5 and 2.5 (such as about any of 0.7, 0.9, 1.1, 1.3, 1.4, 1.5, 1.7, 1.9, 2.1, and 2.3, including any ranges between these values) mL/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 2 (such as at least about any of 2.2, 2.4, 2.6, 2.8, 3, 3.2, 3.4, 3.6, 3.8, 4, 4.5, 5, or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 2 (such as at least about any of 2.2, 2.4, 2.6, 2.8, 3, 3.1, 3.2, 3.4, 3.6, 3.8, 4, 4.5, 5, or more) min. In some embodiments, the polysorbate is polysorbate 20 or polysorbate 80. In some embodiments, the concentration of the polysorbate in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the composition further comprises N-acetyl tryptophan and/or methionine. In some embodiments, the concentration of N-acetyl tryptophan in the composition ranges from about 0.1 mM to about 10 mM (such as about any of 0.2, 0.5, 1, 2, 3, 4, 5, 6, 7, 8, or 9 mM, including any ranges between these values). In some embodiments, the concentration of methionine in the composition ranges from about 0.1 mM to about 100 mM (such as about any of 0.2, 0.5, 1, 2, 3, 4, 5, 6, 7, 8, 9, 10, 20, 30, 40, 50, 60, 70, 80, or 90 mM, including any ranges between these values). In some embodiments, the polypeptide concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic protein is a polyclonal antibody, a monoclonal antibody, a humanized antibody, a human antibody, a chimeric antibody, a multispecific antibody, glycoengineered antibody, antibody fragment, an antibody drug conjugate, a THIOMAB™, a THIOMAB™ drug conjugate. In some embodiments, the mixed mode cation exchange chromatography material comprises a reversed phase, strong cation exchange polymer. In some embodiments, the mixed mode cation exchange chromatography material comprises a sulfonic acid moiety. In some embodiments, the mixed mode cation exchange chromatography material comprises a solid support. In some embodiments, the mixed mode cation exchange chromatography material is contained in a column. In some embodiments, the mixed mode cation exchange chromatography material is a high performance liquid chromatography (HPLC) material. In some embodiments, the mixed mode cation exchange chromatography material is an Oasis® MCX chromatography material. In some embodiments, the non-ionic detergent is quantified by Evaporative Light Scattering (ELSD) or by using a Charged Aerosol Detector (CAD). In some embodiments, the quantification of the polysorbate comprises less than about 10% (such as less than about any of 9%, 8%, 7%, 6%, 5%, 4%, 3%, 2%, 1%, 0.5%, 0.1%, 0.05%, 0.01%, or less) interference from the polypeptide.

In some embodiments, there is provided a method for quantifying a polysorbate in a composition comprising the polysorbate, a polypeptide, and N-acetyl tryptophan, wherein the method comprises the steps of a) applying the composition to a mixed mode cation exchange chromatography material, wherein the composition is loaded onto the chromatography material in a solution comprising a first ratio of a mobile phase B to a mobile phase A, wherein mobile phase A comprises ammonium hydroxide in water and mobile phase B comprises ammonium hydroxide in an organic solvent; b) eluting the polypeptide from the mixed mode cation exchange chromatography material with a solution comprising a second ratio of mobile phase B to mobile phase A, wherein the second ratio is greater than the first ratio; c) eluting the polysorbate from the chromatography material with a solution comprising a third ratio of mobile phase B to mobile phase A, wherein the third ratio is greater than the second ratio; and d) quantifying the polysorbate in the eluate of step c), wherein the quantification of the polysorbate comprises less than about 10% (such as less than about any of 9%, 8%, 7%, 6%, 5%, 4%, 3%, 2%, 1%, 0.5%, 0.1%, 0.05%, 0.01%, or less) interference from the polypeptide and the NAT. In some embodiments, the polypeptide binds to the chromatography material specifically and non-specifically, and at least about 90% (such as at least about any of 91, 92, 93, 94, 95, 96, 97, 98, or 99%) of the polypeptide elutes in step b). In some embodiments, the eluate from step c) comprises non-specifically bound polypeptide. In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the eluate from step c) comprises less than about 5% (such as less than about any of 4%, 3%, 2%, 1%, 0.5%, 0.1%, 0.05%, 0.01%, or less) of the total NAT in the composition. In some embodiments, the organic solvent of mobile phase B is methanol. In some embodiments, the organic solvent of mobile phase B is acetonitrile. In some embodiments, the first ratio of mobile phase B to mobile phase A is between about 0:100 and about 20:80 (such as about any of 2:98, 4:96, 6:94, 8:92, 10:90, 12:88, 14:86, 16:84, and 18:82, including any ranges between these ratios). In some embodiments, the second ratio is between about 35:65 and about 55:45 (such as about any of 36:64, 38:62, 40:60, 42:58, 44:56, 46:54, 48:52, 50:50, 52:48, and 54:46, including any ranges between these ratios). In some embodiments, the third ratio is between about 80:20 and about 100:0 (such as about any of 82:18, 84:16, 86:14, 88:12, 90:10, 92:8, 94:6. 96:4, and 98:2, including any ranges between these values). In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in the organic solvent (e.g., methanol or acetonitrile). In some embodiments, the flow rate of the chromatography is between about 0.5 and 2.5 (such as about any of 0.7, 0.9, 1.1, 1.3, 1.4, 1.5, 1.7, 1.9, 2.1, and 2.3, including any ranges between these values) mL/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) μL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 2 (such as at least about any of 2.2, 2.4, 2.6, 2.8, 3, 3.2, 3.4, 3.6, 3.8, 4, 4.5, 5, or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 2 (such as at least about any of 2.2, 2.4, 2.6, 2.8, 3, 3.1, 3.2, 3.4, 3.6, 3.8, 4, 4.5, 5, or more) min. In some embodiments, the polysorbate is polysorbate 20 or polysorbate 80. In some embodiments, the concentration of the polysorbate in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the concentration of N-acetyl tryptophan in the composition ranges from about 0.1 mM to about 10 mM (such as about any of 0.2, 0.5, 1, 2, 3, 4, 5, 6, 7, 8, or 9 mM, including any ranges between these values). In some embodiments, the composition further comprises methionine. In some embodiments, the concentration of methionine in the composition ranges from about 0.1 mM to about 100 mM (such as about any of 0.2, 0.5, 1, 2, 3, 4, 5, 6, 7, 8, 9, 10, 20, 30, 40, 50, 60, 70, 80, or 90 mM, including any ranges between these values). In some embodiments, the polypeptide concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic protein is a polyclonal antibody, a monoclonal antibody, a humanized antibody, a human antibody, a chimeric antibody, a multispecific antibody, glycoengineered antibody, antibody fragment, an antibody drug conjugate, a THIOMAB™, a THIOMAB™ drug conjugate. In some embodiments, the mixed mode cation exchange chromatography material comprises a reversed phase, strong cation exchange polymer. In some embodiments, the mixed mode cation exchange chromatography material comprises a sulfonic acid moiety. In some embodiments, the mixed mode cation exchange chromatography material comprises a solid support. In some embodiments, the mixed mode cation exchange chromatography material is contained in a column. In some embodiments, the mixed mode cation exchange chromatography material is a high performance liquid chromatography (HPLC) material. In some embodiments, the mixed mode cation exchange chromatography material is an Oasis® MCX chromatography material. In some embodiments, the non-ionic detergent is quantified by Evaporative Light Scattering (ELSD) or by using a Charged Aerosol Detector (CAD).

In some embodiments, there is provided a method for quantifying a polysorbate in a composition comprising the polysorbate, a polypeptide, and N-acetyl tryptophan, wherein the method comprises the steps of a) applying the composition to a mixed mode cation exchange chromatography material wherein the composition is loaded onto the chromatography material in a solution comprising a first ratio of a mobile phase B to a mobile phase A, wherein mobile phase A comprises ammonium hydroxide in water and mobile phase B comprises ammonium hydroxide in an organic solvent; b) eluting the polypeptide from the mixed mode cation exchange chromatography material with a solution comprising a second ratio of mobile phase B to mobile phase A, wherein the second ratio is greater than the first ratio; c) eluting the polysorbate from the chromatography material with a solution comprising a third ratio of mobile phase B to mobile phase A, wherein the third ratio is greater than the second ratio; and d) quantifying the polysorbate in the eluate of step c), wherein the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition and less than about 5% (such as less than about any of 4%, 3%, 2%, 1%, 0.5%, 0.1%, 0.05%, 0.01%, or less) of the total NAT in the composition. In some embodiments, the organic solvent of mobile phase B is methanol. In some embodiments, the organic solvent of mobile phase B is acetonitrile. In some embodiments, the first ratio of mobile phase B to mobile phase A is between about 0:100 and about 20:80 (such as about any of 2:98, 4:96, 6:94, 8:92, 10:90, 12:88, 14:86, 16:84, and 18:82, including any ranges between these ratios). In some embodiments, the second ratio is between about 35:65 and about 55:45 (such as about any of 36:64, 38:62, 40:60, 42:58, 44:56, 46:54, 48:52, 50:50, 52:48, and 54:46, including any ranges between these ratios). In some embodiments, the third ratio is between about 80:20 and about 100:0 (such as about any of 82:18, 84:16, 86:14, 88:12, 90:10, 92:8, 94:6, 96:4, and 98:2, including any ranges between these values). In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in the organic solvent (e.g., methanol or acetonitrile). In some embodiments, the flow rate of the chromatography is between about 0.5 and 2.5 (such as about any of 0.7, 0.9, 1.1, 1.3, 1.4, 1.5, 1.7, 1.9, 2.1, and 2.3, including any ranges between these values) ml/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) μL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 2 (such as at least about any of 2.2, 2.4, 2.6, 2.8, 3, 3.2, 3.4, 3.6, 3.8, 4, 4.5, 5, or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 2 (such as at least about any of 2.2, 2.4, 2.6, 2.8, 3, 3.1, 3.2, 3.4, 3.6, 3.8, 4, 4.5, 5, or more) min. In some embodiments, the polysorbate is polysorbate 20 or polysorbate 80. In some embodiments, the concentration of the polysorbate in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the concentration of N-acetyl tryptophan in the composition ranges from about 0.1 mM to about 10 mM (such as about any of 0.2, 0.5, 1, 2, 3, 4, 5, 6, 7, 8, or 9 mM, including any ranges between these values). In some embodiments, the composition further comprises methionine. In some embodiments, the concentration of methionine in the composition ranges from about 0.1 mM to about 100 mM (such as about any of 0.2, 0.5, 1, 2, 3, 4, 5, 6, 7, 8, 9, 10, 20, 30, 40, 50, 60, 70, 80, or 90 mM, including any ranges between these values). In some embodiments, the polypeptide concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic protein is a polyclonal antibody, a monoclonal antibody, a humanized antibody, a human antibody, a chimeric antibody, a multispecific antibody, glycoengineered antibody, antibody fragment, an antibody drug conjugate, a THIOMAB™, a THIOMAB™ drug conjugate. In some embodiments, the mixed mode cation exchange chromatography material comprises a reversed phase, strong cation exchange polymer. In some embodiments, the mixed mode cation exchange chromatography material comprises a sulfonic acid moiety. In some embodiments, the mixed mode cation exchange chromatography material comprises a solid support. In some embodiments, the mixed mode cation exchange chromatography material is contained in a column. In some embodiments, the mixed mode cation exchange chromatography material is a high performance liquid chromatography (HPLC) material. In some embodiments, the mixed mode cation exchange chromatography material is an Oasis® MCX chromatography material. In some embodiments, the non-ionic detergent is quantified by Evaporative Light Scattering (ELSD) or by using a Charged Aerosol Detector (CAD). In some embodiments, the quantification of the polysorbate comprises less than about 10% (such as less than about any of 9%, 8%, 7%, 6%, 5%, 4%, 3%, 2%, 1%, 0.5%, 0.1%, 0.05%, 0.01%, or less) interference from the polypeptide and the NAT.

In some embodiments, there is provided a method for quantifying a polysorbate in a composition comprising the polysorbate, a polypeptide, and N-acetyl tryptophan, wherein the method comprises the steps of a) applying the composition to a mixed mode cation exchange chromatography material, wherein the composition is loaded onto the chromatography material in a solution comprising a first ratio of a mobile phase B to a mobile phase A, wherein mobile phase A comprises ammonium hydroxide in water and mobile phase B comprises ammonium hydroxide in methanol; b) eluting the polypeptide from the mixed mode cation exchange chromatography material with a solution comprising a second ratio of mobile phase B to mobile phase A, wherein the second ratio is greater than the first ratio; c) eluting the polysorbate from the chromatography material with a solution comprising a third ratio of mobile phase B to mobile phase A, wherein the third ratio is greater than the second ratio; and d) quantifying the polysorbate in the eluate of step c). In some embodiments, the polypeptide binds to the chromatography material specifically and non-specifically, and at least about 90% (such as at least about any of 91, 92, 93, 94, 95, 96, 97, 98, or 99%) of the polypeptide elutes in step b). In some embodiments, the eluate from step c) comprises non-specifically bound polypeptide. In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the eluate from step c) comprises less than about 5% (such as less than about any of 4%, 3%, 2%, 1%, 0.5%, 0.1%, 0.05%, 0.01%, or less) of the total NAT in the composition. In some embodiments, the first ratio of mobile phase B to mobile phase A is between about 0:100 and about 20:80 (such as about any of 2:98, 4:96, 6:94, 8:92, 10:90, 12:88, 14:86, 16:84, and 18:82, including any ranges between these ratios). In some embodiments, the second ratio is between about 35:65 and about 55:45 (such as about any of 36:64, 38:62, 40:60, 42:58, 44:56, 46:54, 48:52, 50:50, 52:48, and 54:46, including any ranges between these ratios). In some embodiments, the third ratio is between about 80:20 and about 100:0 (such as about any of 82:18, 84:16, 86:14, 88:12, 90:10, 92:8, 94:6, 96:4, and 98:2, including any ranges between these values). In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in methanol. In some embodiments, the flow rate of the chromatography is between about 0.5 and 2.5 (such as about any of 0.7, 0.9, 1.1, 1.3, 1.4, 1.5, 1.7, 1.9, 2.1, and 2.3, including any ranges between these values) mL/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 2 (such as at least about any of 2.2, 2.4, 2.6, 2.8, 3, 3.2, 3.4, 3.6, 3.8, 4, 4.5, 5, or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 2 (such as at least about any of 2.2, 2.4, 2.6, 2.8, 3, 3.1, 3.2, 3.4, 3.6, 3.8, 4, 4.5, 5, or more) min. In some embodiments, the polysorbate is polysorbate 20 or polysorbate 80. In some embodiments, the concentration of the polysorbate in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the concentration of N-acetyl tryptophan in the composition ranges from about 0.1 mM to about 10 mM (such as about any of 0.2, 0.5, 1, 2, 3, 4, 5, 6, 7, 8, or 9 mM, including any ranges between these values). In some embodiments, the composition further comprises methionine. In some embodiments, the concentration of methionine in the composition ranges from about 0.1 mM to about 100 mM (such as about any of 0.2, 0.5, 1, 2, 3, 4, 5, 6, 7, 8, 9, 10, 20, 30, 40, 50, 60, 70, 80, or 90 mM, including any ranges between these values). In some embodiments, the polypeptide concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic protein is a polyclonal antibody, a monoclonal antibody, a humanized antibody, a human antibody, a chimeric antibody, a multispecific antibody, glycoengineered antibody, antibody fragment, an antibody drug conjugate, a THIOMAB™, a THIOMAB™ drug conjugate. In some embodiments, the mixed mode cation exchange chromatography material comprises a reversed phase, strong cation exchange polymer. In some embodiments, the mixed mode cation exchange chromatography material comprises a sulfonic acid moiety. In some embodiments, the mixed mode cation exchange chromatography material comprises a solid support. In some embodiments, the mixed mode cation exchange chromatography material is contained in a column. In some embodiments, the mixed mode cation exchange chromatography material is a high performance liquid chromatography (HPLC) material. In some embodiments, the mixed mode cation exchange chromatography material is an Oasis® MCX chromatography material. In some embodiments, the non-ionic detergent is quantified by Evaporative Light Scattering (ELSD) or by using a Charged Aerosol Detector (CAD). In some embodiments, the quantification of the polysorbate comprises less than about 10% (such as less than about any of 9%, 8%, 7%, 6%, 5%, 4%, 3%, 2%, 1%, 0.5%, 0.1%, 0.05%, 0.01%, or less) interference from the polypeptide and the NAT.

In some embodiments, there is provided a method for quantifying a polysorbate in a composition comprising the polysorbate, a polypeptide, and N-acetyl tryptophan, wherein the method comprises the steps of a) applying the composition to a mixed mode cation exchange chromatography material, wherein the composition is loaded onto the chromatography material in a solution comprising a first ratio of a mobile phase B to a mobile phase A, wherein mobile phase A comprises ammonium hydroxide in water and mobile phase B comprises ammonium hydroxide in acetonitrile; b) eluting the polypeptide from the mixed mode cation exchange chromatography material with a solution comprising a second ratio of mobile phase B to mobile phase A, wherein the second ratio is greater than the first ratio; c) eluting the polysorbate from the chromatography material with a solution comprising a third ratio of mobile phase B to mobile phase A, wherein the third ratio is greater than the second ratio; and d) quantifying the polysorbate in the eluate of step c). In some embodiments, the polypeptide binds to the chromatography material specifically and non-specifically, and at least about 90% (such as at least about any of 91, 92, 93, 94, 95, 96, 97, 98, or 99%) of the polypeptide elutes in step b). In some embodiments, the eluate from step c) comprises non-specifically bound polypeptide. In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the eluate from step c) comprises less than about 5% (such as less than about any of 4%, 3%, 2%, 1%, 0.5%, 0.1%, 0.05%, 0.01%, or less) of the total NAT in the composition. In some embodiments, the first ratio of mobile phase B to mobile phase A is between about 0:100 and about 20:80 (such as about any of 2:98, 4:96, 6:94, 8:92, 10:90, 12:88, 14:86, 16:84, and 18:82, including any ranges between these ratios). In some embodiments, the second ratio is between about 35:65 and about 55:45 (such as about any of 36:64, 38:62, 40:60, 42:58, 44:56, 46:54, 48:52, 50:50, 52:48, and 54:46, including any ranges between these ratios). In some embodiments, the third ratio is between about 80:20 and about 100:0 (such as about any of 82:18, 84:16, 86:14, 88:12, 90:10, 92:8, 94:6, 96:4, and 98:2, including any ranges between these values). In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in acetonitrile. In some embodiments, the flow rate of the chromatography is between about 0.5 and 2.5 (such as about any of 0.7, 0.9, 1.1, 1.3, 1.4, 1.5, 1.7, 1.9, 2.1, and 2.3, including any ranges between these values) mL/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 2 (such as at least about any of 2.2, 2.4, 2.6, 2.8, 3, 3.2, 3.4, 3.6, 3.8, 4, 4.5, 5, or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 2 (such as at least about any of 2.2, 2.4, 2.6, 2.8, 3, 3.1, 3.2, 3.4, 3.6, 3.8, 4, 4.5, 5, or more) min. In some embodiments, the polysorbate is polysorbate 20 or polysorbate 80. In some embodiments, the concentration of the polysorbate in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the concentration of N-acetyl tryptophan in the composition ranges from about 0.1 mM to about 10 mM (such as about any of 0.2, 0.5, 1, 2, 3, 4, 5, 6, 7, 8, or 9 mM, including any ranges between these values). In some embodiments, the composition further comprises methionine. In some embodiments, the concentration of methionine in the composition ranges from about 0.1 mM to about 100 mM (such as about any of 0.2, 0.5, 1, 2, 3, 4, 5, 6, 7, 8, 9, 10, 20, 30, 40, 50, 60, 70, 80, or 90 mM, including any ranges between these values). In some embodiments, the polypeptide concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic protein is a polyclonal antibody, a monoclonal antibody, a humanized antibody, a human antibody, a chimeric antibody, a multispecific antibody, glycoengineered antibody, antibody fragment, an antibody drug conjugate, a THIOMAB™, a THIOMAB™ drug conjugate. In some embodiments, the mixed mode cation exchange chromatography material comprises a reversed phase, strong cation exchange polymer. In some embodiments, the mixed mode cation exchange chromatography material comprises a sulfonic acid moiety. In some embodiments, the mixed mode cation exchange chromatography material comprises a solid support. In some embodiments, the mixed mode cation exchange chromatography material is contained in a column. In some embodiments, the mixed mode cation exchange chromatography material is a high performance liquid chromatography (HPLC) material. In some embodiments, the mixed mode cation exchange chromatography material is an Oasis® MCX chromatography material. In some embodiments, the non-ionic detergent is quantified by Evaporative Light Scattering (ELSD) or by using a Charged Aerosol Detector (CAD). In some embodiments, the quantification of the polysorbate comprises less than about 10% (such as less than about any of 9%, 8%, 7%, 6%, 5%, 4%, 3%, 2%, 1%, 0.5%, 0.1%, 0.05%, 0.01%, or less) interference from the polypeptide and the NAT.

In some embodiments, there is provided a method for quantifying a polysorbate in a composition comprising the polysorbate, a polypeptide, and N-acetyl tryptophan, wherein the method comprises the steps of a) applying the composition to a mixed mode cation exchange chromatography material wherein the composition is loaded onto the chromatography material in a solution comprising a first ratio of a mobile phase B to a mobile phase A between about 5:95 and about 15:85, wherein mobile phase A comprises ammonium hydroxide in water and mobile phase B comprises ammonium hydroxide in an organic solvent; b) eluting the polypeptide from the mixed mode cation exchange chromatography material with a solution comprising a second ratio of mobile phase B to mobile phase A between about 40:60 and about 50:50; c) eluting the polysorbate from the chromatography material with a solution comprising a third ratio of mobile phase B to mobile phase A between about 90:10 and about 100:0; and d) quantifying the polysorbate in the eluate of step c). In some embodiments, the polypeptide binds to the chromatography material specifically and non-specifically, and at least about 90% (such as at least about any of 91, 92, 93, 94, 95, 96, 97, 98, or 99%) of the polypeptide elutes in step b). In some embodiments, the eluate from step c) comprises non-specifically bound polypeptide. In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the eluate from step c) comprises less than about 5% (such as less than about any of 4%, 3%, 2%, 1%, 0.5%, 0.1%, 0.05%, 0.01%, or less) of the total NAT in the composition. In some embodiments, the organic solvent of mobile phase B is methanol. In some embodiments, the organic solvent of mobile phase B is acetonitrile. In some embodiments, the first ratio of mobile phase B to mobile phase A is about 10:90. In some embodiments, the second ratio is about 45:55. In some embodiments, the third ratio is about 100:0. In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in the organic solvent (e.g., methanol or acetonitrile). In some embodiments, the flow rate of the chromatography is between about 0.5 and 2.5 (such as about any of 0.7, 0.9, 1.1, 1.3, 1.4, 1.5, 1.7, 1.9, 2.1, and 2.3, including any ranges between these values) mL/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 2 (such as at least about any of 2.2, 2.4, 2.6, 2.8, 3, 3.2, 3.4, 3.6, 3.8, 4, 4.5, 5, or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 2 (such as at least about any of 2.2, 2.4, 2.6, 2.8, 3, 3.1, 3.2, 3.4, 3.6, 3.8, 4, 4.5, 5, or more) min. In some embodiments, the polysorbate is polysorbate 20 or polysorbate 80. In some embodiments, the concentration of the polysorbate in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the concentration of N-acetyl tryptophan in the composition ranges from about 0.1 mM to about 10 mM (such as about any of 0.2, 0.5, 1, 2, 3, 4, 5, 6, 7, 8, or 9 mM, including any ranges between these values). In some embodiments, the composition further comprises methionine. In some embodiments, the concentration of methionine in the composition ranges from about 0.1 mM to about 100 mM (such as about any of 0.2, 0.5, 1, 2, 3, 4, 5, 6, 7, 8, 9, 10, 20, 30, 40, 50, 60, 70, 80, or 90 mM, including any ranges between these values). In some embodiments, the polypeptide concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic protein is a polyclonal antibody, a monoclonal antibody, a humanized antibody, a human antibody, a chimeric antibody, a multispecific antibody, glycoengineered antibody, antibody fragment, an antibody drug conjugate, a THIOMAB™, a THIOMAB™ drug conjugate. In some embodiments, the mixed mode cation exchange chromatography material comprises a reversed phase, strong cation exchange polymer. In some embodiments, the mixed mode cation exchange chromatography material comprises a sulfonic acid moiety. In some embodiments, the mixed mode cation exchange chromatography material comprises a solid support. In some embodiments, the mixed mode cation exchange chromatography material is contained in a column. In some embodiments, the mixed mode cation exchange chromatography material is a high performance liquid chromatography (HPLC) material. In some embodiments, the mixed mode cation exchange chromatography material is an Oasis® MCX chromatography material. In some embodiments, the non-ionic detergent is quantified by Evaporative Light Scattering (ELSD) or by using a Charged Aerosol Detector (CAD). In some embodiments, the quantification of the polysorbate comprises less than about 10% (such as less than about any of 9%, 8%, 7%, 6%, 5%, 4%, 3%, 2%, 1%, 0.5%, 0.1%, 0.05%, 0.01%, or less) interference from the polypeptide and the NAT.

In some embodiments, there is provided a method for quantifying a polysorbate in a composition comprising the polysorbate, a polypeptide, and N-acetyl tryptophan, wherein the method comprises the steps of a) applying the composition to a mixed mode cation exchange chromatography material, wherein the composition is loaded onto the chromatography material in a solution comprising a first ratio of a mobile phase B to a mobile phase A between about 5:95 and about 15:85, wherein mobile phase A comprises ammonium hydroxide in water and mobile phase B comprises ammonium hydroxide in methanol; b) eluting the polypeptide from the mixed mode cation exchange chromatography material with a solution comprising a second ratio of mobile phase B to mobile phase A between about 40:60 and about 50:50; c) eluting the polysorbate from the chromatography material with a solution comprising a third ratio of mobile phase B to mobile phase A between about 90:10 and about 100:0; and d) quantifying the polysorbate in the eluate of step c), wherein the quantification of the polysorbate comprises less than about 10% (such as less than about any of 9%, 8%, 7%, 6%, 5%, 4%, 3%, 2%, 1%, 0.5%, 0.1%, 0.05%, 0.01%, or less) interference from the polypeptide and the NAT. In some embodiments, the polypeptide binds to the chromatography material specifically and non-specifically, and at least about 90% (such as at least about any of 91, 92, 93, 94, 95, 96, 97, 98, or 99%) of the polypeptide elutes in step b). In some embodiments, the eluate from step c) comprises non-specifically bound polypeptide. In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the eluate from step c) comprises less than about 5% (such as less than about any of 4%, 3%, 2%, 1%, 0.5%, 0.1%, 0.05%, 0.01%, or less) of the total NAT in the composition. In some embodiments, the first ratio of mobile phase B to mobile phase A is about 10:90. In some embodiments, the second ratio is about 45:55. In some embodiments, the third ratio is about 100:0. In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in methanol. In some embodiments, the flow rate of the chromatography is between about 0.5 and 2.5 (such as about any of 0.7, 0.9, 1.1, 1.3, 1.4, 1.5, 1.7, 1.9, 2.1, and 2.3, including any ranges between these values) mL/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 2 (such as at least about any of 2.2, 2.4, 2.6, 2.8, 3, 3.2, 3.4, 3.6, 3.8, 4, 4.5, 5, or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 2 (such as at least about any of 2.2, 2.4, 2.6, 2.8, 3, 3.1, 3.2, 3.4, 3.6, 3.8, 4, 4.5, 5, or more) min. In some embodiments, the polysorbate is polysorbate 20 or polysorbate 80. In some embodiments, the concentration of the polysorbate in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the concentration of N-acetyl tryptophan in the composition ranges from about 0.1 mM to about 10 mM (such as about any of 0.2, 0.5, 1, 2, 3, 4, 5, 6, 7, 8, or 9 mM, including any ranges between these values). In some embodiments, the composition further comprises methionine. In some embodiments, the concentration of methionine in the composition ranges from about 0.1 mM to about 100 mM (such as about any of 0.2, 0.5, 1, 2, 3, 4, 5, 6, 7, 8, 9, 10, 20, 30, 40, 50, 60, 70, 80, or 90 mM, including any ranges between these values). In some embodiments, the polypeptide concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic protein is a polyclonal antibody, a monoclonal antibody, a humanized antibody, a human antibody, a chimeric antibody, a multispecific antibody, glycoengineered antibody, antibody fragment, an antibody drug conjugate, a THIOMAB™, a THIOMAB™ drug conjugate. In some embodiments, the mixed mode cation exchange chromatography material comprises a reversed phase, strong cation exchange polymer. In some embodiments, the mixed mode cation exchange chromatography material comprises a sulfonic acid moiety. In some embodiments, the mixed mode cation exchange chromatography material comprises a solid support. In some embodiments, the mixed mode cation exchange chromatography material is contained in a column. In some embodiments, the mixed mode cation exchange chromatography material is a high performance liquid chromatography (HPLC) material. In some embodiments, the mixed mode cation exchange chromatography material is an Oasis® MCX chromatography material. In some embodiments, the non-ionic detergent is quantified by Evaporative Light Scattering (ELSD) or by using a Charged Aerosol Detector (CAD).

In some embodiments, there is provided a method for quantifying a polysorbate in a composition comprising the polysorbate, a polypeptide, and N-acetyl tryptophan, wherein the method comprises the steps of a) applying the composition to a mixed mode cation exchange chromatography material, wherein the composition is loaded onto the chromatography material in a solution comprising a first ratio of a mobile phase B to a mobile phase A between about 5:95 and about 15:85, wherein mobile phase A comprises ammonium hydroxide in water and mobile phase B comprises ammonium hydroxide in methanol; b) eluting the polypeptide from the mixed mode cation exchange chromatography material with a solution comprising a second ratio of mobile phase B to mobile phase A between about 40:60 and about 50:50; c) eluting the polysorbate from the chromatography material with a solution comprising a third ratio of mobile phase B to mobile phase A between about 90:10 and about 100:0; and d) quantifying the polysorbate in the eluate of step c), wherein the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition and less than about 5% (such as less than about any of 4%, 3%, 2%, 1%, 0.5%, 0.1%, 0.05%, 0.01%, or less) of the total NAT in the composition. In some embodiments, the first ratio of mobile phase B to mobile phase A is about 10:90. In some embodiments, the second ratio is about 45:55. In some embodiments, the third ratio is about 100:0. In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in methanol. In some embodiments, the flow rate of the chromatography is between about 0.5 and 2.5 (such as about any of 0.7, 0.9, 1.1, 1.3, 1.4, 1.5, 1.7, 1.9, 2.1, and 2.3, including any ranges between these values) mL/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) μL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 2 (such as at least about any of 2.2, 2.4, 2.6, 2.8, 3, 3.2, 3.4, 3.6, 3.8, 4, 4.5, 5, or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 2 (such as at least about any of 2.2, 2.4, 2.6, 2.8, 3, 3.1, 3.2, 3.4, 3.6, 3.8, 4, 4.5, 5, or more) min. In some embodiments, the polysorbate is polysorbate 20 or polysorbate 80. In some embodiments, the concentration of the polysorbate in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the concentration of N-acetyl tryptophan in the composition ranges from about 0.1 mM to about 10 mM (such as about any of 0.2, 0.5, 1, 2, 3, 4, 5, 6, 7, 8, or 9 mM, including any ranges between these values). In some embodiments, the composition further comprises methionine. In some embodiments, the concentration of methionine in the composition ranges from about 0.1 mM to about 100 mM (such as about any of 0.2, 0.5, 1, 2, 3, 4, 5, 6, 7, 8, 9, 10, 20, 30, 40, 50, 60, 70, 80, or 90 mM, including any ranges between these values). In some embodiments, the polypeptide concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic protein is a polyclonal antibody, a monoclonal antibody, a humanized antibody, a human antibody, a chimeric antibody, a multispecific antibody, glycoengineered antibody, antibody fragment, an antibody drug conjugate, a THIOMAB™, a THIOMAB™ drug conjugate. In some embodiments, the mixed mode cation exchange chromatography material comprises a reversed phase, strong cation exchange polymer. In some embodiments, the mixed mode cation exchange chromatography material comprises a sulfonic acid moiety. In some embodiments, the mixed mode cation exchange chromatography material comprises a solid support. In some embodiments, the mixed mode cation exchange chromatography material is contained in a column. In some embodiments, the mixed mode cation exchange chromatography material is a high performance liquid chromatography (HPLC) material. In some embodiments, the mixed mode cation exchange chromatography material is an Oasis® MCX chromatography material. In some embodiments, the non-ionic detergent is quantified by Evaporative Light Scattering (ELSD) or by using a Charged Aerosol Detector (CAD). In some embodiments, the quantification of the polysorbate comprises less than about 10% (such as less than about any of 9%, 8%, 7%, 6%, 5%, 4%, 3%, 2%, 1%, 0.5%, 0.1%, 0.05%, 0.01%, or less) interference from the polypeptide.

In some embodiments, there is provided a method for quantifying a polysorbate in a composition comprising the polysorbate, a polypeptide, and N-acetyl tryptophan, wherein the method comprises the steps of a) applying the composition to a mixed mode cation exchange chromatography material, wherein the composition is loaded onto the chromatography material in a solution comprising a first ratio of a mobile phase B to a mobile phase A between about 5:95 and about 15:85, wherein mobile phase A comprises ammonium hydroxide in water and mobile phase B comprises ammonium hydroxide in acetonitrile; b) eluting the polypeptide from the mixed mode cation exchange chromatography material with a solution comprising a second ratio of mobile phase B to mobile phase A between about 40:60 and about 50:50; c) eluting the polysorbate from the chromatography material with a solution comprising a third ratio of mobile phase B to mobile phase A between about 90:10 and about 100:0; and d) quantifying the polysorbate in the eluate of step c), wherein the quantification of the polysorbate comprises less than about 10% (such as less than about any of 9%, 8%, 7%, 6%, 5%, 4%, 3%, 2%, 1%, 0.5%, 0.1%, 0.05%, 0.01%, or less) interference from the polypeptide and the NAT. In some embodiments, the polypeptide binds to the chromatography material specifically and non-specifically, and at least about 90% (such as at least about any of 91, 92, 93, 94, 95, 96, 97, 98, or 99%) of the polypeptide elutes in step b). In some embodiments, the eluate from step c) comprises non-specifically bound polypeptide. In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the eluate from step c) comprises less than about 5% (such as less than about any of 4%, 3%, 2%, 1%, 0.5%, 0.1%, 0.05%, 0.01%, or less) of the total NAT in the composition. In some embodiments, the first ratio of mobile phase B to mobile phase A is about 10:90. In some embodiments, the second ratio is about 45:55. In some embodiments, the third ratio is about 100:0. In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in acetonitrile. In some embodiments, the flow rate of the chromatography is between about 0.5 and 2.5 (such as about any of 0.7, 0.9, 1.1, 1.3, 1.4, 1.5, 1.7, 1.9, 2.1, and 2.3, including any ranges between these values) mL/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 2 (such as at least about any of 2.2, 2.4, 2.6, 2.8, 3, 3.2, 3.4, 3.6, 3.8, 4, 4.5, 5, or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 2 (such as at least about any of 2.2, 2.4, 2.6, 2.8, 3, 3.1, 3.2, 3.4, 3.6, 3.8, 4, 4.5, 5, or more) min. In some embodiments, the polysorbate is polysorbate 20 or polysorbate 80. In some embodiments, the concentration of the polysorbate in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the concentration of N-acetyl tryptophan in the composition ranges from about 0.1 mM to about 10 mM (such as about any of 0.2, 0.5, 1, 2, 3, 4, 5, 6, 7, 8, or 9 mM, including any ranges between these values). In some embodiments, the composition further comprises methionine. In some embodiments, the concentration of methionine in the composition ranges from about 0.1 mM to about 100 mM (such as about any of 0.2, 0.5, 1, 2, 3, 4, 5, 6, 7, 8, 9, 10, 20, 30, 40, 50, 60, 70, 80, or 90 mM, including any ranges between these values). In some embodiments, the polypeptide concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic protein is a polyclonal antibody, a monoclonal antibody, a humanized antibody, a human antibody, a chimeric antibody, a multispecific antibody, glycoengineered antibody, antibody fragment, an antibody drug conjugate, a THIOMAB™, a THIOMAB™ drug conjugate. In some embodiments, the mixed mode cation exchange chromatography material comprises a reversed phase, strong cation exchange polymer. In some embodiments, the mixed mode cation exchange chromatography material comprises a sulfonic acid moiety. In some embodiments, the mixed mode cation exchange chromatography material comprises a solid support. In some embodiments, the mixed mode cation exchange chromatography material is contained in a column. In some embodiments, the mixed mode cation exchange chromatography material is a high performance liquid chromatography (HPLC) material. In some embodiments, the mixed mode cation exchange chromatography material is an Oasis® MCX chromatography material. In some embodiments, the non-ionic detergent is quantified by Evaporative Light Scattering (ELSD) or by using a Charged Aerosol Detector (CAD).

In some embodiments, there is provided a method for quantifying a polysorbate in a composition comprising the polysorbate, a polypeptide, and N-acetyl tryptophan, wherein the method comprises the steps of a) applying the composition to a mixed mode cation exchange chromatography material, wherein the composition is loaded onto the chromatography material in a solution comprising a first ratio of a mobile phase B to a mobile phase A between about 5:95 and about 15:85, wherein mobile phase A comprises ammonium hydroxide in water and mobile phase B comprises ammonium hydroxide in acetonitrile; b) eluting the polypeptide from the mixed mode cation exchange chromatography material with a solution comprising a second ratio of mobile phase B to mobile phase A between about 40:60 and about 50:50; c) eluting the polysorbate from the chromatography material with a solution comprising a third ratio of mobile phase B to mobile phase A between about 90:10 and about 100:0; and d) quantifying the polysorbate in the eluate of step c), wherein the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition and less than about 5% (such as less than about any of 4%, 3%, 2%, 1%, 0.5%, 0.1%, 0.05%, 0.01%, or less) of the total NAT in the composition. In some embodiments, the first ratio of mobile phase B to mobile phase A is about 10:90. In some embodiments, the second ratio is about 45:55. In some embodiments, the third ratio is about 100:0. In some embodiments, mobile phase A comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in water. In some embodiments, mobile phase B comprises between about 0.5% and about 5% (v/v) (such as about any of 0.75%, 1%, 1.5%, 2%, 2.5%, 3%, 3.5%, 4%, and 4.5%, including any ranges between these values) ammonium hydroxide in acetonitrile. In some embodiments, the flow rate of the chromatography is between about 0.5 and 2.5 (such as about any of 0.7, 0.9, 1.1, 1.3, 1.4, 1.5, 1.7, 1.9, 2.1, and 2.3, including any ranges between these values) ml/minute. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) μL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 2 (such as at least about any of 2.2, 2.4, 2.6, 2.8, 3, 3.2, 3.4, 3.6, 3.8, 4, 4.5, 5, or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 2 (such as at least about any of 2.2, 2.4, 2.6, 2.8, 3, 3.1, 3.2, 3.4, 3.6, 3.8, 4, 4.5, 5, or more) min. In some embodiments, the polysorbate is polysorbate 20 or polysorbate 80. In some embodiments, the concentration of the polysorbate in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the concentration of N-acetyl tryptophan in the composition ranges from about 0.1 mM to about 10 mM (such as about any of 0.2, 0.5, 1, 2, 3, 4, 5, 6, 7, 8, or 9 mM, including any ranges between these values). In some embodiments, the composition further comprises methionine. In some embodiments, the concentration of methionine in the composition ranges from about 0.1 mM to about 100 mM (such as about any of 0.2, 0.5, 1, 2, 3, 4, 5, 6, 7, 8, 9, 10, 20, 30, 40, 50, 60, 70, 80, or 90 mM, including any ranges between these values). In some embodiments, the polypeptide concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic protein is a polyclonal antibody, a monoclonal antibody, a humanized antibody, a human antibody, a chimeric antibody, a multispecific antibody, glycoengineered antibody, antibody fragment, an antibody drug conjugate, a THIOMAB™, a THIOMAB™ drug conjugate. In some embodiments, the mixed mode cation exchange chromatography material comprises a reversed phase, strong cation exchange polymer. In some embodiments, the mixed mode cation exchange chromatography material comprises a sulfonic acid moiety. In some embodiments, the mixed mode cation exchange chromatography material comprises a solid support. In some embodiments, the mixed mode cation exchange chromatography material is contained in a column. In some embodiments, the mixed mode cation exchange chromatography material is a high performance liquid chromatography (HPLC) material. In some embodiments, the mixed mode cation exchange chromatography material is an Oasis® MCX chromatography material. In some embodiments, the non-ionic detergent is quantified by Evaporative Light Scattering (ELSD) or by using a Charged Aerosol Detector (CAD). In some embodiments, the quantification of the polysorbate comprises less than about 10% (such as less than about any of 9%, 8%, 7%, 6%, 5%, 4%, 3%, 2%, 1%, 0.5%, 0.1%, 0.05%, 0.01%, or less) interference from the polypeptide.

In some embodiments, there is provided a method for quantifying polysorbate 20 in a composition comprising polysorbate 20, a polypeptide, and N-acetyl tryptophan, wherein the method comprises the steps of a) applying the composition to a mixed mode cation exchange chromatography material, wherein the composition is loaded onto the chromatography material in a solution comprising a ratio of about 10:90 of a mobile phase B to a mobile phase A, wherein mobile phase A comprises about 1.5% ammonium hydroxide in water and mobile phase B comprises about 1.5% ammonium hydroxide in methanol; b) eluting the polypeptide from the mixed mode cation exchange chromatography material with a solution comprising a ratio of about 45:55 of mobile phase B to mobile phase A; c) eluting the polysorbate 20 from the chromatography material with a solution comprising a ratio of about 100:0 of mobile phase B to mobile phase A; and d) quantifying the polysorbate 20 in the eluate of step c). In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the eluate from step c) comprises less than about 5% (such as less than about any of 4%, 3%, 2%, 1%, 0.5%, 0.1%, 0.05%, 0.01%, or less) of the total NAT in the composition. In some embodiments, the flow rate of the chromatography is between about 0.5 and 2.5 (such as about any of 0.7, 0.9, 1.1, 1.3, 1.4, 1.5, 1.7, 1.9, 2.1, and 2.3, including any ranges between these values) mL/minute. In some embodiments, the flow rate of the chromatography is about 1.40 mL/min. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) IL. In some embodiments, the volume of the composition applied to the chromatography material is about 25 μL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 2 (such as at least about any of 2.2, 2.4, 2.6, 2.8, 3, 3.2, 3.4, 3.6, 3.8, 4, 4.5, 5, or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 2 (such as at least about any of 2.2, 2.4, 2.6, 2.8, 3, 3.1, 3.2, 3.4, 3.6, 3.8, 4, 4.5, 5, or more) min. In some embodiments, the concentration of polysorbate 20 in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the concentration of N-acetyl tryptophan in the composition ranges from about 0.1 mM to about 10 mM (such as about any of 0.2, 0.5, 1, 2, 3, 4, 5, 6, 7, 8, or 9 mM, including any ranges between these values). In some embodiments, the composition further comprises methionine. In some embodiments, the concentration of methionine in the composition ranges from about 0.1 mM to about 100 mM (such as about any of 0.2, 0.5, 1, 2, 3, 4, 5, 6, 7, 8, 9, 10, 20, 30, 40, 50, 60, 70, 80, or 90 mM, including any ranges between these values). In some embodiments, the polypeptide concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic protein is a polyclonal antibody, a monoclonal antibody, a humanized antibody, a human antibody, a chimeric antibody, a multispecific antibody, glycoengineered antibody, antibody fragment, an antibody drug conjugate, a THIOMAB™, a THIOMAB™ drug conjugate. In some embodiments, the mixed mode cation exchange chromatography material comprises a reversed phase, strong cation exchange polymer. In some embodiments, the mixed mode cation exchange chromatography material comprises a sulfonic acid moiety. In some embodiments, the mixed mode cation exchange chromatography material comprises a solid support. In some embodiments, the mixed mode cation exchange chromatography material is contained in a column. In some embodiments, the mixed mode cation exchange chromatography material is a high performance liquid chromatography (HPLC) material. In some embodiments, the mixed mode cation exchange chromatography material is an Oasis® MCX chromatography material. In some embodiments, the non-ionic detergent is quantified by Evaporative Light Scattering (ELSD) or by using a Charged Aerosol Detector (CAD). In some embodiments, the quantification of the polysorbate comprises less than about 10% (such as less than about any of 9%, 8%, 7%, 6%, 5%, 4%, 3%, 2%, 1%, 0.5%, 0.1%, 0.05%, 0.01%, or less) interference from the polypeptide and the NAT.

In some embodiments, there is provided a method for quantifying polysorbate 20 in a composition comprising polysorbate 20, a polypeptide, and N-acetyl tryptophan, wherein the method comprises the steps of a) applying the composition to a mixed mode cation exchange chromatography material, wherein the composition is loaded onto the chromatography material in a solution comprising a ratio of about 10:90 of a mobile phase B to a mobile phase A, wherein mobile phase A comprises about 1.5% ammonium hydroxide in water and mobile phase B comprises about 1.5% ammonium hydroxide in acetonitrile; b) eluting the polypeptide from the mixed mode cation exchange chromatography material with a solution comprising a ratio of about 45:55 of mobile phase B to mobile phase A; c) eluting the polysorbate 20 from the chromatography material with a solution comprising a ratio of about 100:0 of mobile phase B to mobile phase A; and d) quantifying the polysorbate 20 in the eluate of step c). In some embodiments, the eluate from step c) comprises less than about 10% (such as less than about any of 9%, 8%, 7%, 6%, 5%, 4%, 3%, 2%, 1%, 0.5%, 0.1%, 0.05%, 0.01%, or less) of the total polypeptide in the composition. In some embodiments, the eluate from step c) comprises less than about 5% (such as less than about any of 4%, 3%, 2%, 1%, 0.5%, 0.1%, 0.05%, 0.01%, or less) of the total NAT in the composition. In some embodiments, the flow rate of the chromatography is between about 0.5 and 2.5 (such as about any of 0.7, 0.9, 1.1, 1.3, 1.4, 1.5, 1.7, 1.9, 2.1, and 2.3, including any ranges between these values) mL/minute. In some embodiments, the flow rate of the chromatography is about 1.40 mL/min. In some embodiments, the volume of the composition applied to the chromatography material is between about 1 and about 50 (such as about any of 1, 2, 3, 4, 5, 6, 7, 8, 9, 10, 15, 20, 25, 30, 35, 40, and 45, including any ranges between these values) µL. In some embodiments, the volume of the composition applied to the chromatography material is about 25 µL. In some embodiments, step b) starts at least about 0.5 (such as at least about any of 0.6, 0.7, 0.8, 0.9, 1, 1.1, 1.2, 1.3, 1.4, 1.5, 1.6, 1.7, 1.8, 1.9, 2, or more) min after step a) is initiated and continues for at least about 2 (such as at least about any of 2.2, 2.4, 2.6, 2.8, 3, 3.2, 3.4, 3.6, 3.8, 4, 4.5, 5, or more) min. In some embodiments, step c) starts at least about 0.05 (such as at least about any of 0.06, 0.07, 0.08, 0.09, 0.1, 0.2, 0.3, 0.4, 0.5, 1, 1.5, 2, or more) min after step b) ends and continues for at least about 2 (such as at least about any of 2.2, 2.4, 2.6, 2.8, 3, 3.1, 3.2, 3.4, 3.6, 3.8, 4, 4.5, 5, or more) min. In some embodiments, the concentration of polysorbate 20 in the composition is in the range of about 0.001% to 1.0% (w/v) (such as about any of 0.005, 0.01, 0.05, 0.1, 0.2, 0.3, 0.4, 0.5, 0.6, 0.7, 0.8, and 0.9%, including any ranges between these values). In some embodiments, the concentration of N-acetyl tryptophan in the composition ranges from about 0.1 mM to about 10 mM (such as about any of 0.2, 0.5, 1, 2, 3, 4, 5, 6, 7, 8, or 9 mM, including any ranges between these values). In some embodiments, the composition further comprises methionine. In some embodiments, the concentration of methionine in the composition ranges from about 0.1 mM to about 100 mM (such as about any of 0.2, 0.5, 1, 2, 3, 4, 5, 6, 7, 8, 9, 10, 20, 30, 40, 50, 60, 70, 80, or 90 mM, including any ranges between these values). In some embodiments, the polypeptide concentration in the composition is about 1 mg/mL to about 250 mg/mL (such as about any of 2, 5, 10, 20, 40, 60, 80, 100, 120, 140, 160, 180, 200, 220, and 240 mg/mL, including any ranges between these values). In some embodiments, the composition has a pH of about 4.5 to about 7.5 (such as about any of 4.6, 4.8, 5.0, 5.2, 5.4, 5.6, 5.8, 6.0, 6.2, 6.4, 6.6, 6.8, 7.0, 7.2, 7.4, including any ranges between these values). In some embodiments, the composition further comprises one or more excipients selected from the group consisting of a stabilizer, a buffer, and a tonicity agent. In some embodiments, the composition is a pharmaceutical formulation suitable for administration to a subject. In some embodiments, the polypeptide is a therapeutic polypeptide. In some embodiments, the therapeutic protein is a polyclonal antibody, a monoclonal antibody, a humanized antibody, a human antibody, a chimeric antibody, a multispecific antibody, glycoengineered antibody, antibody fragment, an antibody drug conjugate, a THIOMAB™, a THIOMAB™ drug conjugate. In some embodiments, the mixed mode cation exchange chromatography material comprises a reversed phase, strong cation exchange polymer. In some embodiments, the mixed mode cation exchange chromatography material comprises a sulfonic acid moiety. In some embodiments, the mixed mode cation exchange chromatography material comprises a solid support. In some embodiments, the mixed mode cation exchange chromatography material is contained in a column. In some embodiments, the mixed mode cation exchange chromatography material is a high performance liquid chromatography (HPLC) material. In some embodiments, the mixed mode cation exchange chromatography material is an Oasis® MCX chromatography material. In some embodiments, the non-ionic detergent is quantified by Evaporative Light Scattering (ELSD) or by using a Charged Aerosol Detector (CAD). In some embodiments, the quantification of the polysorbate comprises less than about 10% (such as less than about any of 9%, 8%, 7%, 6%, 5%, 4%, 3%, 2%, 1%, 0.5%, 0.1%, 0.05%, 0.01%, or less) interference from the polypeptide and the NAT.

In some embodiments of any of the methods described above, the non-ionic surfactant is quantified in the composition comprising the non-ionic surfactant prior to adding the polypeptide to the composition. In some embodiments, the concentration of non-ionic surfactant in the composition will be greater prior to adding the polypeptide (e.g., the non-ionic surfactant in the composition is diluted upon addition of the polypeptide). In some embodiments of any of the methods described above, the non-ionic surfactant is quantified in the composition comprising the non-ionic surfactant prior but without the polypeptide to the composition. Such quantitations may be used as controls or comparators to the compositions comprising the non-ionic surfactant and the polypeptide.

In some embodiments of any of the methods described above, samples of the compositions to be analyzed are added to an autosampler of a chromatography instrument (e.g., HPLC instrument). In some embodiments, the samples in the autosampler are refrigerated (e.g., 5±3° C.). In some embodiments, one or more columns comprising the chromatography material are placed in a column compartment of the chromatography instrument. In some embodiments, a temperature control feature may be employed to keep the column compartment temperature within a narrow range (e.g., ±1° C.) from the set point during analysis. In some embodiments, column effluent is monitored at 280 nm.

In some embodiments of any of the methods described above, samples of the compositions to be analyzed are diluted with a loading buffer to a target polypeptide concentration between about 0.1 mg/mL and about 75 mg/mL (such as about any of 0.2, 0.4, 0.6, 0.8, 1, 1.5, 2, 2.5, 3, 3.5, 4, 4.5, 5, 6, 7, 8, 9, 10, 12, 14, 16, 18, 20, 25, 30, 35, 40, 45, 50, 55, 60, 65, or 70 mg/mL, including any ranges between these values).

In some embodiments of any of the methods described above, the chromatography instrument includes a gradient pump (e.g., a low-pressure quaternary gradient pump), an autosampler (e.g., an autosampler with temperature control capability), a column compartment (e.g., a thermal-controlled column compartment), a UV detector (e.g., a diode array UV detector), and an evaporative light scattering detector (ELSD). In some embodiments, the chromatography instrument further comprises a pH and conductivity monitor (e.g., PCM-3000) to collect pH and conductivity data in real time. Instrument control, data acquisition, and data analysis is performed using appropriate software (e.g., JMP10).

In some embodiments of the invention, ionic strength of the mobile phase, e.g. the elution buffer, is measured by conductivity of the mobile phase. Conductivity refers to the ability of an aqueous solution to conduct an electric current between two electrodes. In solution, the current flows by ion transport. Therefore, with an increasing amount of ions present in the aqueous solution, the solution will have a higher conductivity. The basic unit of measure for conductivity is the Siemen (or mho), mho (mS/cm), and can be measured using a conductivity meter, such as various models of Orion conductivity meters. Since electrolytic conductivity is the capacity of ions in a solution to carry electrical current, the conductivity of a solution may be altered by changing the concentration of ions therein. For example, the concentration of a buffering agent and/or the concentration of a salt (e.g. sodium chloride, sodium acetate, or potassium chloride) in the solution may be altered in order to achieve the desired conductivity. Preferably, the salt concentration of the various buffers is modified to achieve the desired conductivity.

In some embodiments, the mobile phase of the chromatography has an initial conductivity of more than about any of 0.0 mS/cm, 0.5 mS/cm, 1.0 mS/cm, 1.5 mS/cm, 2.0 mS/cm, 2.5 mS/cm, 3.0 mS/cm, 3.5 mS/cm, 4.0 mS/cm, 4.5 mS/cm, 5.0 mS/cm, 5.5 mS/cm, 6.0 mS/cm, 6.5 mS/cm, 7.0 mS/cm, 7.5 mS/cm, 8.0 mS/cm, 8.5 mS/cm, 9.0 mS/cm, 9.5 mS/cm, 10 mS/cm, 11 mS/cm, 12 mS/cm, 13 mS/cm, 14 mS/cm, 15 mS/cm, 16 mS/cm, 17.0 mS/cm, 18.0 mS/cm, 19.0 mS/cm, or 20.0 mS/cm. In some embodiments, the conductivity of the mobile phase is increased over the course of the chromatography, e.g. by an ionic strength gradient. In some embodiments, the conductivity of the mobile phase at the completion of elution is more than about any of 1.0 mS/cm, 1.5 mS/cm, 2.0 mS/cm, 2.5 mS/cm, 3.0 mS/cm, 3.5 mS/cm, 4.0 mS/cm, 4.5 mS/cm, 5.0 mS/cm, 5.5 mS/cm, 6.0 mS/cm, 6.5 mS/cm, 7.0 mS/cm, 7.5 mS/cm, 8.0 mS/cm, 8.5 mS/cm, 9.0 mS/cm, 9.5 mS/cm, 10 mS/cm, 11 mS/cm, 12 mS/cm, 13 mS/cm, 14 mS/cm, 15 mS/cm, 16 mS/cm, 17.0 mS/cm, 18.0 mS/cm, 19.0 mS/cm, or 20.0 mS/cm. In some embodiments, the conductivity of the mobile phase is increased by a linear gradient. In some embodiments, the conductivity of the mobile phase is increased by a step gradient comprising one or more steps.

In some embodiments of any of the methods described herein, the composition comprising a polypeptide and a non-ionic surfactant is loaded on the chromatography material at an amount of the polypeptide of more than any one of about 1, 2, 3, 4, 5, 6, 7, 8, 9, 10, 15, 20, 25, 50, 100, 200, 300, 400, 500, 600, 700, 800, 900, 1000, 2000, 3000, 4000, 5000, 6000, 7000, 8000, 9000, or 10000 μg. In some embodiments, the composition is loaded onto the chromatography material at a concentration of more than any one of about 0.5, 1, 1.5, 2, 2.5, 5, 10, 20, 30, 40, 50, 60, 70, 80, 90, 100, 110, 120, 130, 140, or 150 mg/mL. In some embodiments, the composition is diluted prior to loading onto the chromatography material; for example, diluted 1:1, 1:2, 1:5, 1:10 or greater than 1:10. In some embodiments, the composition is diluted into the mobile phase of the chromatography. In some embodiments, the composition is diluted into a loading buffer.

In some embodiments of the methods described herein, the chromatography material is in a column or cartridge. In some embodiments the column is an HPLC column or cartridge. The column or cartridge may have any dimension compatible with the chromatography instrument. For example, in some embodiments the column or cartridge has any one of the following dimensions: 2.1×20 mm, 4×50 mm, 4×100 mm, 4×150 mm, 4×200 mm, 4×250 mm, or 2×250 mm.

III. Polypeptides

Polypeptides are provided for use in any of the methods of ion exchange chromatography wherein the separation conditions are optimized as described herein. In some embodiments of the invention, compositions of a polypeptide are analyzed by ion exchange chromatography. Such methods are useful in identifying charge variants of the polypeptide within the composition. In some embodiments, the polypeptide is an antibody or fragment thereof. In some embodiments, the polypeptides have a pI ranging from about 6.0 to about 9.5. In some embodiments, the polypeptide is an antibody having a pI ranging from about 6.0 to about 9.5. In some embodiments, the Inflection Point (IP) in a curve of charge vs. pH of the polypeptide is provided by the methods of the invention. In some embodiments, the change in the IP with a change in temperature (dIP/dT) is provided by the methods of the invention.

In some embodiments, the polypeptide is a therapeutic polypeptide. In some embodiments, the polypeptide is an antibody. In some embodiments, the polypeptide is an immunoadhesin.

In some embodiments, the polypeptide has a molecular weight of greater than about any of 5,000 Daltons, 10,000 Daltons, 15.000 Daltons, 25,000 Daltons, 50,000 Daltons, 75,000 Daltons, 100,000 Dalton, 125,000 Daltons, or 150,000 Daltons. The polypeptide may have a molecular weight between about any of 50,000 Daltons to 200,000 Daltons or 100,000 Daltons to 200,000 Daltons. Alternatively, the polypeptide for use herein may have a molecular weight of about 120,000 Daltons or about 25,000 Daltons.

pI is the isoelectric point and is the pH at which a particular molecule or surface carries no net electrical charge. In some embodiments, the method of the invention can be used for plurality of compositions comprising a polypeptide where the pI of the polypeptide in the composition, e.g. an antibody, ranges from about 6.0 to about 9.5. In some embodiments, the polypeptide has a pI greater than about 9.5; e.g., about 9.5 to about 12. In some embodiments of any of the methods described herein, the pI of the polypeptide, e.g. an antibody, may be less that about 7; e.g., about 4 to about 7.

In embodiments of any of the methods described herein, the one or more contaminants in a composition comprising a polypeptide and one or more contaminants are polypeptide charge variants. In some embodiments, the polypeptide charge variant is a polypeptide that has been modified from its native state such that the charge of the polypeptide is altered. In some embodiments, the charge variants are more acidic than the parent polypeptide; i.e. have a lower pI than the parent polypeptide. In other embodiments, the charge variants are more basic than the parent polypeptide; i.e. have a higher pI than the parent polypeptide. In some embodiments, the polypeptide charge variants are engineered. In some embodiments, the polypeptide charge variant is the result of natural processes; for example, oxidation, deamidation, C-terminal processing of lysine residues, N-terminal pyroglutamate formation, and glycation. In some embodiments, the polypeptide charge variant is a glycoprotein where the glycan attached to the protein is modified such that the charge of the glycoprotein is altered compared to parent glycoprotein; for example, by addition of sialic acid or its derivatives. In some embodiments, the polypeptide charge variant is an antibody charge variant.

The polypeptides to be analyzed using the methods described herein are generally produced using recombinant techniques. Methods for producing recombinant proteins are described, e.g., in U.S. Pat. Nos. 5,534,615 and 4,816,567, specifically incorporated herein by reference. In some embodiments, the protein of interest is produced in a CHO cell (see, e.g. WO 94/11026). In some embodiments, the polypeptide of interest is produced in an *E. coli* cell. See, e.g., U.S. Pat. Nos. 5,648,237; 5,789,199, and 5,840,523, which describes translation initiation region (TIR) and signal sequences for optimizing expression and secretion. See also Charlton, Methods in Molecular Biology, Vol. 248 (B. K. C. Lo, ed., Humana Press, Totowa, N.J., 2003), pp. 245-254, describing expression of antibody fragments in *E. coli*. When using recombinant techniques, the polypeptides can be produced intracellularly, in the periplasmic space, or directly secreted into the medium.

The polypeptides may be recovered from culture medium or from host cell lysates. Cells employed in expression of the polypeptides can be disrupted by various physical or chemical means, such as freeze-thaw cycling, sonication, mechanical disruption, or cell lysing agents. If the polypeptide is produced intracellularly, as a first step, the particulate debris, either host cells or lysed fragments, are removed, for example, by centrifugation or ultrafiltration. Carter et al., *Bio/Technology* 10: 163-167 (1992) describe a procedure for isolating polypeptides which are secreted to the periplasmic space of *E. coli*. Briefly, cell paste is thawed in the presence of sodium acetate (pH 3.5), EDTA, and phenylmethylsulfonylfluoride (PMSF) over about 30 μmin. Cell debris can be removed by centrifugation. Where the polypeptide is secreted into the medium, supernatants from such expression systems are generally first concentrated using a commercially available polypeptide concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

In some embodiments, the polypeptide in the composition comprising the polypeptide and one or more contaminants has been purified or partially purified prior to analysis by the methods of the invention. For example, the polypeptide of the methods is in an eluent from an affinity chromatography, a cation exchange chromatography, an anion exchange chromatography, a mixed mode chromatography and a hydrophobic interaction chromatography. In some embodiments, the polypeptide is in an eluent from a Protein A chromatography.

Examples of polypeptides that may be analyzed by the methods of the invention include but are not limited to immunoglobulins, immunoadhesins, antibodies, enzymes, hormones, fusion proteins. Fc-containing proteins, immunoconjugates, cytokines and interleukins.

(A) Antibodies

In some embodiments of any of the methods described herein, the polypeptide for use in any of the methods of analyzing polypeptides and formulations comprising the polypeptides by the methods described herein is an antibody.

Molecular targets for antibodies include (i) CD proteins and their ligands, such as, but not limited to: CD3, CD4, CD8, CD19, CD11a, CD20, CD22, CD27, CD28, CD34, CD40, CD79a (CD79a), CD793 (CD79b), CD122, and CD137; (ii) cytokines such as, but not limited to: IL-13, IL-17, IL-22, and IL-33; (iii) members of the ErbB receptor family such as the EGF receptor, HER2, HER3 or HER4 receptor; (iv) cell adhesion molecules such as LFA-1, Mac1, p150,95, VLA-4, ICAM-1, VCAM and αv/β3 integrin, including either alpha or beta subunits thereof (e.g., anti-CD11a, anti-CD18 or anti-CD11b antibodies); (v) growth factors such as VEGF; TGFβ, IgE; blood group antigens; flk2/flt3 receptor; obesity (OB) receptor, mpl receptor; CTLA-4; protein C, BR3, c-met, tissue factor, 37 etc: (vi) immunomodulatory proteins such as OX40, GITR, ICOS, PD-1, PD-L1, PD-L2, LAG3, TIM-3, and VISTA; and (vii) cell surface and transmembrane tumor-associated antigens (TAA), such as those described in U.S. Pat. No. 7,521,541, including, without limitation, NaPi2b.

Other exemplary antibodies include those selected from, and without limitation, anti-estrogen receptor antibody, anti-progesterone receptor antibody, anti-p53 antibody, anti-HER-2/neu antibody, anti-EGFR antibody, anti-TGF antibody, anti-OX40 antibody, anti-GITR antibody, anti-ICOS antibody, anti-CTLA-4 antibody, anti-PD-1 antibody, anti-PD-L1 antibody, anti-PD-L2 antibody, anti-TIM-3 antibody, anti-VISTA antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD10 antibody, anti-CD11a antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD27 antibody, anti-CD28 antibody, anti-CD30 antibody, anti-CD31 antibody, anti-CD33 antibody, anti-CD34 antibody, anti-CD35 antibody, anti-CD38 antibody, anti-CD40 antibody, anti-CD41 antibody, anti-LCA/CD45 antibody, anti-CD45RO antibody, anti-CD45RA antibody, anti-CD39 antibody, anti-CD 100 antibody, anti-CD95/Fas antibody, anti-CD99 antibody, anti-CD106 antibody, anti-CD122 antibody, anti-CD137 antibody, anti-ubiquitin antibody, anti-CD71 antibody, anti-StaphA antibody, anti-FcRH5 antibody, anti-Ly6E antibody, anti-STEAP antibody, anti-FluB antibody, anti-VEGF antibody, anti-Ang2 antibody, anti-FGFR1 antibody, anti-KLB antibody, anti-c-myc antibody, anti-cytokeratins antibody, anti-vimentin antibody, anti-HPV proteins antibody, anti-kappa light chains antibody, anti-lambda light chains antibody, anti-melanosomes antibody, anti-prostate specific antigen antibody, anti-S-100 antibody, anti-tau antigen antibody, anti-fibrin antibody, anti-keratins antibody, anti-Tn-antigen antibody, and MetMab.

(i) Monoclonal Antibodies

In some embodiments, the antibodies are monoclonal antibodies. Monoclonal antibodies are obtained from a population of substantially homogeneous antibodies, i.e., the individual antibodies comprising the population are identical and/or bind the same epitope except for possible variants that arise during production of the monoclonal antibody, such variants generally being present in minor amounts. Thus, the modifier "monoclonal" indicates the character of the antibody as not being a mixture of discrete or polyclonal antibodies.

For example, the monoclonal antibodies may be made using the hybridoma method first described by Kohler et al., *Nature* 256:495 (1975), or may be made by recombinant DNA methods (U.S. Pat. No. 4,816,567).

In the hybridoma method, a mouse or other appropriate host animal, such as a hamster, is immunized as herein described to elicit lymphocytes that produce or are capable of producing antibodies that will specifically bind to the polypeptide used for immunization. Alternatively, lymphocytes may be immunized in vitro. Lymphocytes then are fused with myeloma cells using a suitable fusing agent, such as polyethylene glycol to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

In some embodiments, the myeloma cells are those that fuse efficiently, support stable high-level production of antibody by the selected antibody-producing cells, and are sensitive to a medium such as HAT medium. Among these, in some embodiments, the mycloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor. *J. Immunol.* 133:3001 (1984); Brodeur et al., *Monoclonal Antibody Production Techniques and Applications* pp. 51-63 (Marcel Dekker. Inc., New York, 1987)).

Culture medium in which hybridoma cells are growing is assayed for production of monoclonal antibodies directed against the antigen. In some embodiments, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.* 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice* pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, polypeptide A-Sepharose®, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). In some embodiments, the hybridoma cells serve as a source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce immunoglobulin polypeptide, to obtain the synthesis of monoclonal antibodies in the recombinant host cells. Review articles on recombinant expression in bacteria of DNA encoding the antibody include Skerra et al., *Curr. Opinion in Immunol.* 5:256-262 (1993) and Plückthun, *Immunol. Revs.,* 130:151-188 (1992).

In a further embodiment, antibodies or antibody fragments can be isolated from antibody phage libraries generated using the techniques described in McCafferty et al., *Nature* 348:552-554 (1990). Clackson et al., *Nature* 352: 624-628 (1991) and Marks et al., *J. Mol. Biol.* 222:581-597 (1991) describe the isolation of murine and human antibodies, respectively, using phage libraries. Subsequent publications describe the production of high affinity (nM range) human antibodies by chain shuffling (Marks et al., *Bio/Technology* 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light chain constant domains in place of the homologous murine sequences (U.S. Pat. No. 4,816,567; Morrison et al., *Proc. Natl Acad. Sci. USA* 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

In some embodiments of any of the methods described herein, the antibody is IgA, IgD, IgE, IgG, or IgM. In some embodiments, the antibody is an IgG monoclonal antibody.

(ii) Humanized Antibodies

In some embodiments, the antibody is a humanized antibody. Methods for humanizing non-human antibodies have been described in the art. In some embodiments, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., *Nature* 321:522-525 (1986); Riechmann et al., *Nature* 332:323-327 (1988); Verhoeyen et al., *Science* 239: 1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework region (FR) for the humanized antibody (Sims et al., *J. Immunol.* 151:2296 (1993); Chothia et al., *J. Mol. Biol.* 196:901 (1987)). Another method uses a particular framework region derived from the consensus sequence of all human antibodies of a particular subgroup of light or heavy chain variable regions. The same framework may be used for several different humanized antibodies (Carter et al., *Proc. Natl. Acad. Sci. USA* 89:4285 (1992); Presta et al., *J. Immunol.* 151:2623 (1993)).

It is further important that antibodies be humanized with retention of high affinity for the antigen and other favorable biological properties. To achieve this goal, in some embodiments of the methods, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

(iii) Human Antibodies

In some embodiments, the antibody is a human antibody. As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA* 90:2551 (1993); Jakobovits et al., *Nature* 362:255-258 (1993); Bruggermann et al., *Year in Immuno.* 7:33 (1993); and U.S. Pat. Nos. 5,591,669; 5,589,369; and 5,545,807.

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat polypeptide gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see. e.g., Johnson, Kevin S, and Chiswell, David J., *Current Opinion in Structural Biology* 3:564-571 (1993). Several sources of V-gene segments can be used for phage display. Clackson et al., *Nature* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See also, U.S. Pat. Nos. 5,565,332 and 5,573,905.

Human antibodies may also be generated by in vitro activated B cells (see U.S. Pat. Nos. 5,567,610 and 5,229,275).

(iv) Antibody Fragments

In some embodiments, the antibody is an antibody fragment. Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10:163-167 (1992)). According to another approach, $F(ab')_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. The antibody fragment may also be a "linear antibody," e.g., as described in U.S. Pat. No. 5,641,870 for example. Such linear antibody fragments may be monospecific or bispecific.

In some embodiments, fragments of the antibodies described herein are provided. In some embodiments, the antibody fragment is an antigen binding fragment. In some embodiments, the antigen binding fragment is selected from the group consisting of a Fab fragment, a Fab' fragment, a $F(ab')_2$ fragment, a scFv, a Fv, and a diabody.

(v) Bispecific Antibodies

In some embodiments, the antibody is a bispecific antibody. Bispecific antibodies are antibodies that have binding specificities for at least two different epitopes. Exemplary bispecific antibodies may bind to two different epitopes. Alternatively, a bispecific antibody binding arm may be combined with an arm that binds to a triggering molecule on a leukocyte such as a T-cell receptor molecule (e.g. CD2 or CD3), or Fc receptors for IgG (FcγR), such as FcγRI (CD64). FcγRII (CD32) and FcγRIII (CD16) so as to focus cellular defense mechanisms to the cell. Bispecific antibodies can be prepared as full length antibodies or antibody fragments (e.g. $F(ab')_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. In some embodiments, the fusion is with an immunoglobulin heavy chain constant domain, comprising at least part of the hinge, CH2, and CH3 regions. In some embodiments, the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In some embodiments of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology* 121:210 (1986).

According to another approach described in U.S. Pat. No. 5,731,168, the interface between a pair of antibody molecules can be engineered to maximize the percentage of heterodimers that are recovered from recombinant cell culture. In some embodiments, the interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229: 81 (1985) describe a procedure wherein intact antibodies are protcolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a heavy chain variable domain ($V_H$) connected to a light chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.* 152:5368 (1994).

Antibodies with more than two valencies are contemplated. For example, trispecific antibodies can be prepared. Tutt et al., *J. Immunol.* 147: 60 (1991).

(vi) Multivalent Antibodies

In some embodiments, the antibodies are multivalent antibodies. A multivalent antibody may be internalized (and/or catabolized) faster than a bivalent antibody by a cell expressing an antigen to which the antibodies bind. The antibodies provided herein can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2) n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

In some embodiments, the antibody is a multispecific antibody. Example of multispecific antibodies include, but are not limited to, an antibody comprising a heavy chain variable domain ($V_H$) and a light chain variable domain ($V_L$), where the $V_H V_L$ unit has polyepitopic specificity, antibodies having two or more $V_L$ and $V_H$ domains with each $V_H V_L$ unit binding to a different epitope, antibodies having two or more single variable domains with each single variable domain binding to a different epitope, full length antibodies, antibody fragments such as Fab, Fv, dsFv, scFv, diabodies, bispecific diabodies, triabodies, tri-functional antibodies, antibody fragments that have been linked covalently or non-covalently. In some embodiment that antibody has polyepitopic specificity; for example, the ability to specifically bind to two or more different epitopes on the same or different target(s). In some embodiments, the antibodies are monospecific; for example, an antibody that binds only one epitope. According to one embodiment the multispecific antibody is an IgG antibody that binds to each epitope with an affinity of 5 µM to 0.001 pM, 3 µM to 0.001 pM, 1 µM to 0.001 pM, 0.5 µM to 0.001 pM, or 0.1 µM to 0.001 pM.

(vii) Other Antibody Modifications

It may be desirable to modify the antibody provided herein with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med* 176:1191-1195 (1992) and Shopes, B. J., *Immunol.* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement mediated lysis and ADCC capabilities. See Stevenson et al., *Anti-Cancer Drug Design* 3:219-230 (1989).

For increasing serum half the serum half life of the antibody, amino acid alterations can be made in the antibody as described in US 2006/0067930, which is hereby incorporated by reference in its entirety.

(B) Polypeptide Variants and Modifications

Amino acid sequence modification(s) of the polypeptides, including antibodies, described herein may be used in the methods of purifying polypeptides (e.g., antibodies) described herein.

(i) Variant Polypeptides

"Polypeptide variant" means a polypeptide, preferably an active polypeptide, as defined herein having at least about 80% amino acid sequence identity with a full-length native sequence of the polypeptide, a polypeptide sequence lacking the signal peptide, an extracellular domain of a polypeptide, with or without the signal peptide. Such polypeptide variants include, for instance, polypeptides wherein one or more amino acid residues are added, or deleted, at the N or C-terminus of the full-length native amino acid sequence. Ordinarily, a TAT polypeptide variant will have at least about 80% amino acid sequence identity, alternatively at least about any of 85%, 90%, 95%, 96%, 97%, 98%, or 99% amino acid sequence identity, to a full-length native sequence polypeptide sequence, a polypeptide sequence lacking the signal peptide, an extracellular domain of a polypeptide, with or without the signal peptide. Optionally, variant polypeptides will have no more than one conservative amino acid substitution as compared to the native polypeptide sequence, alternatively no more than about any of 2, 3, 4, 5, 6, 7, 8, 9, or 10 conservative amino acid substitution as compared to the native polypeptide sequence.

The variant polypeptide may be truncated at the N-terminus or C-terminus, or may lack internal residues, for example, when compared with a full length native polypeptide. Certain variant polypeptides may lack amino acid residues that are not essential for a desired biological activity. These variant polypeptides with truncations, deletions, and insertions may be prepared by any of a number of conventional techniques. Desired variant polypeptides may be chemically synthesized. Another suitable technique involves isolating and amplifying a nucleic acid fragment encoding a desired variant polypeptide, by polymerase chain reaction (PCR). Oligonucleotides that define the desired termini of the nucleic acid fragment are employed at the 5' and 3' primers in the PCR. Preferably, variant polypeptides share at least one biological and/or immunological activity with the native polypeptide disclosed herein.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody.

For example, it may be desirable to improve the binding affinity and/or other biological properties of the polypeptide. Amino acid sequence variants of the polypeptide are prepared by introducing appropriate nucleotide changes into the antibody nucleic acid, or by peptide synthesis. Such modifications include, for example, deletions from, and/or insertions into and/or substitutions of, residues within the amino acid sequences of the polypeptide. Any combination of deletion, insertion, and substitution is made to arrive at the final construct, provided that the final construct possesses the desired characteristics. The amino acid changes also may alter post-translational processes of the polypeptide (e.g., antibody), such as changing the number or position of glycosylation sites.

Guidance in determining which amino acid residue may be inserted, substituted or deleted without adversely affecting the desired activity may be found by comparing the sequence of the polypeptide with that of homologous known polypeptide molecules and minimizing the number of amino acid sequence changes made in regions of high homology.

A useful method for identification of certain residues or regions of the polypeptide (e.g., antibody) that are preferred locations for mutagenesis is called "alanine scanning mutagenesis" as described by Cunningham and Wells, Science 244:1081-1085 (1989). Here, a residue or group of target residues are identified (e.g., charged residues such as Arg, Asp, His, Lys, and Glu) and replaced by a neutral or negatively charged amino acid (most preferably Alanine or Polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 1 below under the heading of "conservative substitutions." If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Conservative Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger. *Biochemistry* second ed., pp. 73-75, Worth Publishers, New York (1975)):
(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties:
  (1) hydrophobic: Norleucine, Met, Ala, Val, Leu, Ile;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro;
  (6) aromatic: Trp, Tyr, Phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the polypeptide to improve its stability (particularly where the antibody is an antibody fragment such as an Fv fragment).

A particularly preferred type of substitutional variant involves substituting one or more hypervariable region residues of a parent antibody (e.g., a humanized antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and target. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the polypeptide alters the original glycosylation pattern of the antibody. The polypeptide may comprise non-amino acid moieties. For example, the polypeptide may be glycosylated. Such glycosylation may occur naturally during expression of the polypeptide in the host cell or host organism, or may be a deliberate modification arising from human intervention. By altering is meant deleting one or more carbohydrate moieties found in the polypeptide, and/or adding one or more glycosylation sites that are not present in the polypeptide.

Glycosylation of polypeptide is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Removal of carbohydrate moieties present on the polypeptide may be accomplished chemically or enzymatically or by mutational substitution of codons encoding for amino acid residues that serve as targets for glycosylation. Enzymatic cleavage of carbohydrate moieties on polypeptides can be achieved by the use of a variety of endo- and exo-glycosidases.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains, acetylation of the N-terminal amine, and amidation of any C-terminal carboxyl group.

(ii) Chimeric Polypeptides

The polypeptide described herein may be modified in a way to form chimeric molecules comprising the polypeptide fused to another, heterologous polypeptide or amino acid sequence. In some embodiments, a chimeric molecule comprises a fusion of the polypeptide with a tag polypeptide which provides an epitope to which an anti-tag antibody can selectively bind. The epitope tag is generally placed at the amino- or carboxyl-terminus of the polypeptide. The presence of such epitope-tagged forms of the polypeptide can be detected using an antibody against the tag polypeptide. Also, provision of the epitope tag enables the polypeptide to be readily purified by affinity purification using an anti-tag antibody or another type of affinity matrix that binds to the epitope tag.

In an alternative embodiment, the chimeric molecule may comprise a fusion of the polypeptide with an immunoglobulin or a particular region of an immunoglobulin. A bivalent form of the chimeric molecule is referred to as an "immunoadhesin."

As used herein, the term "immunoadhesin" designates antibody-like molecules which combine the binding specificity of a heterologous polypeptide with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes. IgA (including IgA-1 and IgA-2), IgE, IgD or IgM.

The Ig fusions preferably include the substitution of a soluble (transmembrane domain deleted or inactivated) form of a polypeptide in place of at least one variable region within an Ig molecule. In a particularly preferred embodiment, the immunoglobulin fusion includes the hinge, $CH_2$ and $CH_3$, or the hinge, $CH_1$, $CH_2$ and $CH_3$ regions of an IgG1 molecule.

(iii) Polypeptide Conjugates

The polypeptide for use in polypeptide formulations may be conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such conjugates can be used. In addition, enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated polypeptides. Examples include $^{212}Bi$, $^{131}I$, $^{131}In$, $^{90}Y$, and $^{186}Re$. Conjugates of the polypeptide and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the polypeptide.

Conjugates of a polypeptide and one or more small molecule toxins, such as a calicheamicin, maytansinoids, a trichothene, and CC 1065, and the derivatives of these toxins that have toxin activity, are also contemplated herein.

Maytansinoids are mitotic inhibitors which act by inhibiting tubulin polymerization. Maytansine was first isolated from the east African shrub *Maytenus serrata*. Subsequently, it was discovered that certain microbes also produce maytansinoids, such as maytansinol and C-3 maytansinol esters. Synthetic maytansinol and derivatives and analogues thereof are also contemplated. There are many linking groups known in the art for making polypeptide-maytansinoid conjugates, including, for example, those disclosed in U.S. Pat. No. 5,208,020. The linking groups include disufide groups, thioether groups, acid labile groups, photolabile groups, peptidase labile groups, or esterase labile groups, as disclosed in the above-identified patents, disulfide and thioether groups being preferred.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Another conjugate of interest comprises a polypeptide conjugated to one or more calicheamicin molecules. The calicheamicin family of antibiotics are capable of producing double-stranded DNA breaks at sub-picomolar concentrations. For the preparation of conjugates of the calicheamicin family, see, e.g., U.S. Pat. No. 5,712,374. Structural analogues of calichcamicin which may be used include, but are not limited to, $\gamma_1^I$, $\alpha_2^I$, $\alpha_3^I$, N-acetyl-$\gamma_1^I$, PSAG and $\theta_1^I$. Another anti-tumor drug that the antibody can be conjugated is QFA which is an antifolate. Both calicheamicin and QFA have intracellular sites of action and do not readily cross the plasma membrane. Therefore, cellular uptake of these agents through polypeptide (e.g., antibody) mediated internalization greatly enhances their cytotoxic effects.

Other antitumor agents that can be conjugated to the polypeptides described herein include BCNU, streptozoicin, vincristine and 5-fluorouracil, the family of agents known collectively LL-E33288 complex, as well as esperamicins.

In some embodiments, the polypeptide may be a conjugate between a polypeptide and a compound with nucleolytic activity (e.g., a ribonuclease or a DNA endonuclease such as a deoxyribonuclease; DNase).

In yet another embodiment, the polypeptide (e.g., antibody) may be conjugated to a "receptor" (such streptavidin) for utilization in tumor pre-targeting wherein the polypeptide receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

In some embodiments, the polypeptide may be conjugated to a prodrug-activating enzyme which converts a prodrug (e.g., a peptidyl chemotherapeutic agent) to an active anti-cancer drug. The enzyme component of the immunoconjugate includes any enzyme capable of acting on a prodrug in such a way so as to convert it into its more active, cytotoxic form.

Enzymes that are useful include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs into free active drugs.

(iv) Other

Another type of covalent modification of the polypeptide comprises linking the polypeptide to one of a variety of nonproteinaceous polymers, e.g., polyethylene glycol polypropylene glycol, polyoxyalkylenes, or copolymers of polyethylene glycol and polypropylene glycol. The polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical *Sciences,* 18th edition. Gennaro, A. R., Ed., (1990).

IV. Obtaining Polypeptides for Use in the Formulations and Methods

The polypeptides used in the methods of analysis described herein may be obtained using methods well-known in the art, including the recombination methods. The following sections provide guidance regarding these methods.

(A) Polynucleotides

"Polynucleotide," or "nucleic acid." as used interchangeably herein, refer to polymers of nucleotides of any length, and include DNA and RNA.

Polynucleotides encoding polypeptides may be obtained from any source including, but not limited to, a cDNA library prepared from tissue believed to possess the polypeptide mRNA and to express it at a detectable level. Accordingly, polynucleotides encoding polypeptide can be conveniently obtained from a cDNA library prepared from human tissue. The polypeptide-encoding gene may also be obtained from a genomic library or by known synthetic procedures (e.g., automated nucleic acid synthesis).

For example, the polynucleotide may encode an entire immunoglobulin molecule chain, such as a light chain or a heavy chain. A complete heavy chain includes not only a heavy chain variable region ($V_H$) but also a heavy chain constant region ($C_H$), which typically will comprise three constant domains: $C_H1$, $C_H2$ and $C_H3$; and a "hinge" region. In some situations, the presence of a constant region is desirable.

Other polypeptides which may be encoded by the polynucleotide include antigen-binding antibody fragments such as single domain antibodies ("dAbs"), Fv, scFv, Fab' and F(ab')$_2$ and "minibodies." Minibodies are (typically) bivalent antibody fragments from which the $C_H1$ and $C_K$ or $C_L$ domain has been excised. As minibodies are smaller than conventional antibodies they should achieve better tissue penetration in clinical/diagnostic use, but being bivalent they should retain higher binding affinity than monovalent antibody fragments, such as dAbs. Accordingly, unless the context dictates otherwise, the term "antibody" as used herein encompasses not only whole antibody molecules but also antigen-binding antibody fragments of the type discussed above. Preferably each framework region present in the encoded polypeptide will comprise at least one amino acid substitution relative to the corresponding human acceptor framework. Thus, for example, the framework regions may comprise, in total, three, four, five, six, seven, eight, nine, ten, eleven, twelve, thirteen, fourteen, or fifteen amino acid substitutions relative to the acceptor framework regions.

V. Exemplary Embodiments

Embodiment 1

In some embodiments, there is provided a method for quantifying a non-ionic surfactant in a composition comprising the non-ionic surfactant and a polypeptide, wherein interference between the non-ionic surfactant and the polypeptide during quantification is reduced, wherein the method comprises the steps of a) applying the composition to a mixed mode anion exchange chromatography material, wherein the composition is loaded onto the chromatography material in a solution comprising a mobile phase A and a mobile phase B, wherein mobile phase A comprises acid in water and mobile phase B comprises acid in methanol, wherein the polypeptide binds to the chromatography material specifically and non-specifically;

b) eluting the polypeptide from the mixed mode anion exchange chromatography material with a solution comprising mobile phase A and mobile phase B wherein the ratio of mobile phase B to mobile phase A is increased compared to step a);

c) eluting the non-ionic surfactant and the non-specifically bound polypeptide from the chromatography material with a solution comprising mobile phase A and mobile phase B wherein the ratio of mobile phase B to mobile phase A is increased compared to step c);

d) quantifying the non-ionic surfactant, wherein interference between the non-ionic surfactant and the polypeptide during quantitation is reduced.

Embodiment 2

In some further embodiments of embodiment 1, the ratio of mobile phase B to mobile phase A in step a) is about 10:90.

Embodiment 3

In some further embodiments of embodiment 1 or 2, the ratio of mobile phase B to mobile phase A is increased to about 40:60 in step b).

Embodiment 4

In some further embodiments of any one of embodiments 1-3, the ratio of mobile phase B to mobile phase A is increased to about 100:0 in step c).

Embodiment 5

In some further embodiments of any one of embodiments 1-4, mobile phase A comprises about 2% acid in water.

Embodiment 6

In some further embodiments of any one of embodiments 1-5, mobile phase B comprises about 2% acid in methanol.

Embodiment 7

In some further embodiments of any one of embodiments 1-6, the acid is formic acid.

Embodiment 8

In some further embodiments of any one of embodiments 1-6, the acid is acetic acid.

Embodiment 9

In some further embodiments of any one of embodiments 1-8, the flow rate of the chromatography is about 1.25 mL/minute.

Embodiment 10

In some further embodiments of embodiment 9, step b) starts at about 1 min after the chromatography is initiated and ends at about 3.4 min after the chromatography is initiated.

Embodiment 11

In some further embodiments of embodiment 9 or 10, step c) starts at about 3.5 min after the chromatography is initiated and ends at about 4.6 min after the chromatography is initiated.

Embodiment 12

In some further embodiments of any one of embodiments 1-11, the non-ionic surfactant is poloxamer (P188) or a polysorbate.

Embodiment 13

In some further embodiments of embodiment 12, the polysorbate is polysorbate 20 or polysorbate 80.

Embodiment 14

In some further embodiments of any one of embodiments 1-13, the concentration of non-ionic surfactant in the composition is in the range of about 0.001% to 1.0% (w/v).

Embodiment 15

In some further embodiments of any one of embodiments 1-14, the protein concentration in the composition is about 1 mg/mL to about 250 mg/mL.

Embodiment 16

In some further embodiments of any one of embodiments 1-15, the formulation has a pH of about 4.5 to about 7.5.

Embodiment 17

In some further embodiments of any one of embodiments 1-16, the composition further comprises one or more excipients selected from the group consisting of a stabilizer, a buffer, and a tonicity agent.

Embodiment 18

In some further embodiments of any one of embodiments 1-17, the composition is a pharmaceutical formulation suitable for administration to a subject.

Embodiment 19

In some further embodiments of any one of embodiments 1-18, the polypeptide is a therapeutic polypeptide.

Embodiment 20

In some further embodiments of embodiment 16, the therapeutic polypeptide is a fusion protein, a polyclonal antibody, a monoclonal antibody, a humanized antibody, a human antibody, a chimeric antibody, a multispecific antibody, a glycoengineered antibody, an antibody fragment, an antibody drug conjugate, a THIOMAB™ or a THIOMAB™ drug conjugate.

Embodiment 21

In some further embodiments of any one of embodiments 1-20, the mixed mode anion exchange chromatography material comprises a reversed phase, strong anion exchange polymer.

Embodiment 22

In some further embodiments of any one of embodiments 1-21, the mixed mode anion exchange chromatography material comprises a quaternary amine moiety.

Embodiment 23

In some further embodiments of any one of embodiments 1-22, the mixed mode anion exchange chromatography material comprises a solid support.

Embodiment 24

In some further embodiments of any one of embodiments 1-23, the mixed mode anion exchange chromatography material is contained in a column.

Embodiment 25

In some further embodiments of any one of embodiments 1-24, the mixed mode anion exchange chromatography material is a high performance liquid chromatography (HPLC) material.

Embodiment 26

In some further embodiments of any one of embodiments 1-25, the mixed mode anion exchange chromatography material is an Oasis® MAX chromatography material.

Embodiment 27

In some further embodiments of any one of embodiments 1-26, the non-ionic detergent is quantified by Evaporative Light Scattering (ELSD) or by using a Charged Aerosol Detector (CAD).

Embodiment 28

In some embodiments, there is provided a method for quantifying a non-ionic surfactant in a composition comprising the non-ionic surfactant and a polypeptide, wherein the method comprises the steps of a) applying the composition to a mixed mode cation exchange chromatography material, wherein the composition is loaded onto the chromatography material in a solution comprising a mobile phase A and a mobile phase B, wherein mobile phase A comprises ammonium hydroxide in water and mobile phase B comprises ammonium hydroxide in an organic solvent;

b) eluting the polypeptide from the mixed mode cation exchange chromatography material with a solution comprising mobile phase A and mobile phase B wherein the ratio of mobile phase B to mobile phase A is increased compared to step a);

c) eluting the non-ionic surfactant from the chromatography material with a solution comprising mobile phase A and mobile phase B wherein the ratio of mobile phase B to mobile phase A is increased compared to step c);

d) quantifying the non-ionic surfactant.

Embodiment 29

In some further embodiments of embodiment 28, the organic solvent of mobile phase B is methanol.

Embodiment 30

In some further embodiments of embodiment 28 or 29, the ratio of mobile phase B to mobile phase A in step a) is about 10:90.

Embodiment 31

In some further embodiments of any one of embodiments 28-30, the ratio of mobile phase B to mobile phase A is increased to about 45:55 in step b).

Embodiment 32

In some further embodiments of any one of embodiments 28-31, the ratio of mobile phase B to mobile phase A is increased to about 100:0 in step c).

Embodiment 33

In some further embodiments of any one of embodiments 28-32, mobile phase A comprises about 2% ammonium hydroxide in water.

Embodiment 34

In some further embodiments of any one of embodiments 28-33, mobile phase B comprises about 2% ammonium hydroxide in methanol.

Embodiment 35

In some further embodiments of any one of embodiments 28-34, the flow rate of the chromatography is about 1.4 mL/minute.

Embodiment 36

In some further embodiments of embodiment 35, step b) starts at about 1 min after the chromatography is initiated and ends at about 4.4 min after the chromatography is initiated.

Embodiment 37

In some further embodiments of embodiment 35 or 36, step c) starts at about 4.5 min after the chromatography is initiated and ends at about 7.6 min after the chromatography is initiated.

Embodiment 38

In some further embodiments of any one of embodiments 28-37, the non-ionic surfactant is a polysorbate.

Embodiment 39

In some further embodiments of embodiment 38, the polysorbate is polysorbate 20 or polysorbate 80.

Embodiment 40

In some further embodiments of embodiment 38 or 39, the concentration of polysorbate in the composition is in the range of about 0.001% to 1.0% (w/v).

Embodiment 41

In some further embodiments of embodiment 28, the organic solvent of mobile phase B is acetonitrile.

Embodiment 42

In some further embodiments of embodiment 41, the ratio of mobile phase B to mobile phase A in step a) is about 10:90.

Embodiment 43

In some further embodiments of embodiment 41 or 42, the ratio of mobile phase B to mobile phase A is increased to about 40:60 is step b).

Embodiment 44

In some further embodiments of any one of embodiments 41-43, the ratio of mobile phase B to mobile phase A is increased to 100:0 is step c).

Embodiment 45

In some further embodiments of any one of embodiments 41-44, mobile phase A comprises about 2% ammonium hydroxide in water.

Embodiment 46

In some further embodiments of any one of embodiments 41-45, mobile phase B comprises about 2% ammonium hydroxide in acetonitrile.

Embodiment 47

In some further embodiments of any one of embodiments 41-46, the non-ionic surfactant is a poloxamer.

Embodiment 48

In some further embodiments of embodiment 48, the poloxamer is poloxamer P188.

Embodiment 49

In some further embodiments of embodiment 48 or 49, the concentration of poloxamer in the composition is in the range of about 0.001% to 1.0% (w/v).

Embodiment 50

In some further embodiments of any one of embodiments 28-49, the composition further comprises N-acetyl tryptophan and/or methionine.

Embodiment 51

In some further embodiments of embodiment 50, the concentration of N-acetyl tryptophan in the composition ranges from about 0.1 mM to about 10 mM.

Embodiment 52

In some further embodiments of embodiment 50, the concentration of methionine in the composition ranges from about 0.1 mM to about 100 mM.

Embodiment 53

In some further embodiments of any one of embodiments 28-52, the polypeptide concentration in the composition is about 1 mg/mL to about 250 mg/mL.

Embodiment 54

In some further embodiments of any one of embodiments 28-53, the formulation has a pH of about 4.5 to about 7.5.

Embodiment 55

In some further embodiments of any one of embodiments 28-54, the composition further comprises one or more excipients selected from the group consisting of a stabilizer, a buffer, and a tonicity agent.

Embodiment 56

In some further embodiments of any one of embodiments 28-55, the composition is a pharmaceutical formulation suitable for administration to a subject.

Embodiment 57

In some further embodiments of any one of embodiments 28-56, the polypeptide is a therapeutic polypeptide.

Embodiment 58

In some further embodiments of embodiment 57, the therapeutic protein is a polyclonal antibody, a monoclonal antibody, a humanized antibody, a human antibody, a chimeric antibody, a multispecific antibody, glycoengineered antibody, antibody fragment, an antibody drug conjugate, a THIOMAB™, a THIOMAB™ drug conjugate.

Embodiment 59

In some further embodiments of any one of embodiments 28-58, the mixed mode cation exchange chromatography material comprises a reversed phase, strong cation exchange polymer.

Embodiment 60

In some further embodiments of any one of embodiments 28-59, the mixed mode cation exchange chromatography material comprises a sulfonic acid moiety.

Embodiment 61

In some further embodiments of any one of embodiments 28-60, the mixed mode cation exchange chromatography material comprises a solid support.

Embodiment 62

In some further embodiments of any one of embodiments 28-61, the mixed mode cation exchange chromatography material is contained in a column.

Embodiment 63

In some further embodiments of any one of embodiments 28-62, the mixed mode cation exchange chromatography material is a high performance liquid chromatography (HPLC) material.

Embodiment 64

In some further embodiments of any one of embodiments 28-63, the mixed mode cation exchange chromatography material is an Oasis® MCX chromatography material.

Embodiment 65

In some further embodiments of any one of embodiments 28-64, the non-ionic detergent is quantified by Evaporative Light Scattering (ELSD) or by using a Charged Aerosol Detector (CAD).

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further details of the invention are illustrated by the following non-limiting Examples. The disclosures of all references in the specification are expressly incorporated herein by reference.

EXAMPLES

The examples below are intended to be purely exemplary of the invention and should therefore not be considered to limit the invention in any way. The following examples and detailed description are offered by way of illustration and not by way of limitation.

Materials and Methods for Examples

The following materials and methods were used for the examples unless otherwise noted.

Materials

All mAbs (A1-A20) were manufactured using stable Chinese Hamster Ovary (CHO) cell lines or *Escherichia coli* cells.

Waters Oasis® MAX cartridges (2.1×20 mm, 30 μm particle size, PN #186002052) and Waters Oasis® MCX cartridges (2.1×20 mm, 30 μm particle size, PN #186002051) were purchased from Waters. Polysorbate 20 was obtained from Sigma (P/N T2700-100ML). Formic acid was obtained from Fluka (P/N 94318-250ML-F). HPLC grade glacial acetic acid was obtained from JT Baker (P/N 9515-03). HPLC grade isopropanol (P/N PX1834-1) and methanol (P/N MX0488-1) were obtained from OmniSolv. HPLC grade water was obtained from HoneyWell (Cat. No. 365-4). Ammonia solution, 27-31%, was obtained from Spectrum Chemicals (P/N AM180).

Example 1. Optimization

A more robust solution is needed to eliminate protein interference and yield consistent PS20 quantitation across all HPLC cartridge lots. As a starting point, an antibody drug conjugate (ADC) formulation was used to evaluate the effectiveness of the modifications to the previous methods before assessing other molecules with the methods of the present invention. Objectives of the experiments were to develop a PS assay to allow robust quantification of PS20 across multiple product formulations by minimizing or completely removing interference from proteins, to demonstrate that the assay of the invention improves accuracy and reproducibility of PS20 quantitation compared to previous assays, including robustness across multiple lots of cartridges, and to perform qualification studies to assess accuracy, precision, specificity, repeatability, and intermediate precision of PS20 in select product formulations.

Methods

For all experiments, the following ELSD settings were used:
  Light source intensity (LED) was set to 75%
  Detector gain (PMT) was set to 1

In the HPLC assay, PS20 esters retain to the cartridge while other excipients, protein, and non-esterified PS20 species elute in the flow through or wash steps. Following the wash step, the evaporative light scattering detector (ELSD) is placed in-line using a divert valve and the esterified polysorbate species are eluted with a step gradient of a higher % organic phase. Non-esterified PS20 species make up about 20% of total PS20 composition (Hewitt, D. et al., 2011, *J. Chromatography A*, 1218: 2138-2145). The HPLC-ELSD assay quantifies only PS20 esters, which is sufficient, so long as the lot of PS20 used for preparation of standards contains similar quantities of PS20 esters compared to the PS20 in the sample. Similar PS20 ester composition of the standards can be ensured by an equivalency protocol (Hewitt, D. et al., 2011, *J. Chromatography A*. 1215:156-160), or by matching the lot of PS20 used to make standards to the lot used in the sample.

HPLC-ELSD conditions for the original method, also referred to as Method 0, were as follows: Agilent 1200 HPLC and Varian 380 ELSD; Cartridge was a Waters Oasis MAX on-line cartridge; Mobile Phase A was 2% formic acid in water; Mobile Phase B was 2% formic acid in isopropanol; the flow rate was 1 mL/min; and the injection volume was 20 µL. The gradient used is shown in Table 2.

TABLE 2

| | Method 0 gradient | | |
|---|---|---|---|
| Time (min) | % Mobile Phase A | % Mobile Phase B | Description of Step |
| 0 | 90 | 10 | Load |
| 1 | 80 | 20 | Wash |
| 3.4 | 80 | 20 | Wash |
| 3.5 | 0 | 100 | Elution |

TABLE 2-continued

| | Method 0 gradient | | |
|---|---|---|---|
| Time (min) | % Mobile Phase A | % Mobile Phase B | Description of Step |
| 4.6 | 0 | 100 | Elution |
| 4.7 | 90 | 10 | Equilibrate |
| 6.6 | 90 | 10 | Equilibrate |

The final method, also referred to as Method 1, with modifications from the original in bold/underlined is summarized below. Table 3 shows the LC gradient and Table 4 shows a typical sequence of injections for this assay. HPLC-ELSD conditions were as follows: Agilent 1200 HPLC and Varian 380 ELSD; Cartridge was a Waters Oasis MAX on-line cartridge; Mobile Phase A was 2% formic acid in water or 2% acetic acid in water; Mobile Phase B was 2% formic acid in isopropanol or 2% acetic acid in methanol; the flow rate was 1.25 mL/min; and the injection volume was 20 µL (PS20 concentration range dependent). Although acetic acid was ultimately chosen for the final conditions, initially some qualification and robustness work was done using 2% formic acid in the mobile phase.

TABLE 3

| | Method 1 Gradient | | |
|---|---|---|---|
| Time (min) | % Mobile Phase A | % Mobile Phase B | Description of Step |
| 0 | 90 | 10 | Load |
| 1 | 60 | 40 | Wash |
| 3.4 | 60 | 40 | Wash |
| 3.5 | 0 | 100 | Elution |
| 4.6 | 0 | 100 | Elution |
| 4.7 | 90 | 10 | Equilibrate |
| 6.6 | 90 | 10 | Equilibrate |

TABLE 4

| Typical Sequence | |
|---|---|
| Number of Injections: | Sample: |
| ~5 | Water |
| 2 | Standard 1 |
| 2 | Standard 2 |
| 2 | Standard 3 |
| 1 | Control at target PS20 concentration |
| 2 | PS20 free formulation buffer |
| 2 | PS20 free protein |
| 3 | PS20 at 50% concentration spiked into PS20-free protein |
| 1 | Control at target PS20 concentration |

Method Optimization

1. Initially Attempted Conditions:

During the course of Method 1 development, a number of different experimental conditions were assessed before the final methanol-based mobile phase was selected, with the goal of minimizing the impact of protein interference. These experiments are summarized in Table 5.

TABLE 5

Brief Overview of other attempted solutions (formic acid in the mobile phase unless otherwise stated)

| Attempted Solution | Results |
|---|---|
| Acclaim mixed mode weak anion exchange (WAX) guard cartridge | No way to quickly optimize method for this cartridge - the multi-step gradient method (see next section) might have been a suitable approach, but this technique had not been developed at time of the WAX cartridge evaluation. |
| Pepsin Digest to cleave antibody - test if peptides would be less hydrophobic than protein and reduce protein interference | Pepsin digest was added to sample prep, and no reduction of interference shown |
| Papain digest to cleave drug from linker, and antibody into fragments - test if removal of drug from linker would make ADC protein less hydrophobic and reduce protein interference | Papain digest added to sample prep, and no reduction of interference shown |
| Abbreviated precipitation method - precipitate protein with organic solvent but without removing organic solvent before analysis of supernatant | Observed significant interference when organic solvent remained in the injected sample. |
| POROS ® A Protein A column in-line with Oasis MAX cartridge to tightly retain protein upstream of the PS20 analysis column and eliminate co-elution | PS20 is also retained on the POROS ® A column and cannot be eluted without also eluting protein under conditions tested |
| POROS ® HS CEX column in-line with Oasis ® MAX cartridge to tightly retain protein upstream of the PS20 analysis column and eliminate co-elution | Without changing method protein binds to POROS ® HS column, and PS20 can accurately be analyzed. However, protein cannot be eluted from CEX column with volatile salt - CEX column cannot be regenerated. Method not reproducible. Use of non-volatile salt eluted some protein from the cartridge, but resulted in significant contamination of the detector. |

Method Robustness Experiments

Table 6 and Table 7 describe the products and cartridges used to test method robustness across multiple products.

TABLE 6

Products tested when comparing method accuracy across nine cartridges

| Product (protein concentration) | Target PS20 concentration mg/ml | Tested PS20 concentration (50% of target) | Concentration of PS20 standards used (mg/ml) |
|---|---|---|---|
| A1 ADC (20 mg/mL) | 0.4 | 0.2 | 0.2, 0.4, 0.6 |
| A2 (60 mg/mL) | 0.4 | 0.2 | 0.2, 0.4, 0.6 |
| A3 (18.5 mg/mL) | 0.2 | 0.1 | 0.1, 0.2, 0.3 |
| A4 (21 mg/mL) | 0.1 | 0.05 | 0.05, 0.1, 0.15 |

TABLE 7

Sorbent batch and lots used for method robustness testing

| Cartridge Number | Sorbent Batch # | Cartridge Lot # | HPLC/ELSD system |
|---|---|---|---|
| 1 | 57 | 57333161 | Waters/Varian |
| 2 | 56 | 56331621 | Agilent/Agilent |
| 3 | 57 | 57333161 | Agilent/Agilent |
| 4 | 56 | 56331621 | Agilent/Agilent |
| 5 | 49 | 49321291 | Agilent/Agilent |
| 6 | 9 | T30841 | Agilent/Agilent |
| 7 | 56 | 56330931 | Waters/Varian |
| 8 | 53 | 53323111 | Waters/Varian |
| 9 | 40 | 40390631 | Waters/Varian |
| 11 | 57 | 57333161 | Agilent/Agilent |

1. Method Robustness Across Cartridges:

Table 8 describes the cartridges used to assess method robustness on 12 reference standards (shown in Table 9) using two different cartridges: one that provided acceptable specificity in the Method 0, and another that provided unacceptable specificity in Method 0. The cartridge numbers provided in Table 8 correspond to those numbers provided in Table 7.

TABLE 8

Cartridges used to illustrate method robustness across multiple products

| Cartridge | Performance | Sorbent Batch | Lot # | HPLC/ELSD system |
|---|---|---|---|---|
| 1 | Acceptable | 57 | 57333161 | Agilent/Agilent |
| 5 | Unacceptable | 49 | 49321291 | Agilent/Agilent |

TABLE 9

Reference standard panel (20 µL injections)

| Product | PS20 Standards Used (mg/ml) |
|---|---|
| A5 | 0.20, 0.40, 0.60 |
| A2 | 0.20, 0.40, 0.60 |
| A6 ADC | 0.10, 0.20, 0.30 |
| A7 ADC | 0.10, 0.20, 0.30 |
| A8 ADC | 0.10, 0.20, 0.30 |
| A1 ADC | 0.10, 0.20, 0.30 |
| A9 ADC | 0.10, 0.20, 0.30 |
| A10 ADC | 0.05, 0.10, 0.15 |
| A1 | 0.05, 0.10, 0.15 |
| A10 | 0.05, 0.10, 0.15 |
| A6 | 0.05, 0.10, 0.15 |
| A8 | 0.05, 0.10, 0.15 |

Method Qualification

A method qualification was completed by assessing linearity, accuracy, precision (including intermediate precision), and specificity. Table 10 describes the instruments and cartridges used for intermediate precision.

TABLE 10

Conditions for intermediate precision

| Day | System (HPLC/ELSD) | Cartridge Number (Table 7) | Analyst |
|---|---|---|---|
| 1 | Agilent 1200/Agilent 380 | 1 | 1 |
| 2 | Waters 2695/Varian 380 | 5 | 1 |
| 3 | Agilent 1200/Agilent 380 | 7 | 2 |

Results:
Method Optimization
Multi-Step Gradient Experiments:

During evaluation of different mobile phases, a method was needed to determine whether polysorbate could be completely separated from the other constituents of a typical protein formulation. To perform this analysis, multi-step gradient experiments were performed (FIG. 1). These experiments entailed equilibrating the cartridge with mobile phase consisting of 2% volatile acid (either formic, trifluoroacetic, or acetic acid) in 10% organic solvent, increasing the concentration of organic solvent in the mobile phase in steps of 5%, and holding at each concentration for 1 minute to simulate the wash step of the PS20 quantification method. These 5% steps were repeated until 98% organic (+2% volatile acid) mobile phase was reached. A constant flow rate of 1 mL/min was maintained during this method. These experiments were performed both with a sample of PS20 free protein to determine the mobile phase composition that completely eluted all constituents of the formulation other than PS20, and a PS20 standard in water to determine the mobile phase composition that began to elute PS20 ester species. These two mobile phase organic solvent concentrations were compared to determine if an optimal mobile phase composition could be found that completely separated protein matrix constituents and polysorbate esters. This optimal mobile phase composition would be used during the wash step of the analytical method to remove any protein that may have retained to the cartridge. The multi-step gradient was desirable over a linear gradient for two reasons. First, a linear gradient does not simulate the wash step of the method, and second, it is difficult to determine the discrete mobile phase composition that causes elution of each constituent during a linear gradient.

Figure 2:
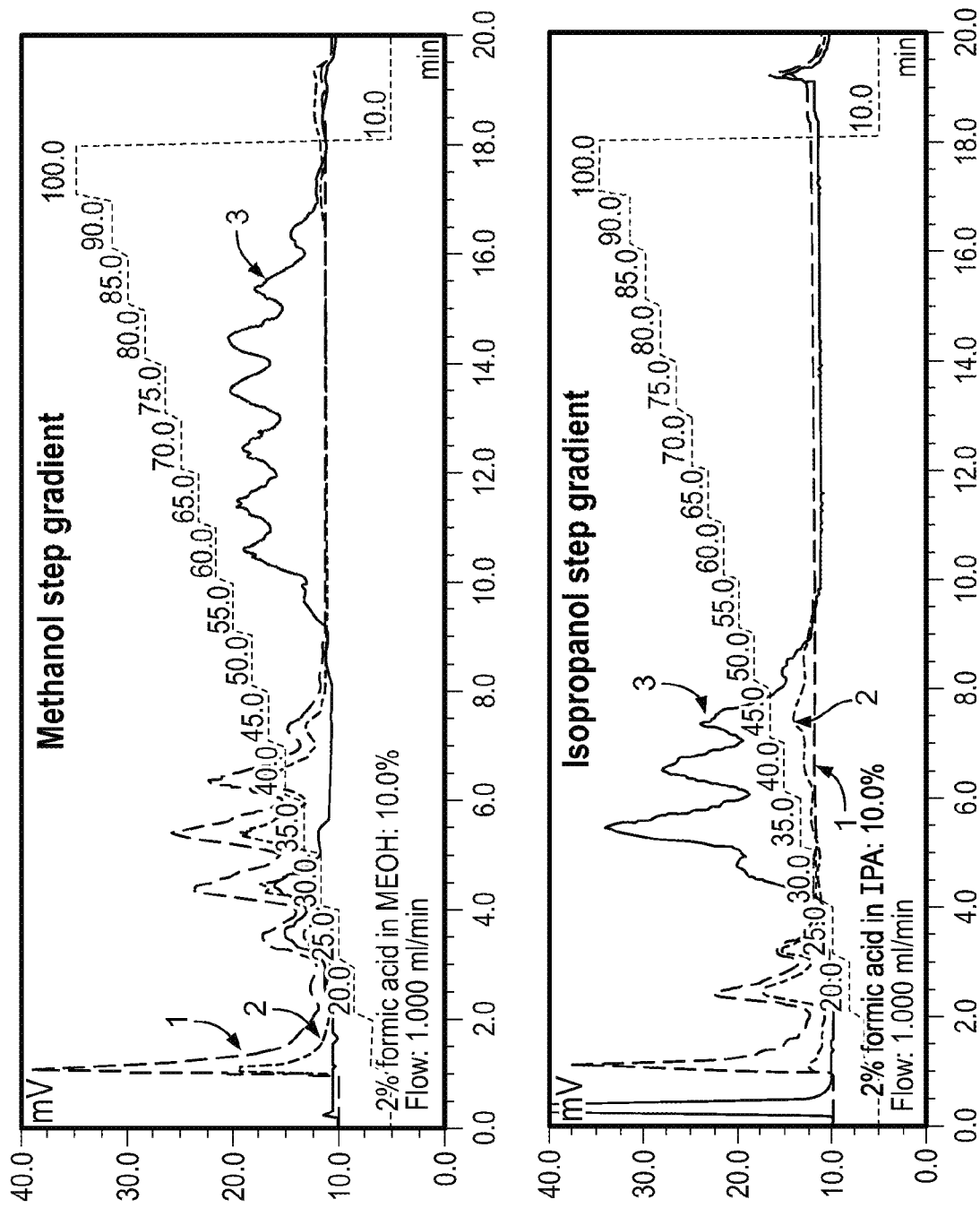
FIG. 2 shows comparison of a methanol multi-step gradient experiment and an isopropanol step gradient experiment (both containing 2% formic acid) on different cartridges. For each overlay, there is PS20-free A1 ADC on a first cartridge (trace 1), PS20-free A1 ADC on a second cartridge (trace 2), and PS20 standard (trace 3).

The multi-step gradient experiments revealed that the optimal methanol concentration to wash protein from cartridge, but retain PS20 ester species, was between 40% and 50% (FIG. 1 and FIG. 2). It is noted that 2% formic acid was still in mobile phase. Both 40% and 50% methanol wash steps were tested and both eliminated protein interference from A1 ADC. The PS20 peak area with 40% methanol wash was on average 38% greater (n=8) than the PS20 peak with 50% methanol wash. Therefore, 40% methanol was chosen to improve PS20 sensitivity. The lower peak area with the 50% wash may indicate that some of the less hydrophobic PS20 esters eluted during the protein wash step, but this possibility was not investigated further.

FIG. 1 shows an example of a typical step gradient overlay (PS20 free product and PS20 standard). This overlay illustrates that all protein is eluted with 40%-50% methanol, and PS20 esters start to elute at 50% methanol. Note that the valve between the HPLC and ELSD is in the divert mode during the first minute of the protein sample to avoid saturation of the detector. The multiple peaks shown in the PS20 standard can most likely be attributed to the different polysorbate species eluting from the cartridge in order of increasing hydrophobicity. The different protein peaks eluting at each step change have not been characterized. This overlay provides a quick way to find the optimal concentration of methanol to wash protein from the cartridge while retaining PS20 esters.

The multi-step gradient experiment was repeated using isopropanol in order to compare the elution of the protein and PS20 regions to methanol. FIG. 2 illustrates the different multi-step elution profiles of methanol and isopropanol for PS20-free A1 ADC and PS20 standard on two different cartridges. The first cartridge (trace 1) had been previously assessed; the first cartridge performed normally with Method 0 (trace 1), however the second cartridge was non-optimal (trace 2). The multi-step gradient experiment with isopropanol showed that the optimal isopropanol concentration in the wash step was 20%. This is consistent with the Method 0, which uses a 20% isopropanol wash between 1 and 3.4 minutes. However, separation of protein and PS20 esters with an isopropanol wash was not consistent across different cartridges and illustrates the variability of protein interference from cartridge to cartridge. On certain cartridges (for example, the cartridge used in FIG. 2), a portion of the protein eluted at the same isopropanol concentration as PS20 esters. This behavior indicated that these particular cartridges would exhibit a significant amount of protein interference when quantifying PS20 with the isopropanol method and this effect was confirmed experimentally.

In contrast to the lower panel of FIG. 2, the upper panel demonstrated that the methanol multi-step gradient on different cartridges consistently eluted all protein by the 40% methanol step, and PS20 esters starting at 50% methanol illustrating a wider separation window of protein region to PS20 region compared to the isopropanol step gradient. This result indicated that using a 40% methanol wash would consistently separate protein from PS20 esters and thus, decrease the variability of PS20 quantitation between cartridges.

The multi-step gradient experiments were used to quickly assess the separation of PS20 and protein across different cartridges and mobile phase compositions (FIG. 1 and FIG. 2).

This approach successfully determined wash conditions for the PS20 assay and could potentially be used to assess the effectiveness of a wash step for the separation of other analytes using different cartridges and mobile phases.

Design of Experiment:

A 2 level full factorial Design of Experiment (DoE) was used to optimize the modified PS20 method containing formic acid. The parameters examined were as follows:
Methanol concentration during wash step (40%, 50%)
Wash duration (1.8 min, 3.0 min)
Flow rate (0.75 mL/min, 1.25 mL/min)
Mass of PS20 loaded (4 µg, 12 µg)

Note that the "Wash" step refers to a part of the HPLC method where the organic concentration is held constant to wash any residual protein from the cartridge. In addition to the 2-level full factorial permutations, midpoints (45% organic wash, 2.4 min wash duration, 1 mL/min flow rate, 8 µg PS20 load) were tested at the beginning and end of the sequence. This experiment was run separately for three samples: PS20 in water, PS20-free A1 ADC, and PS20 spiked in PS20-free A1 ADC. For the PS20-free A1 ADC sample, the PS20 load parameter did not apply.

The criteria used for optimization were as follows:
Minimize protein interference at retention time of PS20 (only for PS20-free A1 ADC sample)

Maximize resolution between protein and PS20 peak (for PS20+A1 ADC sample)

Minimize PS20 peak width at 10% peak height (PS20 in water sample)

Maximize PS20 peak area (PS20 in water sample)

The results of the DoE showed that all conditions tested eliminated protein interference. No protein interference was observed when injecting PS20-free A1 ADC. Similarly, it was found that the resolution between protein and PS20 peaks was greater than 3 for all cases, where resolution was calculated by the following equation (Equation 1):

Resolution $$R = 1.18 * \left| \frac{t_{RefPeak} - t_R}{W_{50\% \, RefPeak} + W_{50\% \, R}} \right| \quad \text{Equation 1}$$

Where t is the retention time of each peak and $W_{50\%}$ is the peak width at 50% height.

Figure 3:
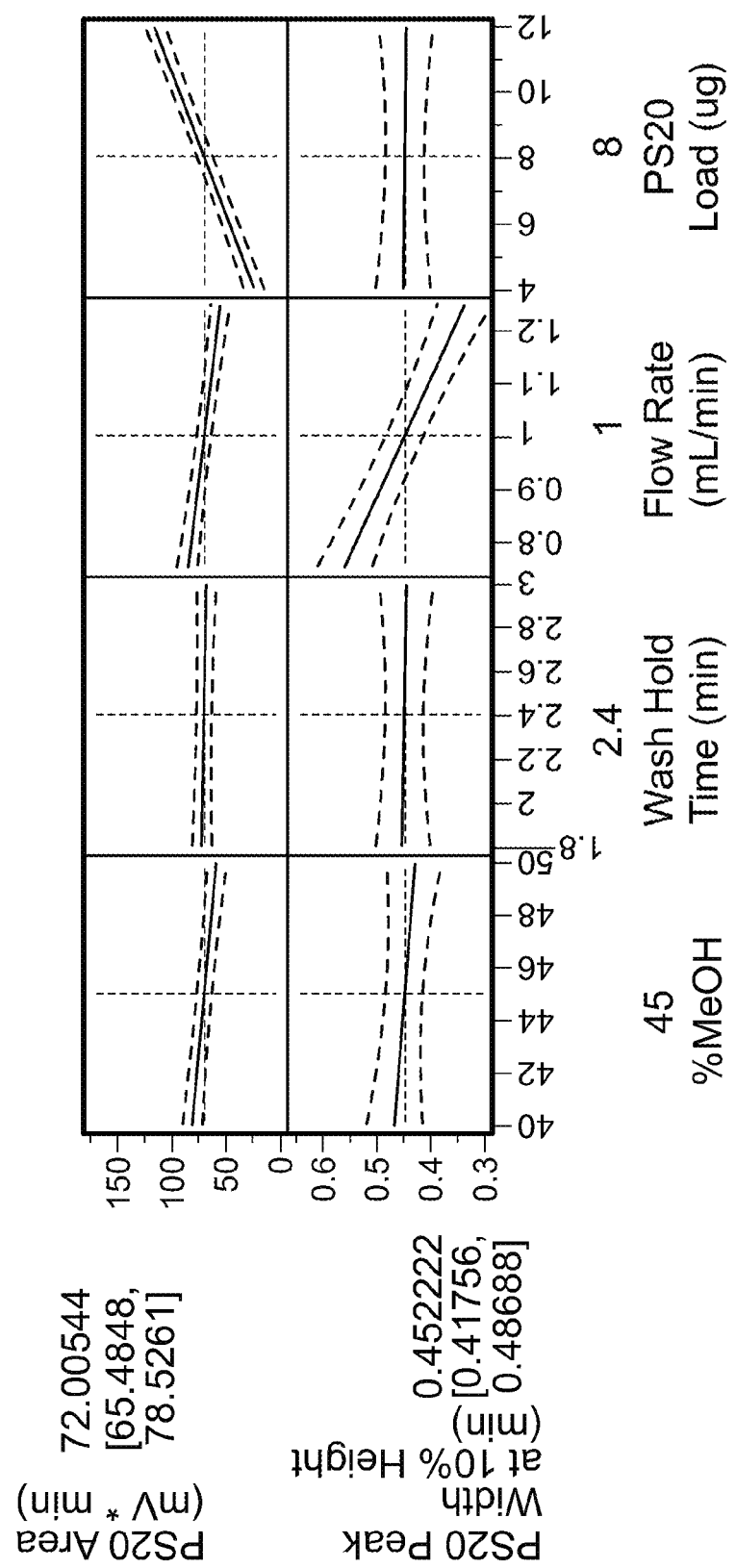
FIG. 3 shows results from the design of experiment method optimization. The solid lines show the directionality according to the statistical model that JMP10 software fits to the data. The dotted lines bounding each solid line indicate error associated with the fit. The slopes of the lines indicate the effect that each factor had on the PS20 peak area and PS20 peak width.

Because no effect on protein interference or resolution was observed for all conditions tested, PS20 peak area and width were optimized for sensitivity and peak shape. A summary of the effect of flow rate, methanol wash concentration and wash time on PS20 peak area and width is illustrated in FIG. 3. Increasing the flow rate decreased PS20 peak width, and decreasing the methanol concentration from 50% to 40% in the wash step increased PS20 peak area by 38%. With a 50% methanol wash, an additional PS20 peak eluted during the wash step, at a retention time later than the non-esterified PS20 species, and it is suspected that this additional peak is due to the earlier elution of the less hydrophobic PS20 esters. The most relevant findings were that PS20 peak area decreases with increasing MeOH concentration in the wash phase, and increasing flow rate decreases peak width.

Figure 4:
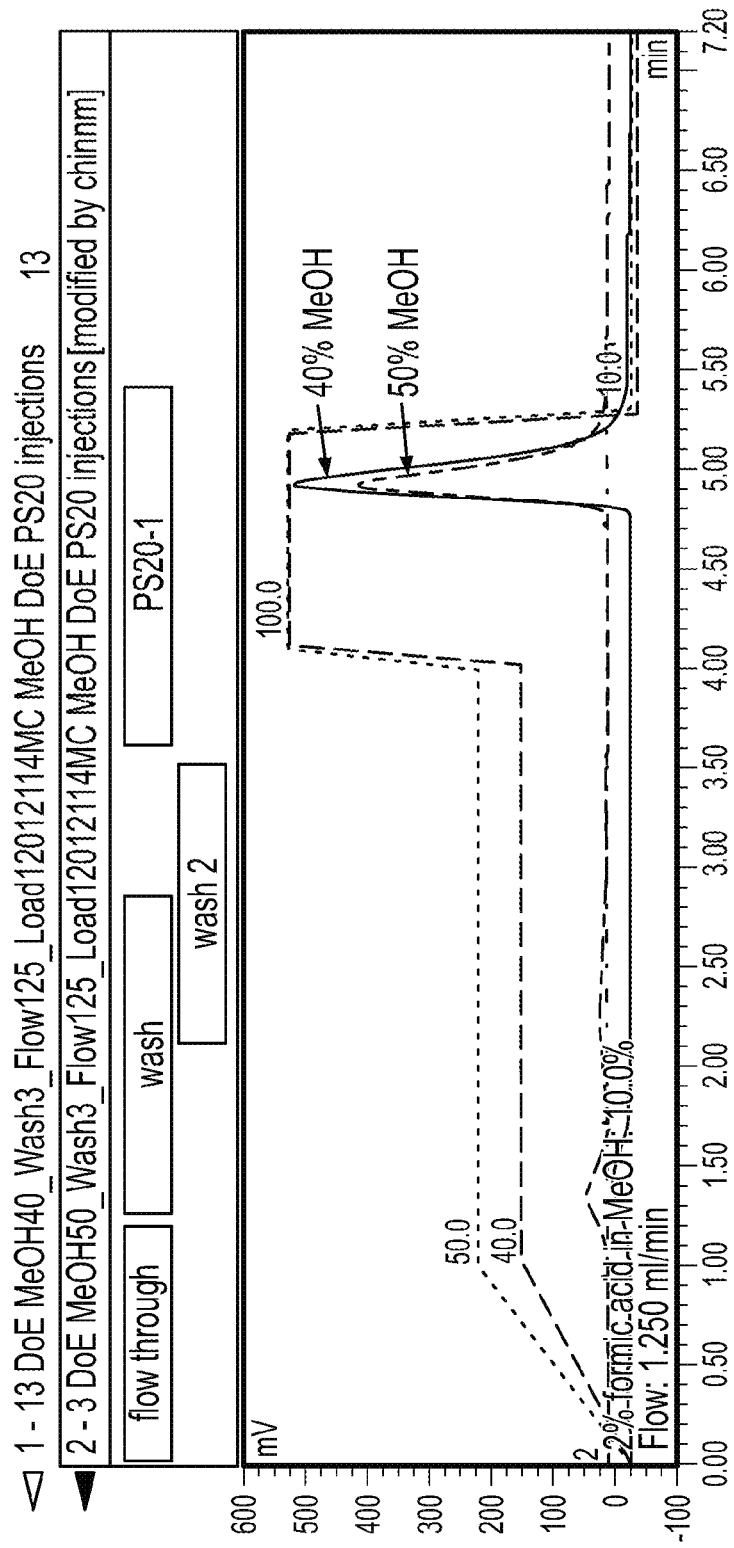
FIG. 4 shows a comparison of PS20 method chromatograms from the DoE method optimization with a 40% MeOH wash and 50% MeOH wash. For these experiments, the flow rate was 1.25 mL/min, 12 µg of PS20 was loaded, and the wash duration was 3 minutes.

A comparison of the 40% and 50% methanol wash is illustrated in FIG. 4. This additional peak from approximately 1.8-3.5 minutes was not present with a 45% methanol wash. It was found the PS20 loads tested had no effect on any of the evaluation criteria. The lowest methanol wash concentration (40%), highest flow rate (1.25 mL/min), and midpoint wash time (2.4 min) were chosen as the optimized parameters for Method 1. The final conditions chosen are shown in Table 3.

Method Robustness Experiments

Once the optimal methanol wash concentration was determined using the multi-step gradient experiments, Method 1 (formic acid+methanol) was tested for improvements relative to Method 0 (formic acid+isopropanol).

Method Robustness Across Products

To further compare the impact of protein interference between Method 1 (formic acid+methanol) and Method 0 (formic acid+isopropanol), PS20 was quantified in 12 different reference standards using 2 cartridges. The cartridges were chosen so that one cartridge (cartridge 1) was deemed acceptable, yielding accurate results with Method 0, and one cartridge (cartridge 5) was deemed unacceptable due to high levels of protein interference with Method 0. The goal of this experiment was to demonstrate the extent by which Method 1 decreased the variability between "acceptable" and "unacceptable" cartridges for multiple products. Consistency of PS20 quantitation using each method was compared on the cartridges and reference standards described in the methods in Table 8 and Table 9, respectively.

The reference standards and their measured PS20 concentrations for each method are listed in Table 11. The accuracy of each method was not calculated because the PS20 concentration listed in the C of A for each reference standard cannot be treated as a theoretical value as is done in the case for spiked samples. Thus, the accuracy of each method cannot be assessed for these reference standards.

TABLE 11

Comparison of Methods: Inter-Cartridge Differences in Measured PS20 Concentrations for Various Reference Standards

| Product | Cartridge number 1 (Table 7) | | Cartridge number 5 (Table 7) | | MeOH/FA* Method absolute | IPA/FA* Method absolute |
|---|---|---|---|---|---|---|
| | MeOH/FA* method (mg/ml) | IPA/FA* method (mg/ml) | MeOH/FA* method (mg/ml) | IPA/FA* method (mg/ml) | % difference in PS20 quantitation | % difference in PS20 quantitation |
| A5 | 0.168 | 0.164 | 0.161 | 0.940 | 3.93% | 474.98% |
| A2 | 0.406 | 0.435 | 0.421 | 0.426 | 3.70% | 2.04% |
| A6 ADC | 0.211 | 0.235 | 0.207 | 0.259 | 1.89% | 10.12% |
| A7 ADC | 0.155 | 0.171 | 0.150 | 0.200 | 3.10% | 16.90% |
| A8 ADC | 0.146 | 0.169 | 0.141 | 0.190 | 3.76% | 12.35% |
| A1 ADC | 0.154 | 0.176 | 0.148 | 0.200 | 3.84% | 13.65% |
| A9 ADC | 0.210 | 0.238 | 0.203 | 0.263 | 2.91% | 10.50% |
| A10 ADC | 0.106 | 0.112 | 0.105 | 0.130 | 1.32% | 16.24% |
| A1 | 0.084 | 0.087 | 0.085 | 0.094 | 1.08% | 8.55% |
| A10 | 0.092 | 0.103 | 0.095 | 0.105 | 3.17% | 2.14% |
| A6 | 0.093 | 0.105 | 0.091 | 0.105 | 2.58% | 0.85% |
| A8 | 0.097 | 0.106 | 0.092 | 0.108 | 4.94% | 2.08% |

*FA = Formic acid
**Absolute % difference in PS20 quantitation for each method is calculated by Equation 2

The data in Table 11 show that the difference in PS20 quantitation between the two cartridges using methanol in the mobile phase is consistently less than 5%. In contrast, the differences in PS20 quantitation when using isopropanol in the mobile phase show a much greater degree of variability between cartridges. Method 0 (formic acid+isopropanol) is more sensitive to cartridge variation. The data in Table 11 show that the use of formic acid+methanol in the mobile phase yields more consistent PS20 quantitation across different cartridges for all products, regardless of how the cartridge performs in Method 0. The absolute % difference in PS20 quantification was calculated using Equation 2:

|100*([Cartridge 5Concentration]−[Cartridge 1 Concentration])/[Cartridge 1 Concentration]|
Equation 2: Absolute % difference in PS20 quantitation Method Robustness Across Cartridges Method 0 and Method 1 (formic acid+methanol) were compared by testing both conditions across nine cartridges with four products. PS20 was spiked into PS20-free protein matrix at 50% of each product's target formulation concentration. This approach represented the lowest PS20 concentration that the assay would need to quantify for each product based on the certificate of analysis acceptance criterion. Standards and controls were prepared by spiking PS20 into water. Two HPLC/ELSD systems (Agilent 1200/Agilent 380 and Waters 2695/Varian 380) were used for testing. The products and cartridges tested are described in detail in the methods section, Table 6 and Table 7, respectively. The cartridges tested were purposely chosen to cover a wide range of lots, age, and historical performance.

A sample of PS20-free product and a PS20-spiked sample were tested to evaluate protein interference with the PS20 assay and the accuracy of PS20 quantitation, respectively. A1 ADC, A2, A3, and A4 samples were tested on 9 cartridges both with formic acid+methanol and with formic acid+isopropanol (Method 0). The average recoveries, relative standard deviations, and ranges across all cartridges using both methods are shown in Table 12.

TABLE 12

Recovery and % RSD of PS20 spiked into PS20-free protein across nine Waters Oasis ® MAX cartridges.

| Sample | | 2% formic acid + MeOH | 2% formic acid + IPA |
|---|---|---|---|
| 0.2 mg/ml PS20 in 20 mg/ml A1 ADC | Average Recovery (%) | 96% | 127% |
| | % RSD | 3.0% | 39.4% |
| | Range (min recovery-max recovery) | 92%-101% | 100%-257% |
| 0.2 mg/ml PS20 in 60 mg/ml A2 | Average Recovery (%) | 103% | 145% |
| | % RSD | 6.7% | 35.6% |
| | Range (min recovery-max recovery) | 86%-110% | 110%-264% |
| 0.05 mg/ml PS20 in 20 mg/ml A4 | Average Recovery (%) | 110% | 168% |
| | % RSD | 10.6% | 64.2% |
| | Range (min recovery-max recovery) | 87%-133% | 98%-449% |
| 0.1 mg/ml PS20 in 18.5 mg/ml A3 | Average Recovery (%) | 122% | 161% |
| | % RSD | 10.6% | 30% |
| | Range (min recovery-max recovery) | 95%-144% | 105%-272% |

Table 12 illustrates that the use of methanol in the mobile phase improves the accuracy of PS20 quantitation (average recoveries are closer to 100%) and reduces variability across cartridges (% RSD are decreased). These data show that using methanol instead of isopropanol in the mobile phase works particularly well for PS20 quantitation in A1 ADC and A2 formulations. Biased over-recoveries of PS20 in the A4 formulation may be due to a decreased signal to noise ratio with only 1 µg of PS20 loaded onto the cartridge (20 µL injection, 0.05 mg/mL PS20 concentration). Increased PS20 loads (50 µL injection) were used during R&D method qualification (formic acid+methanol), and over-recovery was not observed.

Over-recovery of A3 was observed when using methanol in the mobile phase, however, this was still an improvement over the isopropanol mobile phase. It is hypothesized that the low pI of this molecule, which is due, in part, to the increased abundance of sialic acid groups on its gylcans, causes retention of the protein by electrostatic attraction on the positively charged quaternary amine group of the stationary phase.

Further Method Optimization

Selection of Mobile Phase Acid

Experiments were performed using step gradients with the methanol based mobile phase and different mobile phase organic acids to determine the best additive for the method with respect to minimizing protein interference. Methanol step gradient experiments were run with PS20-free A1 ADC and PS20-free A10 ADC using either formic, acetic, or trifluoroacetic acids with ELSD detection to monitor the impact of the acid on the elution of the protein. PS20 standards in water were used to monitor the retention of PS20.

Figure 5:
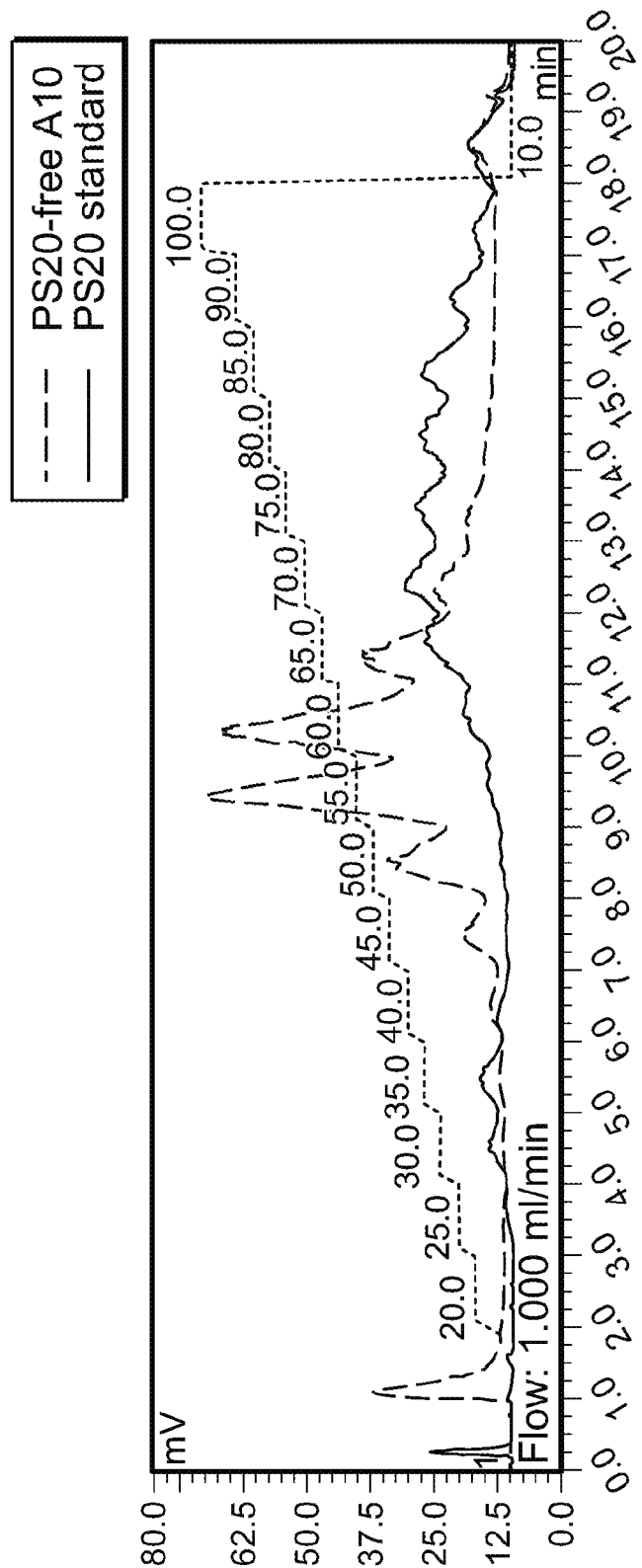
FIG. 5 shows PS20-free 10 mg/ml A10 ADC and 0.6 mg/ml PS20 standard with 0.2% trifluoroacetic acid in the mobile phase.
Figure 6:
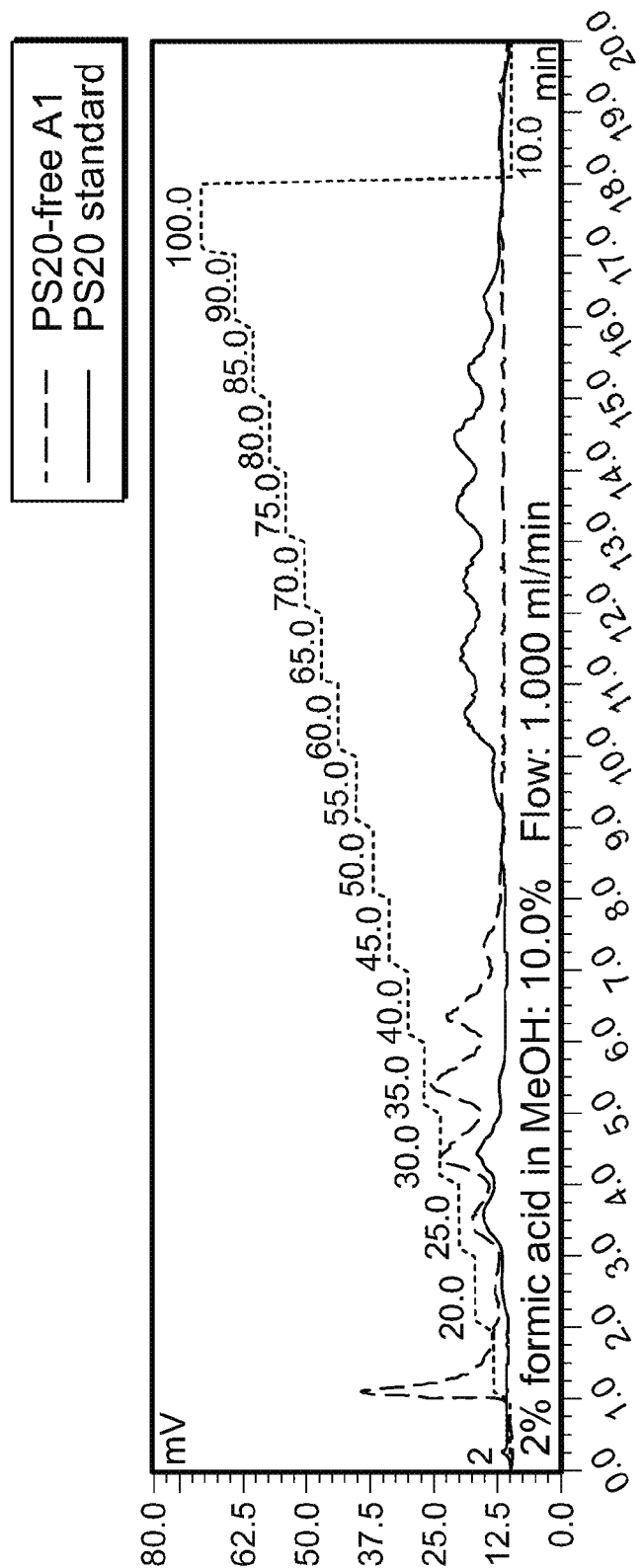
FIG. 6 shows PS20-free 20 mg/ml A1 ADC and 0.6 mg/ml PS20 standard with 2% formic acid in the mobile phase.
Figure 7:
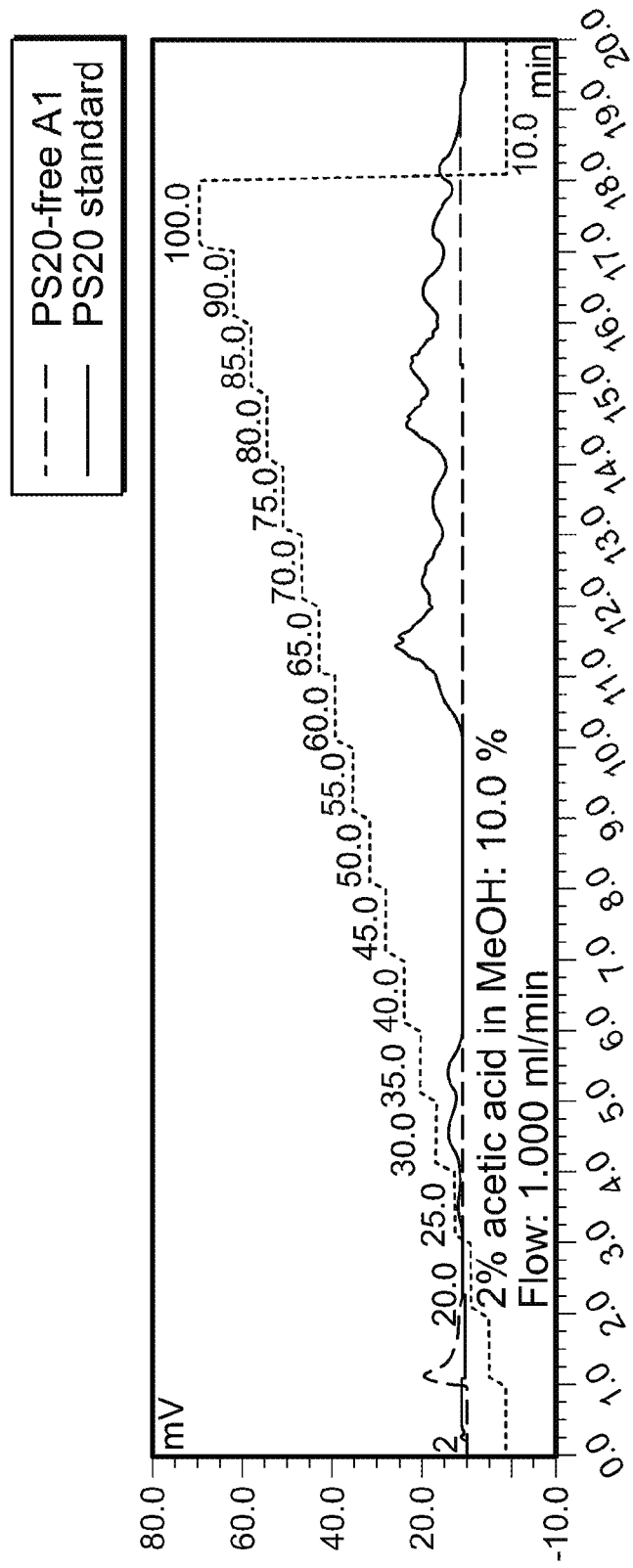
FIG. 7. shows PS20 free 20 mg/ml A1 ADC and 0.7 mg/ml PS20 standard with 2% acetic acid in the mobile phase.

Altering the mobile phase additive has given insight to how protein is retained on the cartridge. FIGS. 5, 6, and 7 show methanol multi-step gradient overlays of PS20-free ADC and PS20 standards with trifluoroacetic acid, formic acid, and acetic acid, respectively, in the mobile phase. For all mobile phase additives, PS20 esters start to elute at 50% methanol. FIG. 5 shows the PS20-free A10 ADC and PS20 standard with trifluoroacetic acid in the mobile phase. The protein elution was completed at approximately 80% methanol. Thus, much of the protein would co-elute with the PS20 esters and interfere with PS20 quantitation. FIG. 6 shows the PS20-free A1 ADC and PS20 standard with formic acid in the mobile phase. The protein eluted completely at about 40% methanol, indicating that a 40% methanol wash would separate protein from polysorbate. This result was consistent with the Method 1 that had been developed. FIG. 7 shows the PS20-free A1 ADC and PS20 standard with acetic acid in the mobile phase. In this case, protein was completely eluted by 15% methanol. This finding indicates that protein could be separated from PS20 esters by any methanol wash ranging from 15%-50%. The ion pairing strength of these mobile phase additives was as follows: trifluoroacetic acid>formic acid>acetic acid. Correspondingly, protein was retained more strongly with increasing strength of the ion pairing agent in the mobile phase, as would be expected if the protein is binding via hydrophobic interactions with the reversed phase stationary phase.

Without being bound by theory, the low pH of the acidic mobile phase creates a net positive charge on the protein. The interaction of the positively charged protein with the positively charged Oasis® MAX stationary phase should be coulombically unfavorable, leading to the protein not being retained by the stationary phase. By contrast, the ion pairing mobile phase additive may interact with the protein to effectively make the protein more hydrophobic (Xindu, G., & Regnier, F. E. *Journal of Chromatography A,* 296:15-30, 1984). This interaction would cause the protein to retain to the cartridge by a hydrophobic interaction mechanism with a strong enough ion-pairing agent (e.g., such as TFA). Reducing the strength of the ion-pairing agent in the mobile phase would subsequently reduce the protein/stationary phase interaction. As the weakest ion-pairing agent of the three tested, acetic acid in the mobile phase appears to significantly reduce protein retention on the cartridge. Thus, acetic acid as a mobile phase additive allowed for a better separation between protein and PS20 esters than the other additives that were tested.

Figure 8:
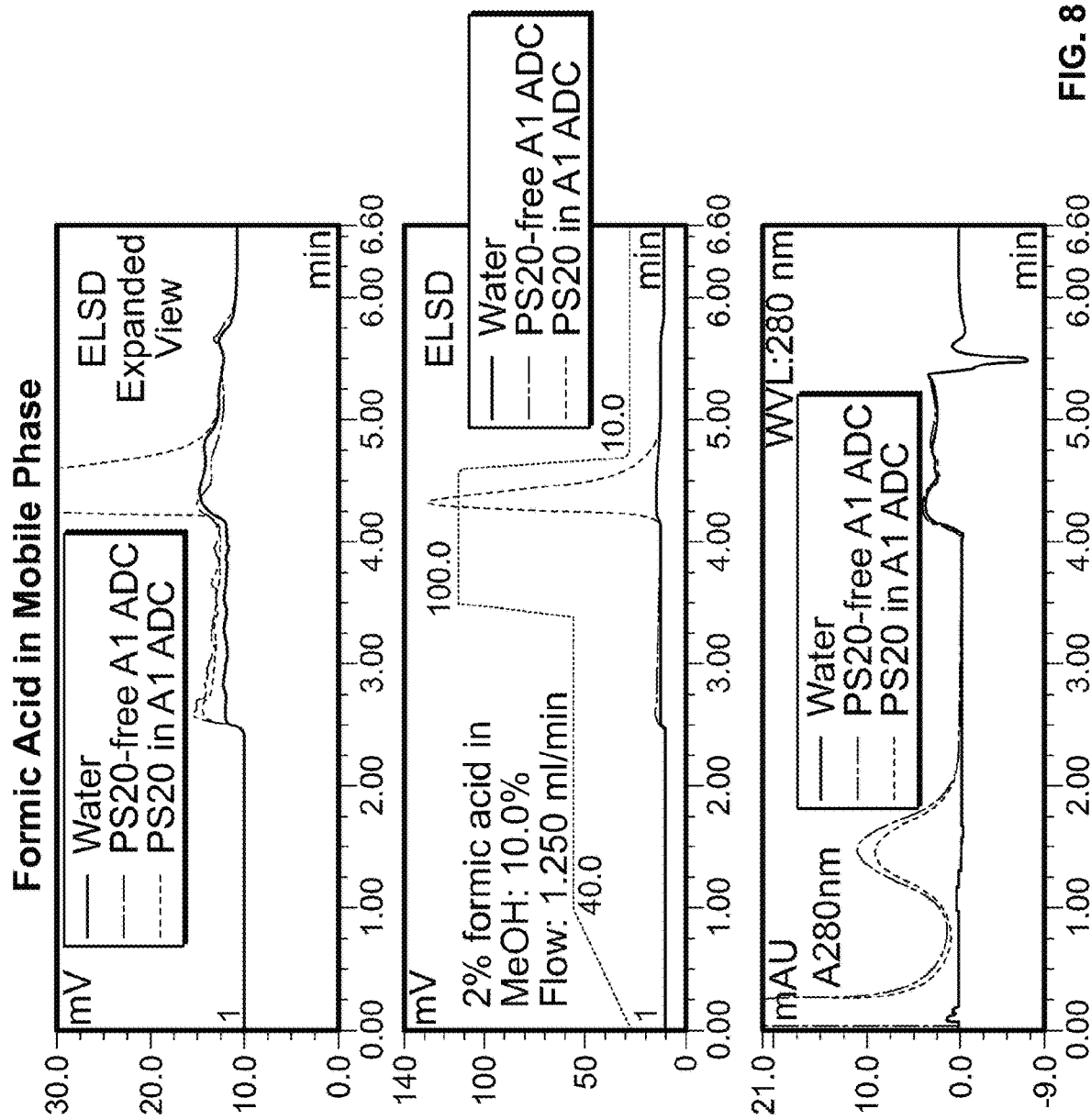
FIG. 8 shows a comparison between formic acid and acetic acid containing mobile phases using the following samples: water (trace 1). PS20-free A1 ADC, 20 mg/mL (trace 2), and 0.2 mg/mL PS20 spiked into A1 ADC, 20 mg/mL (trace 3).
Figure 8:
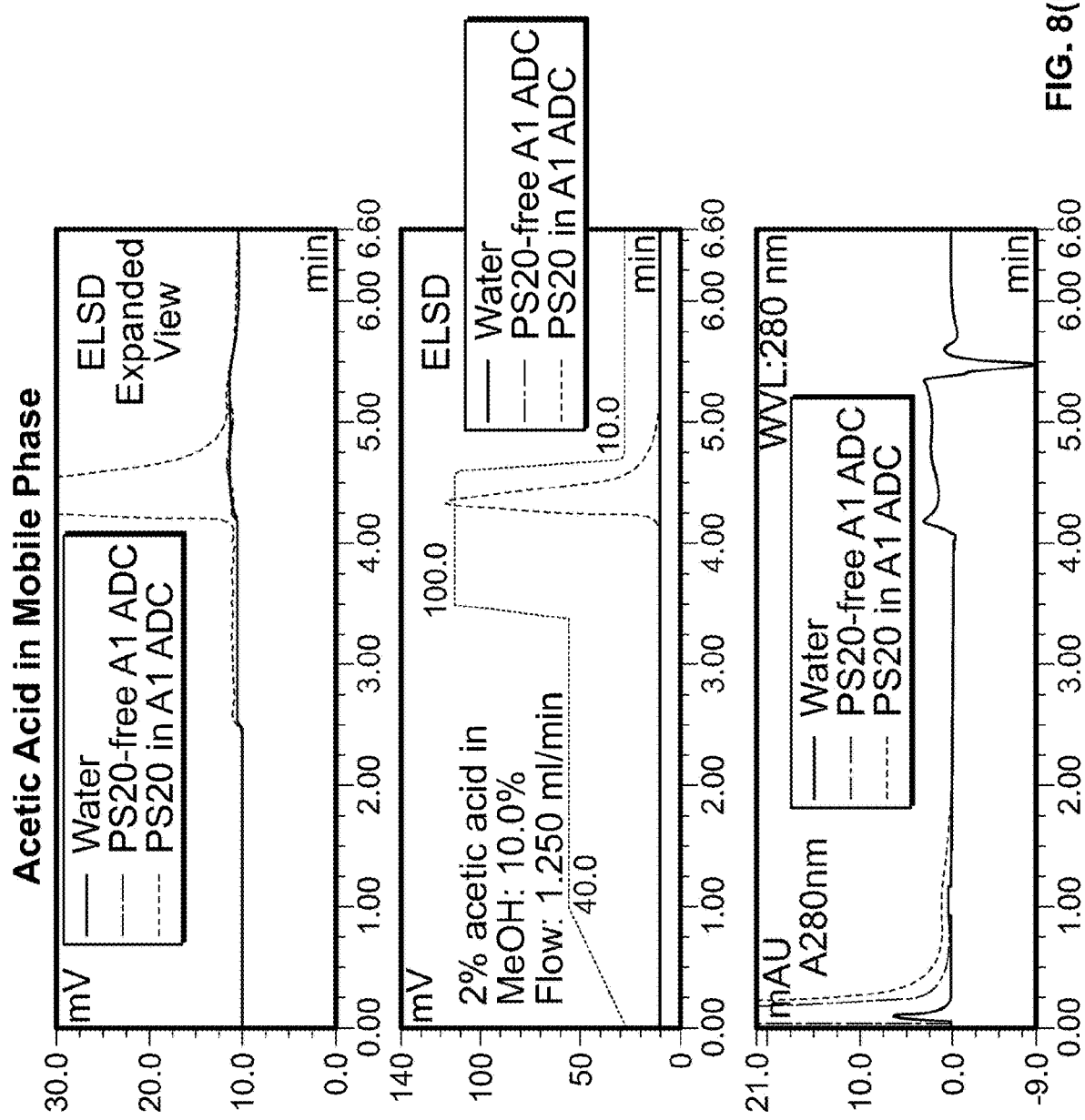

FIG. 8 shows a comparison of analytical method performance between acetic and formic acid as mobile phase additives. As seen in FIG. 8, a very small increase (~3 mV) in baseline is observed for protein injections compared to the water injection with formic acid as the mobile phase additive. Although this interference is considered minimal, it is observed that a protein matrix injection does not increase the ELSD baseline when acetic acid is the additive in the mobile phase. Furthermore, the absorbance at 280 nm was monitored for diagnostic purposes in order to observe the protein retention and clearance. When using acetic acid in the mobile phase, the protein is almost entirely cleared in the void volume, whereas the protein is weakly retained on the cartridge when formic acid is used as the additive, and elutes at a retention time between 1-2 minutes. Because the LC flow is diverted into the ELSD at 2.4 minutes, there is an increased chance that the protein will not be completely cleared when formic acid is the additive, allowing for some protein interference.

Figure 9:
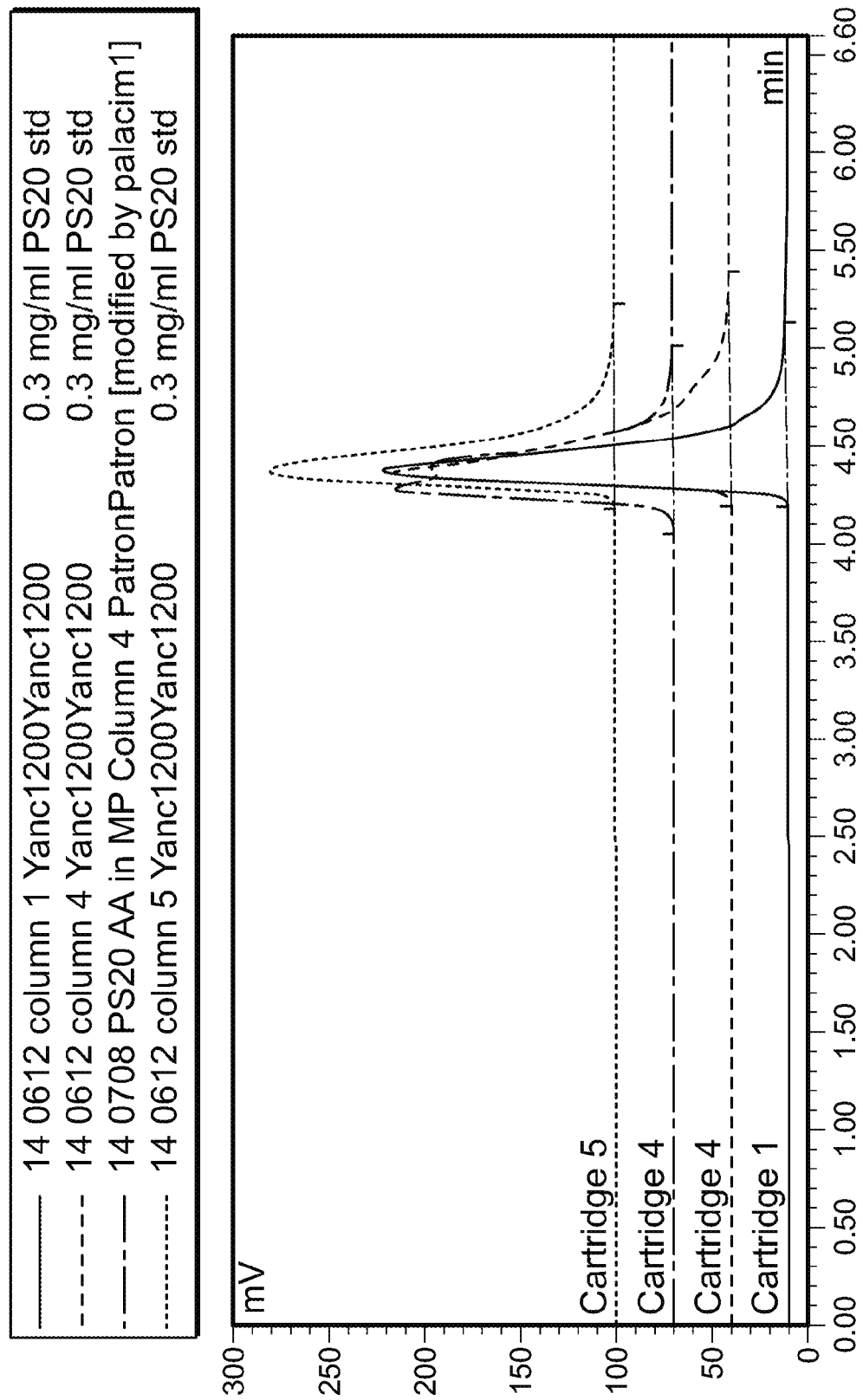
FIG. 9 shows various profiles of the PS20 standard run on different OASIS® MAX cartridges using elution with methanol/acetic acid. Typical profile (trace 1), peak with tailing (trace 2), peak showing splitting (trace 3), and peak with slight tailing (trace 4). This variability in profile does not affect the quantitation of the standards, controls or protein samples.

Representative chromatograms using different cartridges (refer to Table 7 for lot specific details) from the acetic acid+methanol elution conditions are shown in FIG. 9. Although the peak shape from cartridge 1 is typical (trace 1), these data demonstrate that the PS20 peak profiles can vary across the different cartridges. On certain cartridges, such as cartridge 4 (trace 2), the PS20 peak tends to tail; with further usage of this cartridge, the tailing can eventually become PS20 peak splitting (trace 3). This behavior has not been common, as cartridge 2 (data not shown) and 4 are the only cartridges tested that have exhibited peak splitting throughout method development. In others cases, such as cartridge 5 (trace 4), there is slight peak tailing observed. Incidentally, the cartridges which show increased peak tailing and peak splitting with the methanol mobile phase are also subject to increased levels of protein interference when isopropanol is used in the mobile phase. This finding may indicate that the cartridges that show increased peak tailing retain hydrophobic molecules more strongly. Regardless of the peak shape, PS20 quantitation and integration processing methods were unaffected.

A final Method 1 for PS20 quantification will be implemented with 2% acetic acid in the mobile phase, as it was shown to improve separation of protein and PS20 relative to formic acid on the Oasis® MAX cartridge (FIG. 9).

Method Qualification

After using step gradient experiments to optimize the wash step and performing method robustness experiments, it was found that using 2% acetic acid in place of 2% formic acid in the mobile phase improved separation of protein and PS20 esters. Therefore, this example describes qualification experiments performed with both a formic acid/methanol mobile phase (from initial method development) and an acetic acid/methanol mobile phase (final method).

The method used to qualify the assay was consistent with the HPLC-ELSD assay in Method 0 except for the following parameters:

Flow Rate=1.25 mL/min

Mobile phase A=2% formic acid in water OR 2% acetic acid in water

Mobile phase B=2% formic acid in methanol OR 2% acetic acid in methanol

The gradient in Table 3 was used

Injection volume was adjusted depending on the concentration of PS20 in the formulation to result in similar loads onto the cartridge. See Table 13.

The qualification study was performed with PS20-free A1 ADC, PS20-free A1. PS20-free A4, PS20-free A5, and PS20-free A11. A known amount of PS20 was spiked into each sample in order to determine the accuracy of the assay. The assay (refer to Table 13 for additive used per product) was evaluated for accuracy, precision, specificity, repeatability, and intermediate precision.

Accuracy and Precision:

PS20 (Lot MKBL2646V) was spiked into PS20-free protein samples at known concentrations (product dependent; see Table 13) in order to determine the accuracy of the assay. This experiment was performed using a high concentration PS20 stock solution (25 mg/ml), so that dilution of the protein by spiking was minimized. For each concentration, samples spiked with PS20 were injected in triplicate unless otherwise noted. PS20 recovery was used to determine the accuracy of PS20 quantitation. The range of average recoveries was used to determine precision. Linearity over the specified range (Table 13) was also determined. Table 13 shows the concentrations of PS20 spiked into each product. Note that 2 ranges of DNIB0600S were used to cover the worst case (i.e. lowest) PS20 concentration (0.4 mg/ml) and a higher concentration (0.7 mg/ml) prior to the Phase III formulation lock. Two separate ranges were used because the ELSD settings would need to be altered in order to accurately quantify PS20 over a range of 0.2 mg/ml-1 mg/ml PS20. For each range, the injection volume was altered, rather than changing the detector settings. Following formulation lock, another assessment was performed for the final formulation (1.2 mg/mL PS20) and higher protein concentration (40 mg/mL) using a single range.

TABLE 13

Products assessed during method qualification

| Product (Protein concentration) | PS20 Concentration Range (mg/mL) | Injection Volume (μL) | PS20 Load Range (μg) | Qualification w/formic or acetic acid |
|---|---|---|---|---|
| A1 ADC (20 mg/mL) | 0.20-0.60 | 20 | 4.0-12.0 | Formic |
| A1 ADC (20 mg/mL) | 0.50-1.00 | 10 | 5.0-10.0 | Formic |
| A1 ADC (40 mg/mL) | 0.60-1.60 | 10 | 6.0-16.0 | Acetic |
| A1 (20 mg/mL) | 0.025-0.30 | 50 | 1.3-15.0 | Formic |
| A1 (50 mg/mL) | 0.025-0.30 | 50 | 1.3-15.0 | Acetic |
| A4 (21 mg/mL) | 0.025-0.30 | 50 | 1.3-15.0 | Formic |
| A5 (60 mg/mL) | 0.20-0.60 | 20 | 4.0-12.0 | Acetic |
| A11 (83 mg/mL) | 0.10-0.30 | 25 | 2.5-7.5 | Acetic |
| A4 TAC (65 mg/mL)* | 0.10-0.30 | 50 | 5.0-15.0 | Acetic |
| A12/A13 (73 mg/mL)* | 0.10-0.30 | 50 | 5.0-15.0 | Acetic |
| A14/A15 (150 mg/mL)* | 0.15-0.45 | 20 | 3.0-9.0 | Acetic |

*Duplicate injections at three PS20 concentrations

Standards for each set of concentrations were made from PS20 in water. Standards were injected in duplicate prior to protein samples. Every 6th injection of test article was bracketed with a PS20 in water control sample. The PS20 control was prepared separately from the standards (from PS20 Lot MKBJ7237V). Concentrations of standards were chosen to cover the range of PS20 concentrations that were spiked into each PS20-free protein product.

Concentrations of PS20 controls were chosen based on possible or actual PS20 concentrations for each product's drug substance formulation. Table 14 shows the concentrations of the standard and control PS20 samples used for the analysis over each concentration range.

TABLE 14

PS20 concentrations used for standard curve and control for each product

| Product (protein concentration) | PS20 concentration (mg/mL) | | | |
|---|---|---|---|---|
| | Standard 1 | Standard 2 | Standard 3 | Control |
| A1 ADC (20 mg/mL)* | 0.10 | 0.40 | 0.70 | 0.40 |
| A1 ADC (20 mg/mL)* | 0.50 | 0.75 | 1.00 | 0.70 |
| A1 ADC (40 mg/mL)** | 0.60 | 1.20 | 1.60 | 1.20 |
| A1 (20 mg/mL) | 0.05 | 0.15 | 0.30 | 0.10 |
| A1 (50 mg/mL) | 0.05 | 0.15 | 0.30 | 0.10 |
| A4 (21 mg/mL) | 0.05 | 0.15 | 0.30 | 0.10 |
| A5 (60 mg/mL) | 0.20 | 0.40 | 0.60 | 0.40 |
| A11 (83 mg/mL) | 0.10 | 0.20 | 0.30 | 0.20 |
| A4 TAC (65 mg/mL) | 0.10 | 0.20 | 0.30 | 0.10 |
| A12/A13 (73 mg/mL) | 0.10 | 0.20 | 0.30 | 0.10 |
| A14/A15 (150 mg/mL) | 0.15 | 0.30 | 0.45 | 0.30 |

The accuracy and precision of Method 1 was tested for multiple products. Acceptable results for accuracy should show that the average recovery at each spiked concentration is 80%-120%. Results for each product are shown in Table 15.

TABLE 15

Average % Recovery and Range

| Product (mg/mL) | Mobile Phase acid (formic or acetic acid) | Inj. Vol. (µL) | PS20 conc. range (mg/mL) | No. of Replicates per conc. (n) | Average % Recovery across all PS20 concs. | % Recovery Range |
|---|---|---|---|---|---|---|
| A1 ADC (20) | Formic | 20 | 0.20-0.60 | 3 | 101.6 | 95.7-106.2 |
| A1 ADC (20) | Formic | 10 | 0.50-1.00 | 3 | 101.2 | 97.7-108.3 |
| A1 ADC (40) | Acetic | 10 | 0.60-1.60 | 3 | 105.0 | 101.3-106.4 |
| A1 (20) | Formic | 50 | 0.025-0.30 | 3 | 92.5 | 86.4-97.3 |
| A1 (50) | Acetic | 50 | 0.025-0.30 | 3 | 106.1 | 100.0-114.0 |
| A4 (21) | Formic | 50 | 0.025-0.30 | 3 | 93.1 | 82.4-99.2 |
| A5 (60) | Acetic | 20 | 0.20-0.60 | 2 | 102.5 | 100.5-105.7 |
| A11 (83) | Acetic | 25 | 0.10-0.30 | 2 | 108.3 | 100.5-114.8 |
| A4 TAC (65) | Acetic | 50 | 0.10-0.30 | 2 | 107.4 | 103.0-112.8 |
| A12/A13 (73) | Acetic | 50 | 0.10-0.30 | 2 | 104.7 | 99.8-110.5 |
| A14/A15 (150) | Acetic | 20 | 0.15-0.45 | 2 | 101.5 | 95.1-110.4 |

As shown in Table 15, the average % Recovery for all products tested, at all concentrations, met the acceptance criteria (80%-120%) and ranged from 82.4% to 114.8%. Therefore, this assay demonstrated acceptable accuracy and precision for all products over the PS20 ranges tested.

Because injection volumes varied, assay range can also be expressed in terms of PS20 mass (rather than by PS20 concentration in the formulation). These results showed that 1.25 (0.025 µg/µL×50 µL)–16 µg (1.60 µg/µL×10 µL) of PS20 can be loaded onto the cartridge and quantified accurately.

Linearity

Linearity was evaluated by determining the Pearson's correlation coefficient (r)>0.99. These values are shown in Table 16 for each range of PS20 concentrations.

TABLE 16

Pearson's Correlation Coefficient over PS20 concentration ranges

| Product | Mobile Phase acid (formic or acetic acid) | PS20 Conc. Range (mg/ml) | Pearson's correlation coefficient (r) |
|---|---|---|---|
| A1 ADC | Formic | 0.20-0.60 | 0.997 |
| A1 ADC | Formic | 0.50-1.00 | 0.995 |
| A1 ADC | Acetic | 0.60-1.60 | 1.000 |
| A1 | Formic | 0.025-0.30 | 1.000 |
| A1 | Acetic | 0.025-0.30 | 1.000 |
| A4 | Formic | 0.025-0.30 | 1.000 |
| A5 | Acetic | 0.20-0.60 | 0.999 |
| A11 | Acetic | 0.10-0.30 | 0.995 |
| A4 TAC | Acetic | 0.10-0.30 | 1.000 |
| A12/A13 | Acetic | 0.10-0.30 | 1.000 |
| A14/A15 | Acetic | 0.15-0.45 | 0.994 |

All values of Pearson's correlation coefficient were ≥0.99 for the PS20 ranges tested. Therefore, linearity was acceptable for this assay across multiple products.

Figure 10:
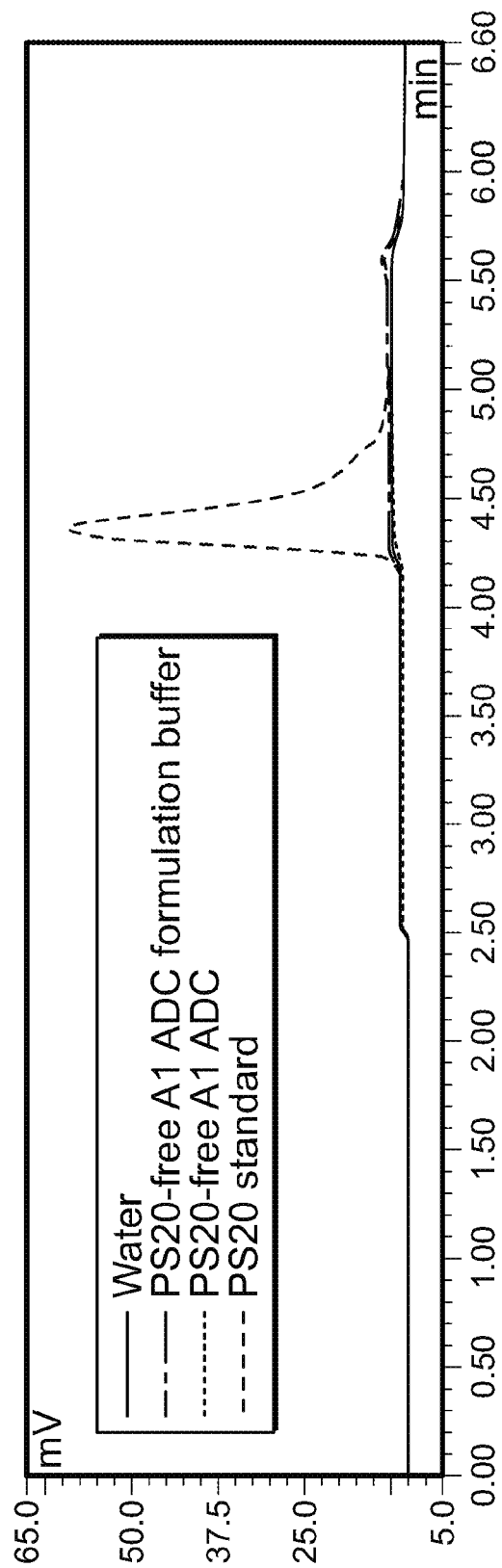
FIG. 10 shows the MeOH/Acetic Acid method. Typical 20 µL injections of water (trace 1), PS20-free A1 ADC formulation buffer (trace 2), PS20-free A1 ADC (trace 3), and the lowest PS20 standard at 0.1 mg/mL (trace 4).

Specificity:

Specificity was determined for nine products by confirming that injections of PS20-free formulation buffer and PS20-free product would not contribute to the PS20 peak. The injections for the formulation buffer and PS20-free protein sample were performed in duplicate. The peak areas in PS20 free formulation buffer and PS20 free protein matrices were compared to the response of a standard at 50% of each product's target PS20 concentration. The acceptance criteria are fulfilled if the peak areas in the PS20 free samples are ≤10% of the peak area in the lowest standard. When there was some protein interference visible in the PS20 region, the following equation was used to derive a numerical estimate of the specificity:

Specificity=(Area of PS20-free protein/Area of 50% of PS20 specification)*100   Equation 3: Specificity Calculation As shown in FIG. 10 (with A1 ADC), neither the PS20-free formulation buffer nor the PS20-free protein sample interferes with the PS20 peak. Specificity values for all other products are given in Table 17. Because the target PS20 concentration was chosen for A1 ADC after the formic acid method qualification experiments, a lower target PS20 concentration was used to calculate specificity for the samples (denoted with an asterisk). Using a lower target PS20 concentration will result in a higher specificity value, but all values reported are still well under 10%.

TABLE 17

Specificity

| Product | Mobile Phase acid (formic or acetic acid) | Target PS20 Concentration (mg/mL) | Specificity (%) |
|---|---|---|---|
| A1 ADC | Formic | 1.2 | 0.7 |
| A1 ADC | Formic | 1.2 | 0.5 |
| A1 ADC | Acetic | 1.2 | N/A |
| A1 | Formic | 0.1 | 1.1 |
| A1 | Acetic | 0.1 | 8.6 |
| A4 | Formic | 0.1 | 1.6 |
| A5 | Acetic | 0.4 | 1.5 |
| A11 | Acetic | 0.2 | 5.4 |
| A4 TAC | Acetic | 0.2 | 2.5 |
| A12/A13 | Acetic | 0.2 | 8.2 |
| A14/A15 | Acetic | 0.3 | 5.6 |

N/A: PS20-free protein injection is the same as water injection.

Repeatability:

Samples containing 0.4 mg/mL PS20 spiked into 20 mg/mL PS20-free A1 ADC and 0.3 mg/mL PS20 spiked into 150 mg/mL PS20-free A14/A15 were injected 6 times. The PS20 peak areas for these injections and corresponding concentrations are shown in Table 18. The % RSD for the area and concentrations for the repeat injections demonstrated acceptable injection repeatability.

TABLE 18

Injection Repeatability

| Injection # | 0.4 mg/mL PS20 in A1 ADC (formic acid) Area (mV * min) | 0.3 mg/mL PS20 in A14/A15 bispecific mAb (acetic acid) Area (mV * min) |
|---|---|---|
| 1 | 73.64 | 54.90 |
| 2 | 75.17 | 55.10 |
| 3 | 74.30 | 55.00 |
| 4 | 73.35 | 54.60 |
| 5 | 73.65 | 53.70 |
| 6 | 73.81 | 54.20 |
| Mean | 73.99 | 54.58 |
| SD | 0.66 | 0.54 |
| % RSD | 0.89% | 0.99% |

The % RSD for the area and concentrations for the repeat injections demonstrated the assay's repeatability.

Intermediate Precision:

Intermediate precision (formic acid+methanol only) was determined for three cartridges, on two different HPLC-ELSD systems, with 3 different PS20 standard and buffer preparations, and by 2 different analysts. For each sample on each day, the mean of 2 injections is reported in Table 19. The mean and standard deviation of all injections are reported at the bottom of Table 19. Samples injected were 0.4 mg/ml PS20 spiked into 20 mg/mL PS20-free A1 ADC, 0.1 mg/ml PS20 spiked into PS20-free A1, and 0.1 mg/ml PS20 spiked into PS20-free A4. Conditions for each day are shown in Table 10 in the methods section. Intermediate precision was done using formic acid before acetic acid was finalized as the modifier for Method 1. Intermediate precision was not repeated with acetic acid in the mobile phase since all other parameters of the qualification were comparable between the two modifiers and because the sample preparation was identical for either condition.

The % RSD for all three samples across the 3 days testing intermediate precision was less than 10%. These results show that the assay was consistent for various cartridges, sample preparations, HPLC-ELSD systems, and analysts. There was a slightly lower trend noticed for the concentrations on Day 2.

TABLE 19

Intermediate Precision (all experiments performed with formic acid)

| Day (instrument no.) | Cartridge number (from Table 7) | A1 ADC: 0.4 mg/ml PS20 | A1: 0.1 mg/ml PS20 | A4: 0.1 mg/ml PS20 |
|---|---|---|---|---|
| 1 (instrument 1) | 1 | 0.418 | 0.097 | 0.099 |
| 2 (instrument 2) | 5 | 0.389 | 0.087 | 0.092 |
| 3 (instrument 1) | 7 | 0.411 | 0.100 | 0.097 |
| Mean | | 0.406 | 0.095 | 0.096 |
| SD | | 0.0138 | 0.0073 | 0.0058 |
| % RSD | | 3.39% | 7.74% | 6.04% |

Conclusions:

The following modifications were made to ELSD Method 0 assay during development of the new version of the method:

Mobile phase B switched from isopropanol to methanol
Additive changed from 2% formic acid to 2% acetic acid
Concentration of organic in wash step from 1-3.4 minutes switched from 20% to 40% mobile phase B
Flow rate changed from 1.00 mL/min to 1.25 mL/min Collectively, these modifications significantly reduced both protein interference and cartridge to cartridge performance variability. Changing mobile phase B organic from isopropanol to methanol (FIG. 2) improved the separation of protein and PS20 compared to previous conditions. The results from both methanol/FA and isopropanol/FA comparison experiments (Table 11 and Table 12) showed that Method 1 significantly improved PS20 quantitation and cartridge-to-cartridge reproducibility. Replacing formic acid with acetic acid (FIG. 8) as the mobile phase additive further reduced retention of protein to the cartridge. Furthermore, changing the organic wash step from 20% to 40% significantly minimized protein interference.

The results from the qualification of this modified assay for multiple products showed that this assay was suitable for quantifying PS20 across a variety of molecule formats, protein concentrations, and PS20 concentrations, thus indicating that Method 1 is a candidate for a platform PS20 quantification assay.

Example 2. Development of an HPLC-ELSD Polysorbate 20 Quantitation Method for N-Acetyl Tryptophan-Containing Formulations During the course of assessing the PS20 method described above (Method 1), it was discovered that N-acetyl tryptophan (NAT) significantly interferes with polysorbate 20 (PS20) when present as an additional excipient in the formulation. Although Method 1 of Example 1 showed minimized protein interference as well as decreased variability across cartridges for the majority of the formulations that have been tested, N-acetyl tryptophan was retained on the cartridge under the conditions of this method and eluted at the same retention time as PS20. Without being bound by theory, NAT may be retained on the cartridge due to the presence of a carboxylate group on the molecule that interacts with the mixed-mode anion exchange resin (MAX) cartridge used in Method 1.

As described below, Method 1 was modified to eliminate NAT interference by:

1) changing the cartridge from the MAX resin to a mixed-mode cation exchange resin (MCX)
2) changing the mobile phase additive from acetic acid to ammonium hydroxide Additionally, further optimization of the method, also referred to as Method 2, was performed by increasing the organic wash from 40% B to 45% B and increasing the wash step time and elution step time by +1 minute and +2 minutes, respectively. The development of the conditions to allow PS20 quantitation for projects formulated with NAT is described in this example. The new conditions were evaluated using three products containing NAT in the formulation, by assessing Method 2 for accuracy, precision, linearity, specificity, repeatability and robustness.

Previous LC-ELSD assays which used the MAX cartridge observed higher protein interference with low pI molecules. Therefore, assessment of low pI molecules was performed on both Method 1 and Method 2 to determine which method is more suitable for correct PS20 quantification.

Materials

HPLC/ELSD system: e.g., Agilent 1200 HPLC—Varian 380 ELSD
Polysorbate 20: Sigma P/N: T2700-100ML
HPLC grade Glacial Acetic Acid: JT Baker
Strong Ammonia Solution, 27-31%: Spectrum Chemicals
HPLC grade Water HoneyWell
HPLC grade Methanol: OmniSolv
Waters Oasis® MAX cartridge 2.1×20 mm, 30 μm particle size
Waters Oasis® MCX cartridge 2.1×20 mm, 30 μm particle size (Table 20)
NAT-containing products (Table 21)

TABLE 20

MCX Cartridges used during Method 2 development

| Cartridge Number | Sorbent Batch # | Cartridge Lot # |
|---|---|---|
| 1 | 0093 | 0093333511 |
| 2 | 0093 | 0093341961 |
| 3 | 0093 | 0093341961 |
| 4 | 0093 | 0093341961 |
| 5 | 0102 | 0102342141 |
| 6 | 0103 | 0103342141 |

TABLE 21

Product information

| Product | Nominal Protein Concentration (mg/mL) | Formulation | Target PS20 (mg/mL) |
|---|---|---|---|
| PS20-free A16/A17 | 80 | 20 mM His-HCl, 1 mM NAT, 5 mM Met, 240 mM Sucrose, pH 5.5 | 0.2 |
| A16/A17 | 80 | 0.2 mg/mL PS20, 20 mM His-HCl, 1 mM NAT, 5 mM Met, 240 mM Sucrose, pH 5.5 | 0.2 |
| PS20-free A18/A19 | 150 | 200 mM ArgSuccinate, 20 mM His, 0.3 mM NAT, 5 mM Met, pH 5.8 | 0.2 |
| A18/A19 | 150 | 0.2 mg/mL PS20, 20 mM His-HCl, 1 mM NAT, 5 mM Met, 240 mM Sucrose, pH 5.5 | 0.2 |

TABLE 21-continued

Product information

| Product | Nominal Protein Concentration (mg/mL) | Formulation | Target PS20 (mg/mL) |
|---|---|---|---|
| PS20-free A14/A20 | 150 | 20 mM His-Ace, 0.3 mM NAT, 5 mM Met, 240 mM sucrose, pH 6.0 | 0.2 |

Methods:

The ELSD light source intensity (LED) was set to 75% and detector gain (PMT) was set to 1 for all experiments. A summary of the final modifications to the method to make the assay compatible with NAT-containing formulations is as follows:

Agilent 1200 HPLC (or equivalent) and Varian 380 ELSD (or equivalent)
Cartridge: Waters Oasis® MCX online cartridge
Mobile Phase A: 1.5% ammonium hydroxide in water
Mobile Phase B: 1.5% ammonium hydroxide in methanol
Flow Rate: 1.40 mL/min
Divert Valve Timing: Flow to ELSD at 4.00 min
Injection volume: 25* μL (*product dependent)

TABLE 22

Modified PS20 Method Gradient (Method 2)

| Time (min) | % Mobile Phase A | % Mobile Phase B | Description of Step |
|---|---|---|---|
| 0 | 90 | 10 | Load |
| 1 | 55 | 45 | Wash |
| 4.4 | 55 | 45 | Wash |
| 4.5 | 0 | 100 | Elution |
| 7.6 | 0 | 100 | Elution |
| 7.7 | 90 | 10 | Equilibrate |
| 9.6 | 90 | 10 | Equilibrate |

Results:

Determination of Interference

The initial focus of method development was to determine if NAT was the source of the interference observed in previous assays. This work was conducted by studying a series of buffers that either contained NAT or excluded it (buffer details provided in the Materials section (Table 21) and in the Results section (Table 23)).

PS20-free A16/A17 formulation buffer (20 mM histidine-HCl, 1 mM NAT, 5 mM methionine, 240 mM sucrose, pH 5.5) and PS20-free A16/A17 at target concentration (nominal=80 mg/mL), were initially assessed using Method 1 of Example 1. The composition of each sample is provided below:

PS20-free formulation buffer—20 mM histidine-HCl, 1 mM NAT, 5 mM methionine, 240 mM sucrose, pH 5.5.

PS20-free A16/A17 sample—80 mg/mL (nominal) in 20 mM histidine-HCl, 1 mM NAT, 5 mM methionine, 240 mM sucrose, pH 5.5.

Figure 11A:
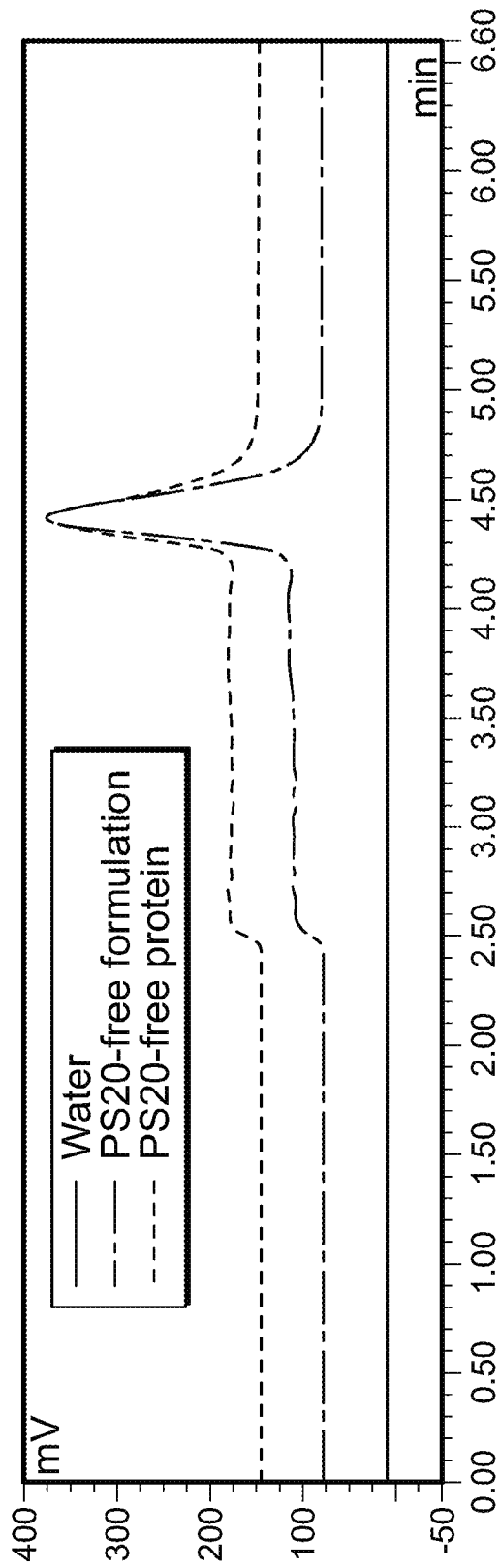
FIGS. 11A and 11B show the assessment of PS20-free A16/A17 using Method 1 of Example 1.

FIG. 11A displays the ELSD results of this evaluation, in which significant interference was observed in the ELSD at the retention time of PS20 (~4.5 minutes) for both samples. Water (trace 1), PS20 free formulation buffer (trace 2), and PS20-free protein sample (trace 3) injections are shown. Additionally, FIG. 11B displays the UV (280 nm) signal for each sample, where a component is detected at the approximate retention time of PS20. Because the magnitude of the observed interference when the PS20-free formulation was injected was approximately the same as the protein sample, it was apparent that the source could not be solely due to protein and led us to the hypothesis that there was an excipient in the buffer being retained by the cartridge.

Figure 11B:
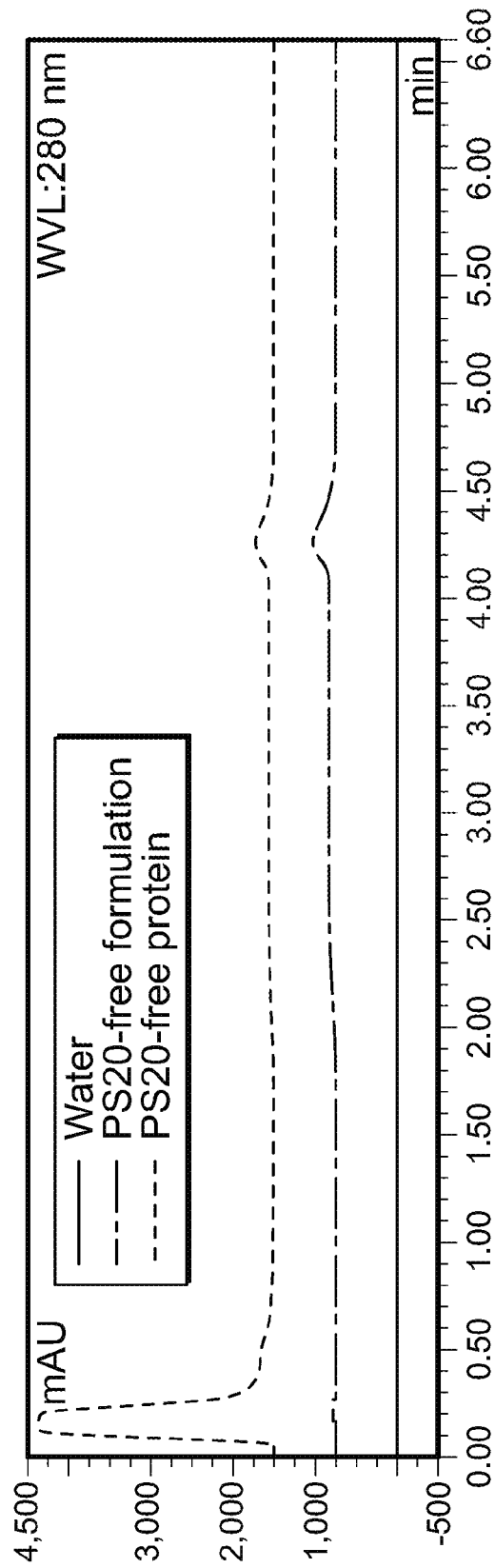

We determined that n-acetyl tryptophan (NAT) was the interferent observed in FIGS. 11A and 11B for the following reasons 1) NAT-containing formulations had not been previously tested with Method 1, therefore this stood out as a key difference from prior assessments; 2) NAT has an apparent pKa of 4.1 and possesses a carboxylate group that might cause it to retain to the ammonium cation resin of the MAX cartridge in its deprotonated, anionic form; and 3) the NAT absorbance maximum is near 280 nm (H. Edelhoch, *Biochemistry*, vol. 6, no. 7, July 1967), and 280 nm absorbance was observed at the PS20 retention time (~4.3 minutes) with NAT formulation samples (FIG. 11B).

To confirm that NAT was interfering with PS20, as described above, a series of A16/A17 formulation buffers, either with or without NAT, were tested. FIGS. 12A and 12B show the HPLC-ELSD results of this assessment with buffers that contain NAT displayed in FIG. 12A and those without NAT displayed in FIG. 12B. Each NAT-containing buffer in FIG. 12A also exhibited a peak at the retention time of PS20. By contrast, all buffers in which NAT was excluded did not exhibit an interfering peak. Together, the data shown in FIGS. 11A, 11B, 12A, and 12B indicate that NAT was retained on the Oasis® MAX cartridge, and co-eluted with PS20, rather than that the interference was caused by protein or other excipients.

TABLE 23

Buffers Tested with Method 1 and Method 2

| Buffer | Contains NAT? |
|---|---|
| 20 mM His-HCl, 1 mM NAT, 5 mM Met, 240 mM Sucrose, pH 5.5 (target A16/A17 formulation, without PS20) | Yes |
| Formulation buffer without Met, PS20 | Yes |
| Formulation buffer without NAT, PS20 | No |
| 25 mM Met in 20 mM His-HCl | No |
| 5 mM NAT in 20 mM His-HCl | Yes |
| 20 mM His-HCl | No |

NAT contains a carboxylate group, and may retain via anion-exchange to the resin found in the cartridge. We explored the use of an alternate Oasis® cartridge (Oasis® MCX) to better separate NAT from PS20. Unlike the Oasis® MAX cartridge, which contains an ammonium based cationic resin, the Oasis® MCX cartridge contains an anionic sulfite resin. Initially, the MCX cartridge was assessed using the same mobile phase (methanol+acetic acid) used in Method 1. However, under these conditions protein interference was found to be elevated to unacceptable levels (data not shown). The Waters Oasis® sample extraction method recommends use of ammonium hydroxide as the mobile phase additive in solid phase extraction procedures in the plate format of the MCX resin (Waters, "Oasis Sample Extraction Products," 2011). Therefore, the mobile phase was modified by replacing 2% acetic acid with 1.5% ammonium hydroxide to better mimic the conditions recommended by the manufacturer. With these method modifications, the different derivatives of A16/A17 buffers were assessed using the MCX cartridge and the data are shown in FIGS. 13A and 13B).

Figure 13A:
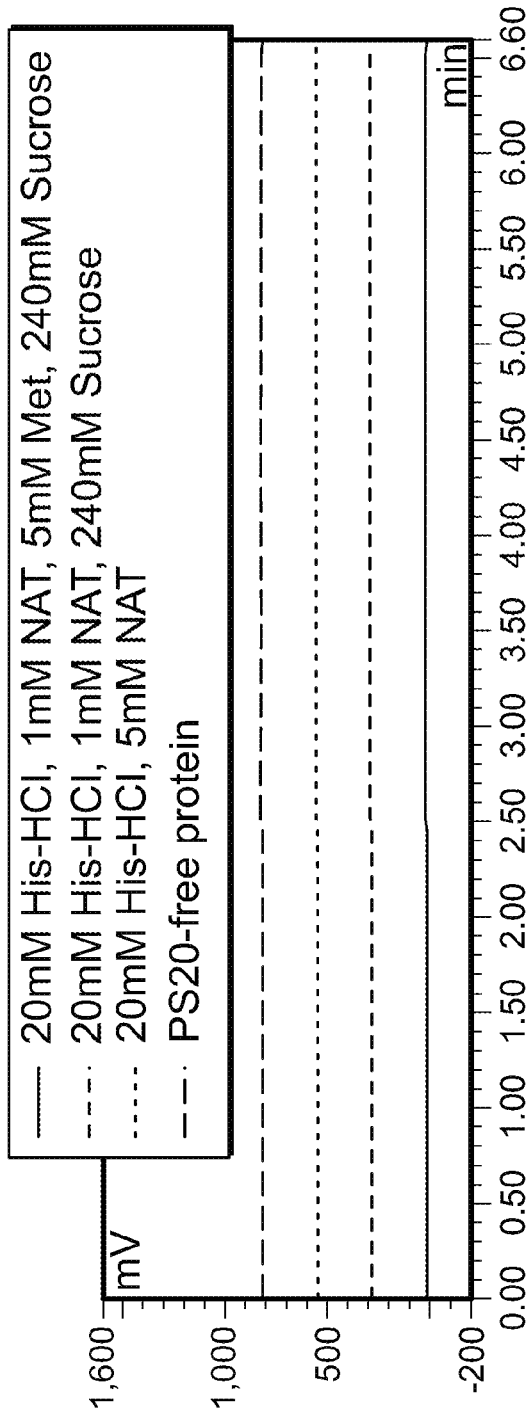
FIGS. 13A and 13B show ELSD chromatograms of different buffer components using a modified method (MCX cartridge and ammonium hydroxide in the mobile phase).
Figure 13B:
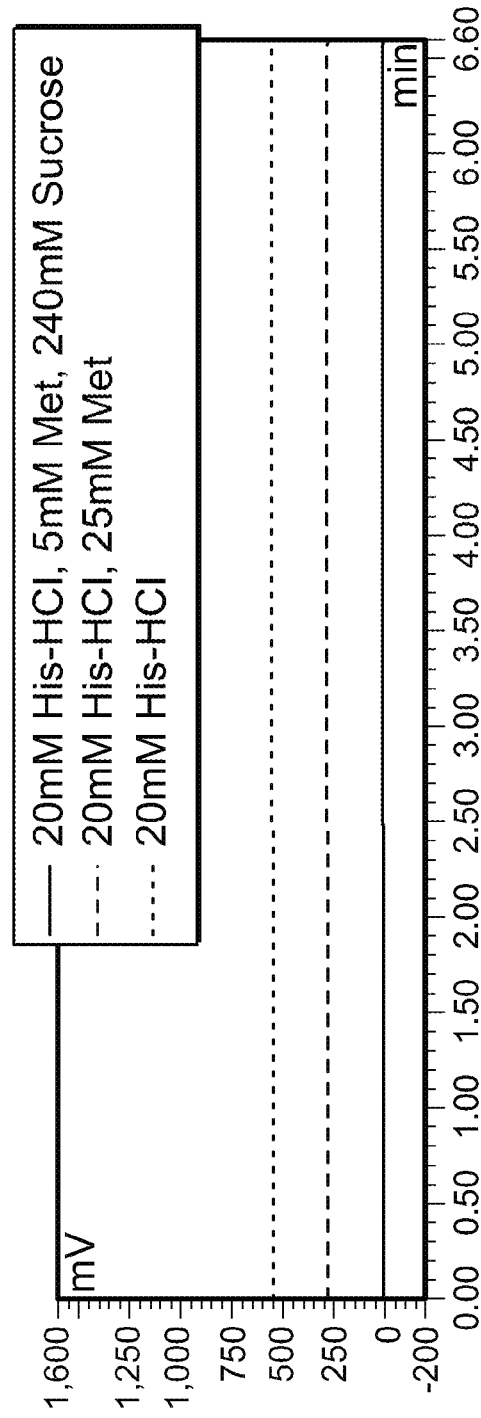

Unlike the results obtained with Method 1, no interference was observed at the retention time of PS20, with or without NAT, and all excipients were eluted from the cartridge prior to 1 minute (FIGS. 13A and 13B). Additionally, no interference was observed in the PS20-region in the ELSD when 50 µL of PS20-free A16/A17 protein (FIG. 13A, trace 4) was injected, indicating that the method has the potential to separate protein from PS20. The MCX cartridge, along with ammonium hydroxide as the mobile phase additive, was selected for use to assess PS20 quantitation for NAT containing formulations.

Method Modification

Once preliminary conditions for analyzing NAT-containing formulations were established, as described above, the following parameters were examined in further detail:
 Ammonium hydroxide % in mobile phase
 % B used in wash step (tested 20-60% B)
 Wash time (2.4 min and 3.4 min) and Injection volumes (25 and 50 µL injection volumes)
 Flow rate (0.8 mL/min to 1.6 mL/min)
 Elution time (1.1 min, 3.1 min)

Ammonium Hydroxide % in Mobile Phase

Figure 14A:
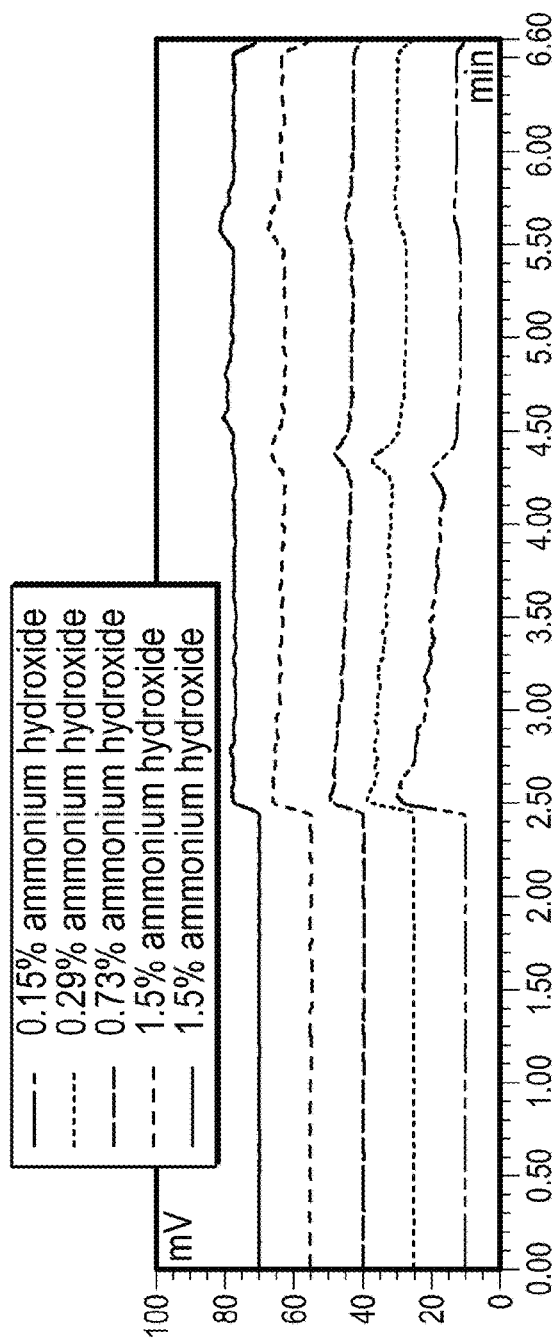
FIGS. 14A and 14B show assessment of PS20-free A16/A17 protein with 0.15-1.50% ammonium hydroxide additive in the mobile phase.
Figure 14B:
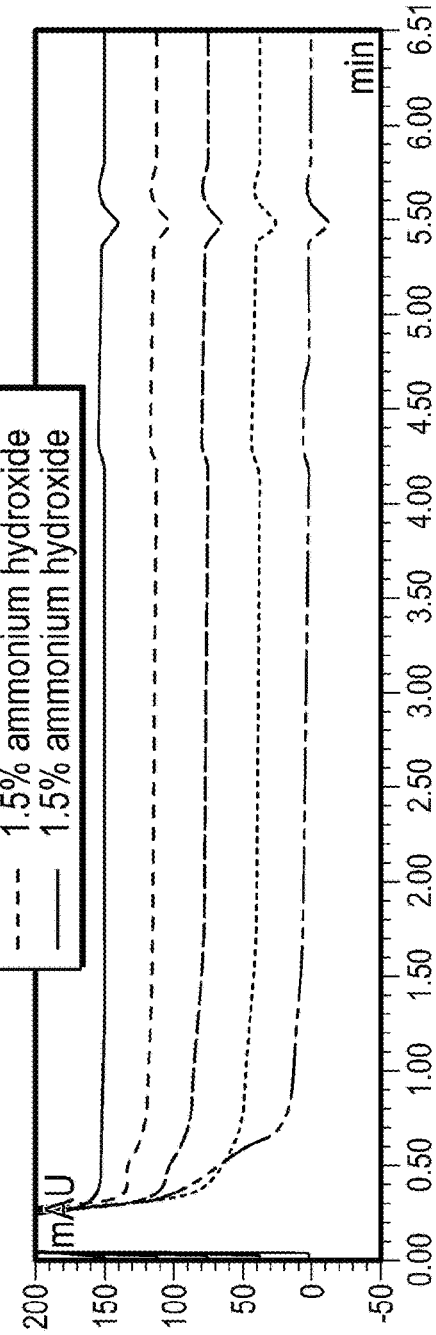

The Waters Oasis® sample extraction method recommends use of ammonium hydroxide as the mobile phase additive in solid phase extraction procedures in the plate format of the MCX resin (Waters, "Oasis Sample Extraction Products," 2011). The experiment was performed with detection by both ELSD (FIG. 14A) and UV (FIG. 14B). PS20-free A16/A17 protein was the sample used to assess both protein and NAT elution from the cartridge using 0.15, 0.29, 0.73 or 1.5% ammonium hydroxide in the mobile phase (FIGS. 14A and 14B, traces 1, 2, 3, and 4, respectively). Since the UV detector is in-line before the divert valve, analytes with a chromophore (e.g. NAT and protein) that elute before PS20 can be detected. In order to assess the ability to clear NAT, A16/A17 PS20-free formulation buffer was injected as well (FIGS. 14A and 14B, trace 5).

When the cartridge effluent was introduced into the ELSD at 2.4 minutes by switching the divert valve, a slight interference was observed with 0.15% ammonium hydroxide (FIG. 14A, trace 1) in the mobile phase, as evidenced by the slightly higher baseline; the UV trace also shows that protein and/or NAT were mostly eluted from the cartridge before the effluent entered the ELSD. The majority of these potential interferents eluted in the void volume. As the percentage of ammonium hydroxide additive was increased (from 0.29 to 1.5%), there was minimal difference in the extent of protein or NAT interference observed by ELSD (FIG. 14A, traces 2-4). Additionally, the UV trace shows the method cleared protein and NAT sufficiently at all levels of ammonium hydroxide tested (FIG. 14B, traces 2-4). When PS20-free protein was injected with 1.5% ammonium hydroxide in the mobile phase (FIG. 14A, trace 4), there appeared to be less protein interference when the effluent was introduced at 2.4 minutes in the PS20-region (4.0-5.5 minutes) compared to the same protein injected with the lower ammonium hydroxide percentages. PS20-free formulation buffer (FIG. 14B trace 5) UV trace shows that NAT is cleared efficiently with 1.5% ammonium hydroxide in the mobile phase. Therefore this percentage of additive was selected for use in the method.

The absorbance at 280 nm (FIG. 14B) shows that the protein and NAT were cleared sufficiently when using 0.15-1.5% ammonium hydroxide in the mobile phase with some tailing of these interferents present at ~2.5 min. Because of this finding, the methanol+ammonium hydroxide method was changed to divert the flow to the ELSD at 3.0 min, rather than 2.4 min, in order to prevent the detector from being contaminated and to ensure minimal protein and NAT interference in the ELSD. Since the elution of the PS20 is at about 4.5 min, this change should not affect that peak.

% B Used in Wash Step (Tested 20-60%)

Figure 15A:
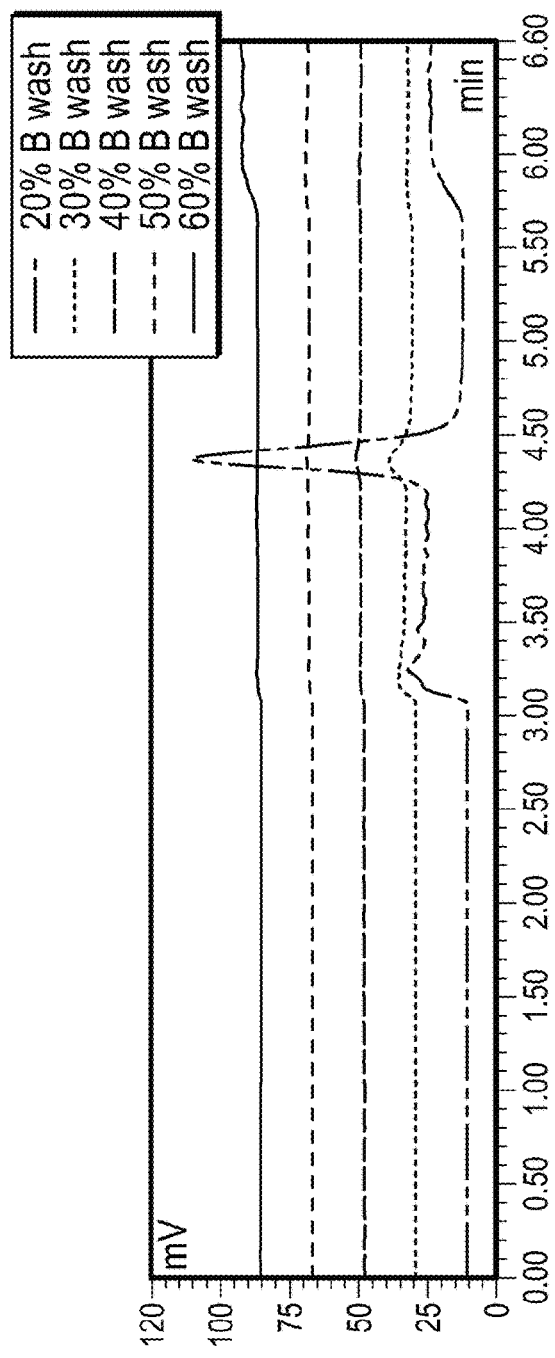
FIGS. 15A and 15B show assessment of 20-60% mobile phase B wash step.

Previously, for the development of Method 1 in formulations without NAT, the % methanol used during the wash step to separate protein from PS20 was optimized using a step gradient approach. The % methanol used in Method 2 development was reconsidered due to the unknown impact on protein retention of several key changes to the method; the stationary phase was changed to a MCX resin, and the mobile phase additive was revised to ammonium hydroxide. In this experiment, four different levels in 10% (v/v) increments of % B (methanol+1.5% ammonium hydroxide) were tested over a range of concentrations from 20-60%. Both ELSD and UV detection were used to monitor protein elution under each tested condition. Polysorbate free A16/A17 sample was used for the assessment, and the ELSD and UV data are shown in FIGS. 15A and 15B, respectively.

Figure 15B:
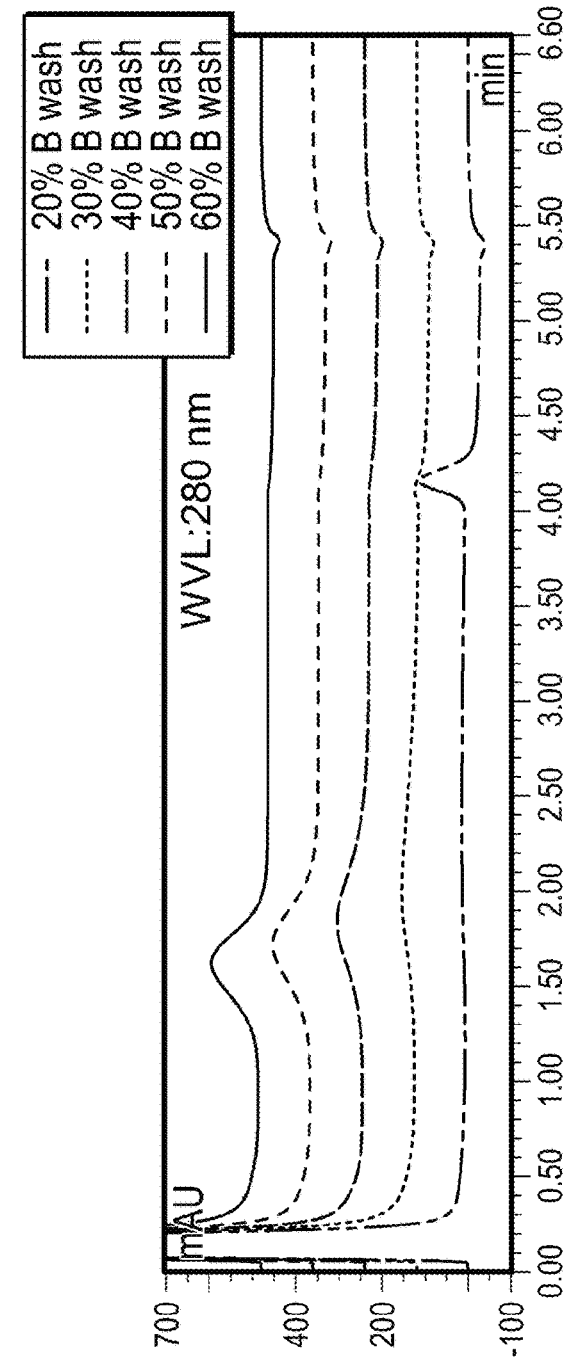

In FIG. 15B, the 280 nm absorbance chromatogram exhibits a well-defined peak at the retention time of PS2- (~4.5 minutes), suggesting that there was protein and/or NAT retention on the cartridge with 20% B wash (trace 1) when 15 µL of PS20-free A16/A17 protein was injected. A much larger peak was also observed in the void volume, which is likely a mixture of protein and NAT. A well-defined peak was also detected in the ELSD as interference in the PS20 region (FIG. 15A) for this same condition. When the % B for the wash step was increased to 30%, the NAT and protein clearance was improved (trace 2), as evidenced by the decrease of the peak in the PS20 region in both the UV and ELSD traces. The NAT and protein were cleared more efficiently with 40% B, however there was still slight interference present in the PS20-region in the ELSD (FIG. 15A). NAT and protein were most efficiently cleared with 50 and 60% B wash (traces 4 and 5, respectively), with minimal interference present. 45% B in the wash step was selected for use in the method. During previous development of Method 1, we had also tested up to 50% methanol as the wash condition, but it was observed that a small portion of the PS20 would elute earlier under these conditions (at 45% methanol this small peak was not observed). These peaks may have been the shorter chain-length esters, which are less hydrophobic, and were indicative that the 50% methanol condition was approximately the point where esterified species would elute. Due to this previous observation, and the present result showing that 40% B was sufficient to remove the protein, we decided on the 45% B condition for the washing step to provide a compromise between robust protein removal and PS20 retention. Furthermore, the UV data in FIG. 15B show that the protein eluted slightly earlier at the 50% B wash condition.

Wash Time (2.4 min and 3.4 min) and Injection Volumes (25 and 50 µL Injection Volumes)

Figure 16:
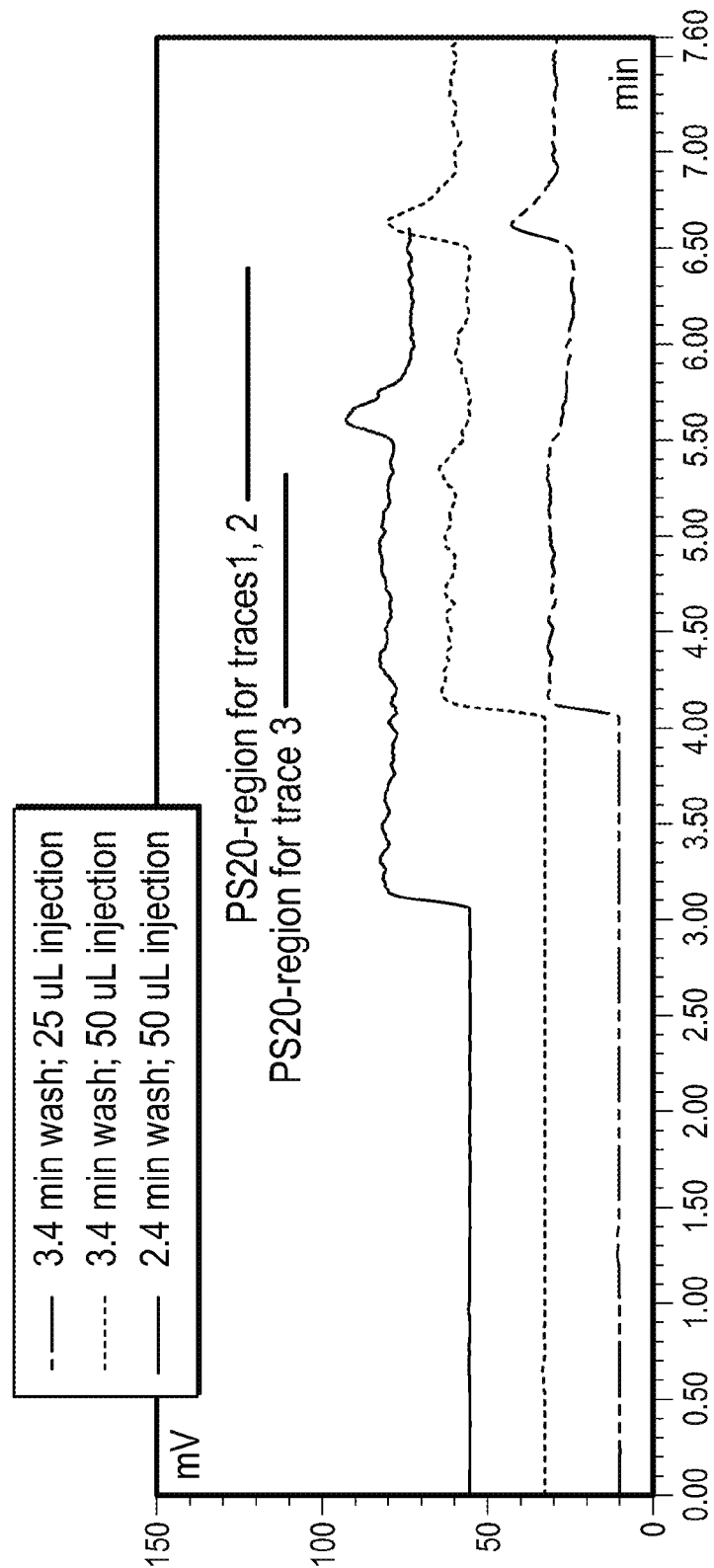
FIG. 16 shows assessment of wash times and injection volumes for PS20-free A16/A17 protein by ELSD chromatography. 25 µL PS20-free A16/A17 sample injection: 3.4 minute wash step (trace 1). 50 µL PS20-free A16/A17 sample injection: 3.4 minute wash step (trace 2) and 2.4 minute wash step (trace 3).

In order to further minimize interference in the PS20-region, 2.4 minute and 3.4 minute wash steps were assessed. As shown in FIG. 16, the PS20-region is similar between the 2.4 or 3.4 minute washes (trace 3 and trace 2, respectively). Because the specificity was improved slightly and there were no apparent negative impacts at the longer wash time, a 3.4 minute wash was selected for use in the method. Additionally, the flow was selected to be diverted to the ELSD at 4.0 minutes instead of at 2.4 minutes.

The impact of injection volume on the baseline was also assessed by decreasing sample volume from 50 µL to 25 µL (FIG. 16, trace 2 and trace 1, respectively). The baseline of the 25 µL injection trace appears slightly cleaner, which is expected since there are less protein and excipients to be removed from the cartridge. Ultimately, the injection volume did not significantly impact the performance with respect to specificity.

Flow Rate (0.8 mL/min to 1.6 mL/min)

Figure 17A:
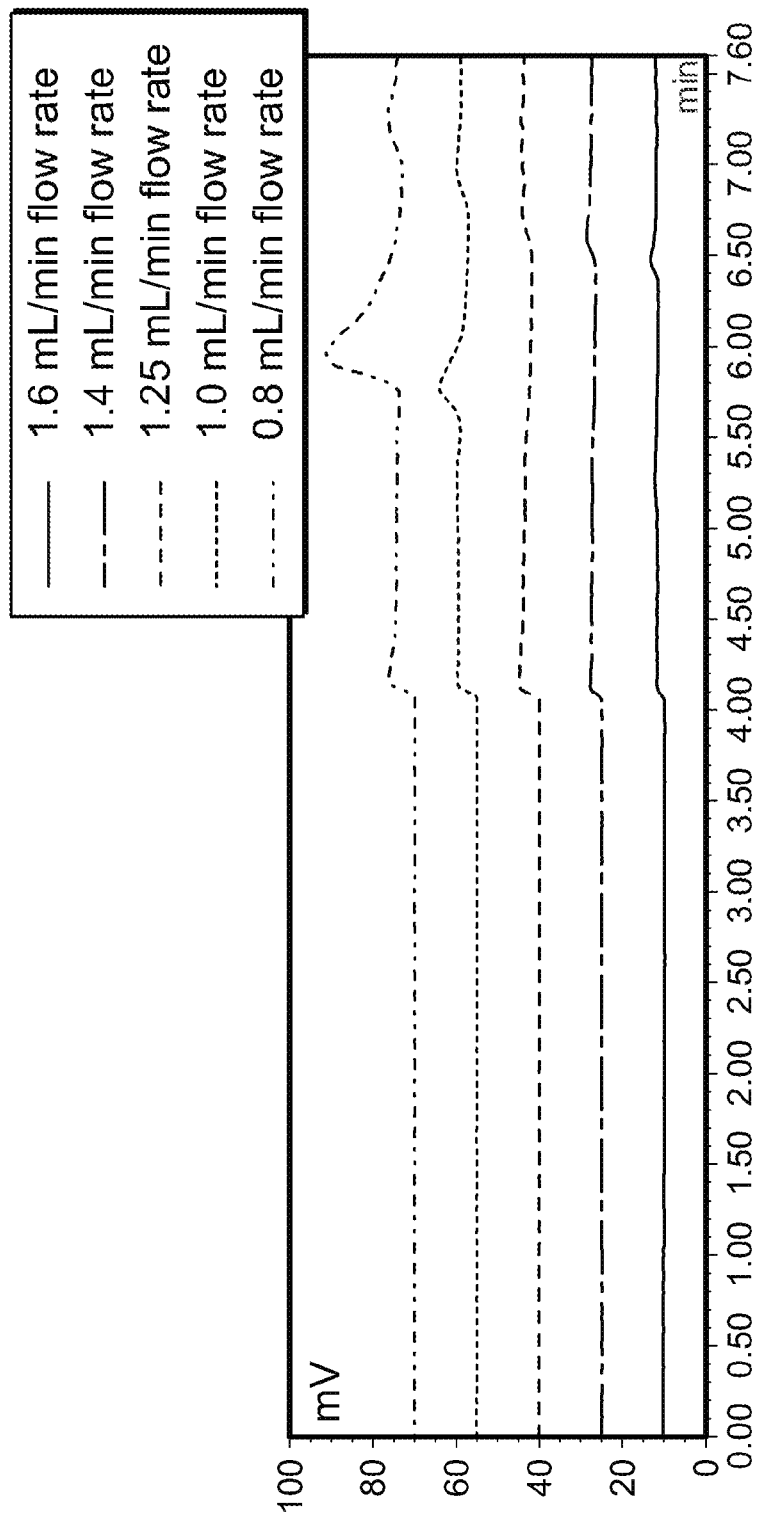
FIGS. 17A and 17B show assessment of different flow rates for PS20-free A18/A19.
Figure 17B:
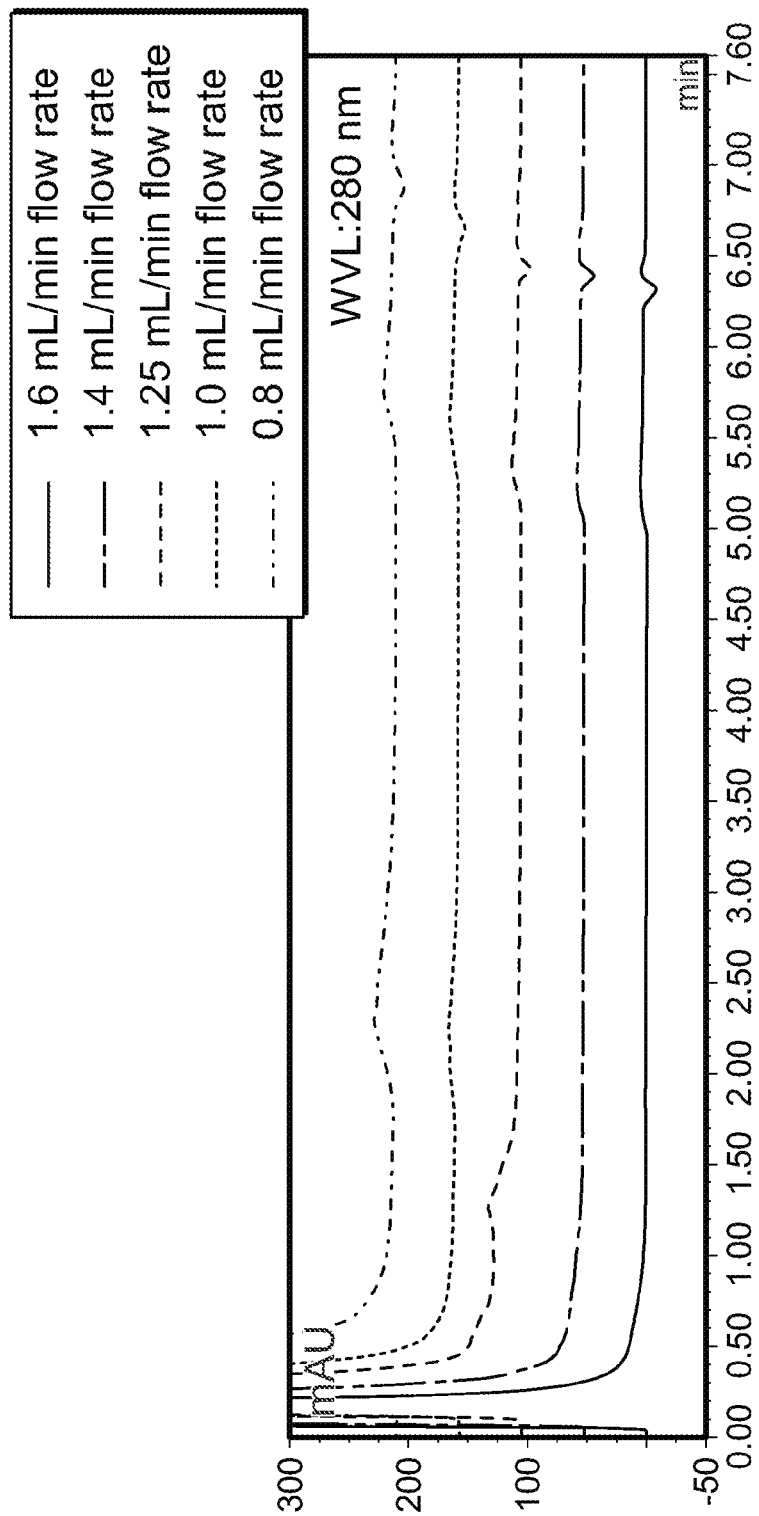

Flow rate was assessed to ensure that the protein and NAT were being cleared efficiently. The flow rate was varied between 0.8-1.6 mL/min. FIGS. 17A and 17B show 25 µL sample injections of PS20-free A18/A19 protein at 150 mg/ml using 1.60, 1.40, 1.25, 1.00, and 0.80 mL/min flow rates (traces 1, 2, 3, 4, and 5, respectively).

At the slowest flow rate, 0.8 mL/min (trace 5), there were still protein and excipients eluting in the PS20 region as indicated by the peak in the ELSD (FIG. 17A). The UV trace (FIG. 17B) of this condition also exhibited increased interferents eluting later than with the higher flow rates. When the flow rate was increased to 1.00 mL/min (trace 4) the interference was decreased, and became almost negligible once the flow rate was increased to 1.25 mL/min (trace 3). When the flow rate was increased to 1.40 and 1.60 mL/min (traces 2 and 1, respectively), the UV trace shows most of the protein and excipients were eluted from the cartridge more completely by 2.0 minutes than with the lower flow rates, and a flow rate of 1.40 mL/min was selected for use in the method. We did not increase to 1.6 mL/min because the performance was nearly equivalent at 1.4 mL/min, and because we wanted to minimize the risk of leaks due to the higher backpressure at 1.6 mL/min.

Elution Time (1.1 min, 3.1 min)

Figure 18:
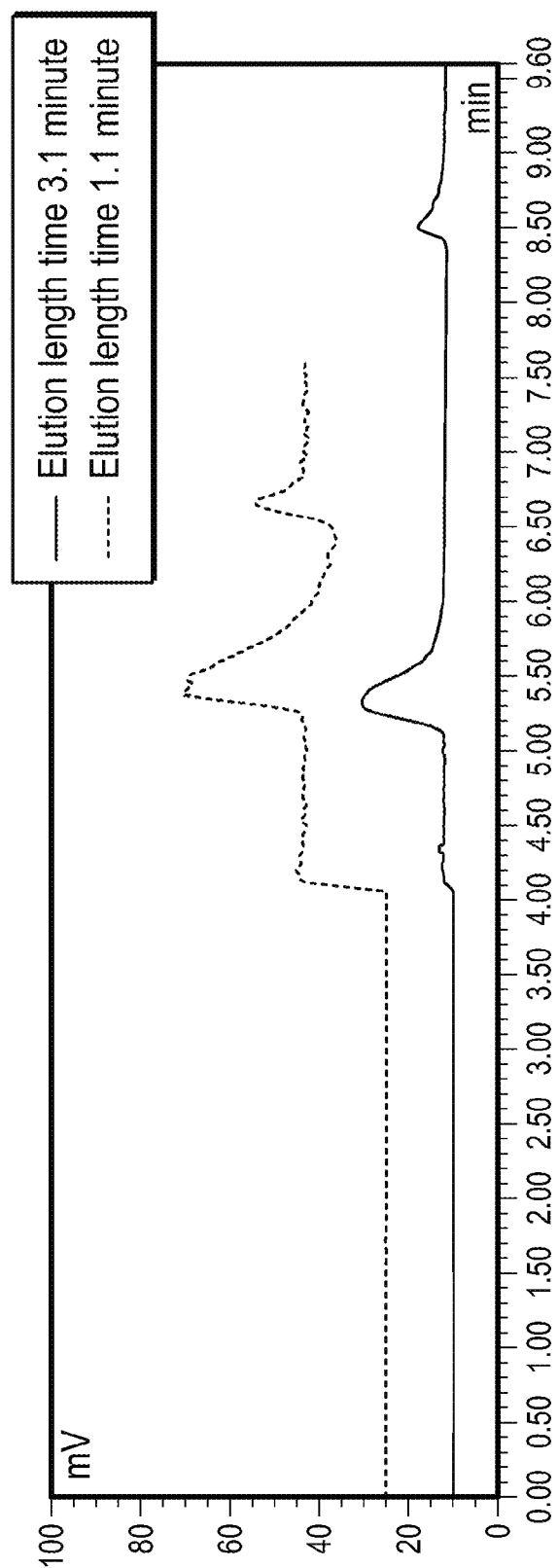
FIG. 18 shows assessment of different elution times for PS20 in water by ELSD chromatography. 50 µL injection of 0.1 mg/mL PS20 in water, 3.1 minute elution step (trace 1) or 1.1 minute elution step (trace 2).
Figure 19:
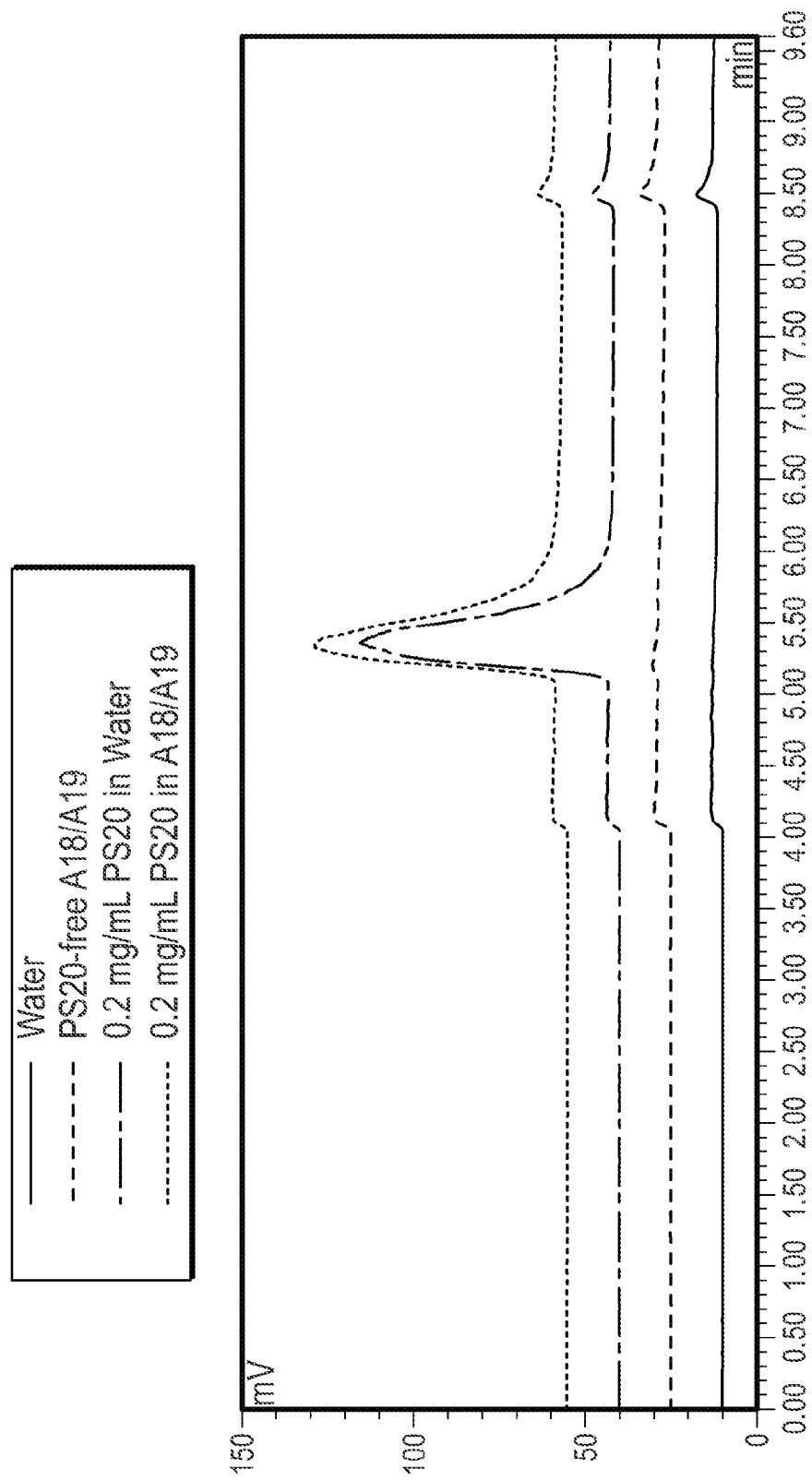
FIG. 19 shows assessment of finalized Method 2 by ELSD chromatography. 25 µL injection of water (trace 1), 150 mg/mL PS20-free A18/A19 (trace 2), 0.2 mg/mL PS20 spiked into water (trace 3), and 0.2 mg/mL PS20 spiked in A18/A19 (trace 4) using the finalized parameters for Method 2.

The elution step at 100% B in Method 1 is held for 1.1 minutes. There is a peak of unknown identity that elutes at ~6.5 minutes that was observed in every injection, independent of the sample and including water blanks. The unknown peak seems to elute after the mobile phase % B is returned to the re-equilibration conditions. To test whether the peak could be better separated from PS20, the elution time was extended. FIG. 18 illustrates the integration of the PS20 peak, which starts at ~5.2 minutes and ends approximately when this unknown peak begins (trace 2). Although this did not significantly affect the quantitation, to prevent potential interference from this peak in the future the elution step was increased to a hold time of 3.1 minutes (trace 1), allowing for better separation and integration of the PS20 region. FIG. 19 illustrates results for water, 150 mg/mL PS20-free A18/A19, 0.2 mg/mL PS20 spiked into water, and 0.2 mg/mL PS20 spiked in A18/A19 (traces 1, 2, 3 and 4, respectively) using Method 2 with the finalized parameters.

Method Qualification Experiments

Specificity

Specificity was determined by confirming that injections of PS20-free formulation buffer and PS20-free product do not contribute to any peaks that may interfere in the PS20-region; these were compared to the lowest PS20 calibration standard, which is typically at 50% of the target PS20 concentration.

Figure 20A:
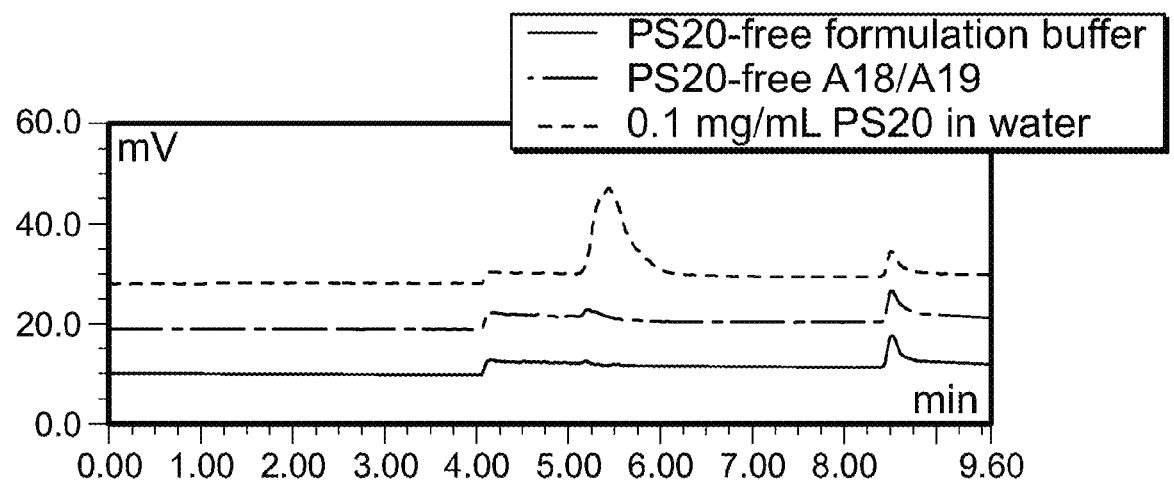
FIGS. 20A-20F show assessment of specificity for three different products.
Figure 20B:
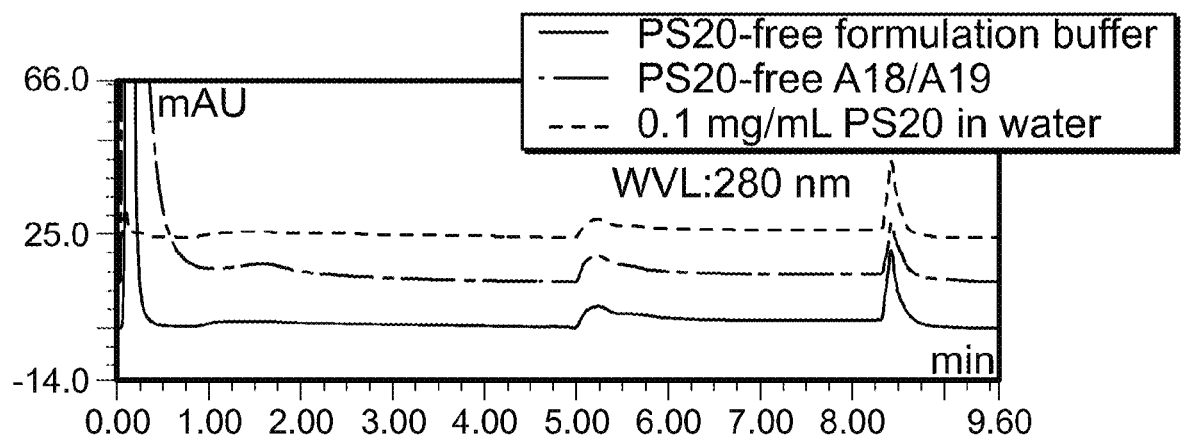
Figure 20C:
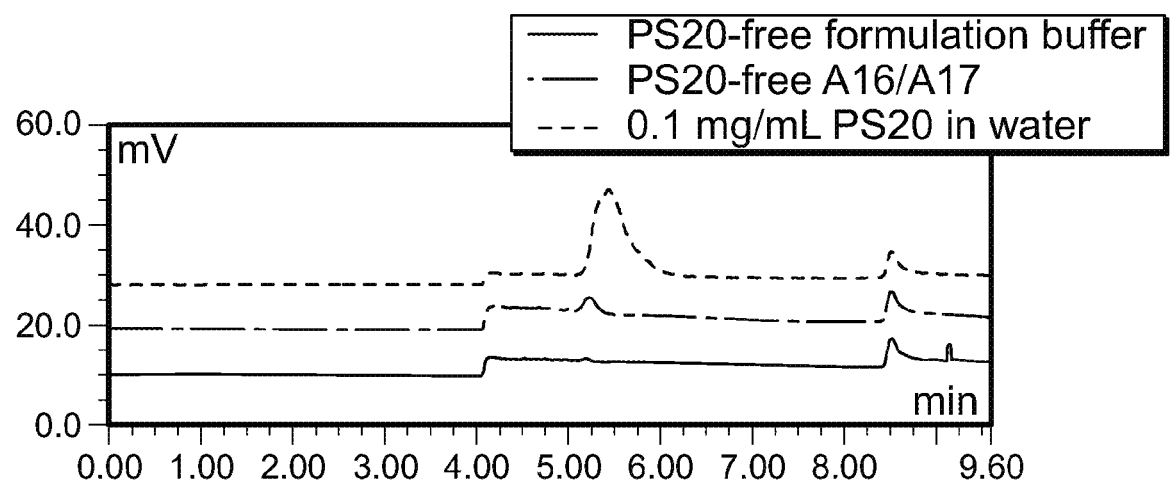
Figure 20D:
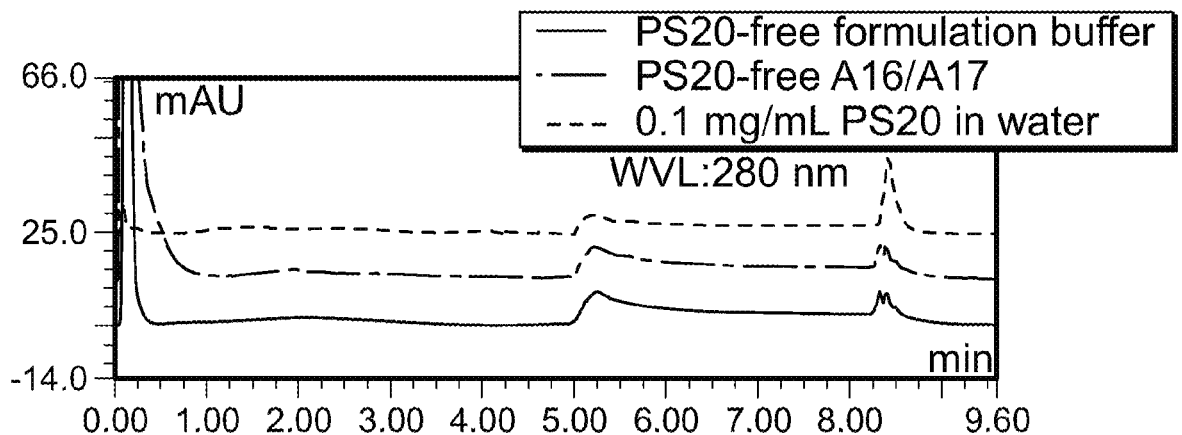
Figure 20E:
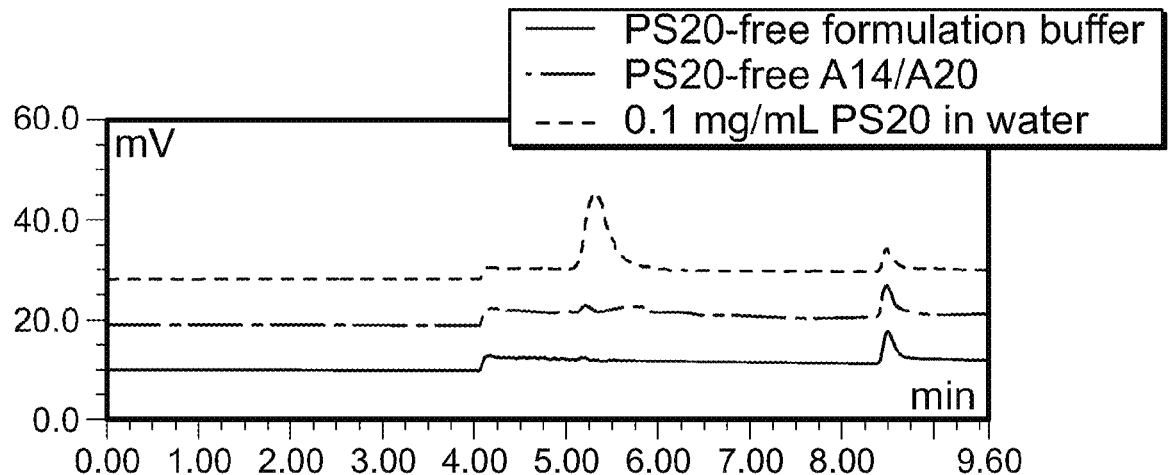
Figure 20F:
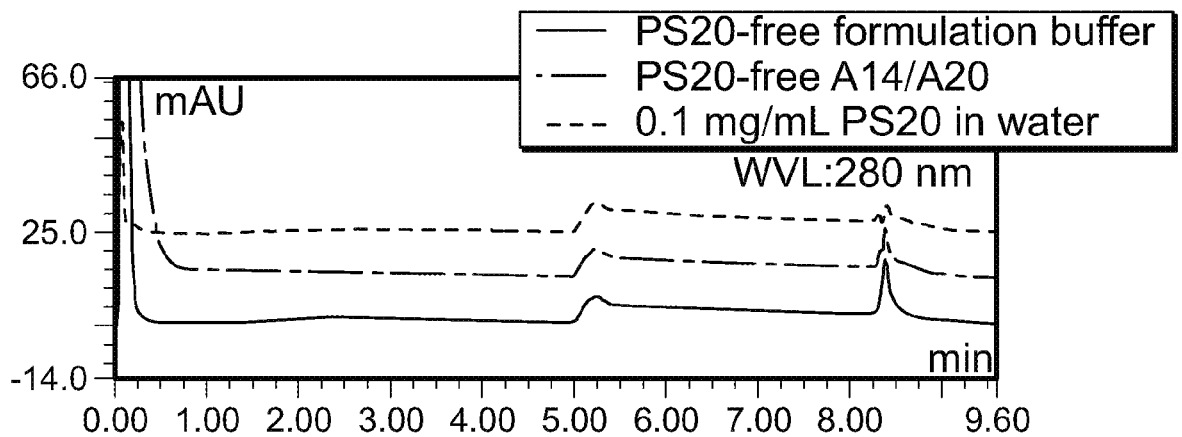

Typical chromatograms for PS20-free formulation buffer, PS20-free protein and 0.1 mg/mL PS20 (50% target) spiked into water are shown in FIGS. 20A-20F. Three different PS20-free products were assessed. A18/A19 (FIGS. 20A and 20B). A16/A17 (FIGS. 20C and 20D), and A14/A20 (FIGS. 20E and 20F) have protein concentrations of 150, 80, and 150 mg/mL, respectively. More detail on these products is provided in Table 21. Visually, all products had some interference in the PS20-region in the ELSD when the PS20-free protein sample was injected (FIGS. 20A, 20C, and 20E, trace 2). However, the PS20-free formulation buffer showed no visual interference in the PS20-region (FIGS. 20A, 20C, and 20E, trace 1), indicating that the interference was mainly from protein.

The acceptance criteria of the method are fulfilled if the peak areas in the PS20 free samples are ≤10% of the peak area in the lowest standard. Because there was some protein interference visible in the PS20 region, specificity must be determined using an equation. There are different approaches used to determine specificity. For this study, the following equation was used to derive a numerical estimate of the specificity:

Interference (%)=(Area of PS20-free protein/Area of 50% of PS20 specification)*100    Equation 1: Specificity Using this equation, the % interference was calculated for the three products (Table 24). It was determined that PS20-free A16/A17 (80 mg/mL) (FIG. 20C) had 7% specificity when compared to 0.1 mg/mL PS20 in water (50% target). PS20-free A18/A19 (150 mg/mL) (FIG. 20A) had only 4% interference, whereas A14/A20 (150 mg/mL) (FIG. 20E) had 13% interference when compared to 0.1 mg/mL PS20 in water (50% target).

The UV traces at 280 nm (FIGS. 20B, 20D, and 20F) for all products show that the protein and NAT were efficiently cleared by the time the flow was diverted into the ELSD at 4.0 minutes. Although A14/A20 had an interference of 13%, the repeatability, accuracy, and linearity in the subsequent assessments for this product were acceptable.

TABLE 24

Specificity of the three products

|  | A18/A19 | A16/A17 | A14/A20 |
|---|---|---|---|
| Area of PS20-free protein | 0.3 | 0.5 | 0.8 |
| Area of 0.1 mg/ml PS20 in water | 7.1 | 7.1 | 6.2 |
| Specificity (%) | 4 | 7 | 13 |

Accuracy

In order to determine the accuracy of the assay, a known amount of PS20 was spiked into PS20-free protein and the recoveries for each concentration were determined (Table 25). The typical validation acceptance criteria require that the % recovery be within 80-120%.

PS20-free A18/A19 (150 mg/mL) and PS20-free A16/A17 (80 mg/mL) were evaluated by spiking PS20 at a range of 0.1-0.6 mg/mL. The accuracy data are summarized in Table 25. At the PS20 concentrations tested, the range of recoveries for A16/A17 and A18/A19 were 94-100% and 78-100%, respectively. The sample with 78% recovery occurred with 0.4 mg/mL PS20 spiked into PS20-free A18/A19. The recoveries of the bracketing PS20 concentrations (0.2 and 0.6 mg/mL) were within the specification, suggesting sample preparation or injection error for this one sample. If the 0.4 mg/mL sample is excluded, the range of recoveries is 88-100% for A18/A19.

The accuracy of PS20-free A14/A20 (150 mg/mL) was assessed by spiking PS20 at a range of 0.1-0.3 mg/mL. The PS20 recoveries for A14/A20 ranged from 92-109%. Overall, the data from spiked recovery experiments for all three products tested demonstrate that the method is accurate. Additionally, these results demonstrate that 2.5 µg (0.1 µg/µL*25 µL)–15 µg (0.6 µg/µL*25 µL) of PS20 can be loaded onto the cartridge and quantified accurately.

TABLE 25

Accuracy

| Product (protein concentration) | Injection Volume (µL) | Number of Replicates | Spiked PS20 (mg/mL) | Area (mV * min) | Amount (mg/mL) | % Recovery |
|---|---|---|---|---|---|---|
| A18/A19 (150 mg/mL) | 25 | 1 | 0.10 | 9.2 | 0.09 | 88 |
|  |  |  | 0.20 | 26.4 | 0.19 | 95 |
|  |  |  | 0.40 | 51.8 | 0.31 | 78 |
|  |  |  | 0.60 | 125.0 | 0.60 | 100 |
| A16/A17 (80 mg/mL) | 25 | 1 | 0.10 | 10.0 | 0.09 | 94 |
|  |  |  | 0.20 | 27.3 | 0.20 | 98 |
|  |  |  | 0.40 | 72.5 | 0.40 | 100 |
|  |  |  | 0.60 | 124.3 | 0.60 | 99 |
| A14/A20 (150 mg/mL) | 25 | 3 | 0.10 | 7.2 | 0.11 | 109 |
|  |  |  | 0.15 | 12.7 | 0.16 | 104 |
|  |  |  | 0.20 | 19.0 | 0.20 | 101 |
|  |  |  | 0.25 | 25.8 | 0.25 | 98 |
|  |  |  | 0.30 | 31.6 | 0.28 | 92 |

Linearity

Linearity was evaluated by determining the Pearson's correlation coefficient (r)≥0.99 over the ranges tested for the three products. These values are shown in Table 26 for each range of PS20 concentrations for each product. All values of Pearson's correlation coefficient were greater than 0.99 for the PS20 ranges tested. Therefore, linearity was acceptable for this assay across the three products tested.

TABLE 26

Linearity: Pearson's Correlation Coefficient

| Product | PS20 Concentration Range (mg/ml) | Pearson's correlation coefficient (r) |
|---|---|---|
| A18/A19 | 0.1-0.6 | 0.9915 |
| A16/A17 | 0.1-0.6 | 0.9999 |
| A14/A20 | 0.1-0.3 | 0.9994 |

Repeatability

Repeatability was assessed with six replicate injections of A18/A19 sample (nominal 0.2 mg/mL PS20) and six replicate injections of A16/A17 sample (nominal 0.2 mg/mL PS20) and measuring the % RSD of the PS20 peak areas. The results of this assessment are displayed in Table 27, and show that the precision of the assay was acceptable for both products.

TABLE 27

Repeatability of A18/A19 and A16/A17

| Injection # | A18/A19 Area (mV * min) | A18/A19 PS20 Conc (mg/ml) | A16/A17 Area (mV * min) | A16/A17 PS20 Conc (mg/ml) |
|---|---|---|---|---|
| 1 | 23.9 | 0.18 | 35.4 | 0.24 |
| 2 | 25.6 | 0.19 | 35.1 | 0.24 |
| 3 | 24.3 | 0.18 | 35.0 | 0.23 |
| 4 | 24.0 | 0.18 | 35.1 | 0.24 |
| 5 | 24.5 | 0.18 | 35.2 | 0.24 |
| 6 | 23.4 | 0.18 | 34.9 | 0.23 |
| Mean | 24.3 | 0.18 | 35.1 | 0.23 |
| SD | 0.7 | 0.0 | 0.2 | 0.0 |
| RSD % | 3.1 | 2.1 | 0.5 | 0.3 |

The repeatability was also be assessed by testing three replicates of five concentrations and measuring the % RSD of the PS20 peak areas. This experiment was performed with 0.10-0.30 μmg/mL PS20-spiked into PS20-free A14/A20. The results of this assessment are displayed in Table 28, and show that the precision of the assay is acceptable for A14/A20.

TABLE 28

Repeatability of A14/A20

PS20-spiked into A14/A20

| | | | | | |
|---|---|---|---|---|---|
| Theoretical PS20 (mg/mL) | 0.10 | 0.15 | 0.20 | 0.25 | 0.30 |
| Mean Measured PS20 (mg/mL) | 0.11 | 0.16 | 0.20 | 0.25 | 0.28 |
| SD (mg/mL) | 0.001 | 0.002 | 0.002 | 0.001 | 0.003 |
| RSD (%) | 0.5 | 1.5 | 0.9 | 0.4 | 1.1 |

Method Robustness Experiments
Cartridge to Cartridge

Previous work done with Method 1 of Example 1 has shown that even when the sorbent batch of the cartridge is the same, the cartridges may exhibit different behavior with respect to protein clearance and specificity. Three MCX cartridges were assessed to determine the cartridge to cartridge variability. Of these, MCX cartridge 2 and 4 had the same sorbent batch (0093), while 6 was different (0103) (Table 20).

Figure 21:
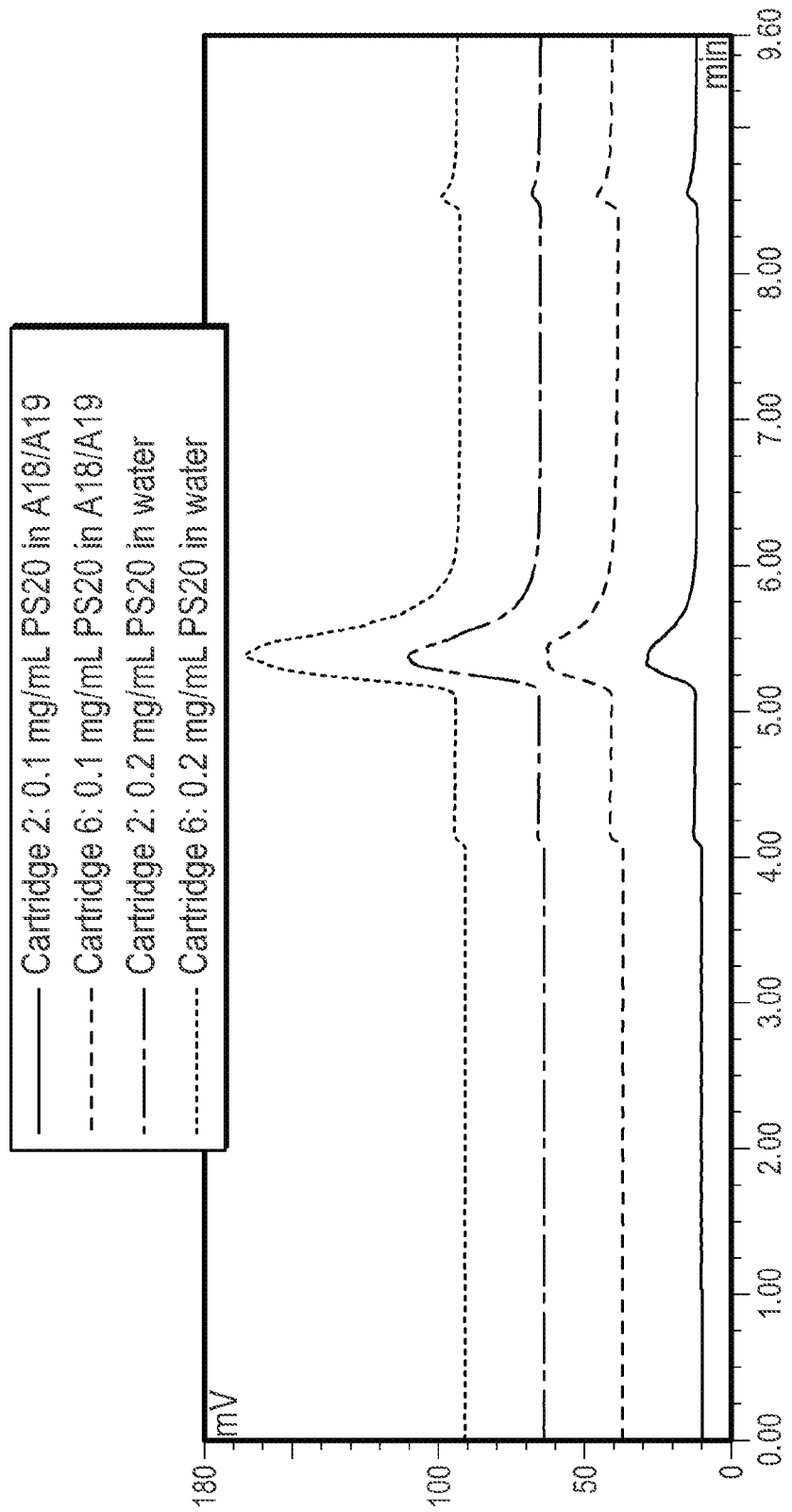
FIG. 21 shows assessment of cartridge to cartridge variability using PS20 spiked in water or PS20-free A18/A19 by ELSD chromatography. Cartridge 2, 0.1 mg/mL PS20 spiked in PS20-free A18/A19 (trace 1); Cartridge 6, 0.1 mg/mL PS20 spiked in PS20-free A18/A19 (trace 2); cartridge 2, 0.2 mg/mL PS20 spiked in water (trace 3); and cartridge 6, 0.2 mg/mL PS20 spiked in water (trace 4).
Figure 22:
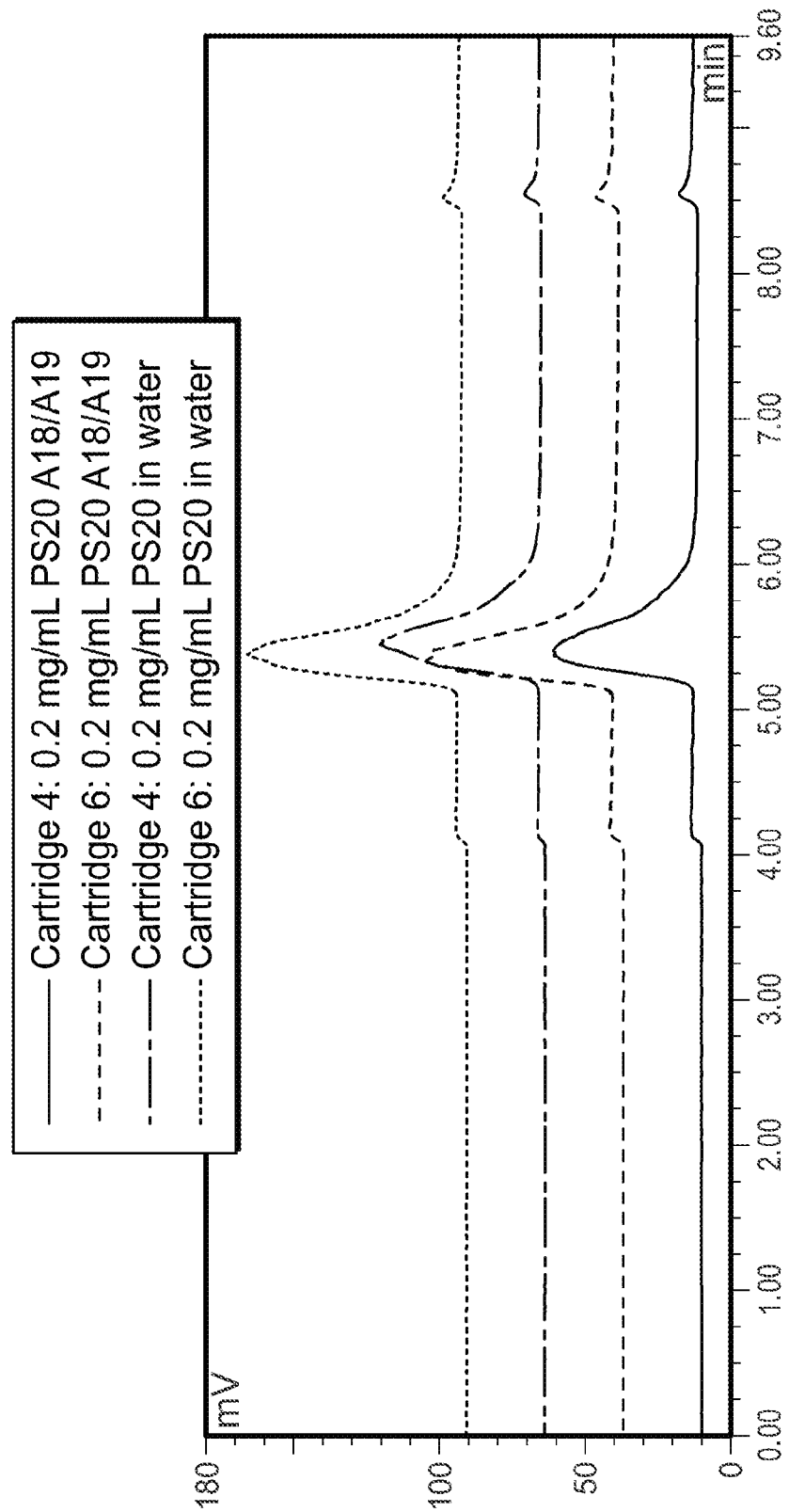
FIG. 22 shows assessment of cartridge to cartridge variability using PS20 spiked in water or PS20-free A18/A19 by ELSD chromatography. Cartridge 4, 0.2 mg/mL PS20 spiked in PS20-free A18/A19 (trace 1); Cartridge 6, 0.2 mg/mL PS20 spiked in PS20-free A18/A19 (trace 2); cartridge 4, 0.2 mg/mL PS20 spiked in water (trace 3); and cartridge 6, 0.2 mg/mL PS20 spiked in water (trace 4).

All three MCX cartridges were assessed with 0.2 mg/mL PS20 spiked into water, and PS20-containing products. FIGS. 21 and 22 show the chromatograms from these assessments, and Table 29 displays a summary of the results. Traces 3 and 4 in FIG. 21 and trace 3 in FIG. 22 illustrate the differences in peak heights and widths for the 0.2 mg/mL PS20 in water samples injected across the three cartridges. Most notably, the peak heights and areas are variable from cartridge to cartridge, with the largest difference observed between cartridge 2 (FIG. 21 trace 1 and 3) and cartridge 6 (FIG. 21 trace 2 and 4). The area of the peak with cartridge 2 was approximately 60% of the area of the peak with cartridge 6 in both sample types tested (i.e. PS20 in water and PS20 in A18/A19). Given that the difference in peak areas was observed to be independent of the sample type (e.g., with or without protein), the variability is not likely caused by protein interference. Although the area counts were very different between two of the cartridges tested, the difference between cartridge 4 and 6 was smaller, with the area of cartridge 4 being approximately 85% of cartridge 6. The variability in PS20 peak area between cartridges does not appear to be solely dependent on the resin batch, as both cartridge 2 and 4 shared the same resin batch and also yielded different peak areas.

Although this variability is not ideal, the concentrations of PS20 determined from the calibration curve analyzed on the same column were accurate compared to the theoretical concentrations across all cartridges once the standards were implemented to obtain the calculated PS20 amount. Based on these data, it will be important to utilize injection amounts of PS20 that provide a response well within the linear range of the ELSD detector. For instance, a maximum detector response of 80% of full scale (e.g., 800 mV) is generally recommended for HPLC-ELSD methods, but given the variability observed from cartridge to cartridge it may be advisable to lower this target response for the MCX method to provide further assurance that the detector will not saturate for certain cartridges. Overall, the cartridge to cartridge variability was minimal with respect to the reported PS20 amount for this method for the samples and cartridges tested.

TABLE 29

Cartridge to Cartridge Variability

| MCX Cartridge | 0.2 mg/mL PS20 spiked in water | | 0.1 mg/mL PS20 spiked in A18/A19 | | | A18/A19 (est. 0.2 mg/mL PS20) | |
|---|---|---|---|---|---|---|---|
| | Area (mv * min) | PS20 Amount (mg/mL) | Area (mv * min) | PS20 Amount (mg/mL) | % Recovery | Area (mv * min) | PS20 Amount (mg/mL) |
| 2 | 15.8 | 0.19 | 6.1 | 0.10 | 99.6 | n/a | n/a |
| 4 | 22.3 | 0.20 | n/a | n/a | n/a | 20.3 | 0.19 |
| 6 | 26.7 | 0.19 | 10.3 | 0.10 | 95.2 | 23.9 | 0.18 |

100× Injection of A18/A19 Sample

Although the experiments described above demonstrate that the OASIS® MCX cartridge can robustly and accurately quantify PS20, we wanted to test the cartridge durability by running long sequences with protein-containing samples. One of the products for which this method was initially being developed for has a very high target protein concentration of 150 mg/mL and may lead to cartridge failure/overpressuring due to protein accumulation on the cartridge. Typically, the pressure was ~25-45 bar when running the method. If the pressure increases above this range, the cartridge has likely accumulated protein and/or excipients and should be closely monitored or the cartridge replaced. If the cartridge starts leaking, it should be discarded and replaced immediately.

Figure 23:
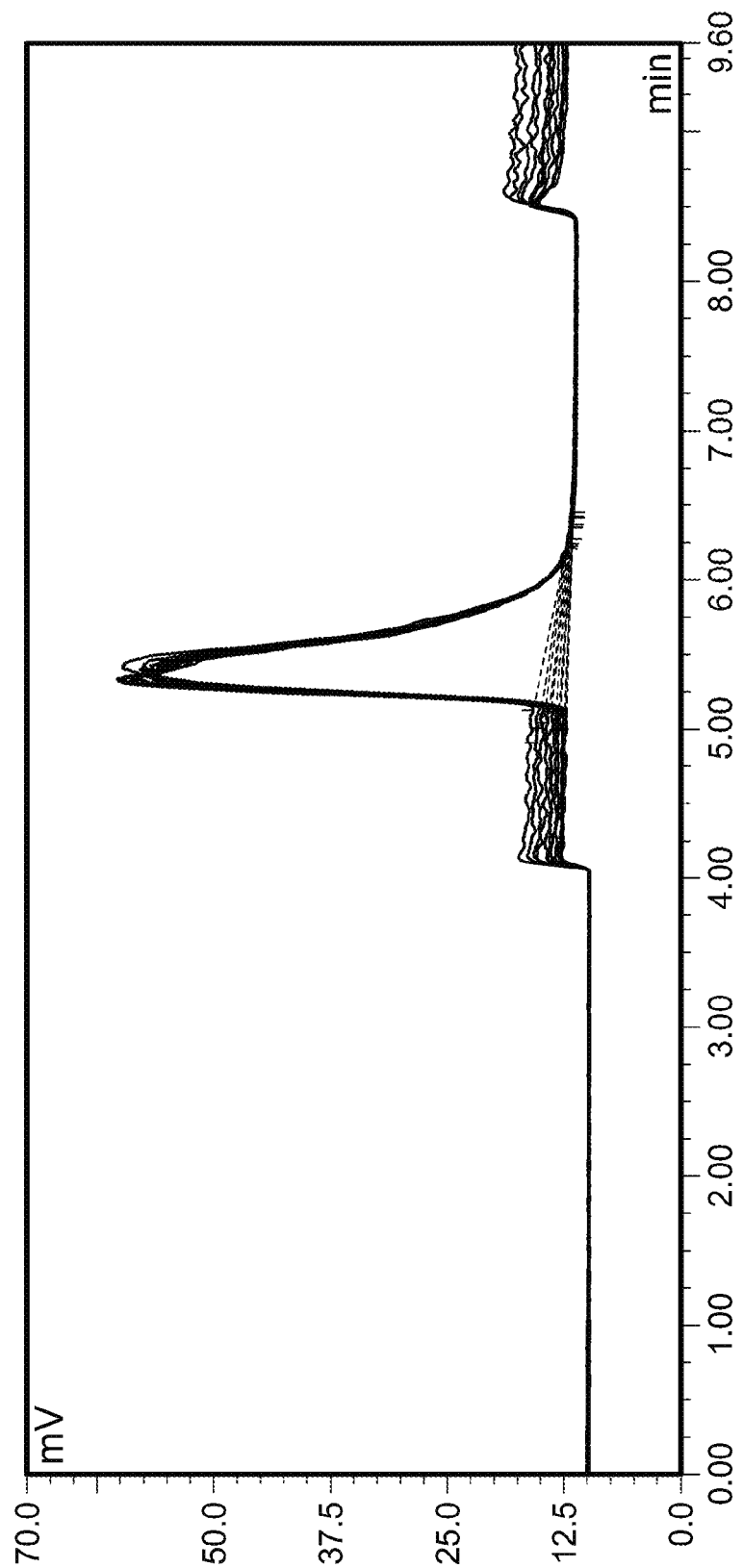
FIG. 23 shows ELSD chromatograms for control samples used in a sequence including 100 A18/A19 injections on a single cartridge. Overlay of 11 control samples injected throughout the sequence.

The cartridges repeatability and ability to consistently clear the protein and NAT was assessed by injecting protein (150 mg/mL) one hundred times (see Table 30 for sequence) using a new cartridge. The controls (n=11) were bracketed every tenth protein injection and were analyzed first to ensure the sequence was valid. FIG. 23 shows the overlay of the controls. Although there was an increase (up to 5 mV) in the beginning of the baseline (at 4.0-5.0 min, and after 8.5 min) and at the back-end of the baseline, these changes did not affect the integration or final PS20 quantitation (Table 31) with an average PS20 amount calculated at 0.2±0.005 (2.8% RSD) mg/mL.

TABLE 30

Sequence (all 25 µL injections)

| Sample | Replicates | Repeat |
|---|---|---|
| water | 5 | 0 |
| standard 1 (0.1 mg/mL in water) | 2 | |
| standard 2 (0.2 mg/mL in water) | 2 | |
| standard 3 (0.3 mg/mL in water) | 2 | |
| PS20-free formulation buffer | 1 | |
| PS20-free A18/A19 | 1 | |
| Formulation Buffer with PS20 | 1 | |
| water | 1 | |
| control (0.2 mg/mL in water) | 1 | |
| A18/A19 (est. 0.2 mg/ml PS20) | 10 | 9 |
| water | 1 | |
| control (0.2 mg/mL in water) | 1 | |
| PS20-free formulation buffer | 1 | 0 |
| PS20-free A18/A19 | 1 | |
| Formulation Buffer with PS20 | 1 | |
| standard 1 (0.1 mg/mL in water) | 2 | |
| standard 2 (0.2 mg/mL in water) | 2 | |
| standard 3 (0.3 mg/mL in water) | 2 | |

TABLE 31

Quantitation of controls used in 100X protein sequence

| Control (0.2 mg/mL PS20 in water) every 10th protein injection | PS20 Area (mV*min) | PS20 Amount (mg/mL) |
|---|---|---|
| Average | 18.5 | 0.2 |
| SD | 0.891 | 0.005 |
| % RSD | 4.8 | 2.8 |

Figure 24:
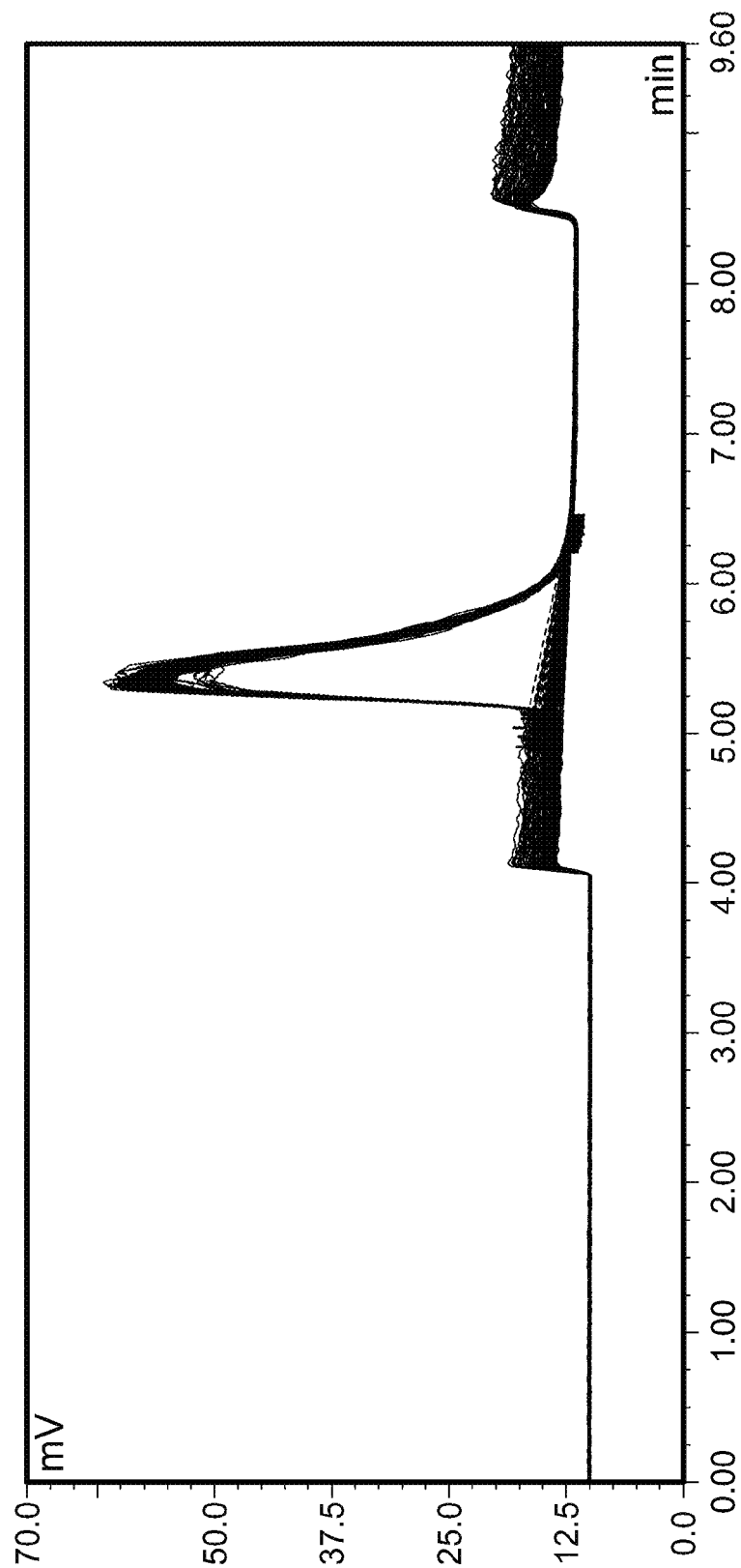
FIG. 24 shows ELSD chromatograms for A18/A19 samples used in a sequence including 100 A18/A19 injections on a single cartridge. Overlay of 100 A18/A19 sample injections throughout the sequence.
Figure 25A:
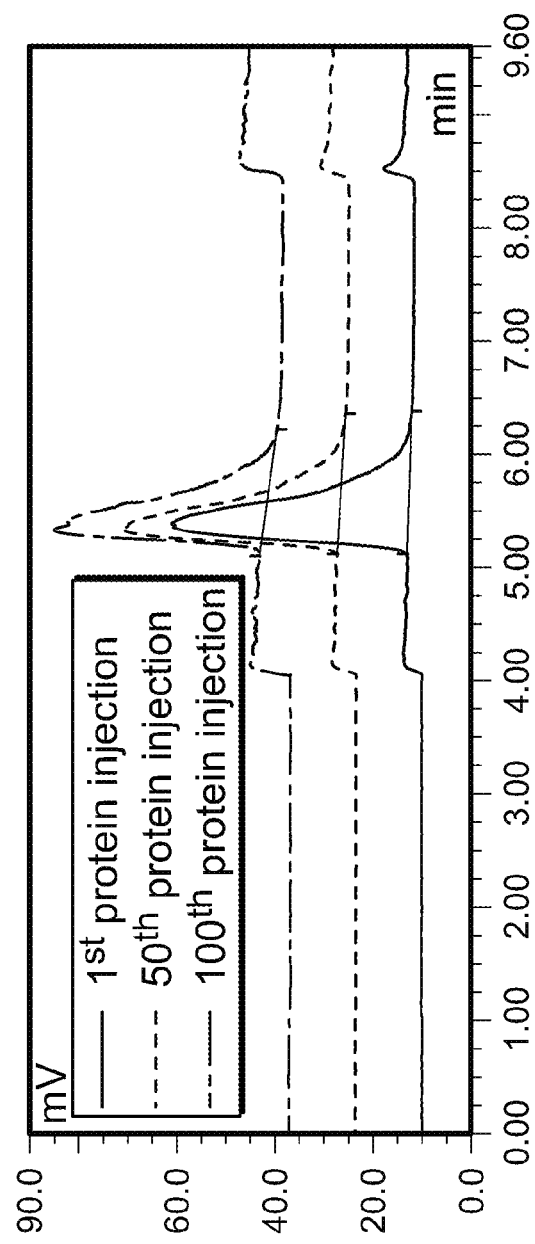
FIGS. 25A and 25B show chromatograms of the $1^{st}$, $50^{th}$, and $100^{th}$ protein injection from one sequence including 100 A18/A19 injections on a single cartridge.
Figure 25B:
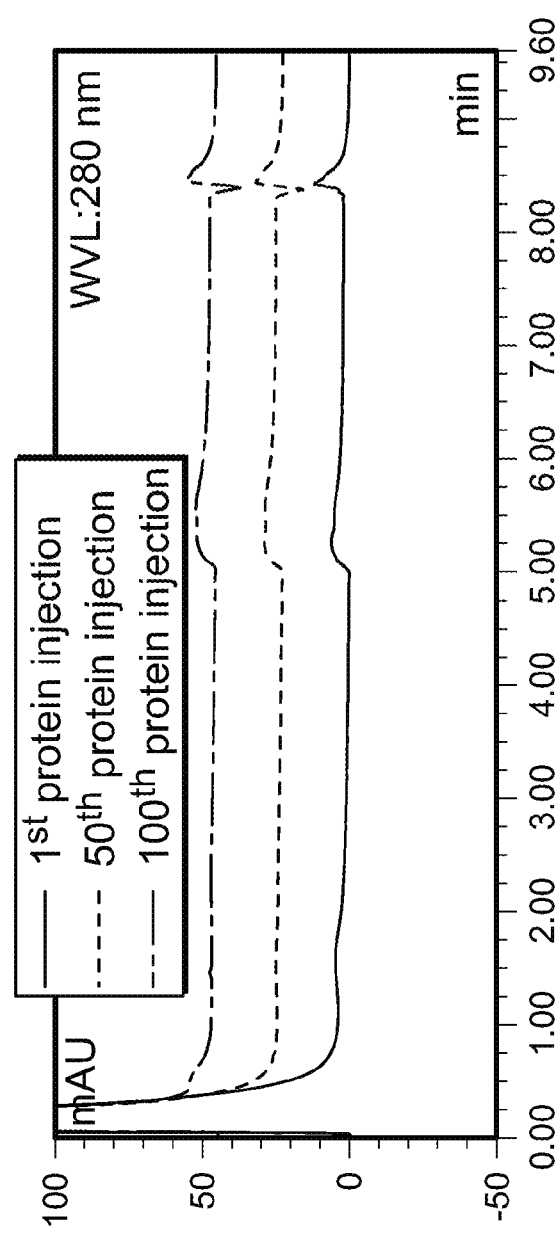
Figure 26A:
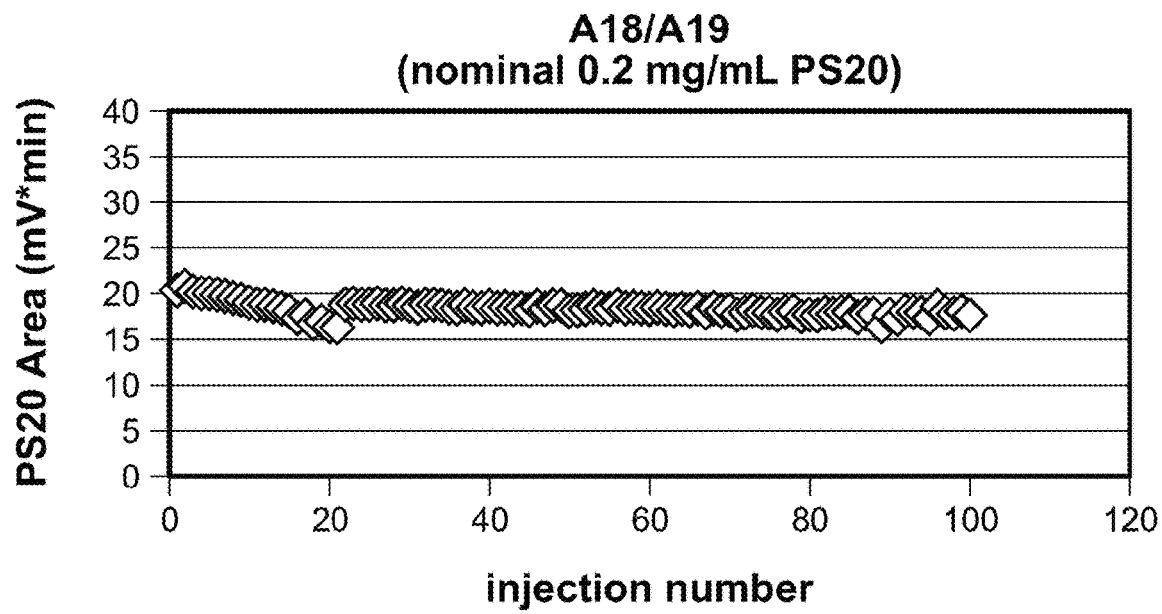
FIGS. 26A and 26B show quantitation results from 100 injections of A18/A19 sample (nominal 0.2 mg/mL PS20)
Figure 26B:
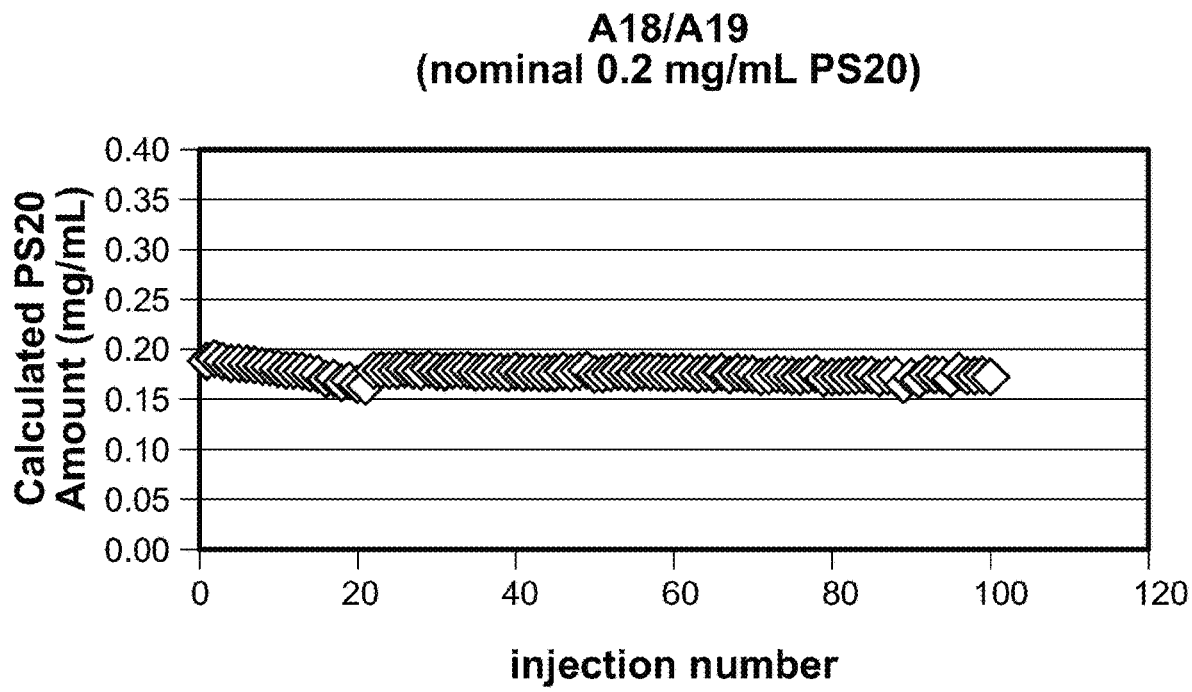

Since the controls were qualitatively and quantitatively consistent throughout the run, the one hundred A18/A19 samples (150 mg/mL) with nominal 0.2 mg/mL PS20 were integrated (FIG. 24) and quantitated (FIG. 26B, Table 32). FIG. 24 illustrates the same trend as the controls, with an increasing baseline (~5 mV) before the PS20 region, at 4.0-5.0 min, and after 8.5 min. Plotting the area vs injection number and amount vs injection number, the quantitation of the protein had minimal deviation, although there was a slight downward trend for the areas and amounts calculated for the first twenty injections, which may be due to the equilibration of the cartridge (FIGS. 26A and 26B). Ultimately, the average areas and amounts of PS20 quantified for the one hundred injections of the A18/A19 sample were 18.3±0.76 (4.2% RSD) mV*min and 0.2±0.005 (2.6% RSD) mg/mL, respectively (Table 32). Note that 375 mg of protein had been loaded onto the cartridge with the one-hundredth injection. The method consistently cleared the protein and excipients sufficiently prior to the effluent entering the ELSD at 4.0 minutes (FIG. 25A) throughout the sequence as depicted in the UV trace (FIG. 25B).

Figure 27A:
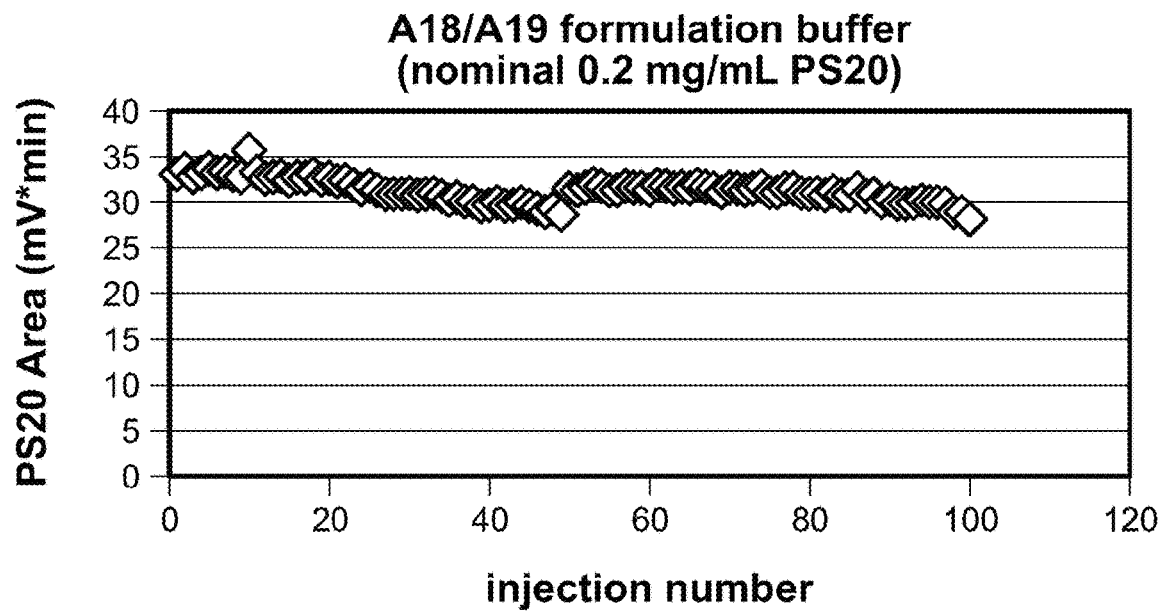
FIGS. 27A and 27B show quantitation results from 100 injections of A18/A19 formulation buffer (nominal 0.2 mg/mL PS20) using cartridge 5.
Figure 27B:
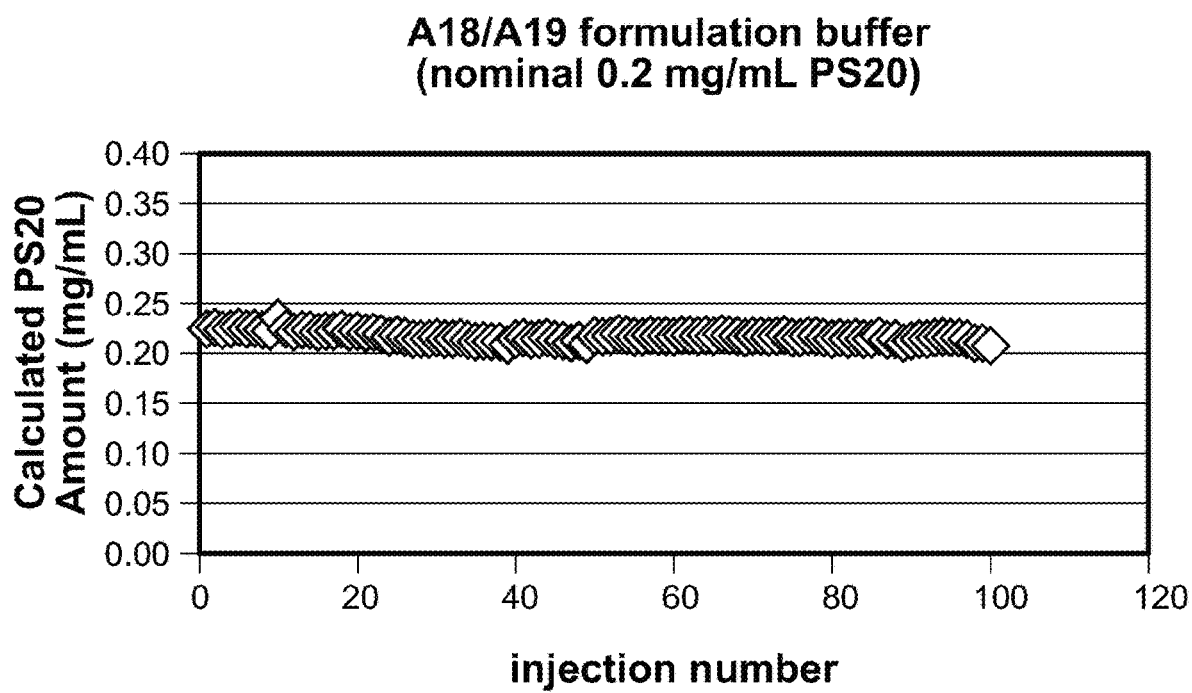

Because of the downward trend, one hundred injections of A18/A19 formulation buffer with nominal 0.2 mg/mL PS20 were assessed with a new MCX cartridge (cartridge 5) in order to determine if this effect is due to protein or formulation or both. Interestingly, there was a similar downward trend in the area counts [n=100, mean 31.3±1.3 (4.1% RSD) mv*min] for the first 49 injections (FIG. 27A). This behavior did not have a major impact on the quantitation [n=100, mean 0.22±0.005 (2.1% RSD)] (FIG. 27B, and Table 32).

Figure 28A:
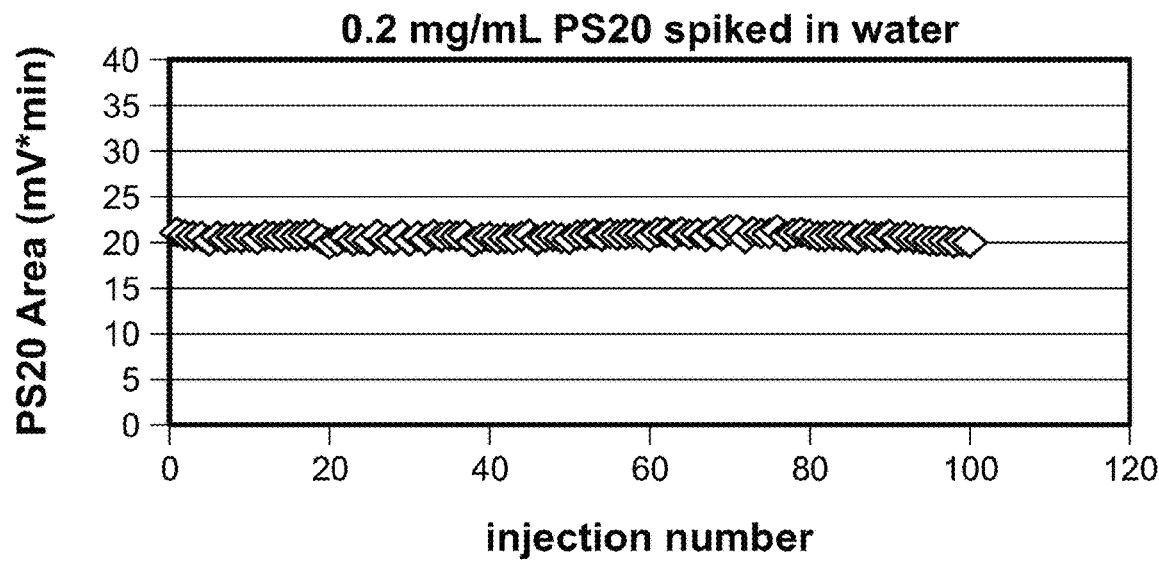
FIGS. 28A and 28B show quantitation results from 100 injections of 0.2 mg/mL PS20 spiked in water using cartridge 3.
Figure 28B:
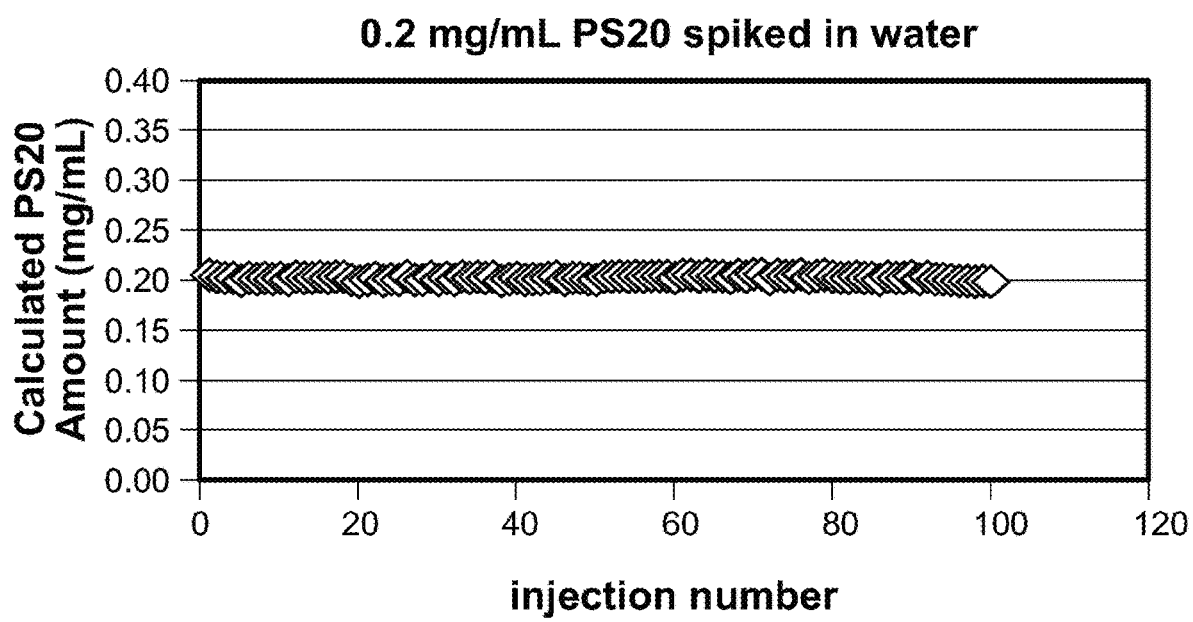
Figure 29A:
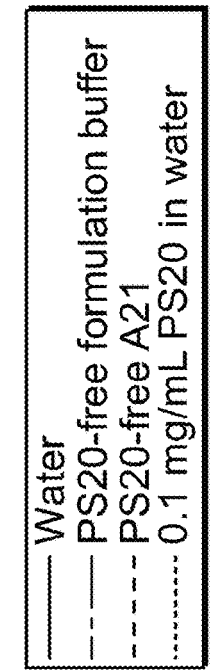
FIGS. 29A-29F show assessment of three low pI products using Method 1 and Method 2 by ELSD chromatography.
Figure 29B:
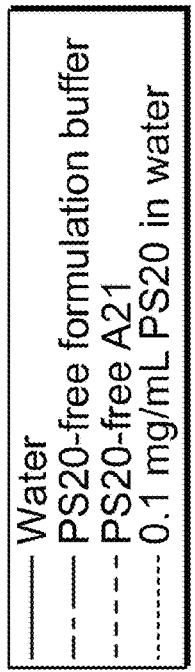
Figure 29C:
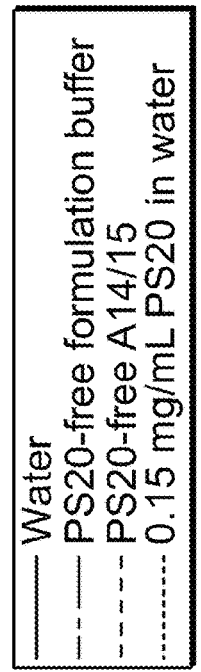
Figures 29D, 29E, 29F:
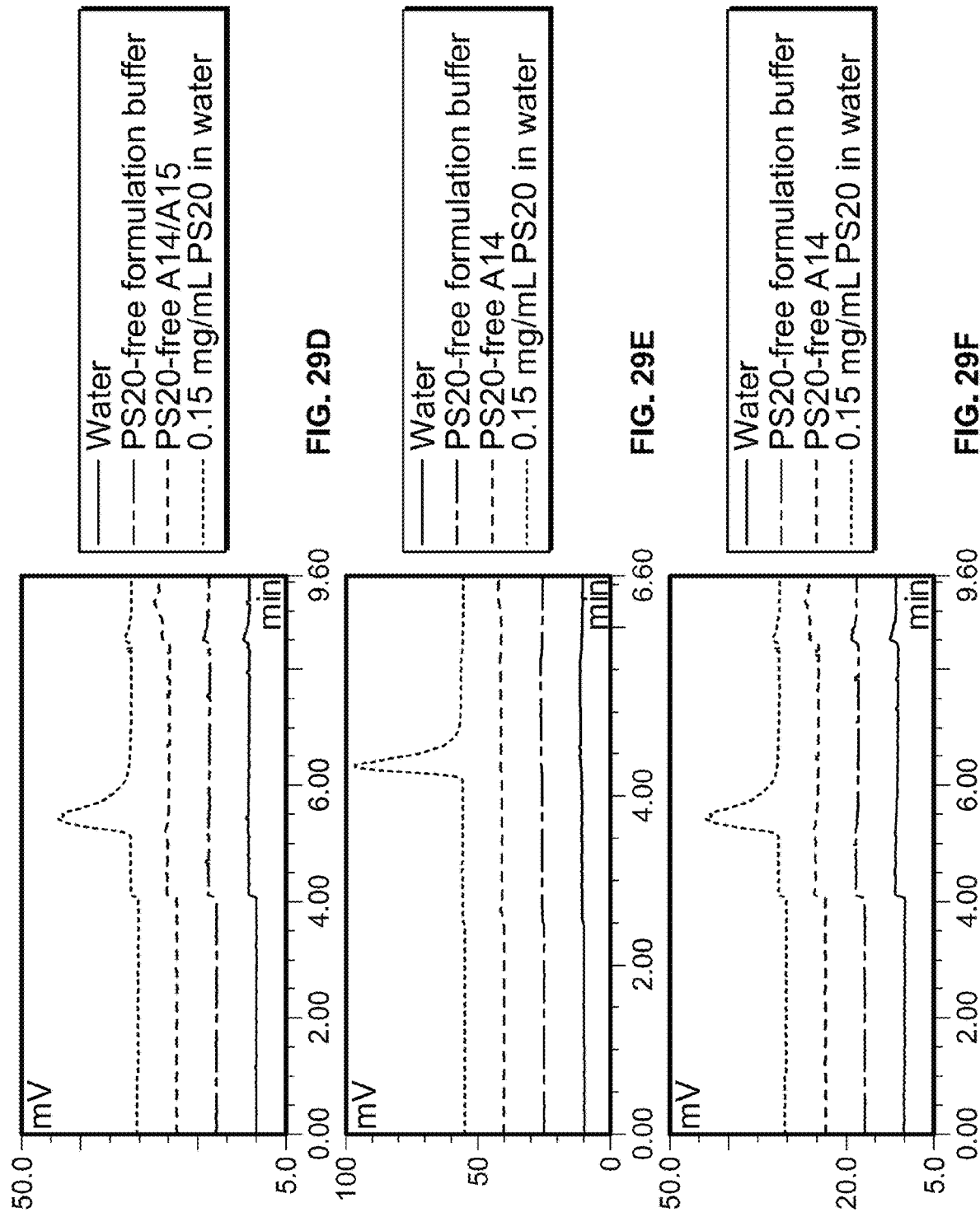

When 0.2 mg/mL PS20 spiked into water was also assessed on a brand new cartridge (cartridge 3), there was no such downward trend. For this sample, the area counts [n=100, mean 20.7±0.3 (1.5% RSD) mv*min] (FIG. 28A) remained consistent, along with the quantitation [n=100, mean 0.20±0.002 (0.9% RSD)] (FIG. 28B, Table 32). This result from the water+PS20 sample may indicate that the downward trend observed previously (FIGS. 26A and 27A) is related to the other excipients in the formulation or the presence of the protein. Another possibility is that it was an effect related to the specific cartridge used, and is not dependent on the other formulation components.

TABLE 32

Quantitation of 100X injections of PS20 spiked in water, A18/A19 formulation buffer, A18/A19 sample

| Sample | Parameter | PS20 Area (mV*min) | PS20 amount (mg/mL) |
|---|---|---|---|
| 0.2 mg/mL spiked in water | Mean | 20.7 | 0.20 |
| | SD | 0.3 | 0.002 |
| | % RSD | 1.5 | 0.92 |
| A18/A19 formulation buffer (est. 0.2 mg/mL PS20) | Mean | 31.3 | 0.22 |
| | SD | 1.3 | 0.005 |
| | % RSD | 4.1 | 2.09 |
| 150 mg/mL A18/A19 sample (est. 0.2 mg/mL PS20) | Mean | 18.3 | 0.18 |
| | SD | 0.8 | 0.005 |
| | % RSD | 4.2 | 2.61 |

Overall, the three cartridges were each able to perform efficiently after 100 PS20 injections, illustrating that the reproducibility and ruggedness of the MCX cartridge is suitable for routine use in a QC environment. More importantly, the absorbance profiles of one hundred protein injections clearly show similar clearance of both protein and NAT throughout the sequence (FIG. 25B). The PS20 quantification remained statistically constant throughout the sequence.

PS20 Quantification Assessment of Three Low pI Products

Three different low pI products, A21, A14/A15 and A14 (Table 33), were assessed with Method 1 (described in Example 1) and Method 2. The cartridges used for this assessment are listed in Table 34. The method performance characteristics tested were specificity, accuracy, linearity and repeatability.

TABLE 33

Molecules assessed

| Product | Buffer | Nominal Protein Concentration (mg/mL) | Nominal PS20 concentration (mg/mL) | pI |
|---|---|---|---|---|
| A21 | 20 mM histidine chloride pH 5 | 150 | 0.2 | 7.2* |
| A14/A15 bispecific | 20 mM HisAce, 240 mM Sucrose, pH 5.8 | 190 | 0.3 | 7.2* |

TABLE 33-continued

Molecules assessed

| Product | Buffer | Nominal Protein Concentration (mg/mL) | Nominal PS20 concentration (mg/mL) | pI |
|---|---|---|---|---|
| A14 | DF buffer 20 mM histidine acetate pH 5.7 | 160 | 0.3 | 6.2** |

*pI determined by the bracketing (calibration curve) approach method
**pI determined by the icIEF control system assay

TABLE 34

Cartridges used during method development

| Cartridge Type | Cartridge Number | Sorbent Batch # | Cartridge Lot # |
|---|---|---|---|
| Mixed mode cation exchange cartridge (MCX) for Method 2 | 7 | 0101 | 0101342141 |
| Mixed mode anion exchange cartridge (MAX) for Method 1 | 8 | 0053 | 0053323111 |

Specificity

The specificity calculated for the three molecules is shown in Table 35. Corresponding chromatograms are shown in FIGS. 29A-29F. A21 (150 mg/mL) had 16% interference when assessed with Method 1 (Oasis® MAX with methanol and acetic acid) and 7% interference when assessed with the Method 2 (Oasis® MCX with methanol and ammonium hydroxide), compared to 0.1 mg/mL PS20 in water (50% target). This may be due to weaker interaction of the low pI product with the cation exchange resin (sulfite anion group), minimizing the protein interference. A14/A15 (192 mg/mL) had 3% interference when assessed with Method 1 and 2% interference when assessed with the Method 2, compared to 0.15 mg/mL PS20 in water (50% target). A14 (161 mg/mL) had ~1% interference when assessed with both methods, compared to 0.15 mg/mL PS20 in water (50% target). The specificity of these products was not significantly impacted by the method.

TABLE 35

Specificity of three low pI molecules

| Product | Method 1 Specificity (%) | Method 2 Specificity (%) |
|---|---|---|
| A21 | 15.6 | 7.1 |
| A14/A15 | 3.4 | 1.9 |
| A14 | 0.8 | 0.6 |

Accuracy

In order to determine the accuracy of the assay, a known amount of PS20 was spiked into PS20-free protein and the recoveries for each concentration were determined (Table 36). The typical validation acceptance criteria require that the % recovery be within 80-120%.

PS20-free A21 was evaluated by spiking PS20 at a range of 0.10-0.30 μmg/mL. The accuracy data are summarized in Table 36. At the PS20 concentrations tested, the range of recoveries, when samples were analyzed using Method 1 and Method 2, were 99-108% and 101-110%, respectively. The accuracies of PS20-free A14/A15 and A14 were assessed by spiking PS20 at a range of 0.15-0.45 mg/mL. The PS20 recoveries for A14/A15, when samples were analyzed using Method 1 and Method 2, ranged from 97-101% and 92-99%, respectively. The PS20 recoveries for A14, when samples were analyzed using Method 1 and Method 2, ranged from 102-108% and 102-110%, respectively. Overall, the data from the spiked recovery experiments for all three products tested demonstrated that both methods are accurate.

TABLE 36

Recovery of three low pI products

| | Method 1 | | | Method 2 | | |
|---|---|---|---|---|---|---|
| Sample | Average Area | Average Amount (mg/mL) | % Recovery Average | Average Area | Average Amount (mg/mL) | % Recovery Average |
| 0.10 mg/mL PS20 in A21 | 6.1 | 0.11 | 108.4 | 3.3 | 0.11 | 109.6 |
| 0.15 mg/mL PS20 in A21 | 9.9 | 0.15 | 98.9 | 5.8 | 0.15 | 101.3 |
| 0.20 mg/mL PS20 in A21 | 16.0 | 0.20 | 100.8 | 9.6 | 0.21 | 102.8 |
| 0.25 mg/mL PS20 in A21 | 22.9 | 0.25 | 101.5 | 14.0 | 0.26 | 102.1 |
| 0.30 mg/mL PS20 in A21 | 30.9 | 0.31 | 102.6 | 19.0 | 0.31 | 101.8 |
| 0.15 mg/mL PS20 in A14/A15 | 8.5 | 0.15 | 97.2 | 4.5 | 0.14 | 91.7 |
| 0.23 mg/mL PS20 in A14/A15 | 18.5 | 0.23 | 100.9 | 11.0 | 0.23 | 98.4 |
| 0.3 mg/mL PS20 in A14/A15 | 27.1 | 0.29 | 97.1 | 15.9 | 0.28 | 93.1 |
| 0.38 mg/mL PS20 in A14/A15 | 41.1 | 0.37 | 98.4 | 25.9 | 0.37 | 96.7 |
| 0.45 mg/mL PS20 in A14/A15 | 54.5 | 0.44 | 98.4 | 36.5 | 0.45 | 99.3 |
| 0.15 mg/mL PS20 in A14 | 10.0 | 0.16 | 106.8 | 6.2 | 0.16 | 109.6 |
| 0.23 mg/mL PS20 in A14 | 20.6 | 0.25 | 107.6 | 13.3 | 0.25 | 109.6 |
| 0.3 mg/mL PS20 in A14 | 30.2 | 0.31 | 103.7 | 19.1 | 0.31 | 103.2 |
| 0.38 mg/mL PS20 in A14 | 44.5 | 0.39 | 103.3 | 29.4 | 0.39 | 103.8 |
| 0.45 mg/mL PS20 in A14 | 57.7 | 0.46 | 101.9 | 38.6 | 0.46 | 102.4 |

Triplicate, 20 μL injections

Linearity

Linearity was evaluated by determining that Pearson's correlation coefficient (r)≥0.99 over the ranges tested for the three low pI products assessed with Method 1 and Method 2. These values are shown in Table 37 for each range of PS20 concentrations for each product. All values of Pearson's correlation coefficient were greater than 0.99 for the PS20 ranges tested. Therefore, linearity was acceptable for Method 1 and Method 2 across the three products tested.

TABLE 37

Linearity of three low pI products

| Product | PS20 concentration range (mg/mL) | Method | Slope (m) | Y-intercept (b) | Linearity Correlation (r) | Residual sum of squares (RSS) |
|---|---|---|---|---|---|---|
| A21 | 0.10-0.30 | Method 1 | 1.4928 | 2.2566 | 0.9974 | 0.00163 |
|  |  | Method 2 | 1.6173 | 2.1165 | 0.9989 | 0.00083 |
| A14/A15 | 0.15-0.45 | Method 1 | 1.6733 | 2.3171 | 0.9994 | 0.00048 |
|  |  | Method 2 | 1.8659 | 2.2018 | 0.9984 | 0.00162 |
| A14 | 0.15-0.45 | Method 1 | 1.5917 | 2.3165 | 0.9996 | 0.00025 |
|  |  | Method 2 | 1.6481 | 2.1578 | 0.9993 | 0.00055 |

Repeatability

The repeatability was assessed by testing three replicates of five concentrations and measuring the % RSD of the PS20 peak areas. This experiment was performed with 0.10-0.30 mg/mL PS20-spiked into PS20-free A21 and 0.15-0.45 mg/mL PS20-spiked into PS20-free A14/A15 and A14. The results of this assessment are displayed in Table 38, and show that the precision of the assay was acceptable for both Method 1 and Method 2 across the three products tested.

TABLE 38

Repeatability of three low pI products

| Sample | Method 1 % RSD (N = 3) | Method 2 % RSD (N = 3) |
|---|---|---|
| 0.10 mg/mL PS20 in A21 | 1.41 | 0.53 |
| 0.15 mg/mL PS20 in A21 | 1.03 | 1.97 |
| 0.20 mg/mL PS20 in A21 | 0.99 | 0.97 |
| 0.25 mg/mL PS20 in A21 | 0.23 | 0.68 |
| 0.30 mg/mL PS20 in A21 | 0.86 | 0.19 |
| 0.15 mg/mL PS20 in A14/A15 | 1.98 | 0.42 |
| 0.23 mg/mL PS20 in A14/A15 | 1.14 | 0.67 |
| 0.30 mg/mL PS20 in A14/A15 | 3.90 | 0.83 |
| 0.38 mg/mL PS20 in A14/A15 | 4.86 | 1.59 |
| 0.45 mg/mL PS20 in A14/A15 | 0.90 | 1.06 |
| 0.15 mg/mL PS20 in A14 | 0.63 | 1.26 |
| 0.23 mg/mL PS20 in A14 | 0.93 | 1.82 |
| 0.30 mg/mL PS20 in A14 | 0.64 | 0.99 |
| 0.38 mg/mL PS20 in A14 | 0.39 | 1.65 |
| 0.45 mg/mL PS20 in A14 | 0.25 | 0.38 |

Triplicate, 20 μL injections

CONCLUSIONS

The following modifications from Method 1 of Example 1 were made to the current ELSD assay, Method 2:

Mobile phase additive switched from 2% acetic acid to 1.5% ammonium hydroxide

Flow rate changed from 1.25 mL/min to 1.40 mL/min

LC flow going from waste into the ELSD from 2.4 minutes changed to 4.0 minutes

Concentration of B % in wash step switched from 40% to 45% mobile phase B

Time of the organic in wash step from 1.0-3.4 minutes switched to 1.0-4.4 minutes Time of the elution step from 3.5-4.6 minutes changed to 4.5-7.6 minutes Time of the equilibration step from 4.7-6.6 minutes changed to 7.7-9.6 minutes These modifications eliminated both NAT and protein interference and had minimal cartridge to cartridge quantitation variability. The results from the qualification of this modified assay for three NAT-containing products showed that this assay was suitable for quantifying polysorbate 20 in these formulations.

Three low pI molecules were assessed with both Method 1 and Method 2. The only instance of failure to meet acceptance criteria was for specificity when using Method 1 with A21. Other than this, both methods passed accuracy, linearity, and repeatability criteria for all three low pI products. These results further indicate that Method 2 is also capable of quantifying PS20, and is particularly useful for non-NAT containing products.

What is claimed is:

1. A method for quantifying a non-ionic surfactant in a composition comprising the non-ionic surfactant and a polypeptide, wherein the method comprises the steps of
   a) applying the composition to a mixed mode anion exchange chromatography material, wherein the composition is loaded onto the chromatography material in a solution comprising a mobile phase A and a mobile phase B, wherein mobile phase A comprises acetic acid in water and mobile phase B comprises acetic acid in methanol, wherein the polypeptide binds to the chromatography material specifically and non-specifically;
   b) eluting the specifically bound polypeptide from the mixed mode anion exchange chromatography material with a solution comprising mobile phase A and mobile phase B wherein the ratio of mobile phase B to mobile phase A is increased compared to step a);
   c) eluting the non-ionic surfactant and the non-specifically bound polypeptide from the chromatography material with a solution comprising mobile phase A and mobile phase B wherein the ratio of mobile phase B to mobile phase A is increased compared to step b);
   d) quantifying the non-ionic surfactant.

2. The method of claim 1, wherein the ratio of mobile phase B to mobile phase A in step a) is about 10:90.

3. The method of claim 1, wherein the ratio of mobile phase B to mobile phase A is increased to about 40:60 in step b).

4. The method of claim 1, wherein the ratio of mobile phase B to mobile phase A is increased to about 100:0 in step c).

5. The method of claim 1, wherein mobile phase A comprises about 2% acetic acid in water.

6. The method of claim 1, wherein mobile phase B comprises about 2% acetic acid in methanol.

7. The method of claim 1, wherein the flow rate of the chromatography is about 1.25 mL/minute.

8. The method of claim 7, wherein step b) starts at about 1 min after the chromatography is initiated and ends at about 3.4 min after the chromatography is initiated and/or step c) starts at about 3.5 min after the chromatography is initiated and ends at about 4.6 min after the chromatography is initiated.

9. The method of claim 1, wherein the non-ionic surfactant is poloxamer (P188) or a polysorbate.

10. The method of claim 9, wherein the polysorbate is polysorbate 20 or polysorbate 80.

11. The method of claim 1, wherein the concentration of non-ionic surfactant in the composition is in the range of about 0.001% to 1.0% (w/v).

12. The method of claim 1, wherein the polypeptide concentration in the composition is about 1 mg/mL to about 250 mg/mL.

13. The method of claim 1, wherein the composition has a pH of about 4.5 to about 7.5.

14. The method of claim 1, wherein the composition further comprises one or more excipients selected from the group consisting of a stabilizer, a buffer, and a tonicity agent.

15. The method of claim 1, wherein the composition is a pharmaceutical formulation suitable for administration to a subject.

16. The method of claim 1, wherein the polypeptide is a therapeutic polypeptide.

17. The method of claim 16, wherein the therapeutic polypeptide is a fusion protein, a polyclonal antibody, a monoclonal antibody, a humanized antibody, a human antibody, a chimeric antibody, a multispecific antibody, a glycoengineered antibody, an antibody fragment, an antibody drug conjugate, a THIOMAB™ or a THIOMAB™ drug conjugate.

18. The method of claim 1, wherein the mixed mode anion exchange chromatography material comprises a reversed phase, strong anion exchange polymer.

19. The method of claim 1, wherein the mixed mode anion exchange chromatography material comprises a quaternary amine moiety.

20. The method of claim 1, wherein the mixed mode anion exchange chromatography material comprises a solid support.

21. The method of claim 1, wherein the mixed mode anion exchange chromatography material is contained in a column.

22. The method of claim 1, wherein the mixed mode anion exchange chromatography material is a high performance liquid chromatography (HPLC) material.

23. The method of claim 1, wherein the non-ionic surfactant is quantified by Evaporative Light Scattering (ELSD) or by using a Charged Aerosol Detector (CAD).

* * * * *